US012765812B2

(12) United States Patent
Andrijauskas et al.

(10) Patent No.: US 12,765,812 B2
(45) Date of Patent: Oct. 20, 2026

(54) SYSTEMS AND METHODS FOR NONINVASIVE MONITORING OF THE BODY FLUID STATUS AND HEMOGLOBIN, AND USING THE SAME FOR AN AUTOMATED DECISION SUPPORT

(71) Applicant: Micro Flow Medix B.V., The Hague (NL)

(72) Inventors: Audrius Andrijauskas, Vilnius (LT); Povilas Andrijauskas, Vilnius (LT); Darius Dilijonas, Kaunas (LT); Mindaugas Leonavičius, The Hague (NL); Vaidotas Marozas, Kaunas (LT); Tomas Jovaiša, Vilnius (LT); Edgaras Stankevičius, Kaunas (LT); Mantas Jucevičius, Kaunas (LT)

(73) Assignee: MICRO FLOW MEDIX B.V., The Hague (NL)

( * ) Notice: Subject to any disclaimer, the term of this patent is extended or adjusted under 35 U.S.C. 154(b) by 0 days.

(21) Appl. No.: 19/209,716

(22) Filed: May 15, 2025

(65) Prior Publication Data

US 2025/0352096 A1 Nov. 20, 2025

Related U.S. Application Data

(60) Provisional application No. 63/647,836, filed on May 15, 2024.

(51) Int. Cl.
*A61B 5/00* (2006.01)
*A61B 5/145* (2006.01)
(Continued)

(52) U.S. Cl.
CPC ........ *A61B 5/14546* (2013.01); *A61B 5/1455* (2013.01); *A61B 5/1495* (2013.01);
(Continued)

(58) Field of Classification Search
None
See application file for complete search history.

(56) References Cited

U.S. PATENT DOCUMENTS 7,209,775 B2 4/2007 Bae et al.
7,788,045 B2 8/2010 Andrijauskas
(Continued)

FOREIGN PATENT DOCUMENTS

CN 107249444 A 10/2017
CN 112924660 A 6/2021
(Continued)

OTHER PUBLICATIONS

Egro FM, Kenny EM, Manders EC, Manders E. A Nomogram for the Rapid Prediction of Hematocrit Following Blood Loss and Fluid Shifts in Neonates, Infants, and Adults. Cureus. Apr. 22, 2020;12(4):e7780. doi: 10.7759/cureus.7780. PMID: 32461853; PMCID: PMC7243637. (Year: 2020).*

(Continued)

*Primary Examiner* — Tse W Chen
*Assistant Examiner* — Martin Nathan Ortega
(74) *Attorney, Agent, or Firm* — Gary J. Gershik

(57) ABSTRACT

Methods and apparatus for multi-wavelength (MW) photoplethysmography (PPG)-based trend monitoring are used to monitor changes in total hemoglobin, fluid accumulation in circulation (plasma volume) and tissues (interstitial fluid volume), total blood volume, and tissue perfusion (microcirculation). The methods and systems provide integration of automated decision support in both medical-grade and non-medical grade wearables for continuous body fluid management guided by MW PPG measurements. Recommendations for optimizing physiological function, including management of fluid intake, restriction or removal, co- (Continued)

administration of cardiovascular medication, and red blood cell transfusion may be provided. Blood loss detection and transfusion-related recommendations may be made based in assessing whole-body hemoglobin mass changes by differentiating dilution-related variations in hemoglobin concentration from net changes in hemoglobin mass due to red blood cell loss or transfusion. Plasma dilution-related fluctuations in plasma volume and corresponding blood volume changes may also be monitored alongside fluctuations in tissue fluid volume and transcapillary fluid shifts. The system may provide clinically relevant trend data for clinician interpretation and real-time alerts for assessing fluid status, including intravascular and extravascular fluid accumulation, total blood volume changes, plasma volume, and net hemoglobin mass variations. Clinical guidance on fluid management, real-time alerts for imminent edema or dehydration risks, and notifications regarding potential blood loss or transfusion effects on hemoglobin levels may be provided. In a non-clinical setting, the system advises on fluid intake or restriction based on fluid accumulation trends in circulation and tissues which are an indication of plasma and tissue hydration status, and prompts users to seek medical attention when a significant reduction in hemoglobin is detected.

20 Claims, 132 Drawing Sheets

(51) Int. Cl.

*A61B 5/1455* (2006.01)
*A61B 5/1495* (2006.01)

(52) U.S. Cl.

CPC ............ *A61B 5/443* (2013.01); *A61B 5/7264* (2013.01); *A61B 5/7275* (2013.01); *A61B 5/742* (2013.01); *A61B 5/7475* (2013.01); *A61B 2560/0223* (2013.01); *A61B 2562/0233* (2013.01)

(56) References Cited

U.S. PATENT DOCUMENTS

| | | | |
|---|---|---|---|
| 8,048,040 | B2 | 11/2011 | Kiani |
| 8,428,673 | B2 | 4/2013 | Cho et al. |
| 9,095,307 | B2 | 8/2015 | Parfenova et al. |
| 9,717,446 | B2 | 8/2017 | Dixon et al. |
| 10,231,667 | B2 | 3/2019 | Mathew et al. |
| 10,285,599 | B2 | 5/2019 | Fortin |
| 10,456,056 | B2 | 10/2019 | Govari et al. |
| 11,026,604 | B2 | 6/2021 | Chen et al. |
| 2007/0178167 | A1* | 8/2007 | Andrijauskas ............ A61P 7/04 424/529 |
| 2008/0146890 | A1 | 6/2008 | Leboeuf et al. |
| 2010/0081942 | A1* | 4/2010 | Huiku ................... A61M 5/145 600/483 |
| 2010/0099964 | A1 | 4/2010 | O'Reilly et al. |
| 2010/0286515 | A1* | 11/2010 | Gravenstein ....... A61B 5/14552 600/437 |
| 2011/0070210 | A1* | 3/2011 | Andrijauskas ......... A61K 35/18 424/93.73 |
| 2013/0317322 | A1 | 11/2013 | Andrijauskas |
| 2014/0058232 | A1 | 2/2014 | Andrijauskas |
| 2017/0266192 | A1 | 9/2017 | Jasper et al. |
| 2019/0320988 | A1* | 10/2019 | Ahmed .................. A61B 5/002 |
| 2020/0297259 | A1* | 9/2020 | Feldschuh .......... A61B 5/14542 |
| 2021/0219882 | A1 | 7/2021 | Huiku et al. |
| 2022/0176088 | A1* | 6/2022 | Salahieh ................ A61B 5/686 |
| 2023/0347029 | A1 | 11/2023 | Corso et al. |
| 2024/0016421 | A1* | 1/2024 | Feldschuh .............. A61B 5/746 |
| 2024/0404689 | A1 | 12/2024 | Andrijauskas et al. |

FOREIGN PATENT DOCUMENTS

| | | | |
|---|---|---|---|
| CN | 114869260 | A | 8/2022 |
| DE | 102015015113 | A1 | 5/2017 |
| DE | 102016006196 | A1 | 11/2017 |
| EP | 2096984 | B1 | 1/2012 |
| EP | 1931239 | B1 | 8/2012 |
| EP | 2839777 | B1 | 12/2015 |
| EP | 3212060 | A1 | 9/2017 |
| EP | 3099224 | B1 | 5/2020 |
| JP | H04158843 | A | 6/1992 |
| JP | H06169902 | A | 6/1994 |
| JP | 2017510390 | A | 4/2017 |
| JP | 2018502612 | A | 2/2018 |
| JP | 2018518323 | A | 7/2018 |
| JP | 6636410 | B2 | 1/2020 |
| JP | 2020516358 | A | 6/2020 |
| JP | 2021522880 | A | 9/2021 |
| JP | 2022153480 | A | 10/2022 |
| TW | 201038249 | A | 11/2010 |
| TW | 201038253 | A | 11/2010 |

OTHER PUBLICATIONS

Yang Y, Huang S, Jia Y, Song G, Ye X, Lu K, Li G, Wang F, Zhu S. A 6-month prognostic nomogram incorporating hemoglobin level for intracerebral hemorrhage in younger adults. BMC Neurol. Jan. 6, 2023;23(1):6. doi: 10.1186/s12883-022-03039-9. PMID: 36609246; PMCID: PMC9817395. (Year: 2023).*

Rosen E, Yap TA, Lee EK, Højgaard M, Mettu NB Development of a Practical Nomogram for Personalized Anemia Management in Patients Treated with Ataxia Telangiectasia and Rad3-related Inhibitor Camonsertib. Clin Cancer Res. Feb. 16, 2024;30(4): 687-694. doi: 10.1158/1078-0432.CCR-23-2080. (Year: 2024).*

Volkova E, Perchik A, Pavlov K, Nikolaev E, Ayuev A, Park J, Chang N, Lee W, Kim JY, Doronin A, Vilenskii M. Multispectral sensor fusion in SmartWatch for in situ continuous monitoring of human skin hydration and body sweat loss. Sci Rep. Aug. 17, 2023;13(1):13371. doi: 10.1038/s41598-023-40339-7. PMID: 37591885; PMCID: PMC10435441.

Castaneda D, Esparza A, Ghamari M, Soltanpur C, Nazeran H. A review on wearable photoplethysmography sensors and their potential future applications in health care. Int J Biosens Bioelectron. 2018;4(4):195-202. doi: 10.15406/ijbsbe.2018.04.00125. Epub Aug. 6, 2018. PMID: 30906922; PMCID: PMC6426305.

Pereira T, Ding C, Gadhoumi K, Tran N, Colorado RA, Meisel K, Hu X. Deep learning approaches for plethysmography signal quality assessment in the presence of atrial fibrillation. Physiol Meas. Dec. 27, 2019;40(12):125002. doi: 10.1088/1361-6579/ab5b84. PMID: 31766037; PMCID: PMC7198064.

Svensen, C. H.; Stankevicius, E.; Broms, J.; Markevicius, V.; Andrijauskas, A., Evaluation of hydration status calculated from differences in venous and capillary plasma dilution during stepwise crystalloid infusions: A randomized crossover study in healthy volunteers. Medicina (Kaunas, Lithuania) 2014, 50 (5), 255-62. https://doi.org/10.1016/j.medici.2014.09.007.

Andrijauskas, A.; Ivakeviius, J.; Porvaneckas, N.; Stankeviius, E.; H. Svensen, C.; Uvarovas, V.; Švedienė, S.; Kvederas, G., A mini volume loading test for indication of preoperative dehydration in surgical patients. Medicina (Kaunas, Lithuania) 2015, 51 (2), 81. https://doi.org/10.1016/j.medici.2015.02.001.

Andrijauskas, A.; Svensen, C. H.; Porvaneckas, N.; Sipylaite, J.; Stankevicius, E.; Cincikas, D.; Uvarovas, V.; Svediene, S.; Satkauskas, I.; Vosylius, S.; Kvederas, G., A mini volume loading test (mVLT) using 2.5-mLkg(-1) boluses of crystalloid for indication of perioperative changes in hydration status. Medicina (Kaunas, Lithuania) 2016, 52 (6), 354-365. https://doi.org/10.1016/j.medici.2016.11.004.

Markevicius, V.; Cincikas, D.; Porvaneckas, N.; Stankevicius, E.; Navikas, D.; Andriukaitis, D.; Sipylaite, J.; Svediene, S.; Uvarovas, V.; Satkauskas, I.; Kvederas, G.; Valinevicius, A.; Zilys, M.; Andrijauskas, A., Revised 7 Evaluation of Hemodilution Response

(56) References Cited

OTHER PUBLICATIONS in the Semi-Closed Loop Infusion System. 2016; vol. 22. https://doi.org/10.5755/j01.eee.22.1.12826.

* cited by examiner

A

B

C

D

E

F

A

B

C

A

B

C

A

B

C

A

B

C

D

RA – Radial artery

SPBRA – Superficial palmar branch of radial artery

FPMA- First palmar metacarpal artery

RIA – Radialis indicis artery

PPA – Princeps Pollicis artery

UDA – Ulnar digital artery

RDA – Radial digital artery

SPA – Superficial palmar arch

DPA- Deep palmar arch

*Figure 1:* The palmar arterial system of the thumb showing major principal arteries of thumb.

LOST PROPORTIONALITY BETWEEN CHANGE IN PV AND TBV
BECAUSE REDUCTION IN tHb (blood loss) counteracts increase in PV LOST PROPORTIONALITY BETWEEN CHANGE IN PV AND TBV
BECAUSE REDUCTION IN tHb (blood loss) counteracts increase in PV

| INTER-SESSION CHANGES & FAR | | | | |
|---|---|---|---|---|
| lwDC | n | 8 | ΔlwDCn+1 | -3,00 |
| | n+1 | 5 | QlwDCn+1 | -0,38 |
| bwDC | n | 9 | ΔbwDCn+1 | -2,00 |
| | n+1 | 7 | QbwDCn+1 | -0,22 |
| **FAR** = Q bwDCn+1 - QlwDCn+1 | | | | **0,15** |

| mPD | mtcPED | FAR | Oedema | Reflux | Urine | Lymph | Blood loss |
|---|---|---|---|---|---|---|---|
| ↓ | ↓ | ↓ | | ↑ | ↑ | | |
| ↑ | ↓ | ↓ | | ↑ | ↑ | ↑ | ↑ |
| ↑ | ↑ | ↑ | ↑ | | ↑ | ↑ | ↑ |
| ↓ | ↑ | ↑ | ↑ | | | | |

FIG. 41

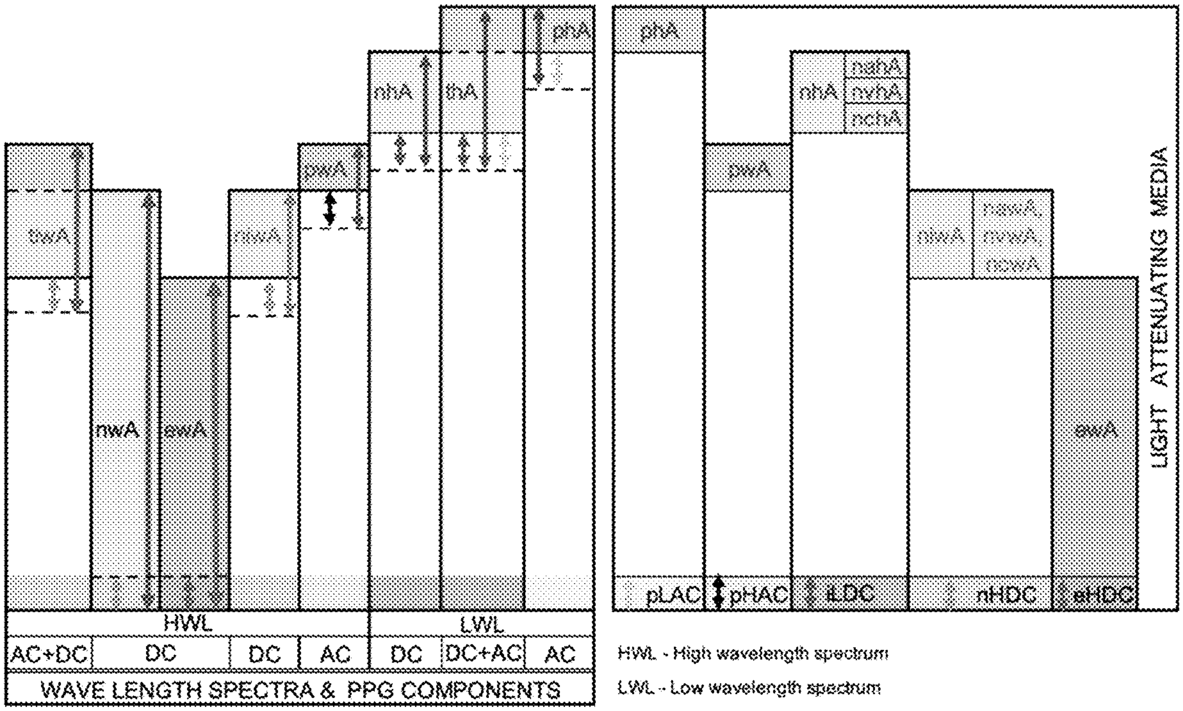

HWL - High wavelength spectrum
LWL - Low wavelength spectrum
AC - PPG AC component
DC - PPG DC component twA - light attenuation by total intravascular water
nwA - attenuation by non-pulsatile water
ewA - attenuation by extravascular water
niwA - attenuation by non-pulsatile intravascular water
pwA - attenuation by pulsatile water
nhA - attenuation by non-pulsatile hemoglobin (mass)
thA - attenuation by total hemoglobin (mass)
phA - attenuation by pulsatile hemoglobin (mass)

pLAC - other pulsatile LWL AC signal confounders
pHAC - other pulsatile HWL AC signal confounders
iLDC - other intravascular non-pulsatile LWL DC signal confounders
nHDC - other intravascular non-pulsatile HWL DC signal confounders
eHDC - other extravascular HWL DC signal confounders
NOTE: All signal confounders are related to NON-EXPANDABLE MEDIA.

FIG. 43B

HYDRATION (TBW) LEVELS:

0 - 1 Severe - life threatening - dehydration
1- 2 Mild dehydration = Alert of imminent dehydration
2 - 3 Normal hydration
3 - 4 Mild overhydration = Alert of imminent edema
4 - 5 Edema
5 - 6 Severe - life-threatening - overhydration
TBW - TOTAL BODY WATER

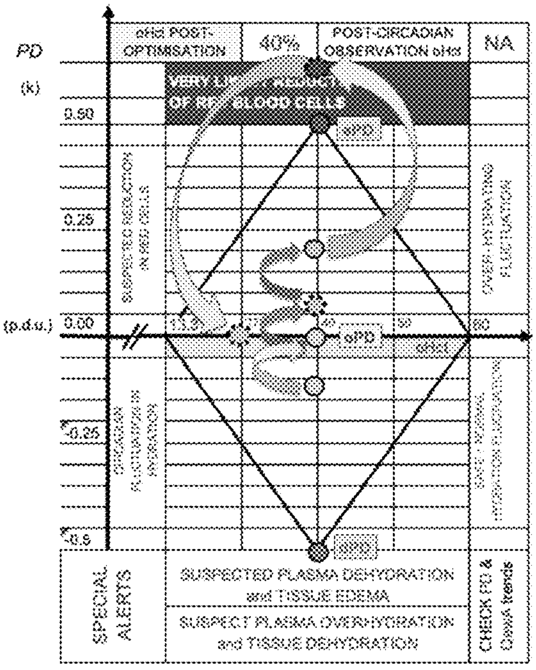
FIG. 72A
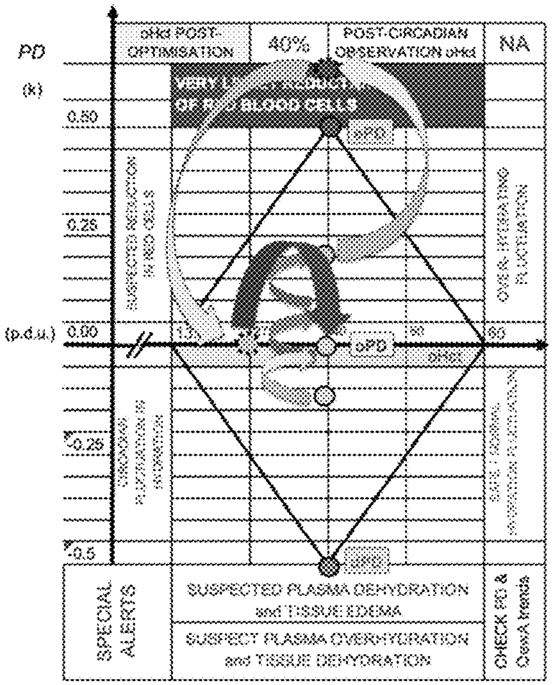
FIG. 72B
| Optimised hematocrit | Optimised hemoglobin concentration | Optimised red cell mass |
|---|---|---|
| oHct | oHb | oRCM |
| 28 | 92 | 1217 |
| 29 | 96 | 1267 |
| 30 | 99 | 1319 |
| 31 | 102 | 1371 |
| 32 | 106 | 1424 |
| 33 | 109 | 1477 |
| 34 | 112 | 1531 |
| 35 | 116 | 1585 |
| 36 | 119 | 1641 |
| 37 | 122 | 1698 |
| 38 | 125 | 1753 |
| 39 | 129 | 1810 |
| 40 | 132 | 1868 |
| 41 | 135 | 1927 |
Loss of RCM related shift in oPD and oHct
Estimated loss of RCM: 1868 - 1267 = 601 (ml)
Estimated transfusion of RCM for return to baseline RCM: 1868 - 1267 = 601 (ml)
FIG. 72C

SYSTEMS AND METHODS FOR NONINVASIVE MONITORING OF THE BODY FLUID STATUS AND HEMOGLOBIN, AND USING THE SAME FOR AN AUTOMATED DECISION SUPPORT

CROSS-REFERENCE TO RELATED APPLICATIONS

The present application claims benefit of and priority to U.S. Provisional Patent Application Ser. No. 63/647,836 filed May 15, 2024 and entitled SYSTEMS AND METHODS FOR NONINVASIVE MONITORING OF THE BODY FLUID STATUS AND HEMOGLOBIN, AND USING THE SAME FOR AN AUTOMATED DECISION SUPPORT, the entire content of which is incorporated by reference herein.

FIELD OF THE DISCLOSURE

The system and method of the present application relate to monitoring body function, and particularly, fluid distribution between the circulation and tissues as well as optimization of fluid intake/infusion or fluid elimination/removal to optimize intravascular (volume) and extravascular (hydration) fluid volume. In embodiments, the system and method of the present application provides a multi-modular body functionality monitor.

The present disclosure further relates to methods and apparatus of using multi-wavelength (MW) photoplethysmography (PPG) to monitor changes in a. estimated whole body quantities: whole body extravascular water (wbe$H_2O$) which is an indication of total nody water (TBW), blood volume (wbBV) which includes hemoglobin mass (wbHb) and intravascular water (wbi$H_2O$);
b. intravascular quantity of light absorbing media (absorbent) in micro vessels, (microcirculation) of derma; total hemoglobin (tHB), intravascular water (i$H_2O$) and total blood volume (tBV) which is a sum of tHb and i$H_2O$;
c. extravascular quantity of absorbent in derma: extravascular water (e$H_2O$) where FIG. 26 illustrates relationships between spectra of light used in PPG measurements and PPG signal components (AC and DC) that may be processed to provide the information discussed above. Definitions and abbreviations in FIG. 26 are applicable only for referring to the quantity of media, while the corresponding definitions and abbreviations in FIG. 43A are applicable only for referring to the photon-saturated fraction of the whole quantity of media in the path of PPG light;
d. intravascular quantity of photon-saturated absorbent in microcirculation of derma as indicated by changes in light attenuation: total hemoglobin (thA), total intravascular water (tiwA), and total blood volume (bA) which is a sum of thA and tiwA;
e. extravascular quantity of photon-saturated absorbent in derma as by changes in light attenuation: extravascular water (ewA);
f. tissue perfusion as indicated by changes in ratio bA to ewA; and
g. transcapillary fluid filtration-absorption ratio (FAR) as indicated by changes in ratio hemodilution in non-pulsatile fraction of total blood volume (bA) to hemodilution in pulsatile fraction of bA, an indication of change in arterio-venous dilution difference.

In embodiments, medical-grade and non-medical wearable devices may be used to obtain PPG information that may be used to provide body fluid management based on the relationships discussed above.

RELATED ART

Conventional systems that monitor whole body hemoglobin mass are based on clinical signs and require invasive measurement of hemoglobin concentration. Such monitoring, however, may be lifesavings in postoperative patients and patients with an increased risk of hemorrhage (bleeding) such as those on blood thinners. When less invasive techniques are used, they lack reliability and result in increased blood loss from the testing process itself. Further, repeated blood testing increases risk of infection. Further, these techniques cannot distinguish blood-loss related decreases in hemoglobin and decreases due to hemodilution.

Conventional systems for monitoring fluid accumulation in tissue are typically based on fluid balance estimates, non-specific low-sensitivity clinical observations and measurements. The techniques are not reliable. Non-invasive techniques such as bioimpedance cannot discriminate between fluid volume in blood Bessel and tissues. Monitoring body hydration status by non-medical wearables is also unreliable. IV therapies are based on rule of thumb estimates, hemodynamic parameters and fluid balance. Fluid consumption in everyday life is based on general diet recommendations. None of these approaches provide reliable and real time indication of tissue fluid accumulation. Accurate tissue fluid monitoring is important for adequate oral fluid consumption in everyday life and clinical settings, as well as for administration of intravenous fluid therapy and prevention of adverse effects such as edema or dehydration. Indeed, detecting imminent edema may be life-saving, however, current methods of doing so are either unreliable, invasive of inconvenient, for example the use of MRI, X-Ray, ultrasound or determining extravascular lung water (EVLW). Undetected development of fluid overload in circulation may lead to heart failure, edema and hypoperfusion-related hypoxia of organs which may be life-threatening Conventional approaches to monitor fluid levels in circulation, which may be used to detect circulation overload are also unreliable and rely in clinical signs and invasive measurements which increase the risk of infection. Delay in detecting hypoperfusion results in poor overall outcomes of treatment and even life-threatening complications.

Conventional approached to monitoring blood supply to organs rely on clinical signs, invasive measurements, and non-invasive optical observations. Less invasive approaches are unreliable and repeated invasive measurement of global markers has a high risk vs. benefit ratio due to invasiveness lack of specificity in the results.

Conventional approaches to monitoring transcapillary fluid shifts are based on pharmacodynamics and volume kinetic analysis used to estimate distribution of fluids and medication. These approaches require multiple blood draws and laboratory analysis which are cumbersome and inconvenient. Limited awareness of capillary permeability status frequently lead to inadequate treatment of global deteriorations of circulation with poor treatment outcomes and even life-threatening consequences Accordingly, a method and system of monitoring hydration that overcomes these and other problems is desirable.

SUMMARY

The present disclosure is directed to methods and system of monitoring hemoglobin and other levels in a subject to provide information including recommendations regarding hydration and blood loss for a subject.

A method for monitoring measurable changes in quantities of hemoglobin, intravascular water and extravascular water in derma of a subject in accordance with an embodiment of the present application includes: obtaining multi-wavelength photoplethysmography information associated with light that has passed through the derma of the subject; processing the multi-wavelength photoplethysmography information to derive: a first parameter associated with a quantity of non-pulsatile hemoglobin (sHb) as indicated by a PPG DC component associated with LWL/ILWL light attenuation (nhA) in tissues through which the light passed in the subject, a second parameter associated with net non-pulsatile water volume (wDC) as indicated by the PPG DC component that associated with HWL/IHWL light attenuation by non-pulsatile water (nwA) in tissues through which the light passed in the subject, a third parameter associated with a quantity of pulsatile hemoglobin (aHb) as indicated by a PPG AC component associated with LWL/ILWL light attenuation (phA) in tissues through which the light passed in the subject, a fourth parameter associated with net pulsatile water volume (wDC) as indicated by the PPG AC component associated with HWL/IHWL light attenuation (pwA) in tissues through which the light passed in the subject, storing the multi-wavelength photoplethysmography information, and the first, second, third and fourth parameters associated with changes in quantity of hemoglobin, intravascular water and extravascular water in derma of a subject over time; repeating steps i) through iii) for a period of time; determining, based on the stored multi-wavelength photoplethysmography information and the stored first, second, third and fourth parameters associated with changes in quantity of hemoglobin, intravascular water and extravascular water in derma of a subject, trends associated with changes in quantity of hemoglobin, intravascular water and extravascular water in derma of a subject; and providing hydration status information associated with the subject based on the multi-wavelength photoplethysmography information, the parameters associated with hemoglobin, intravascular water and extravascular water in derma of a subject and the trends.

In embodiments, a HWL/IHWL DC component value corresponds to net light attenuation by non-pulsatile water (niwA) in the subject and is calculated during step (ii) by adding an intravascular water ($sH_2O$) quantity-related light attenuation value (niwA), extravascular water ($eH_2O$) quantity-related light attenuation value, and a non-expandable water containing media (nDC) quantity-related light attenuation value (nHDC), where light attenuation by nDC has no impact on changes in niwA because the quantity of nDC is not changing in short term.

In embodiments, a HWL/IHWL AC component value corresponds to net light attenuation by pulsatile water (pwA) in the subject and is calculated during step (ii) by adding a non-expandable water containing media (oLAC) quantity-related light attenuation value (pHAC) where light attenuation by nDC has no impact on changes in niwA because the quantity of nDC is not changing in short term.

In embodiments, a LWL/ILWL DC component value corresponds to net light attenuation by non-pulsatile hemoglobin (nhA) in the subject and is calculated during step (ii) by adding attenuation by non-expandable media (oDC) quantity-related light attenuation value (iLDC) where light attenuation by oDC has no impact on changes in nhA because the quantity of oDC is not changing in short term.

In embodiments, a LWL/ILWL AC component value corresponds to net light attenuation by pulsatile hemoglobin (phA) in the subject and is calculated during step (ii) by adding a attenuation by non-expandable media (oLAC) quantity-related light attenuation value (pLAC); light attenuation by oLAC has no impact on changes in phA because the quantity of oLAC is not changing in short term.

In embodiments, the providing step vi) includes providing the stored multi-wavelength photoplethysmography information and stored first, second, third and fourth parameters to a machine learning algorithm, that is trained by a training set including prior wavelength photoplethysmography information, prior parameters associated with extravascular water volume and provides, as an output, trend information associated with the trend associated with extravascular water volume.

In embodiments, the light comprises (i) low wavelength light (LWL) in a wavelength spectrum most sensitive to absorption by hemoglobin, and (ii) high wavelength light (HWL) in a wavelength spectrum most sensitive to absorption by water.

In embodiments, there is an inverse relationship between light absorption by hemoglobin and water at LWL and HWL.

In embodiments the low wavelength light and high wavelength light are determined in calibration and light absorption by hemoglobin at LWL is adjusted by a ratio of light absorption by water of hemoglobin at HWL to minimize impact of light absorption by water in hemoglobin measurements, and impact of light absorption by hemoglobin in water measurements.

In embodiments, the low wavelength spectrum is 400 nm to 600 nm light and a high wavelength spectrum is 850 nm to 1100 nm light.

In embodiments, the determining step includes providing the, based on the stored multi-wavelength photoplethysmography information and the stored first, second, third and fourth parameters associated with changes in quantity of hemoglobin, intravascular water and extravascular water in derma of a subject as inputs to a machine learning algorithm trained using prior multi-wavelength photoplethysmography information and parameters and providing, as an output, trend information associated with the trends.

A method of calibrating a plurality of multi-wavelength photoplethysmography sensor devices arranged in parallel in a system for monitoring changes in the quantity of hemoglobin and water in derma of a subject in accordance with an embodiment of the present disclosure includes activating a first light source emitting light of a first wavelength toward tissue of the subject; activating a second light source emitting light of a second wavelength toward tissue of the subject; wherein the first light source is positioned parallel to the second light source; receiving, by a first light detector first wavelength spectra associated with the first wavelength and by a second light detector second wavelength spectra associated with the second wavelength; generating multi-wavelength photoplethysmography information based on receipt of the first spectra and the second spectra; analyzing the multi-wavelength photoplethysmography information to select a first desired wavelength specifically for measuring light attenuation by hemoglobin based on signal quality, patterns and features, where the first desired wavelength is referred to as individual low wavelength (ILWL); analyzing the multi-wavelength photoplethysmography information to select a second desired wavelength specifically for measuring light attenuation by water based signal quality, patterns and features, the second desired wavelength is referred to as individual high wavelength (IHWL); indicating the individual low wavelength (ILWL) and the individual high wavelength (IHWL) which are associated with the best suitable features, where ILWL is used for PPG measurements that estimate changes in hemoglobin and IHWL is used for PPG measurements that estimate changes in water.

In embodiments, there is an inverse relationship between light absorption by hemoglobin and water at ILWL and IHWL.

A method for monitoring changes in a non-measurable quantity of extravascular (tissue) water of a subject and its changes in accordance with an embodiment of the present disclosure includes" obtaining HWL/IHWL photoplethysmography information associated with light that has passed through tissue of the subject; obtaining multi-wavelength photoplethysmography information associated with net pulsatile water volume (wDC), non-pulsatile water volume (wDC), pulsatile hemoglobin (aHb) and non-pulsatile hemoglobin (sHb), as indicated by pwA, nwA, phA and nhA, and deriving from the above information an estimated quantity of non-pulsatile intravascular water (sH2O) as indicated by a net DC component either during an induced obstruction of circulation under a photoplethysmography sensor providing the photoplethysmography information, or without compression by deriving an estimated quantity of non-pulsatile intravascular water (sH2O) by applying an arterial hemodilution value, which is a ratio of measurable phA to pwA, to a ratio of measurable nhA to non-measurable niwA, with niwA estimated as a result; storing the multi-wavelength photoplethysmography information and the estimated quantities; repeating steps i) through iv) for a period of time; determining, based on the stored multi-wavelength photoplethysmography information and the stored estimated quantities associated with extravascular water amount and accumulation a trend; and providing changes in tissue hydration information associated with the subject based on the multi-wavelength photoplethysmography information and the trend.

In embodiments, the determining providing the multi-wavelength photoplethysmography information and the stored estimated quantities associated with extravascular water amount and accumulation as inputs to a machine learning algorithm trained by a training set including multi-wavelength photoplethysmography information and the stored estimated quantities and providing as an output trend information associate with the trend.

A method for monitoring hydration status and detection of changes in whole body hemoglobin mass in accordance with an embodiment of the present disclosure includes: obtaining multi-wavelength photoplethysmography information associated with light that has passed through the derma of the subject;

setting a minimum Hct value and a maximum Hct value defining lateral boundaries; setting dehydrated plasma dilution (dPD) value as a lower boundary; setting an optimal plasma dilution (oPD) as an upper boundary; processing the multi-wavelength photoplethysmography information to derive: a first parameter associated with plasma dilution (PD); and a second parameter associated with Hct; generating a nomogram including a rhombus shape defined by the minimum Hct, maximum Hct, dehydrated plasma dilution and optimal plasma dilution, fitting the first parameter and the second parameter on the nomogram, wherein normal hydration is indicated where the first parameter and second parameter fit inside the rhombus shape.

In embodiments, the nomogram is displayed on a display to a user such that the rhombus shape is visible.

In embodiments, the nomogram includes indicia indicating waring areas on the nomogram associated with hydration or circulation risks.

In embodiments, the nomogram includes a zoom feature to allow a user a more detailed view of the parameters represented on the nomogram.

In embodiments, the nomogram may include patient identification information identifying the subject.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 41 illustrates a table indicating clinical interpretation of mPD and mtcPED trends Clinical interpretation of mPD and mtcPED trends in accordance with an embodiment of the present disclosure;

FIG. 43B illustrates a chart illustrating the relationship between wavelength spectra and PPG information and light attenuating media in the tissue of the subject in accordance with an embodiment of the present disclosure;

FIGS. 72A-72C illustrate an example of monitoring changes of red cell mass (RCM) and optimized hematocrit (oHct) due to loss of RCM and RCM transfusion, using a revised HBS (revHBS) Nomogram in accordance with an embodiment of the present disclosure;

FIG. 82A illustrates an example of a non-standard Rhombus in a Nomogram in accordance with an embodiment of the present disclosure;

FIG. 82B illustrates an example zooming in on a portion of the non-standard Rhombus in FIG. 82A;

FIG. 82C illustrates an exemplary patient profile screen in accordance with an embodiment of the present disclosure;

FIG. 83 illustrates exemplary system architectures in accordance with an embodiment of the present disclosure;

FIG. 84 illustrates an exemplary architecture for an AI agent that may be used in the system in accordance with an embodiment of the present disclosure;

FIG. 85 illustrates an exemplary workflow for a system in accordance with an embodiment of the present disclosure;

FIG. 86 illustrates an example of a profile screen that may be provided to a user in accordance with an embodiment of the present disclosure;

FIG. 87 illustrates an exemplary screen indicating calibration is in progress in accordance with an embodiment of the present disclosure;

FIG. 88 illustrates an exemplary warning screen that may be displayer to a user based on the monitoring being provided in accordance with an embodiment of the present disclosure; and FIG. 89 illustrate examples of other hydration status screens that may be presented to the user based on the monitoring provided by the system.

Like reference numerals refer to like parts throughout the several views of the drawings.

DETAILED DESCRIPTION

Figure 1:
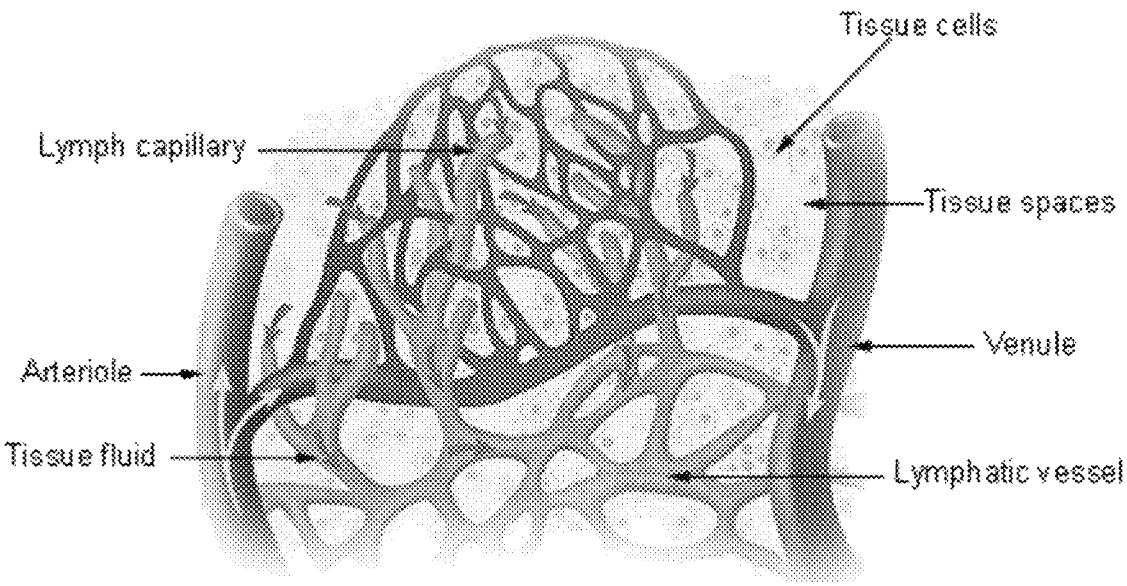
FIG. 1 is a schematic illustration of a typical architecture of a microvascular bed in a subject in accordance with an embodiment of the present disclosure.

The following detailed description is merely exemplary in nature and is not intended to limit the described embodiments or the application and uses of the described embodiments. As used herein, the word “exemplary” or “illustrative” means “serving as an example, instance, or illustration.” Any implementation described herein as “exemplary” or “illustrative” is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms “upper”, “lower”, “left”, “rear”, “right”, “front”, “vertical”, “horizontal”, and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Monitoring these changes may be used to provide automated decision support in both medical-grade and non-medical wearable devices for continuous body fluid management guided by the MW PPG measurements. The system provides recommendations for optimizing physiological function, including management of fluid intake, restriction or removal of fluid, co-administration of cardiovascular medication, and red blood cell transfusion Blood loss detection and transfusion-related recommendations may be provided based on assessment of whole-body hemoglobin mass changes by differentiating dilution-related variations in hemoglobin concentration from net changes in hemoglobin mass due to red blood cell loss or transfusion. Plasma dilution-related fluctuations in plasma volume and corresponding blood volume changes may be monitored with fluctuations in tissue fluid volume and transcapillary fluid shifts.

In a clinical setting, the system monitors tissue perfusion and provides clinically relevant trend data both for clinician interpretation and processing to provide real-time alerts for fluid status, including intravascular and extravascular fluid accumulation, total blood volume changes, plasma volume, and net hemoglobin mass variations. The system offers clinical guidance on fluid management, real-time alerts for imminent edema or dehydration risks, and notifications regarding potential blood loss or transfusion effects on hemoglobin levels. In other applications, the system may provide advice on fluid intake or restriction based on fluid accumulation trends in circulation and tissues which are an indication of plasma and tissue hydration status, and prompts users to seek medical attention when a significant reduction in whole body hemoglobin mass is detected.

The system and method of the present disclosure provide monitoring of fluid distribution in circulation and in tissues and may be used to detect blood loss and optimize fluid intake via infusion or otherwise and/or fluid elimination or removal to optimize intravascular (volume) and extravascular (hydration) fluid volume. The system and method of the present disclosure may provide a unique method for assessment of changes in wbHb by discriminating dilution related changes in hemoglobin concentration from changes in net hemoglobin mass due to loss or transfusion of red blood cells. In embodiments, plasma dilution (PD) relates, increase or decrease in plasma volume (PV), and relate changes in blood volume (BV) may be monitored in parallel to changes in tissue hydration status (changes in $eH_2O$) and related changes in transcapillary fluid shifts (changes in arterio-venous hemodilution changes is as indication of changes in transcapillary fluid filtration absorption ratio-FAR). In embodiments, the system and method includes monitoring and assesssing changes in tissue perfusion where the the clinically relevant information and clinical decision support in medical grade applications includes but is not limited to assessment of fluid status and its changes based on intravascular water and $eH_2O$, wbBV and cBvA, PV and PD, wbHb and tHb. The system and method may generate and provide clinical advice via an automated decision support system regarding the need for fluid intake and/or infusion or fluid restriction and/or removal, as well as providing alerts about suspected imminent edema or dehydration in accordance with the trends of fluid accumulation, as well as reductions or increases in wbHb due to occult or obvious blood loss or transfusion. In non-medical grade applications, the method and system may include but is not limited to generating and providing suggestions for fluid intake or restriction in accordance with the trends of fluid accumulation, as well as suggestions to seek medical advice when significant reduction in hemoglobin is suspected.

In embodiments, the system 100 of the present disclosure includes a Swapping-Layer Sensor System (SLSS) that includes a MW PPG sensor 102 to maximized specificity and sensitivity to light absorption by water ($H_2O$) and hemoglobin mass (Hb) in anatomic compartments and tissues.

Figure 2A:
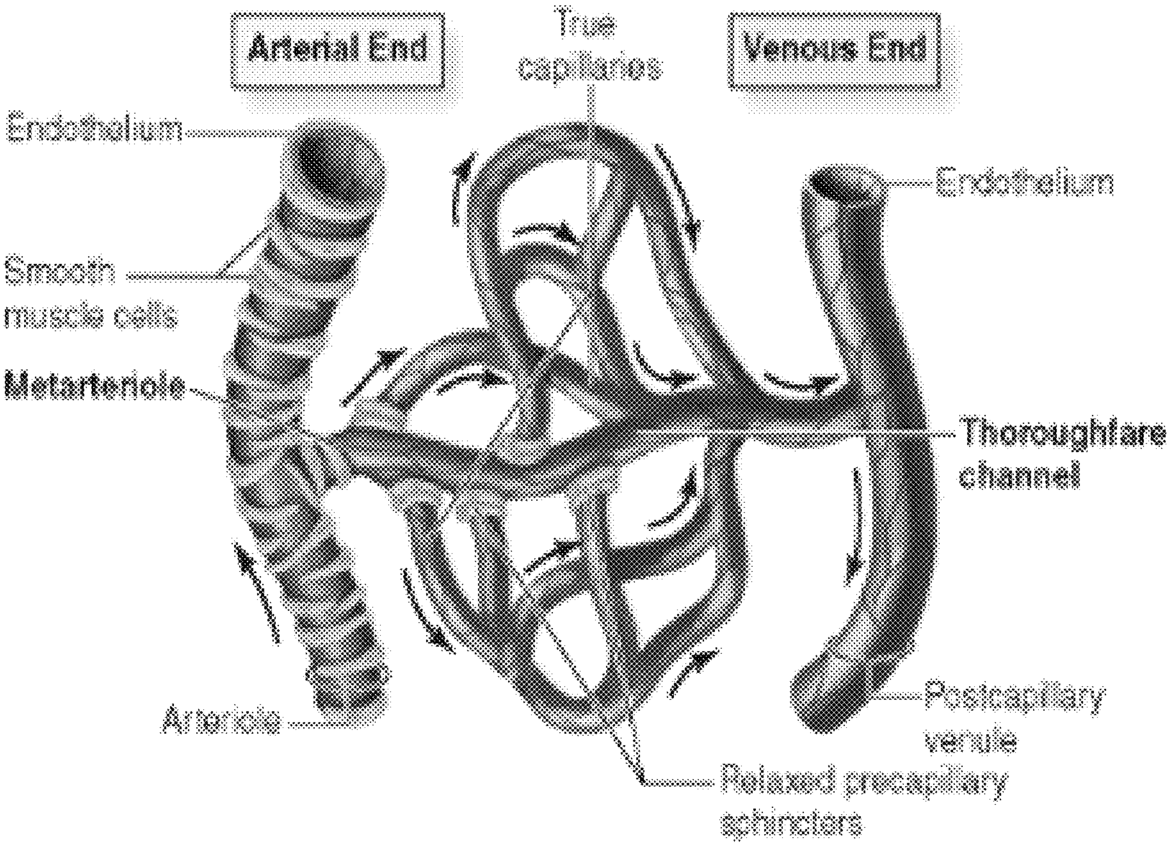
FIG. 2A is another schematic illustration of a typical architecture of a microvascular bed in a subject in accordance with an embodiment of the present disclosure.
Figure 2B:
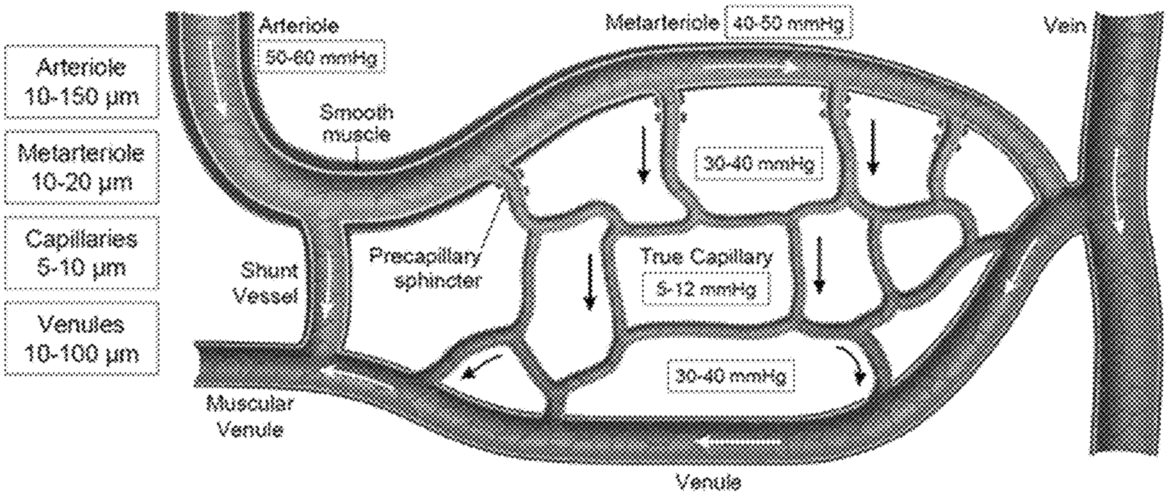
FIG. 2B is another schematic illustration of a typical architecture of a microvascular bed in a subject in accordance with an embodiment of the present disclosure.

FIGS. 1-2 illustrate a typical architecture of a microvascular bed, as is traditionally presented in textbooks. In FIG. 1; blood flow to capillaries is supplied by arterioles, resistance vessels that are surrounded by vascular smooth muscle. Blood entering the capillary bed is controlled by contraction or dilation of arterioles and precapillary sphincters. Blood flows into the capillaries and is carried out to the venous circulation by postcapillary venules. Alternatively, blood may be shunted directly from the arterioles to the venules via metarterioles, bypassing the capillary bed. These mechanisms control the hydrodynamic pressure and volume of blood flow through individual capillary beds to meet the metabolic and respiratory demands of the tissues. In FIG. 2A well perfused true capillaries have fully relaxed sphincters. In FIG. 2B the pressures within a capillary bed are depicted in a completely different schematic microvascular network compered to depiction in FIG. 2A. Therefore, random sections with different anatomy and the everchanging perfusion status in the overlapping capillary beds fall into the PPG sensors 102 scan area and may cause unpredictable and difficult to interpret light absorption patterns. Thus such conventional architectures may be problematic when the PPG sensor signal is interpreted in terms of scanned vessel types and their perfusion status in particular. Actual types of vessels and their perfusion under the sensor is context-sensitive and difficult to predict and monitor. As a result, depending on the specific vessel, the perfusion index (PI) value may be misleading.

Figure 3A:
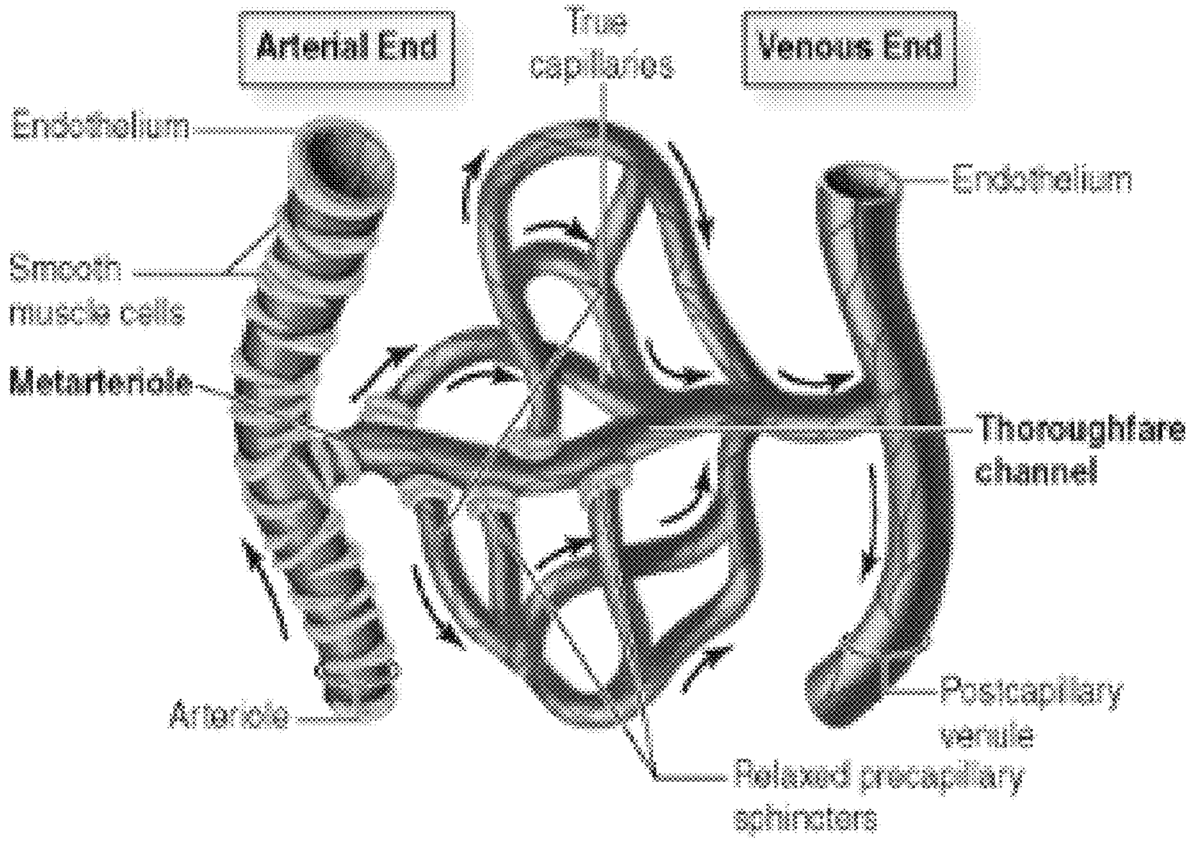
FIG. 3A is another schematic illustration of a typical architecture of a microvascular bed in a subject showing relaxed precapillary sphincters in accordance with an embodiment of the present disclosure.
Figure 3B:
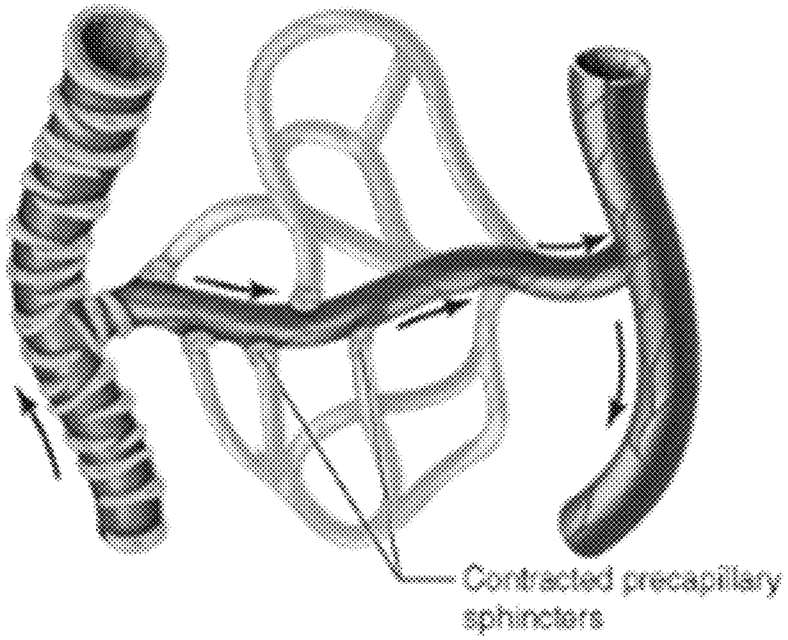
FIG. 3B is another schematic illustration of a typical architecture of a microvascular bed in a subject showing contracted precapillary sphincters in accordance with an embodiment of the present disclosure.
Figure 4:
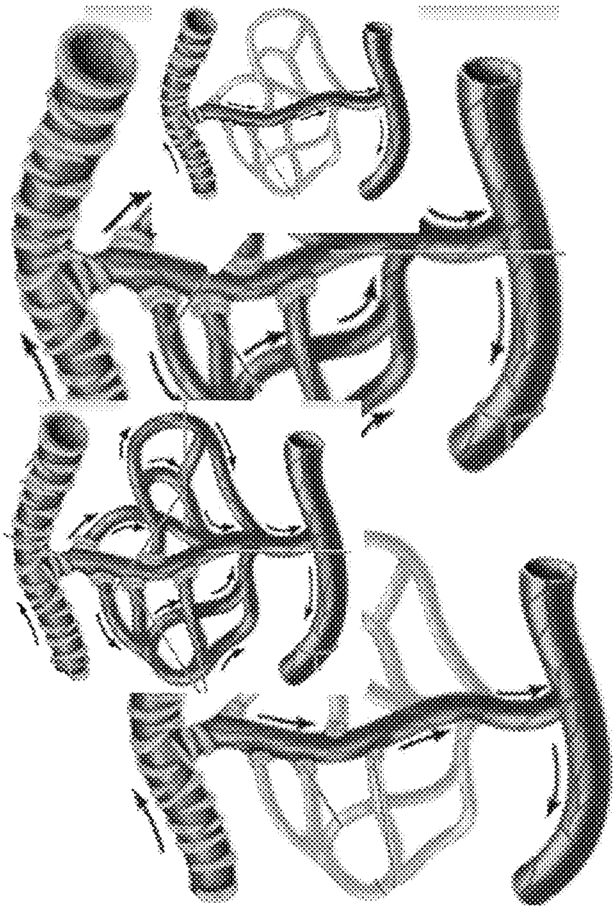
FIG. 4 is a schematic illustration of a typical architecture of a microvascular bed in a subject showing different size and perfusion states of capillary beds overlapping in accordance with an embodiment of the present disclosure.

Perfusion of true capillariesm the microvessels where transcapillary exchange of fluids occurs, depends on the opening of precapillary sphincters. Since transcapillary fluid shifts do not occur in metarteriole (thoroughfare channel or shunt), the hematocrit and hemoglobin concentration changes on the way from arteriola to venule depend solely on hemodilution of blood that enters from true capillaries. In FIG. 3A, true capillaries are perfused when precapillary sphincters are fully open and under normal tissue hydration conditions, as well when tissues are dehydrated, more fluid shifts into the tissues compared to the fluid return to capillaries. As a result, hematocrit and hemoglobin concentration may increase in true capillaries, and when it is mixed with less concentrated metarteriolar blood, the venular hematocrit and hemoglobin concentration are higher compared to arteriolar hematocrit and hemoglobin concentrations; thus arterial hemodilution is higher than venous. In embodiments, the arterio-venous hemodilution difference may thus be positive. Alternatively, when tissues are overloaded with fluids, transcapillary shift of fluid into the true capillaries may be bigger compared to the fluid shift into the tissues such that the arterio-venous hemodilution difference is negative as venular hemodilution is higher than arteriolar. In FIG. 3B, true capillaries are not perfused when precapillary sphincters are fully closed. The arteriovenous dilution difference is null (zero) because there is no influx of true capillary blood into the venulae. However, the PI may remain unchanged or even increase because of increase in blood flow via metarteriolae (arterio-venous shunts) which results in increased pulsatile PPG signal, and thus the perfusion index (PI) value may be misleading. FIG. 4 illustrates different size and perfusion status of capillary beds overlapping in tissue under PPG sensor 102.

Figure 5:
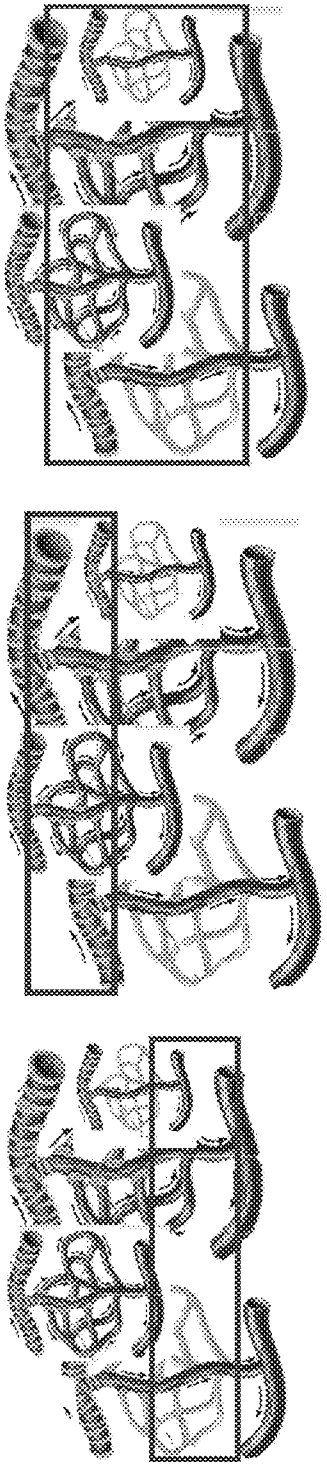
FIGS. 5A-5C illustrate long wavelength PPG scans with a relatively long distance from LED to detector in accordance an embodiment of the present disclosure.
FIGS. 5D-5F illustrate short wavelength PPG scans with short distances between LED and detector in accordance with an embodiment of the present disclosure.
Figure 5:
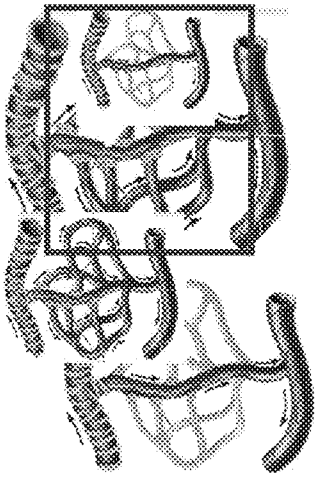
Figure 5:
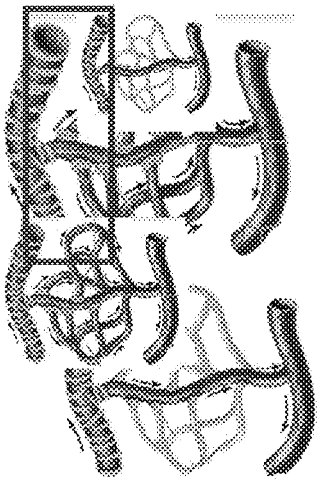
Figure 5:
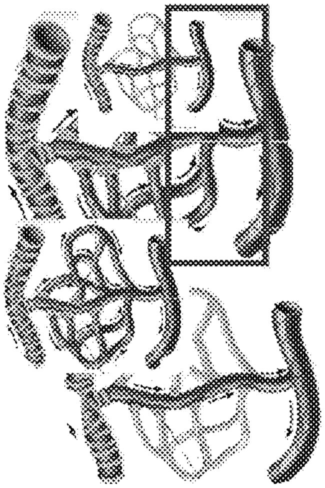

In embodiments, in FIGS. 5A-5C light absorption by $H_2O$ using relatively long waves, and both short and long distances between LEDs and detectors is illustrated. In embodiments, in FIGS. 5D-5F, relatively short waves are used with shorter waves and distances between the light emitting diode (LED) 102L and detector 102D for measuring light absorption by Hb. In embodiments, in either case, the sensor 102 may be implemented as a sensor array with an aim to optimize the signal quality and obtain optimal sensitivity to $H_2O$ and Hb.

Figure 6:
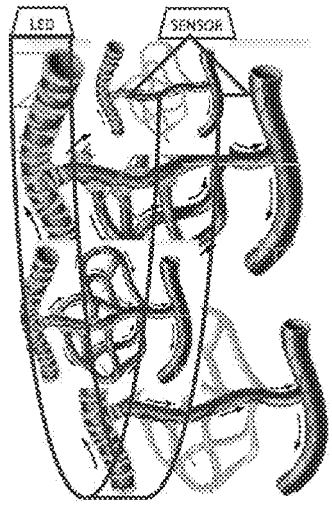
FIG. 6A illustrates short wavelength PPG scans reaching deeper layers of skin and overlapping capillary beds in accordance with an embodiment of the present disclosure.
FIG. 6B illustrates medium wavelength PPG scans reaching fewer capillary beds in accordance with an embodiment of the present disclosure.
FIG. 6C illustrates short wavelength PPG scans reaching shallow capillary beds in accordance with an embodiment of the present disclosure.
Figure 6:
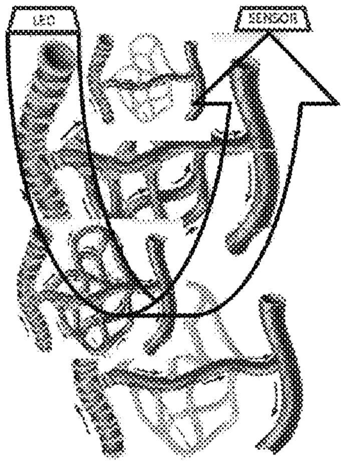
Figure 6:
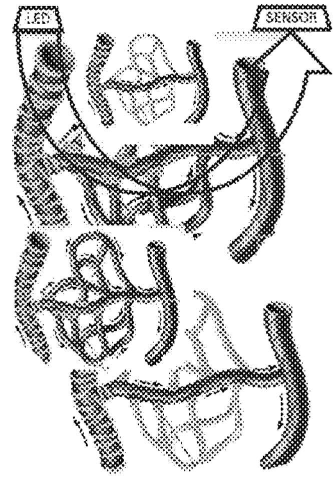

In FIG. 6A, the longest waves from the LED reach deeper layers of skin and light absorption in at least three overlapping capillary beds may be accounted for. In embodiments, medium length waves from the LED may reach fewer capillary beds in a different perfusion status. In FIG. 6C short wavelengths scan superficial capillary beds with different perfusion states, too. In embodiments, the light absorption depends not only the structure and number of the capillary bed segments scanned, but also on their ever-changing perfusion status, which effects the tHb and $tiwH_2O$ within the scanned vessels and tissues. In embodiments, the width of the area scanned also makes a difference in terms of different segments of capillary beds getting scanned, affecting the ratio between the pulsatile (arteriolae and metarteriolae) and non-pulsatile (true capillaries and venulae) micro vessels. In embodiments, the perfusion index (PI), which is an indication of a ratio pulsatile to the non-pulsatile MW PPG signal, does not indicate the state of perfusion of true capillaries because they are generally non-pulsatile micro vessels since the amplitude of vasomotion related pulsation in negligible.

Accordingly, two or more wavelengths of light may be used in the system 100. In embodiments, a low wavelength of light refers to spectra of approximately 500 nm to 650 nm where the relatively minimal light absorption coefficient of $H_2O$ and relatively high absorption coefficient of Hb and melanin is prevalent. In embodiments, change in signal (indicating a trend) may be more sensitive and specific to changes in Hb compared to $H_2O$. In embodiments, a high wavelength of light refers to spectra of approximately 850 nm to 1100 nm which has a relatively minimal light absorption coefficient of Hb and melanin, and relatively high absorption ratio for $H_2O$. In embodiments, a change in signal (trend) is more sensitive and specific to changes in $H_2O$ compared to Hb and melanin. In embodiments, the wavelength of the light may be different than that discussed above. In embodiments, the wavelength used may be optimized. In embodiments, the wavelength may be determined based on the wavelength most sensitive and specific to either Hb (within or outside preferred a LWL spectrum for Hb) or $H_2O$ (within or outside a preferred HWL spectrum for water).

Figure 7:
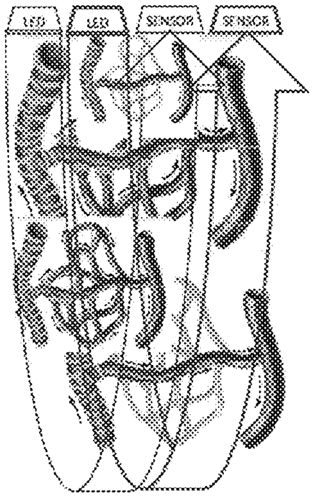
FIGS. 7A-7C illustrate impact of changing the number of sensors and distance between the LED and detector in accordance with an embodiment of the present disclosure.
Figure 7:
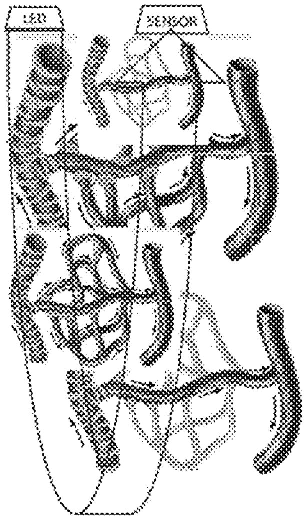
Figure 7:
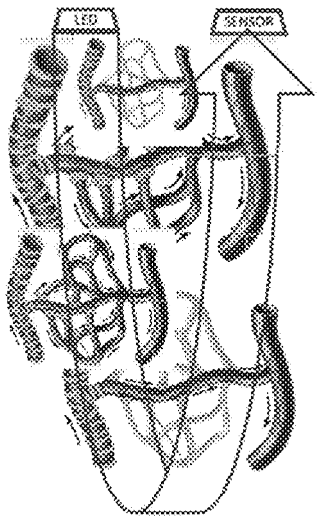
Figure 8:
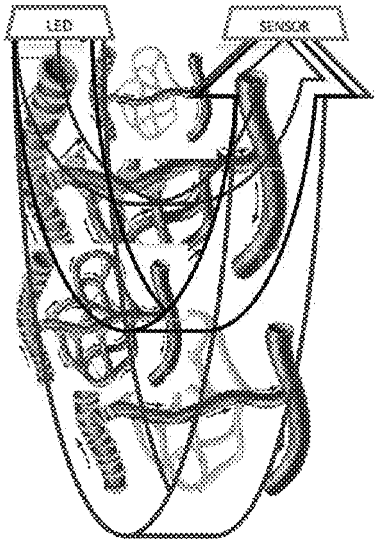
FIGS. 8A-8C illustrate different positioning of sensors in a MW PPG system in accordance with an embodiment of the present disclosure.
Figure 8:
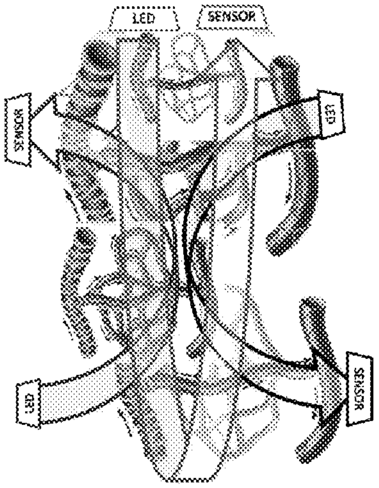
Figure 8:
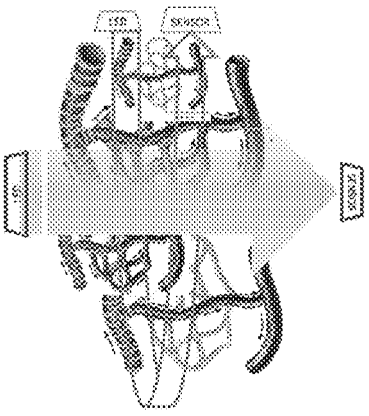

In embodiments, changing the number of sensors systems and the distance between the LED 102L and the sensor (light detector) 102D varies the results. FIG. 7A shows an overlapping scan by a pair of sensor systems 102, 102' that provides a wider-width estimate of the light absorbing components and includes different sections of capillary beds, each with a different perfusion status. FIGS. 7B and 7C show single sensor systems. In FIG. 7B, the relatively low distance between the LED 102L and the sensor (detector) 102D provides a signal from the relatively narrow scan that randomly includes several completely different segments of the overlapping capillary beds. In FIG. 7C, there is a relatively long distance between the LED 102L and the sensor (detectors) 102*s* providing a signal from a relatively wide scan that randomly includes more completely different segments of the overlapping capillary beds, however, the scan is not uniform throughout the tissues and some segments of tissues and micro vessels are poorly scanned. The system 100 includes multiple sensors 102 (LEDs 102L and corresponding sensors (detectros) 102D) with different wavelength LEDs 102L and different distances between the LEDs and sensor (detector) 102D. During calibration, based on test-performance using the unique algorithm, two sensor pairs may be selected for further continuous measurement. In embodiments, one LED/sensor pair includes a sensor 102D from a lower array and one sensor 102 from a higher wavelength sensor array, both with relatively short (less than 2.5 cm) distance from LEDs, and another pair that includes a sensor 102D from a lower array and one from a higher wavelength sensor arrays. In embodiments, this arrangement optimizes the MW PPG measurements after calibration.

In embodiments, the system 100 is a multi-layer and MW PPG sensor system that uses different positioning and sensor characteristics for measuring light absorption by $H_2O$ and Hb in a mixture of vessel types and their ever-changing perfusion status with an aim to provide the average estimates of the volumes of Hb and $H_2O$ in the microcirculation, and $H_2O$ extravascular tissues in relatively big scan area.

In embodiments, the system 100 uses different distances between the light emitting diode (LED) 102L and the detector 102D, which may be a photodiode. In a Low Width Scan (LWS) mode, the distance between LEDs and the detector is approximately 2.5 cm or less and is used for measuring the AC and DC components in the PPG signal using LED emitting light in Low Wave-Length (LWL) and High Wave-Length (HWL) spectra. In a Wide Width Scan (WWS) mode, the distance between the LEDs and the detectors may be approximately more than 2.5 cm and may be used for measuring AC and DC components in PPG using LED emitting light in High Wave-Length (HWL) spectrum, however, Low Wave-Length (LWL) mode may be used in other applications applications within the SLSS technologies as is discussed with resect to the Shallow Narrow Scan which uses LWL spectrum in the Low Width Scan (LWS) mode. In a ShallowWide Scan, the Low Wavelength LEDs may be used in Wide Width Scan (WWS) mode.

In embodiments, swapping signal processing (SSP) hardware may include autonomous wearables, as well as MBF monitor's modules, a Titrated Tissue Compression Spectroscopy (TTCS) module, Multiple Trend Monitoring module, and multi-layer Automated Decision Support System module. A triplet sensor array (TSA) 302 or group of TSA's may be connected to the hardware. In embodiments, the modules may be implemented using a processor of computer system operable connected to a memory including processor executable code that when executed by the computer perform the activities of the module. In embodiments, multiple processors and multiple memories may be used to implement the modules or a single module and memory may be used. In embodiments, multiple memories may be used by one processor or multiple processors may be operable connected to one memory.

In embodiments, each TSA 302 may include three independently driven LEDs 102L and a corresponding detector 102D. Two LEDs 102L use high wavelength LEDs while one LED 102L uses a low wavelength LED. In embodiments, positioning of the independently driven LEDs and dedicated detector, and intermittent activation allows swapping independently driven LEDs in a vicinity of a single TSA system or a group of TSAs depends on: (1) depth and width of an application-specific accessible area of skin, and the target anatomic vicinity for MW PPG measurements, e.g. intravascular and extravascular compartments for measuring the light absorbing constituents such as Hb and $H_2O$, (2) the technique/method of data processing and outcomes of data evaluation, (3) placement of TSA systems includes but is not limited to the finger, wrist, forehead, or torso.

In embodiments, MW PPG light signals from the three LEDs 102D within a single TSA system are measured by the same detector 102D which is at a context-sensitive (e.g. application type and accessibility) distance from the LEDs that depends on the mode of PPG sensing. In embodiments, in transmission mode, all three LEDs 102L in a single TSA system are located at the same distance from the detector 102D, and the distance between the LEDs and the detector depends on the measurement site including but not limited to the fingertip or earlobe where the light travels in a straight path from LEDs to the detector. In embodiments, in reflectance mode, the component positioning architecture optimized the combination of wavelength, its physical features and absorption coefficient of a target anatomical constituent, including but not limited to Hb and $H_2O$, for obtaining the best possible efficacy of MW PPG for measuring light absorption by the target anatomic constituents in a specific depth and width.

In embodiments, one LED 102L uses a low wavelength and a second LED 102L uses a high wavelength positioned alongside each other at the same, relatively low (<=2.5 cm from the detector) distance from the detector 102D. A third LED 102D uses a higher wavelength is positioned at longer distance from the detector 102D compared to the other two LEDs (>2.5 cm). As noted above, the wavelength of the LED may be optimized.

In embodiments, the first LED is used for the "ShallowNarrowScan" function (LWL-LWS technique) with the main objective to measure the light absorption by HJb. The second LED is used for the "DeepNarrowScan" function (HWL-LWS technique) with the main objective to measure the light absorption by $H_2O$. The third LED is used for "DeepWideScan" function (HWL-WWS technique) with the main objective to measure the light absorption by $H_2O$.

Figure 10:
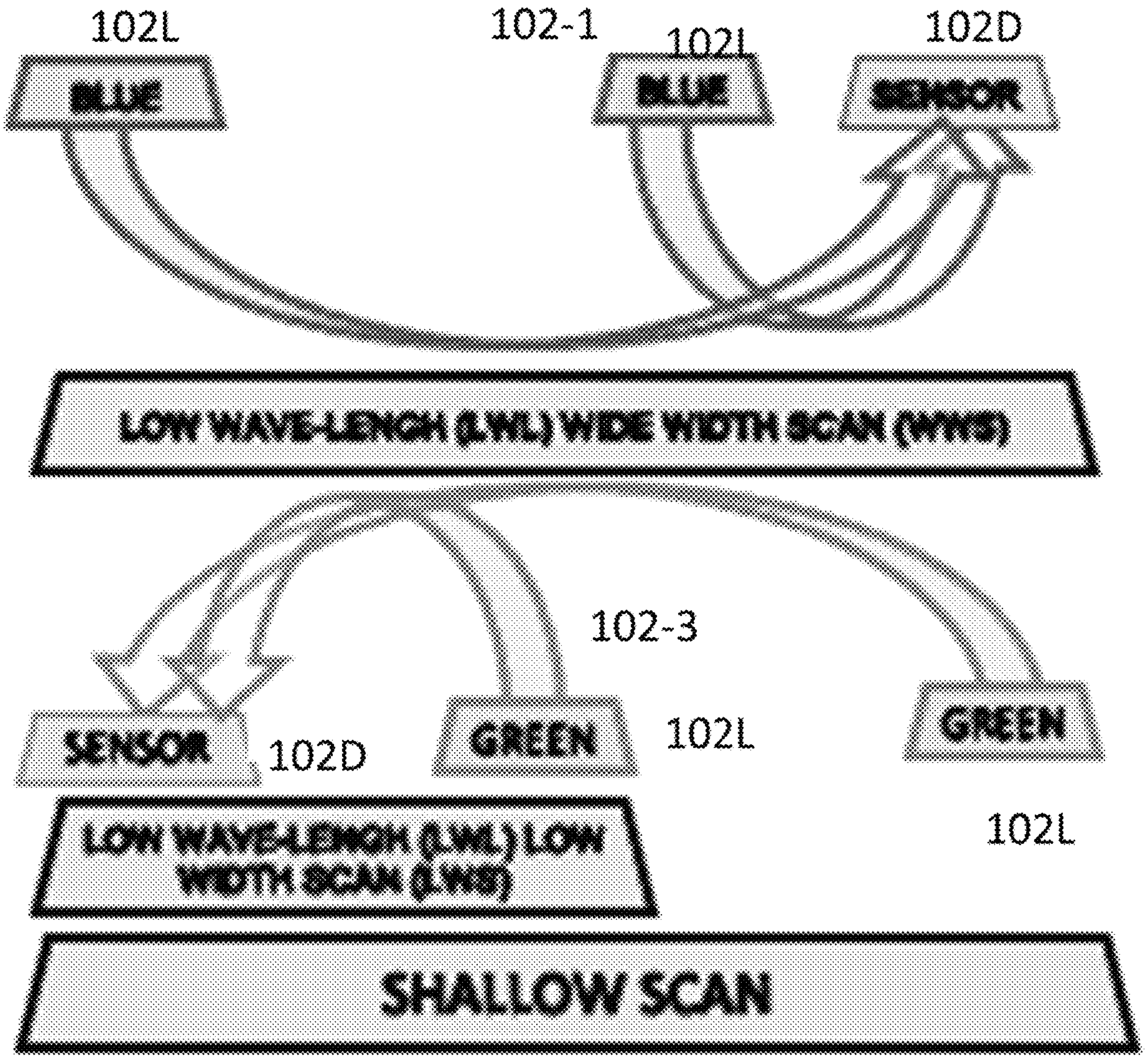
FIG. 10 illustrates an exemplary flat surface array of sensor in accordance with an embodiment of the present disclosure.

In embodiments, where the flat surface array of sensor of FIG. 10 is used the sensors 102 may be applied on the skin on relatively flat anatomic surfaces and may be suitable for use as part of a smart watch or a patch. In contrast, in embodiments where a flexible flat base is used, application may be made on the skin of relatively curved anatomic surfaces which would be suitable for use in wearables such as watch bands, bracelets, cuffs (including inflatable) patches and attachable (sticky) single use sensor systems.

Figure 11A:
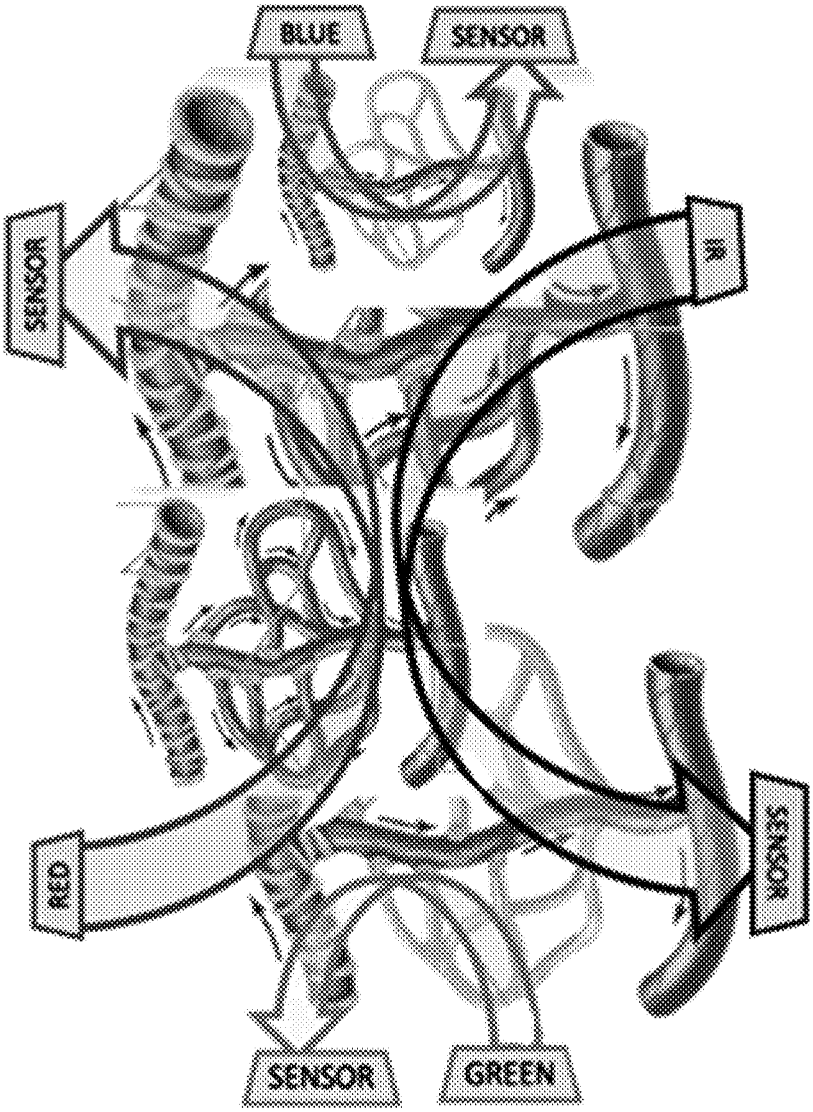
FIG. 11A illustrates a multi-directional sensor system including the capillary beds within the scab area thereof in accordance with an embodiment of the present disclosure.
Figure 11B:
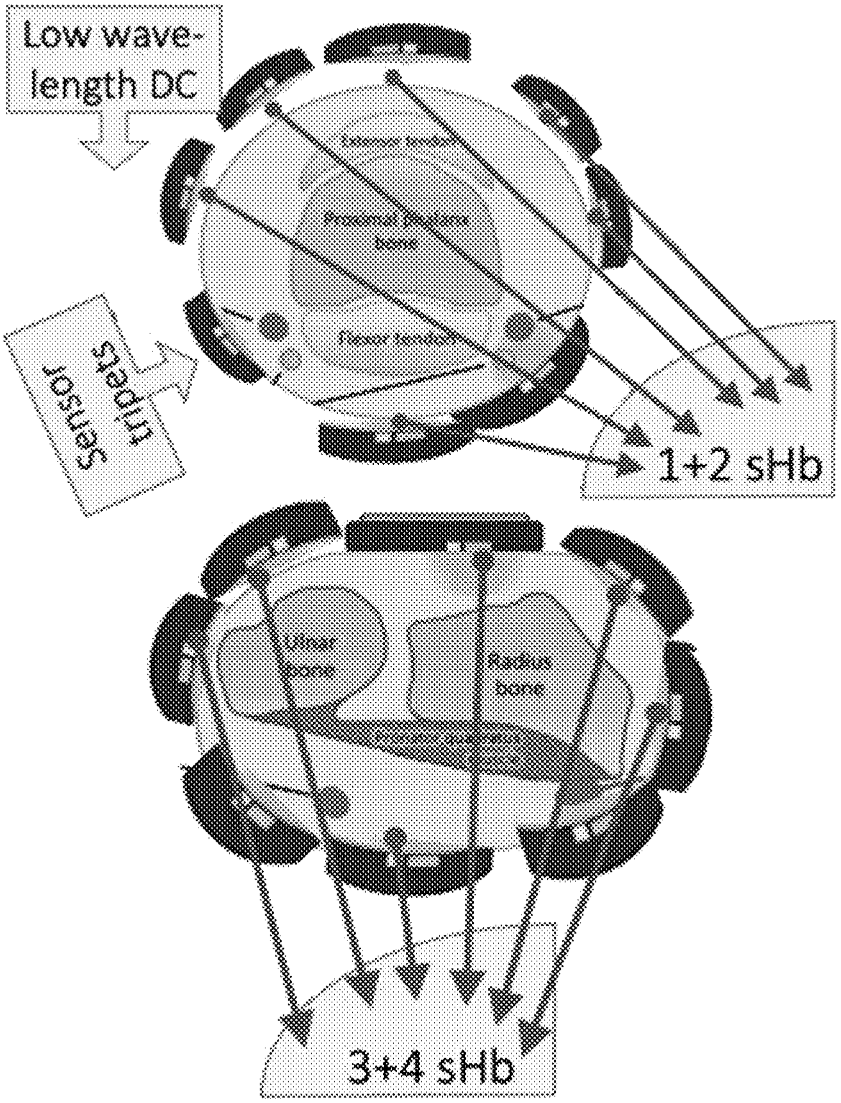
FIG. 11B illustrates an array of sensors for use in scanning capillary beds in accordance with an embodiment of the present disclosure.
Figure 11C:
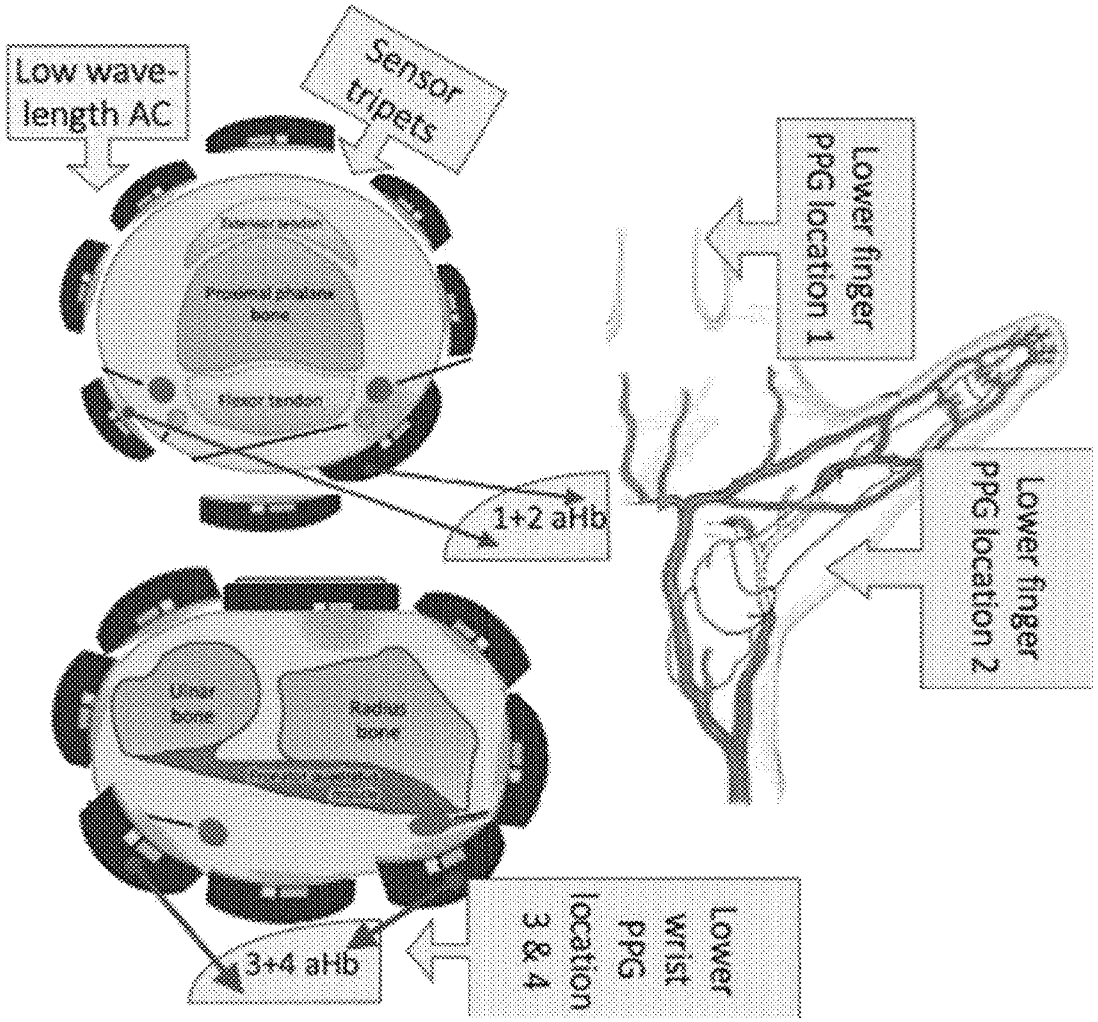
FIG. 11C illustrates an array of sensors for use in scanning larger vessels such as radial and ulnar arteries in accordance with an embodiment of the present disclosure.

FIG. 11 illustrates a multi-directional sensor system embodiment in which the sensors 102-1, 102-2, 102-3 and 102-4 may be arranged in a ring shape. FIG. 11A illustrates a depiction of an empiric combination of capillary beds within a PPG scan area of the sensors 102. FIG. 11B illustrates sensors 102 for scanning the capillary beds. FIG. 11C, the sensors 102-1, 102-2, 102-3 and 102-4 for scanning large vessels such as radial and ulnar arteries.

In embodiments, the system 100 may include two rings of MW PPG sensors 102 (ring arrays) that include an application size-specific number of AC-LWL-LWS type sensors in one ring-row ("1-AC-RING"), and DC-HWL-WWS sensors in a parallel row ("1-DC-RING") within a closed ring frame such as bracelet or finger ring, e.g. soft and size-adjustable or cuffed and inflatable, or solid frames/rings that come in different sizes. In embodiments, the LEDs 102L are activated in a sequence so that only one LED is emitting light at a time and the light rotates around the finger or other extremity depending on the application site. In embodiments, the number of sensors in the AC-LWL-LWS array is two times higher than the number of sensors in the DC-HWL-WWS array and the distance between the paired LED 102L and sensor 102D is twice the length in the latter array since it uses LEDs 102L with longer wavelengths.

In embodiments, a "1-AC-RING" configuration is the AC-LWL-LWS sensor array which is dedicated to measuring light absorption by arterial hemoglobin (aHb) in a pulsatile part of arterial flow. In embodiments, "1-DC-RING" configuration is a DC-HWL-WWS sensor array which is dedicated to measuring light absorption by non-pulsatile $H_2O$ (wDC). In embodiments, the "1-DC-RING" configuration includes eH2O and non-pulsatile intravascular water ($sH_2O$) which includes non-pulsatile water in veins ($vH_2O$), capillaries ($cH_2O$) and non-pulsatile component of arterial flow ($nH_2O$).

In embodiments, an "ACDC-5-RING" or AC-LWS/4/DC-WWS configuration may be used. In embodiments, four MW PPG sensor ring arrays may include an application size-specific number of AC-LWL-LWS type sensors in two parallel ring-arrays dedicated to LWS (low distance between LEDs and sensors), and a third AC-dedicated ring with a half the number of AC-LWL-WWS sensors (higher distance between LEDs and sensors). In embodiments, two parallel arrays of the DC-mode dedicated sensors are used with one array being DC-HWL-WWS and one being DC-LWL-WWS.

In embodiments, a "1-AC-RING" configuration uses the AC-LWL-LWS sensor array which is dedicated to measuring light absorption by arterial hemoglobin (aHb) in a pulsatile part of arterial flow. In embodiments, the "2-AC-RING" configuration uses the AC-HWL-LWS sensor array which is dedicated to measuring light absorption by pulsatile (arterial) water (aH2O) in a pulsatile part of arterial flow. In embodiments, a "3-AC-RING" configuration uses an AC-LWL-WWS sensor array which is dedicated to measuring light absorption by aHb. In embodiments, a "1-DC-RING" configuration uses a DC-HWL-WWS sensor array which is dedicated to measuring light absorption by non-pulsatile water (wDC). In embodiments, this configuration includes $eH_2O$, and $sH_2O$ which includes $vH_2O$, c and $nH_2O$. In embodiments, a "2-DC-RING" configuration uses a DC-LWL-WWS sensor array which is dedicated to measuring net light absorption by arterial, venous, and capillary hemoglobin's, that is, total hemoglobin (tHb).

Figure 12:
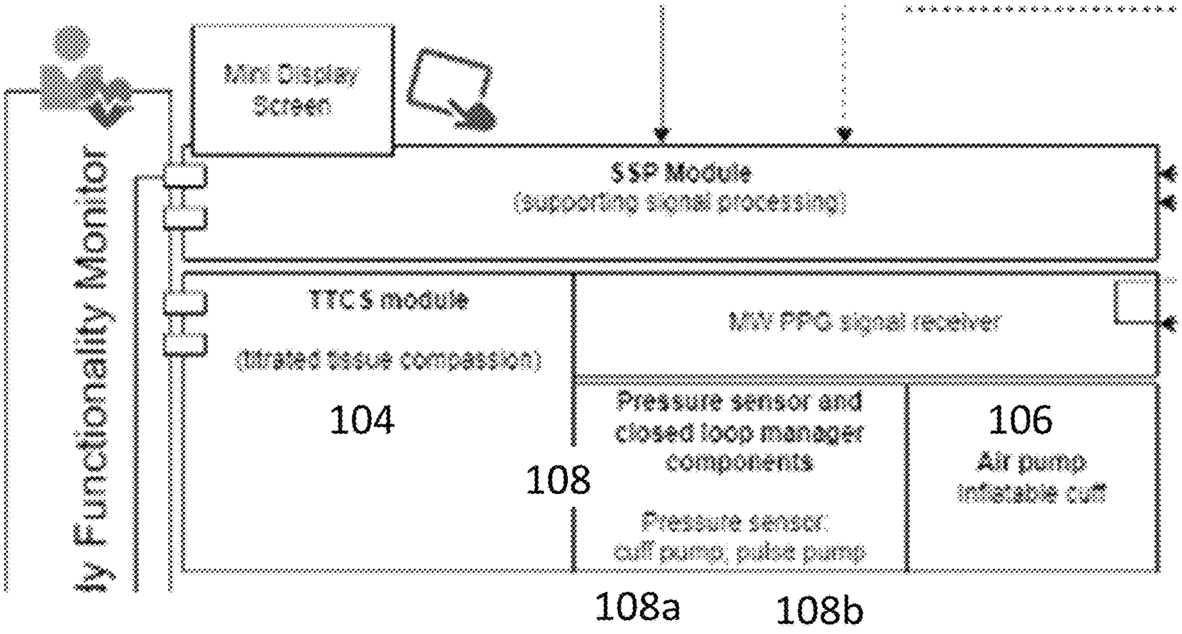
FIG. 12 illustrated an exemplary tissue compression spectroscopy module for a sensor system in accordance with an embodiment of the present disclosure.
Figure 13:
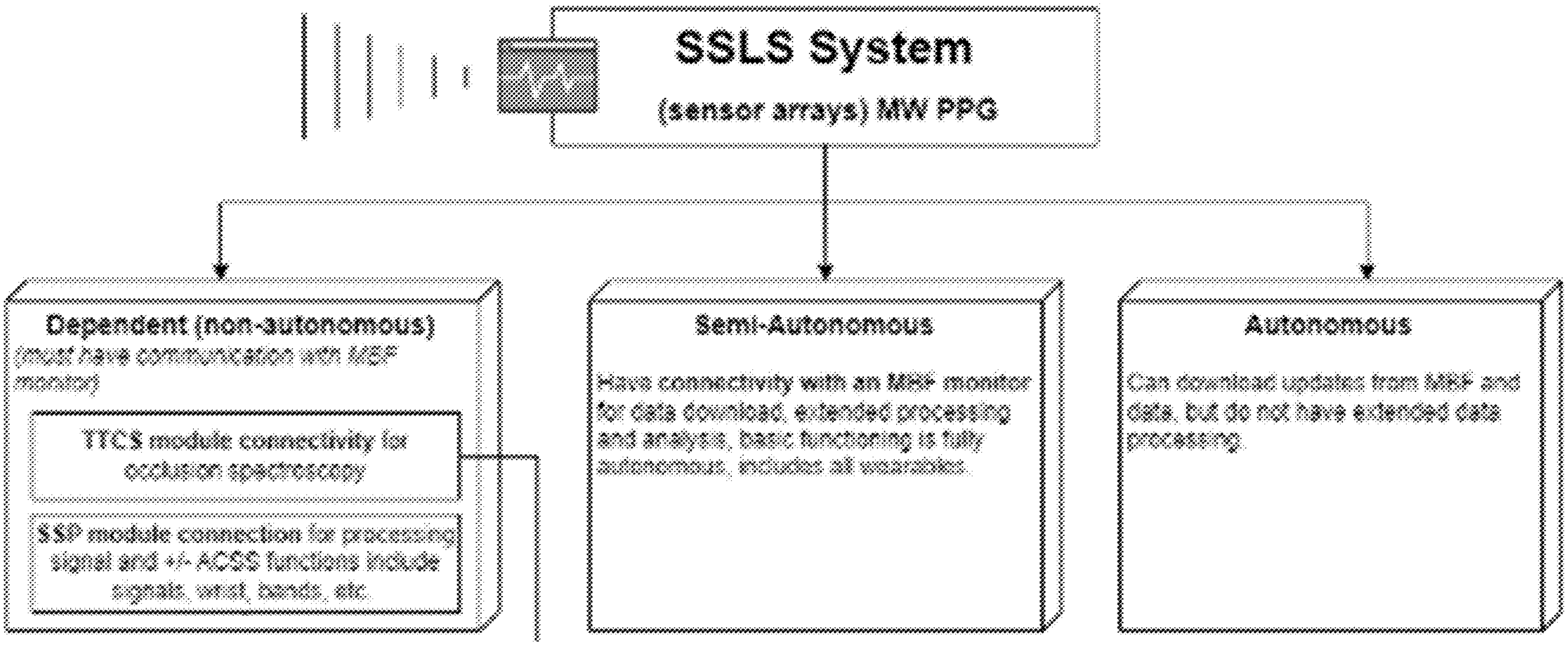
FIG. 13 is illustrates a schematic representation of components of the TTCS in accordance with an embodiment of the present disclosure.

In embodiments, the system 100 may be implemented as a Target-Layer Sensor System (TLSS) in which the number, type and positioning of the LEDs 102L and the detector 102D may be customized for an individual needs. As noted above, for example, the wavelength of the light emitted by the LED may be optimized in accordance with its absorption by either Hb or $H_2O$ In embodiments, the system 100 may include a Titrated Tissue Compression Spectroscopy module (TTCS) 104 (see FIG. 12, for example) which deploys a Stepwise Circulation Occlusion Spectroscopy (SCOS) technique. In embodiments, the TTCS module 104 may include a digital cuff pressurization unit (DCPU) 106 that provides compression closed loop-based operation using an integrated air pump for Closed Loop Cuff Pressurization (CLCP). In embodiments, feedback from a cuff pressure sensor 108 may be provided indicating steadily increasing and decreasing pressurization of the cuff based on external factors that affect the cuff pressure and ameliorating their impact (titrating the flow of air). The module 104 may also include or be connected to a pulsation sensor 108*b* for the detection of a cuff pressure cut-off value at which the arterial pulsation is not sensed, and it serves as indication to switch from inflation to deflation. In this case the TTCS module includes hardware elements beyond a processor and memory as us discussed above and further discussed below.

In embodiments, the module 104 may also include a Closed Loop Cuff Heater 110 that provides heating to target T & feedback energy in-out) and may include a skin heating element 110*a* and may provide a closed control system for providing temperature management of the heating element.

In embodiments, the TTCS module 104 may include additional elements, for example, a tourniquet cuff 110 with may include an inflatable bladder 110*a* adapted to encircle a region of a limb. In embodiments, inflatable bladder pressure sensors 110*b* may be used to provide for inflation pressure management, and sensing the arterial pulse. In embodiments, wireless or wired connections may be provided between the TTCS module 104 and the pressure/pulsation sensors 110*b*. In embodiments, a tube 110*c* may be provided between inflatable bladder 110*a* and the integrated air pump of the digital cuff pressurization unit (DCPU) 106. In embodiments, structural components 112 may be provided on the distal side of the cuff for attaching sensors array systems 102. In embodiments, wireless or wired connections may be provide between the TTCS module 104 and PPG sensors 102.

In embodiments, as noted above, the MW PPG sensors 102 are organized into arrays and may be built into re-usable bands (Flexible Flat base type system) of different sizes. In embodiments, the bands may include parts for attaching sensors (LEDs 102L and detectors 102D) to the distal part of the cuff. In embodiments, the sensors 102 may include size-dependent number of Multi-Directional Sensor Systems (MDSS) which include multiple TSAs. In embodiments, the anatomy of the hand may influence the sites of the TTCS applications.

Figure 14A:
FIG. 14A illustrates a schematic view of a finger including proposed positions for a PPG sensor in accordance with an embodiment of the present disclosure.
Figure 14B:
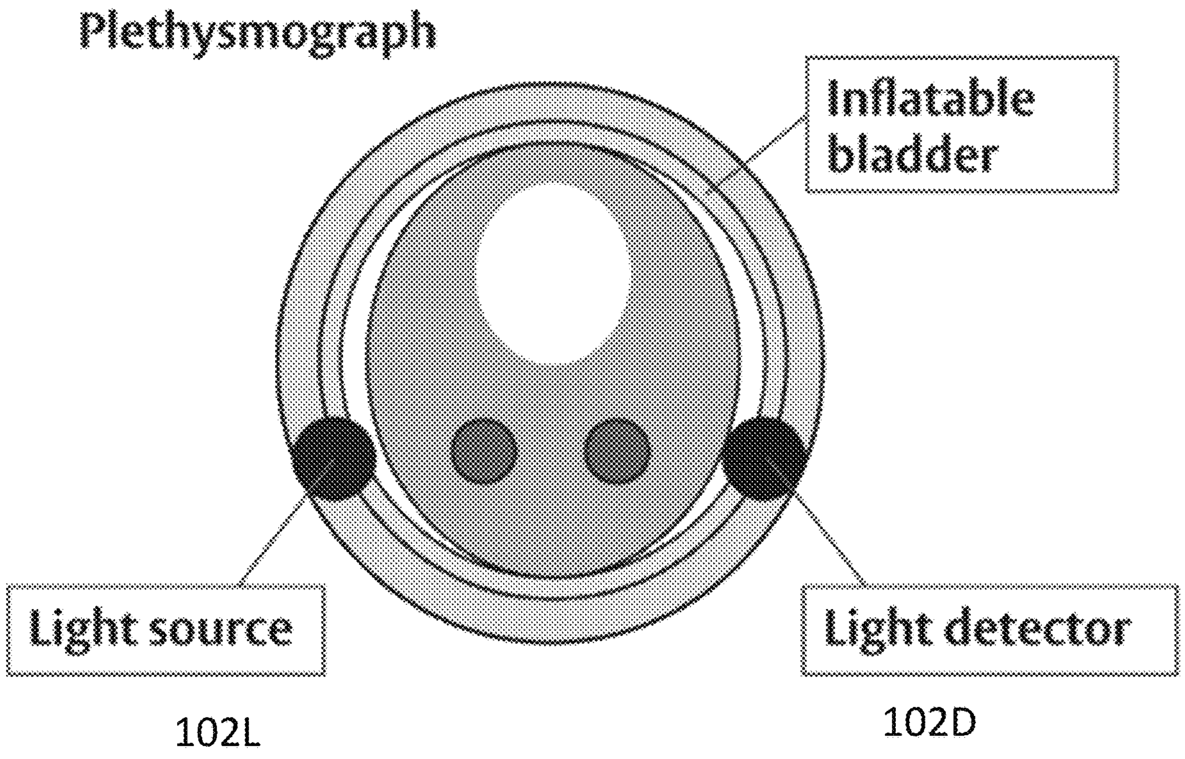
FIG. 14B illustrates a conventional finger cuff for use in blood pressure measurements in accordance with an embodiment of the present disclosure.
Figure 15:
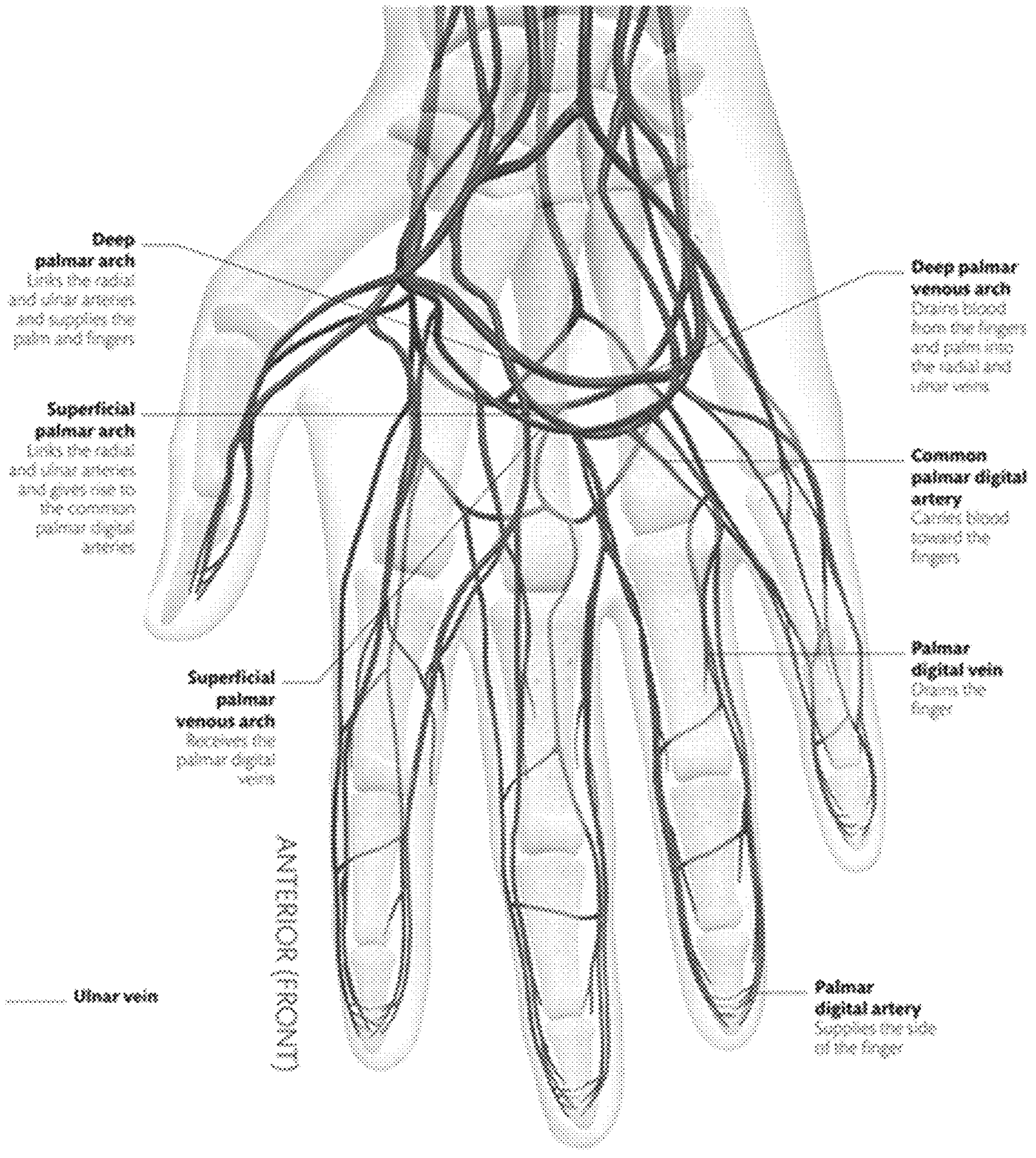
FIG. 15 illustrates the arteries and veins of the hand in accordance with an embodiment of the present disclosure.

FIG. 14A illustrates exemplary sites for application of the TTCS using the numbered arrows 1, 2 and 3 relative to the anatomy of a finger. FIG. 14B illustrates a conventional finger cuff and sensors 102 that may be used for blood pressure measurements.

Figure 16:
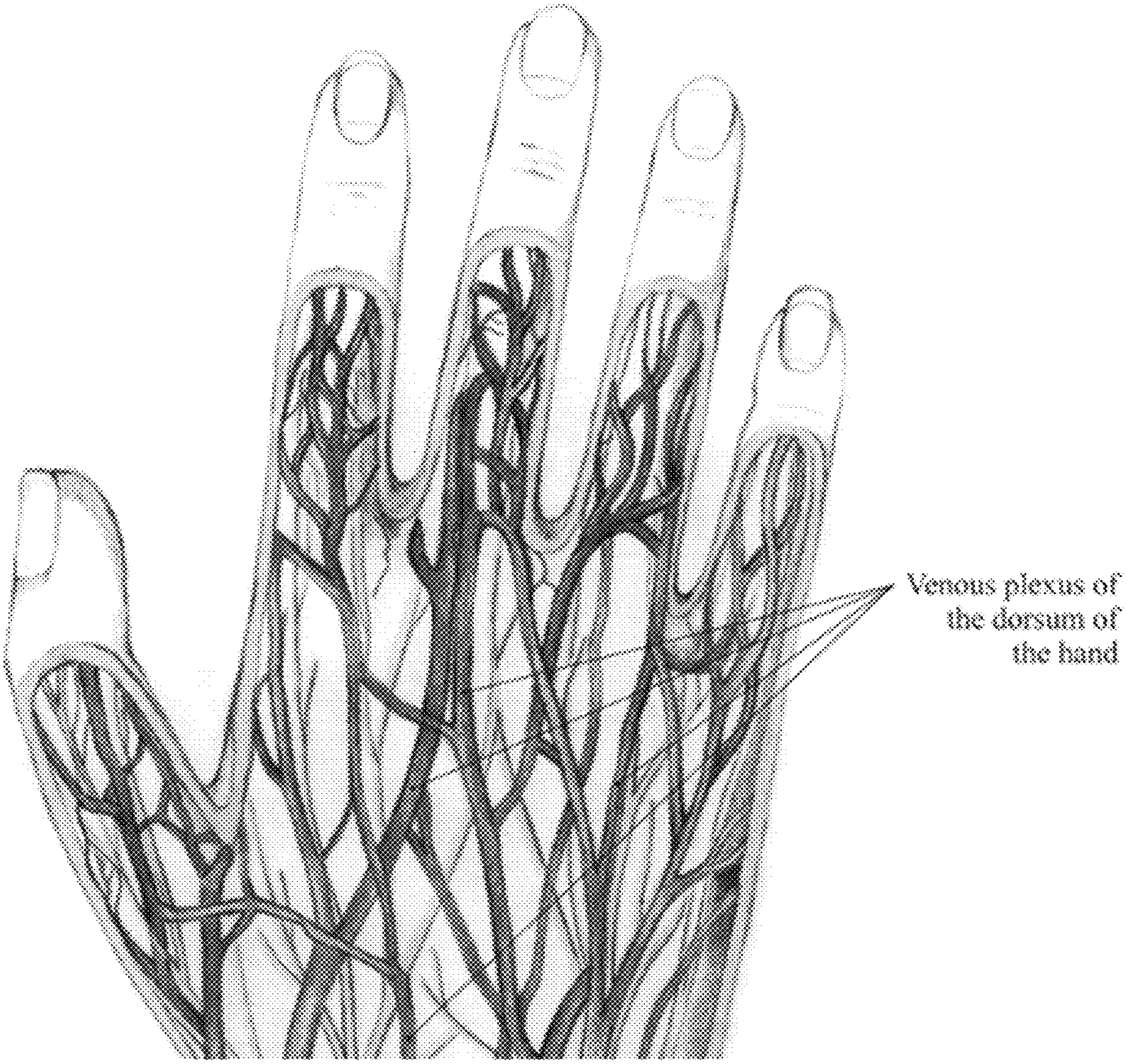
FIG. 16 illustrates the venous architecture of the hand in accordance with an embodiment of the present disclosure.

FIG. 16A illustrates capillary beds which are the main vessels systems within a scan area relative to the entire circulatory system. In FIG. 16B, the capillary bed is supplied by a supply artery which splits into a network of true capillaries where transcapillary exchange of water and oxygen with tissues take place. A metarteriole provides a shortcut between the arterial and venous portions of the circulatory system and does not participate in transcapillary exchange with extravascular tissues. In embodiments, the MW PPG sensors 102 measure LWL light absorption by tHb, net HWL light absorption by intravascular intracellular water in red cells (RCV) and PV, as well as $eH_2O$.

Figure 17A:
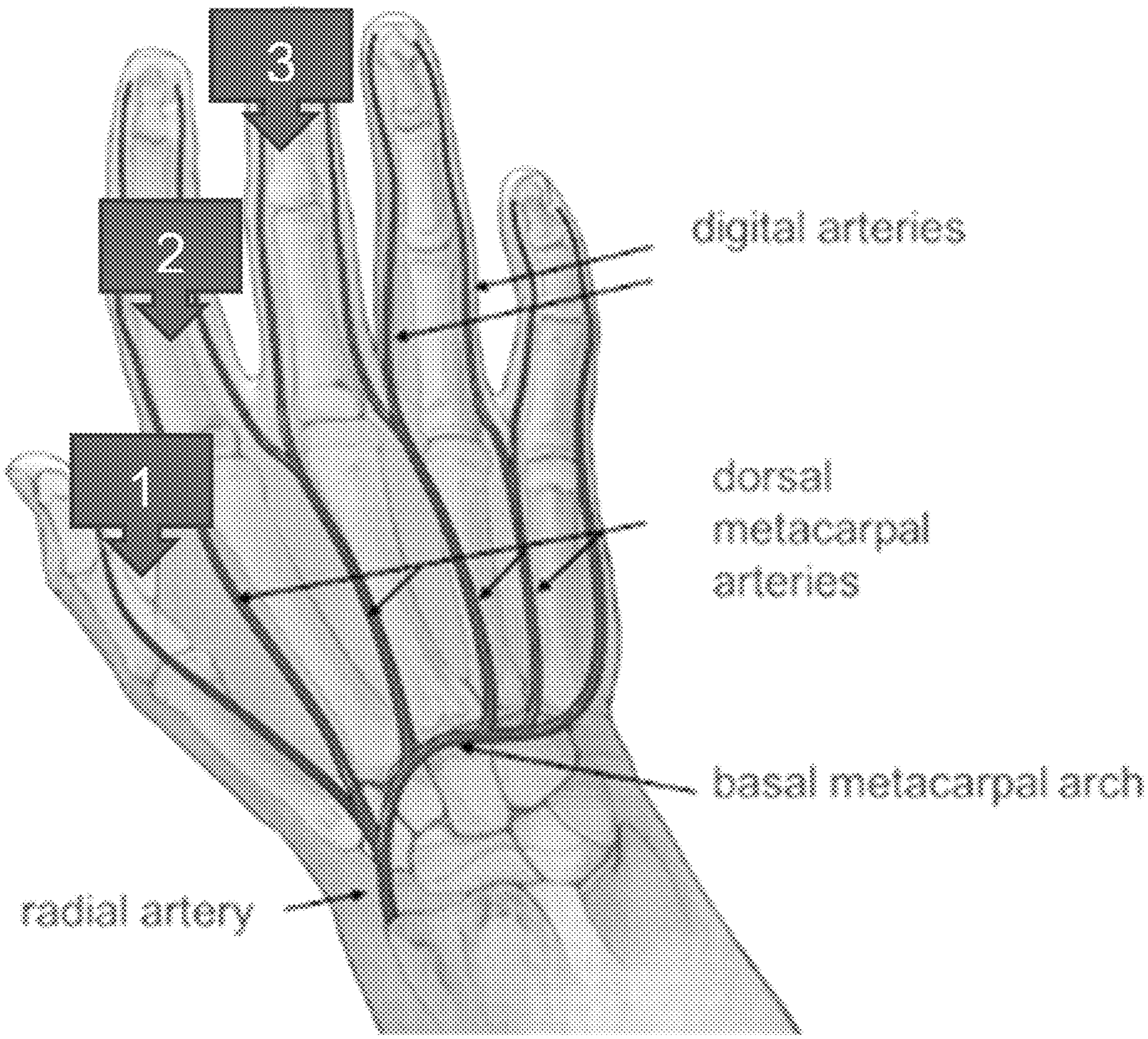
FIG. 17A illustrates arteries of the palm, thumb and fingers with exemplary positions for MW PPG sensors in accordance with an embodiment of the present disclosure.
Figure 17B:
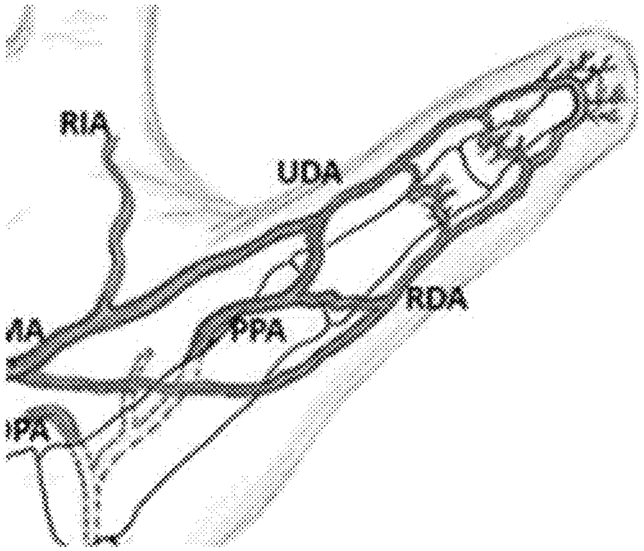
FIG. 17B illustrates arteries and veins of the thumb with exemplary positions for MW PPG sensors in accordance with an embodiment of the present disclosure.
Figure 17C:
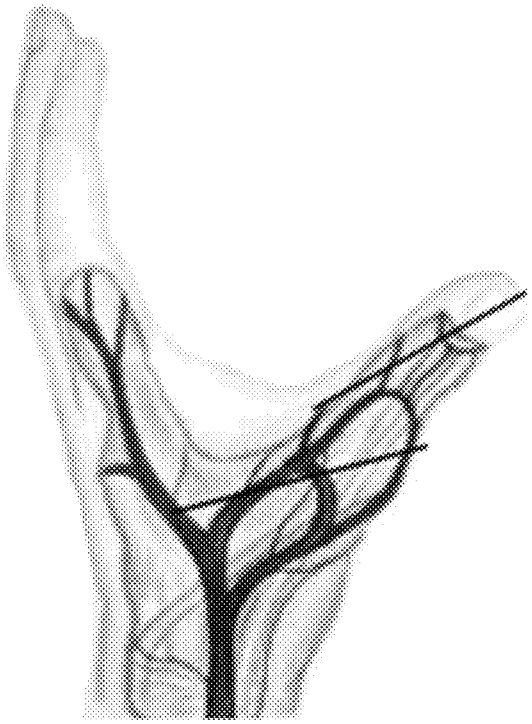
FIG. 17C illustrates arteries, arteriola and capillaries of a finger with exemplary positions for MW PPG sensors in accordance with an embodiment of the present disclosure.
Figure 17D:
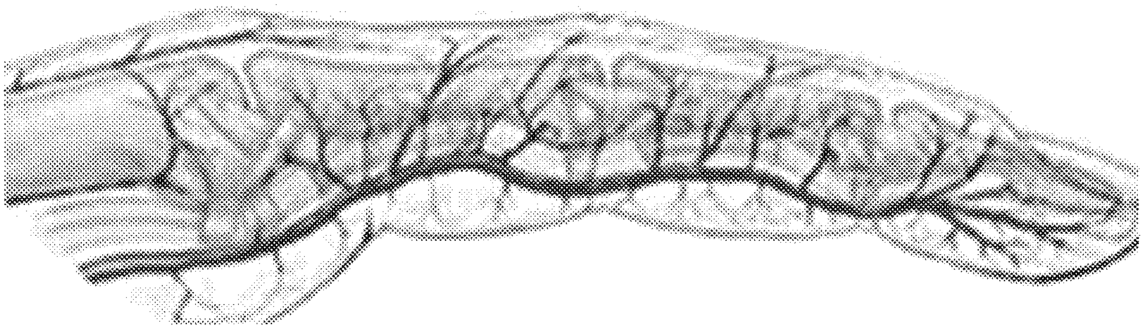
FIG. 17D illustrates veins of a finger with exemplary positions for MW PPG sensors in accordance with an embodiment of the present disclosure.

FIG. 17A illustrates a detailed schematic of a portion of the circulatory system in a user's hand while FIG. 17B highlights the venous architecture thereof. In FIG. 17A arteries of the palm, thumb and fingers are illustrated while in FIG. 17B, the arteries and veins of the thumb as shown. In FIG. 17C, arteries, arteriola and capillaries of a finger are shown. In embodiments, the numbered arrows indicate possible placement sites for the cuffed or ring-shape sensor systems 100, where the numbers indicate a sequence of the site's preference.

Figure 18A:
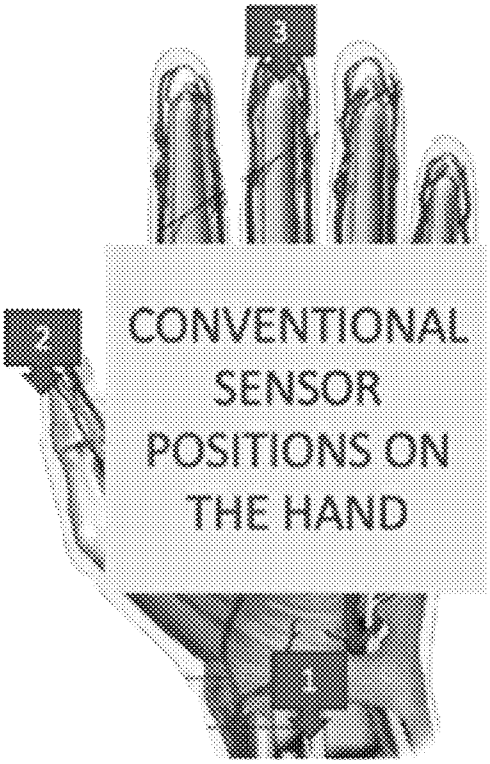
FIG. 18A-18B illustrate the anatomy of a hand exemplary positions for MW PPG sensors and identification of non-compressible tissues in accordance with an embodiment of the present disclosure.
Figure 18B:
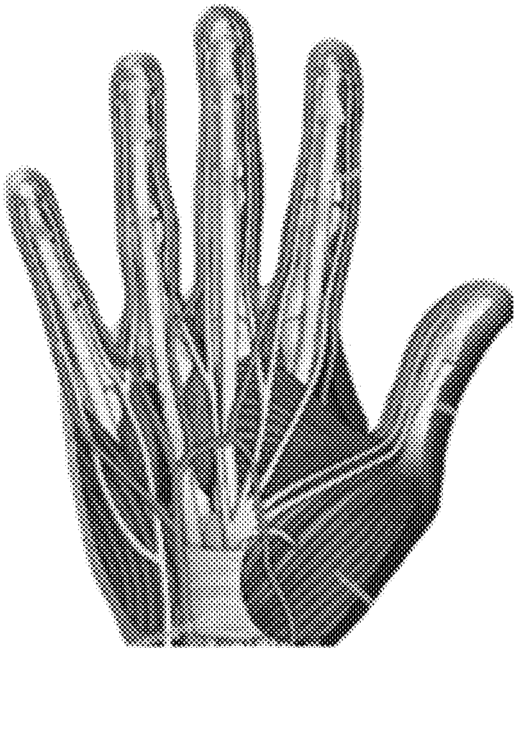
Figure 19A:
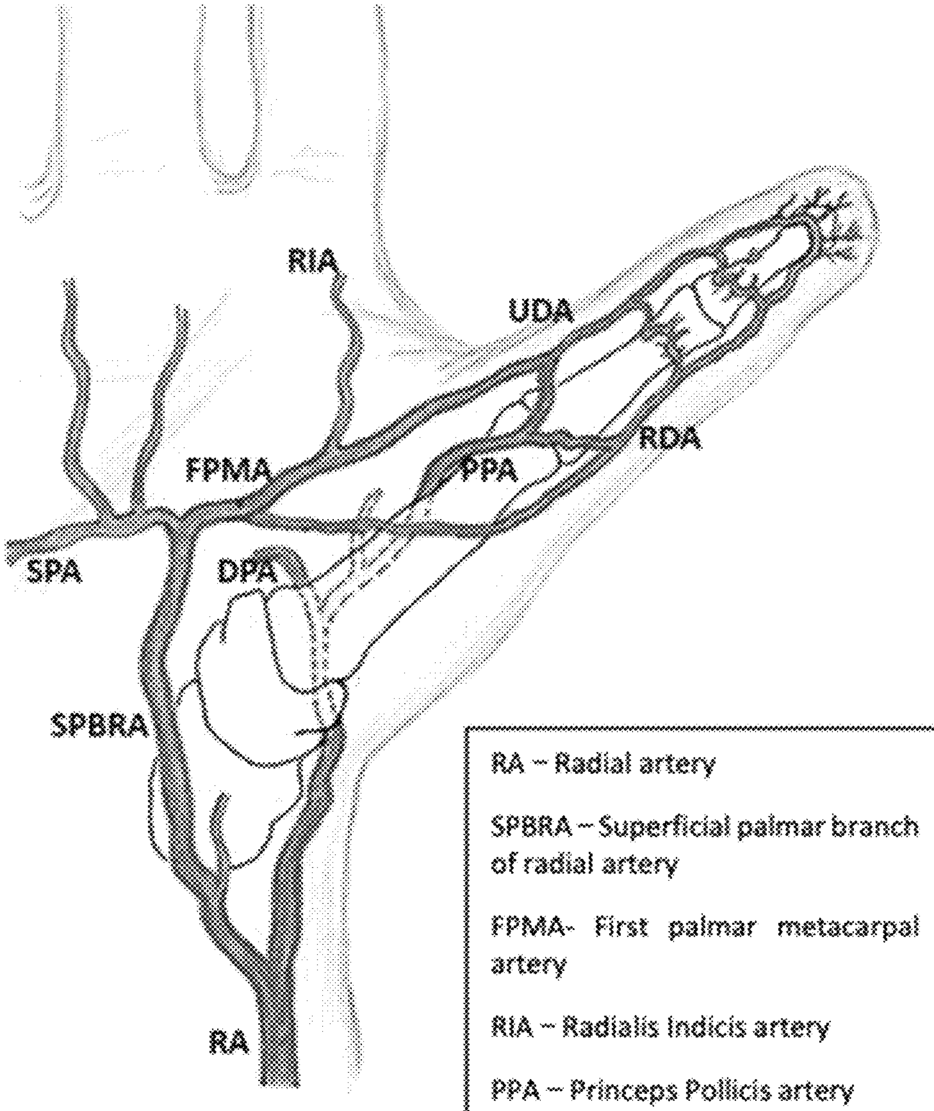
FIGS. 19A-D illustrates dominant arterial vessels, arterial network, venous network and capillary network of the thumb in accordance with an embodiment of the present disclosure.
Figure 19B:
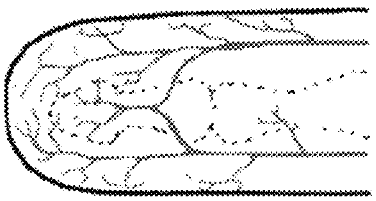
Figure 19C:
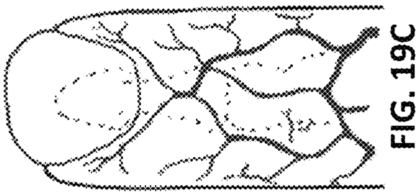
Figure 19D:
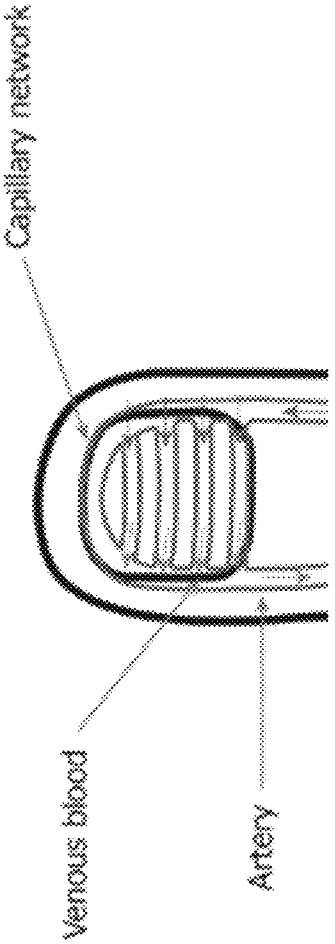
Figure 20A:
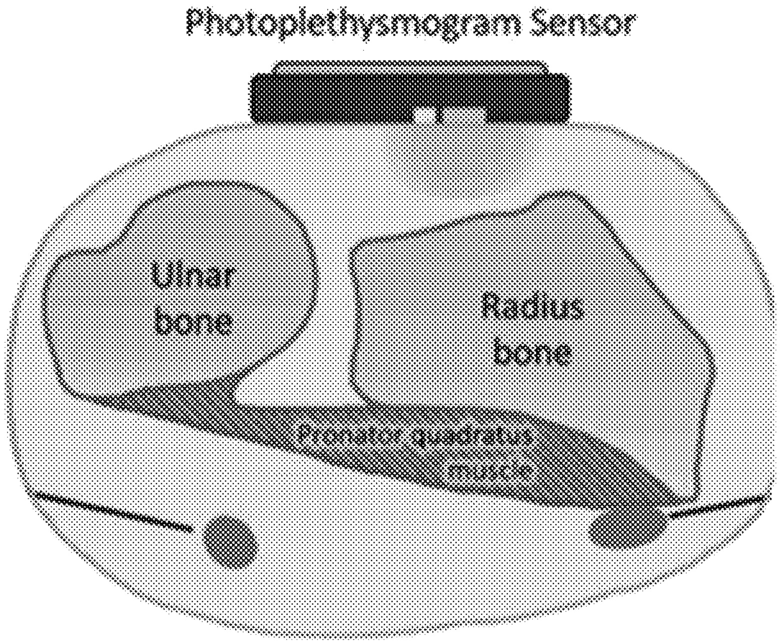
FIG. 20A illustrates placement of a PPG sensor on a wrist in accordance with an embodiment of the present disclosure.
Figure 20B:
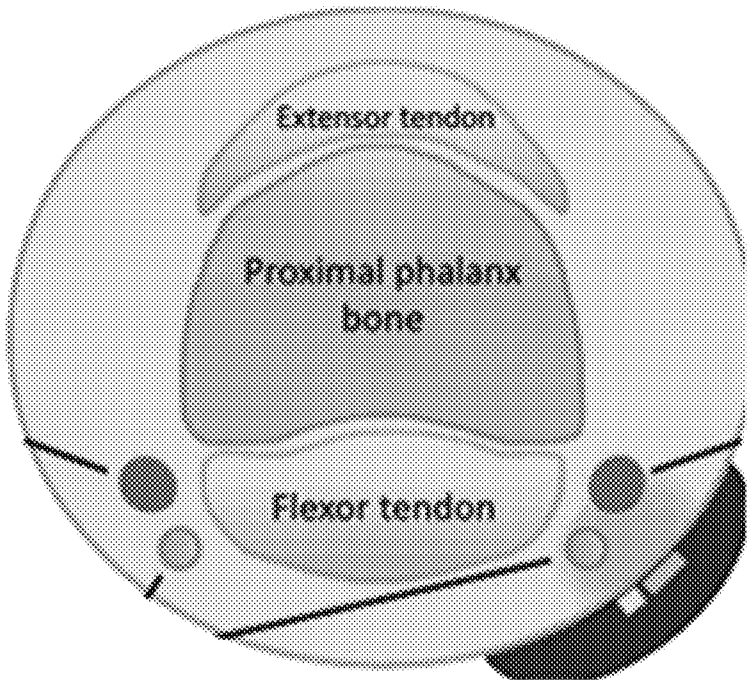
FIG. 20B illustrates placement of a PPG sensor on a finger in accordance with an embodiment of the present disclosure.
Figure 20C:
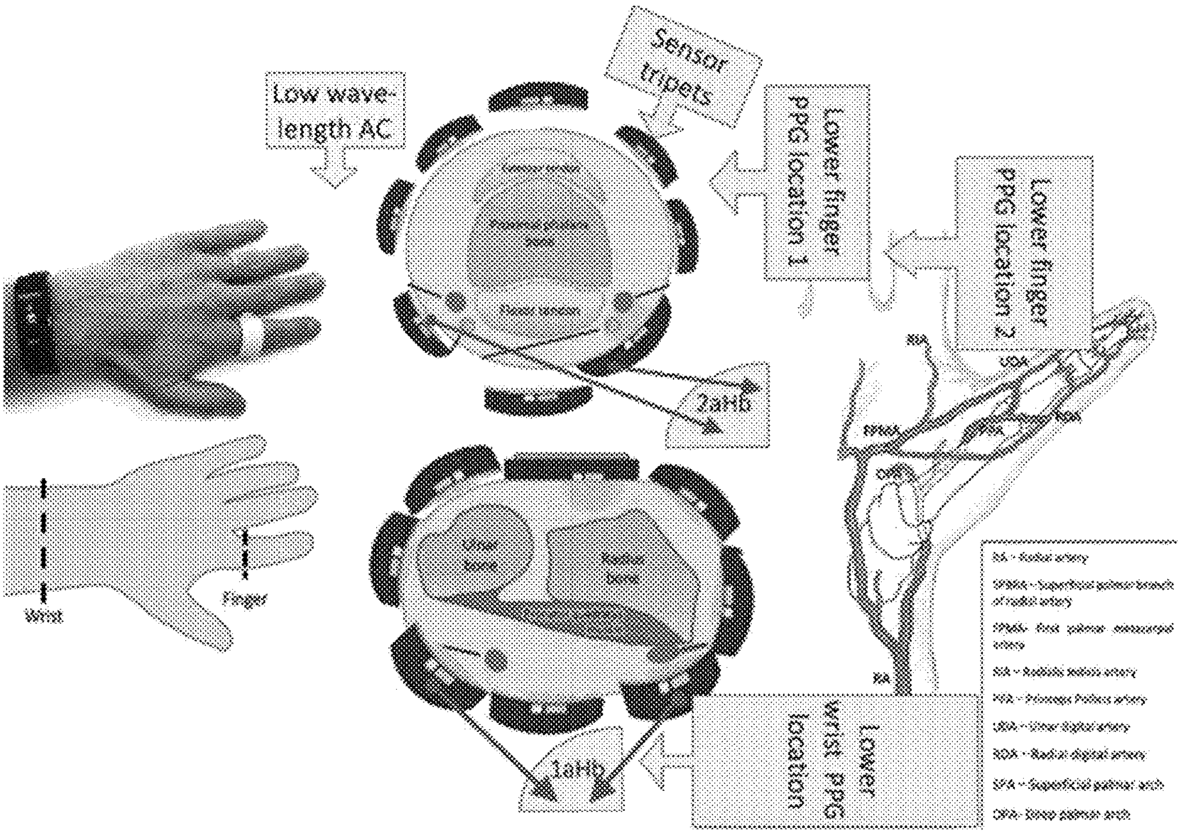
FIG. 20C illustrates used of LWL AC for assessment of changes in pulsatile arterial hemoglobin (aHb) in palmar digital arteries and capillary beds of the skin and LWL DC components for assessment of changes in non-pulsatile hemoglobin (sHb) which is the sum light absorption by non-pulsatile arterial (nHb), capillary (cHb) and venous (vHb) in palmar digital veins and arteries and capillary beds of the skin as well as summarized LWL AC signals from wrist and finger sensors in accordance with an embodiment of the present disclosure.
Figure 21B:
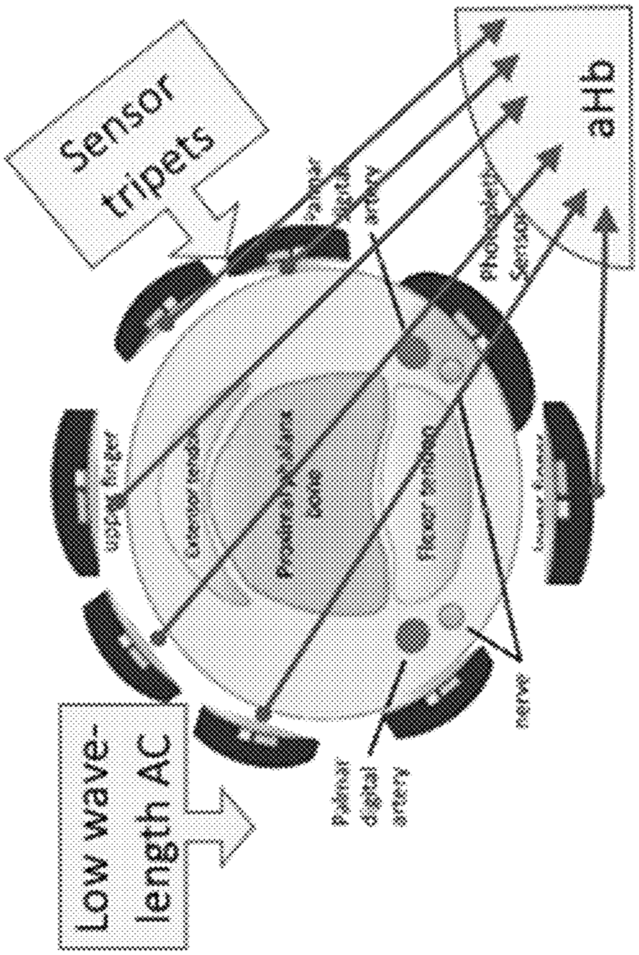
FIG. 21B illustrates an exemplary sensor system for measuring light absorption by water in tissue in capillary beds of skin in accordance with an embodiment of the present disclosure.
Figure 21A:
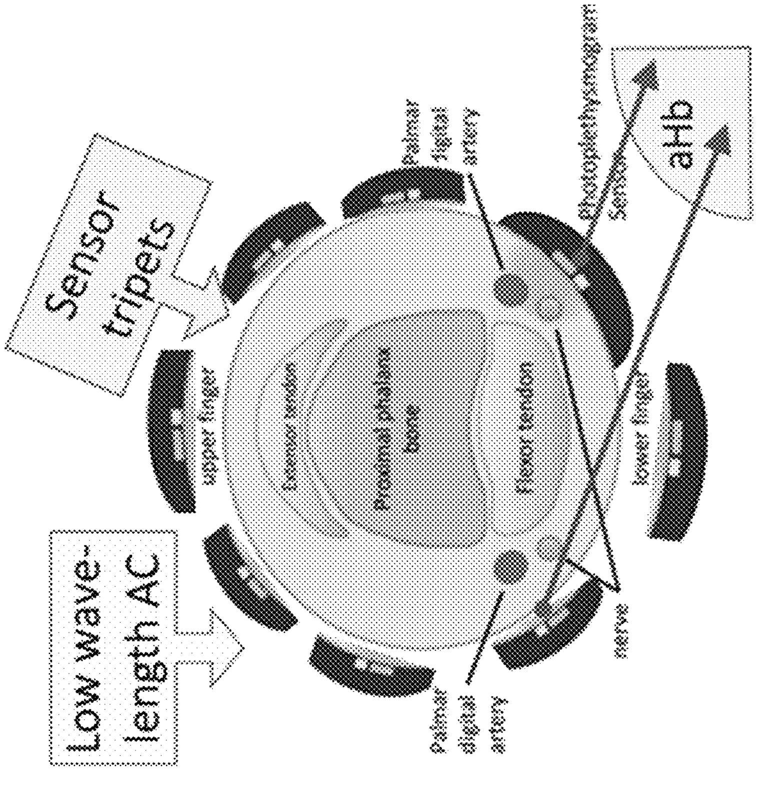
FIG. 21A illustrates an exemplary sensor system for measuring light absorption by water in tissue in palmer digital arteries in accordance with an embodiment of the present disclosure.
Figure 21D:
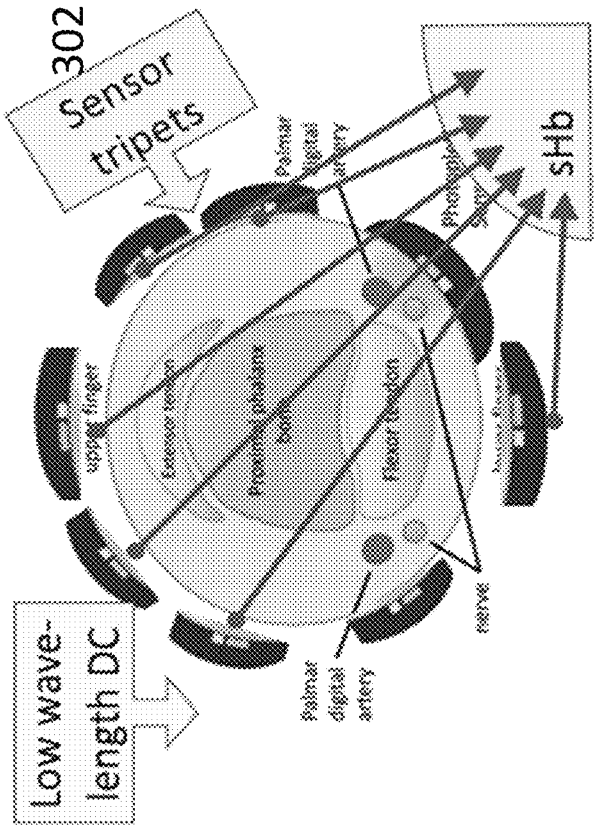
FIGS. 21C-D illustrated an LWL DC component for assessment of changes in non-pulsatile hemoglobin (sHb) in palmar digital veins and arteries and is capillary beds of the skin in accordance with an embodiment of the present disclosure.
Figure 21C:
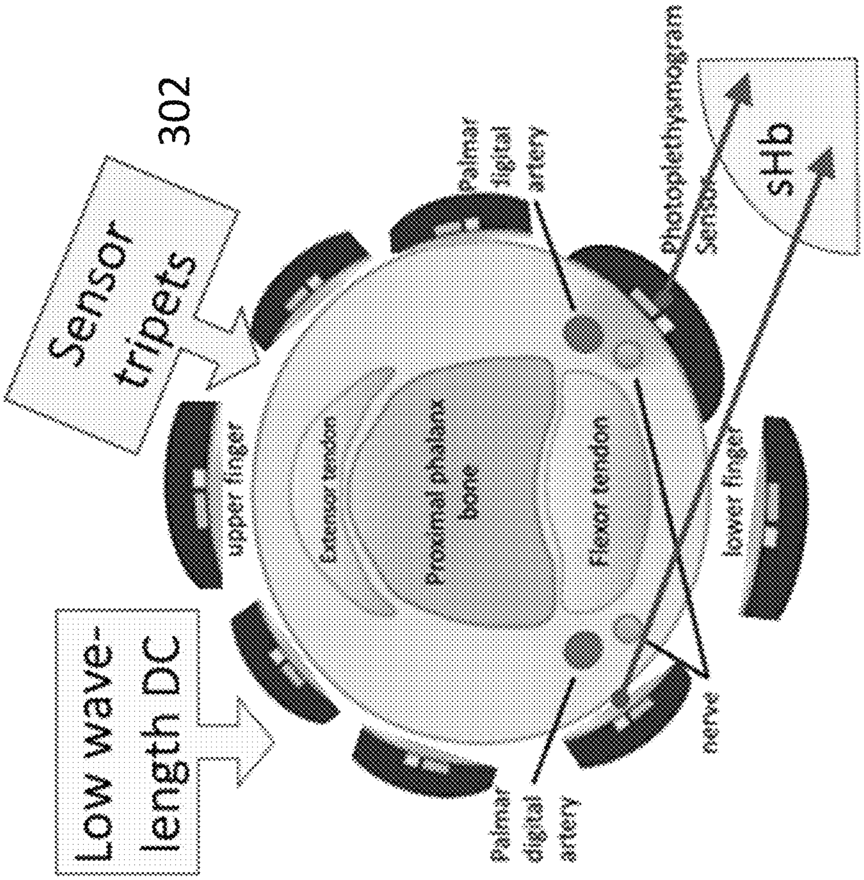
Figure 21E:
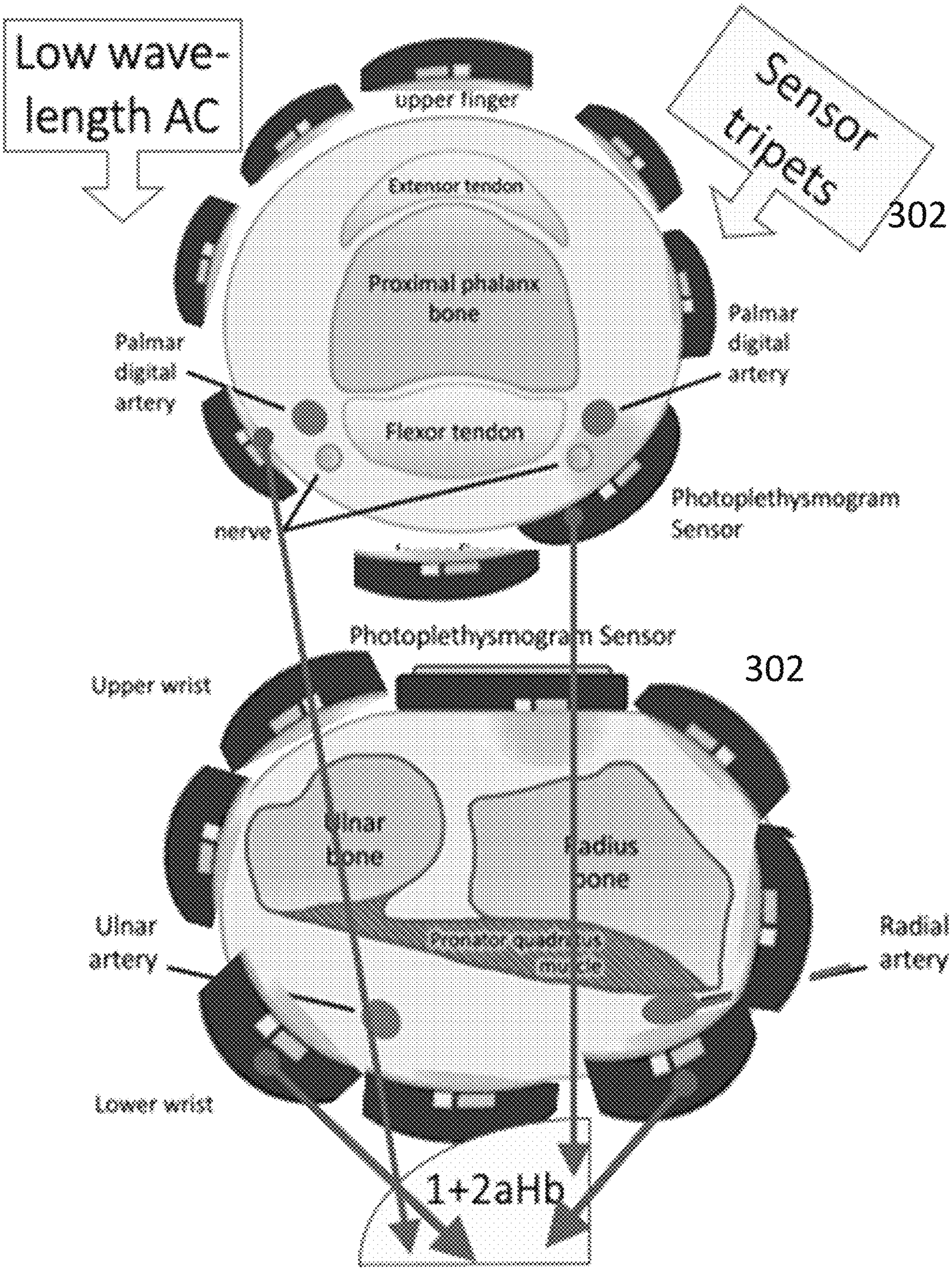
FIG. 21E illustrates summarized LWL AC signals from wrist and finger sensors in accordance with an embodiment of the present disclosure.
Figure 22B:
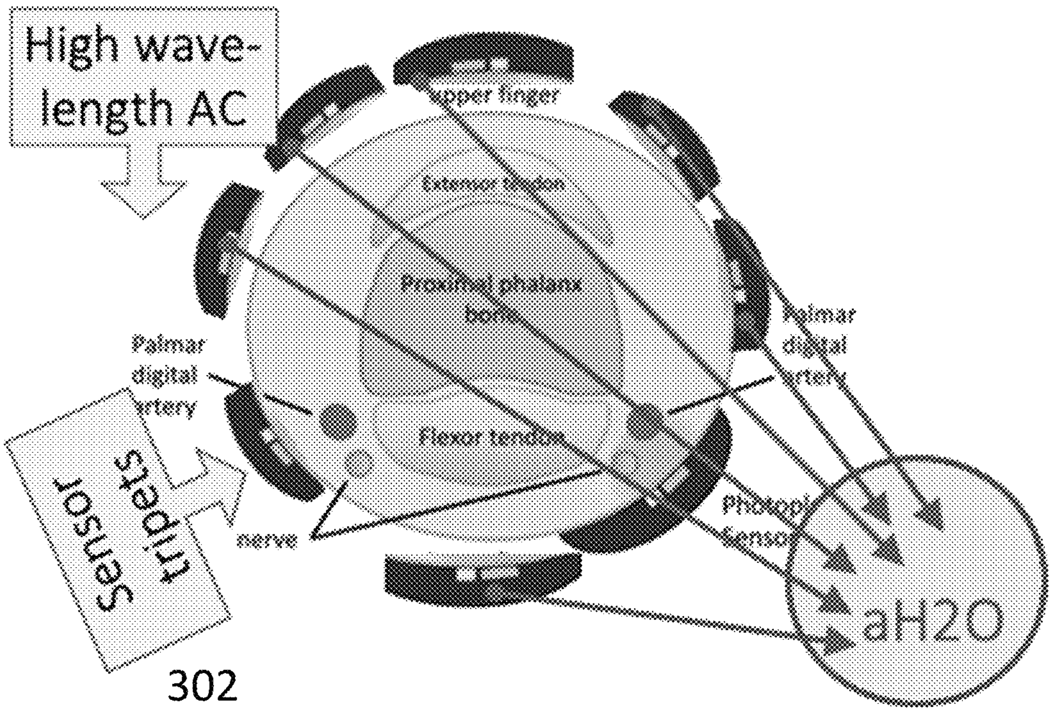
FIGS. 22A-22B illustrate a high wavelength HWL AC component for assessment of changes in pulsatile arterial water ($aH_2O$) in palmar digital arteries and capillary beds of the skin in accordance with an embodiment of the present disclosure.
Figure 22A:
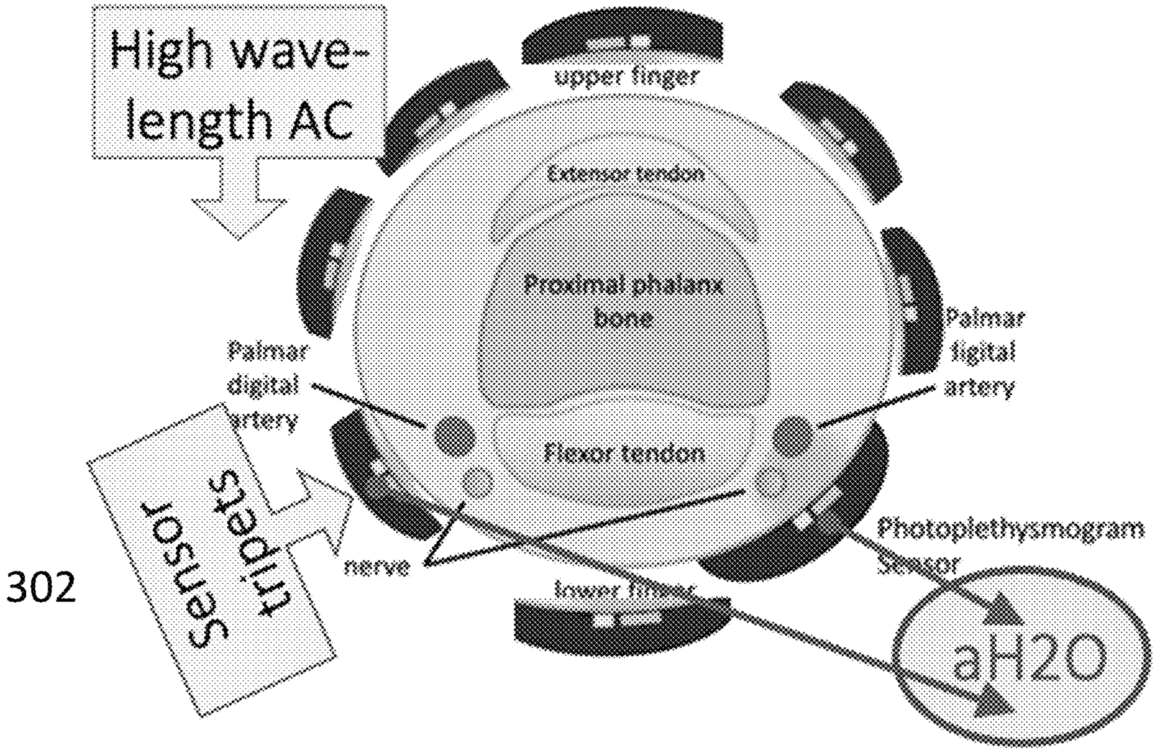
Figure 22C:
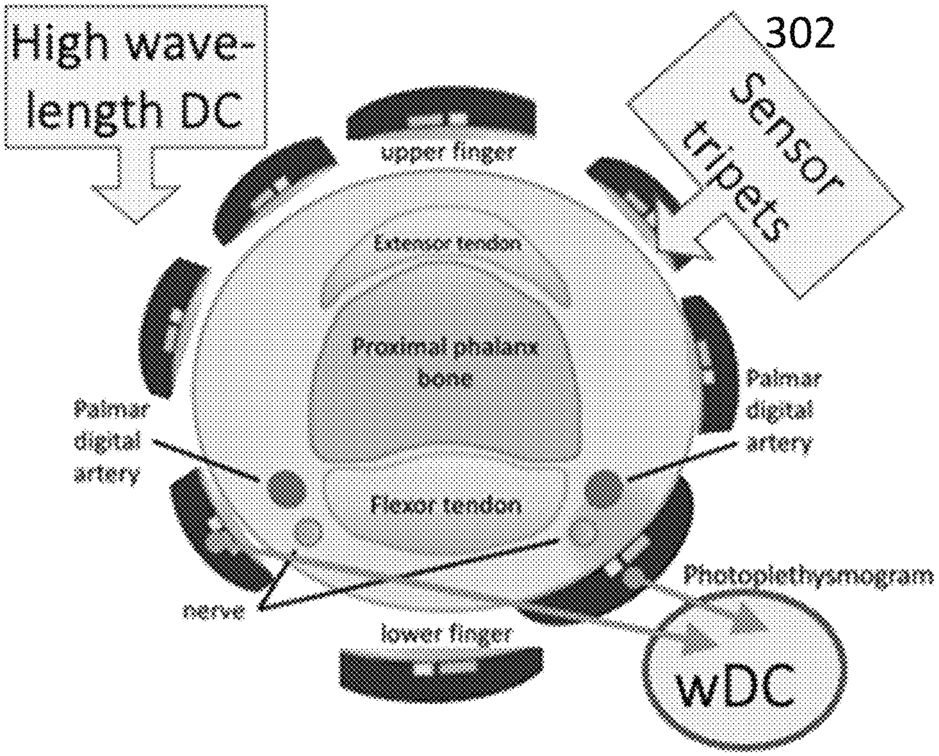
FIGS. 22C-22D illustrate a high wavelength HWL DC component for assessment of changes in non-pulsatile water (wDC) in palmar digital arteries and capillary beds of the skin in accordance with an embodiment of the present disclosure.
Figure 22D:
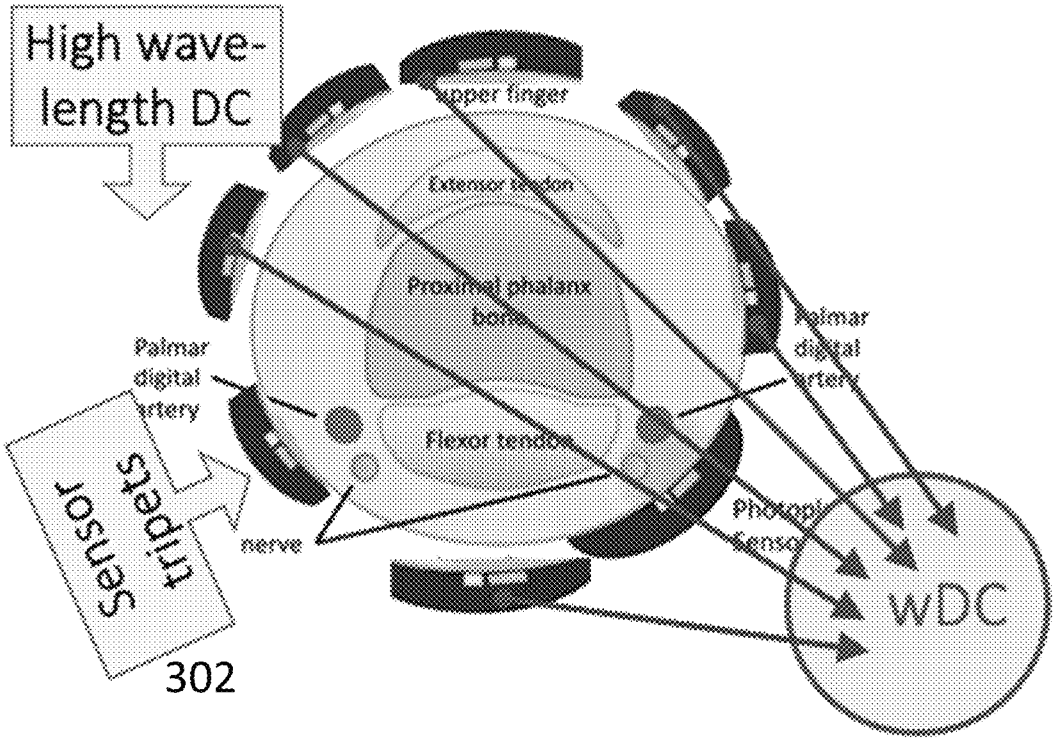
Figure 22E:
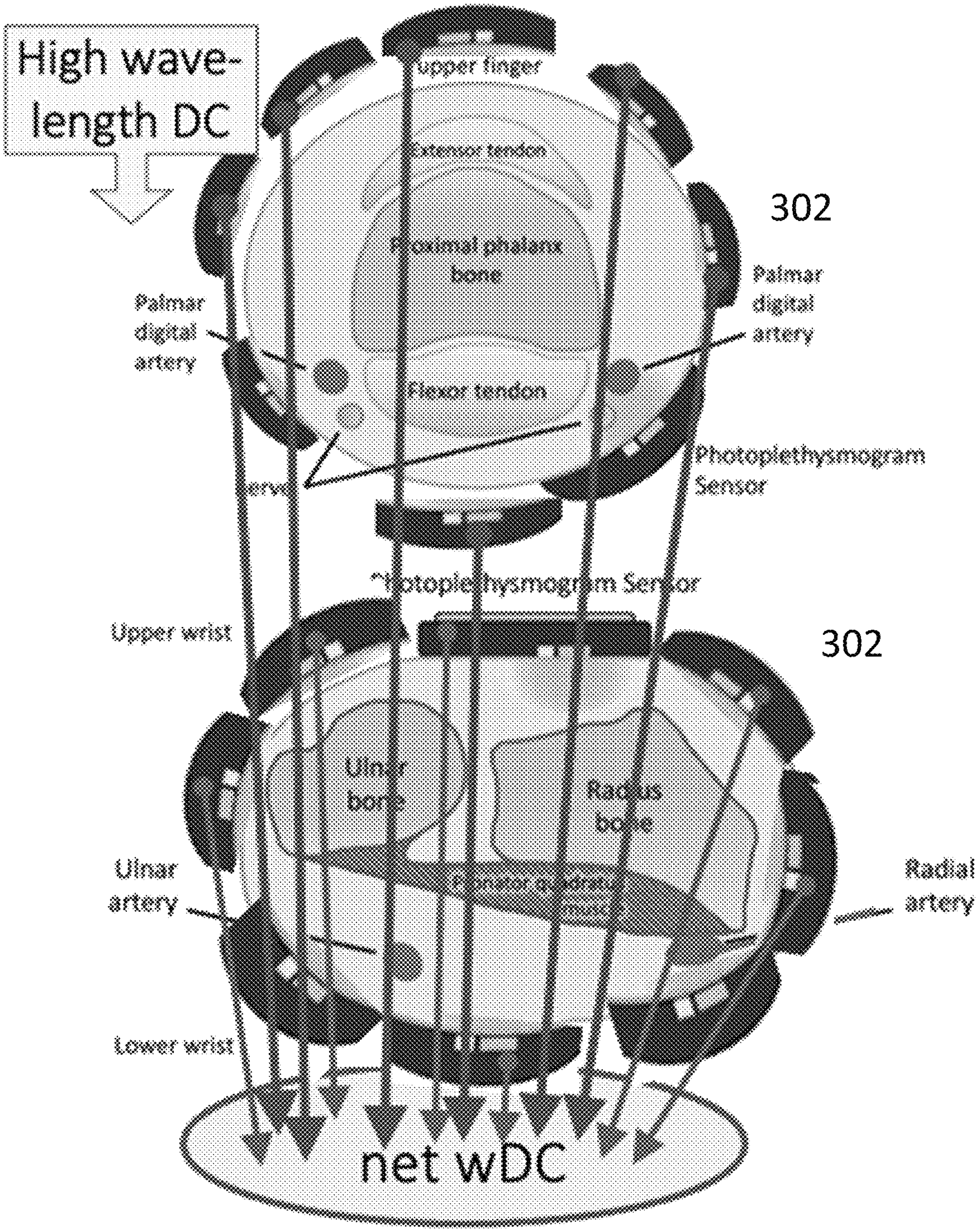
FIG. 22E illustrates summarized HWL DC signals from wrist and finger sensors in accordance with an embodiment of the present disclosure.
Figure 23:
FIG. 23 illustrates an exemplary multiple trend monitorin module in accordance with an embodiment of the present disclosure.
Figure 24:
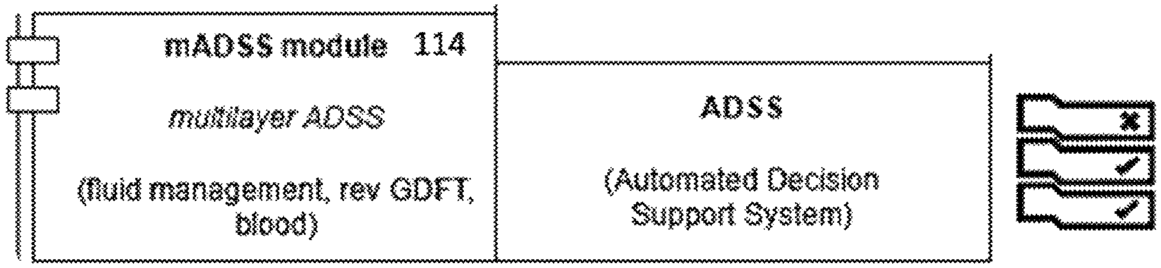
FIG. 24 illustrates an exemplary automated decision support system in accordance with an embodiment of the present disclosure.
Figure 25:
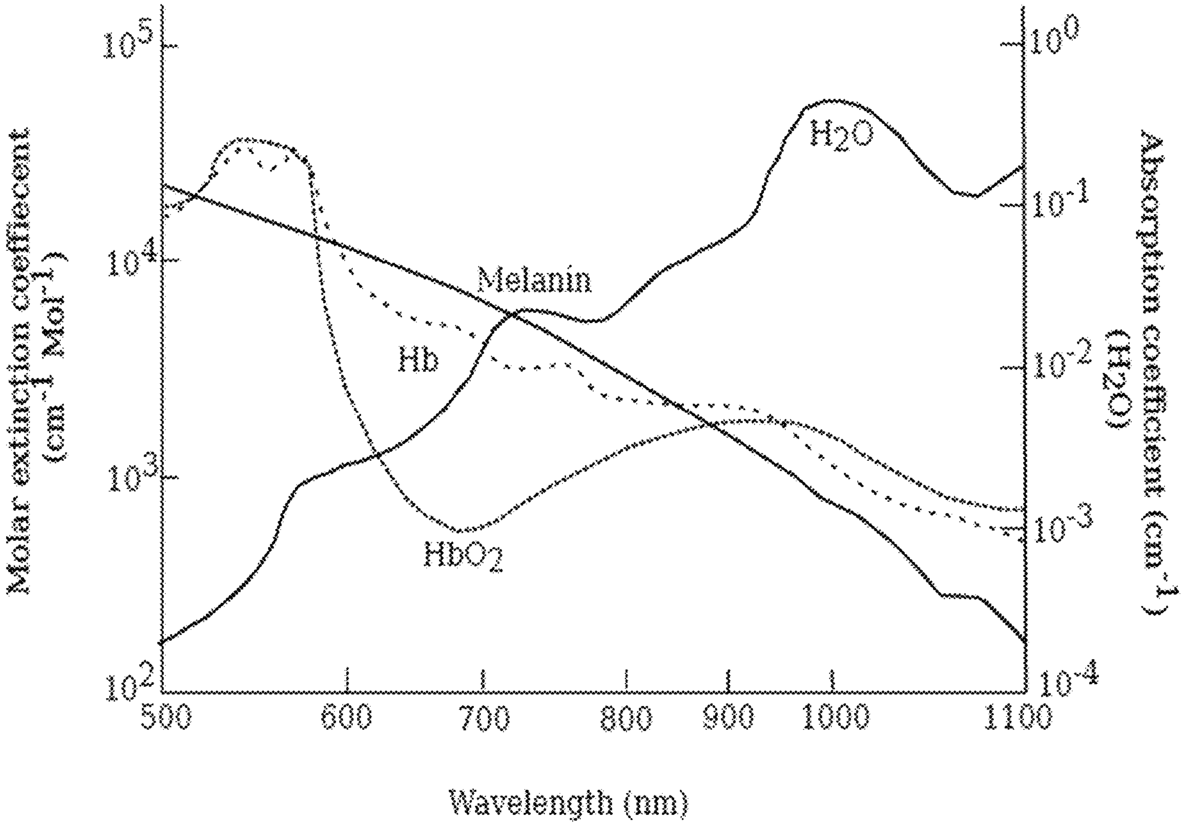
FIG. 25 illustrates a graph showing light absorption in epidermis-hypodermis layers of skin where wavelengths 500-650 nm (between point 1 and 3), and wavelengths 850-1050 nm (between 4 and 2) and water (H2O) has extinction and absorption coefficients for 850-1050 nm which are similar to 550-600 nm for hemoglobin (Hb), oxygenated hemoglobin (Hb O2) and melanin.
Figure 26:
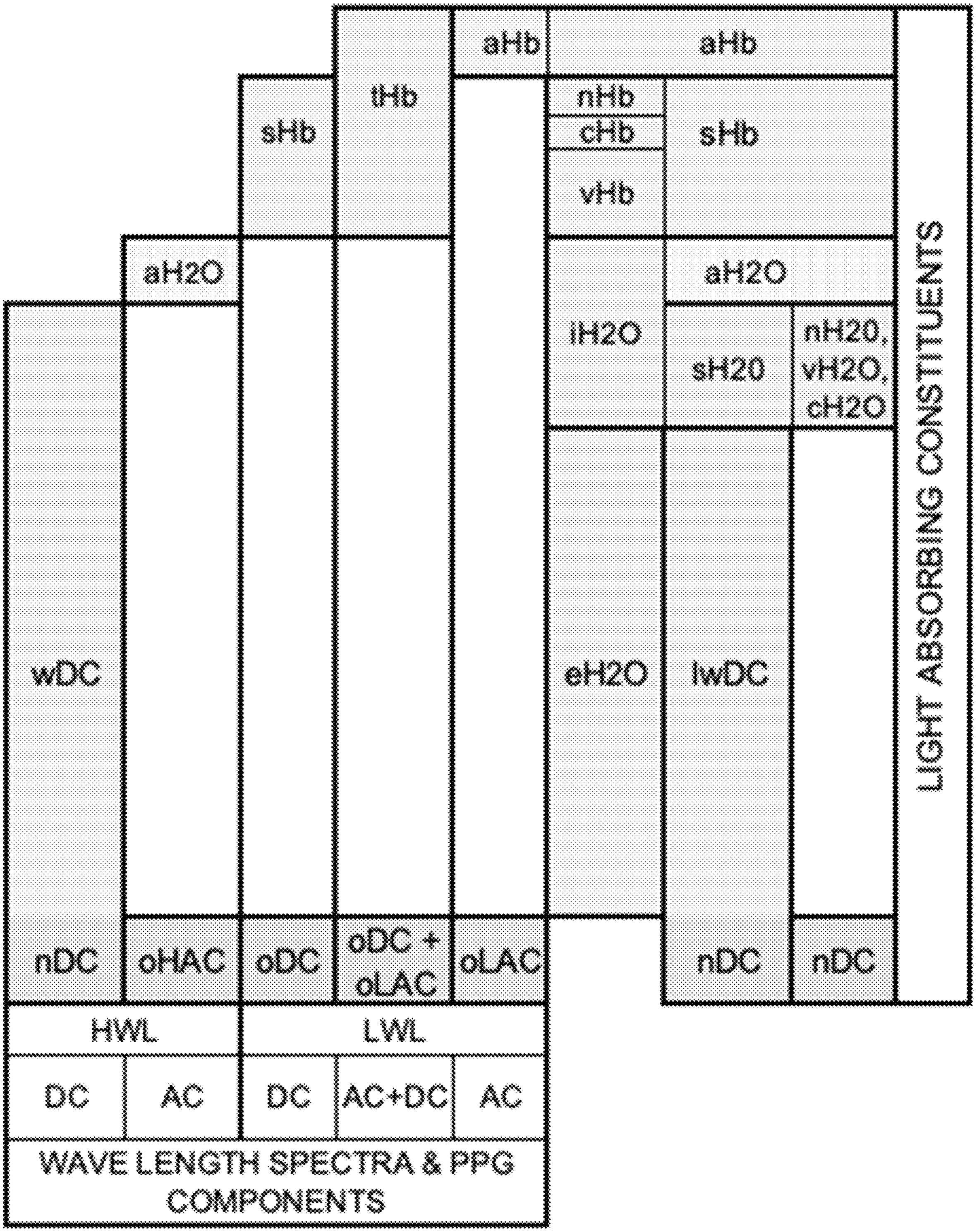
FIG. 26 is a graph illustrating Wavelength spectra and PPG components of the PWPPG information and their relation to light absorbing constituents in tissue in accordance with an embodiment of the present disclosure.
Figure 27:
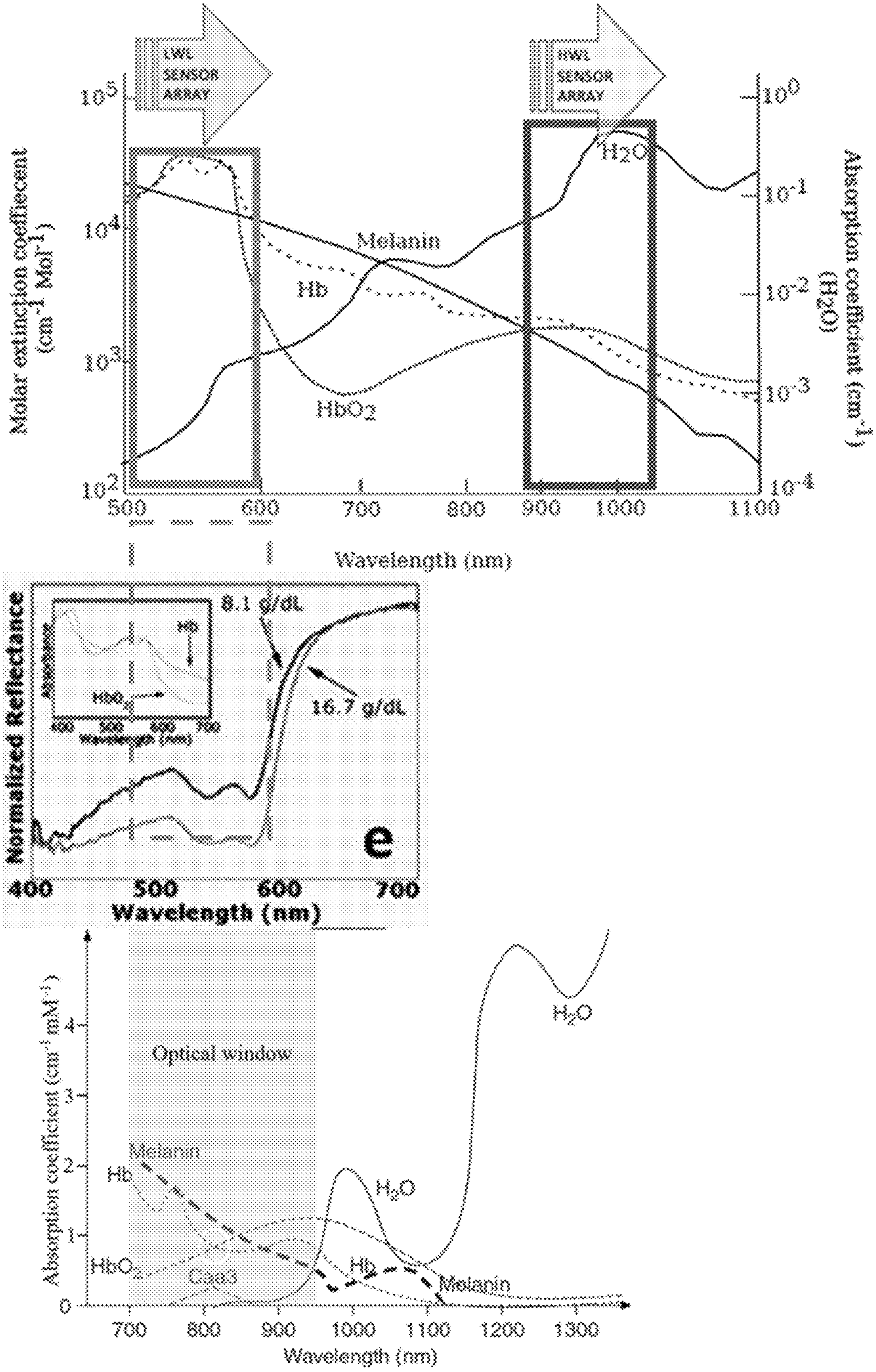
FIG. 27 illustrates light absorption graphs where the left side rectangle zone represents the LWL MW PPG scan spectra for measuring hemoglobin, and right side rectangle represents the HWL MW PPG scan spectra for measuring water.
Figure 28:
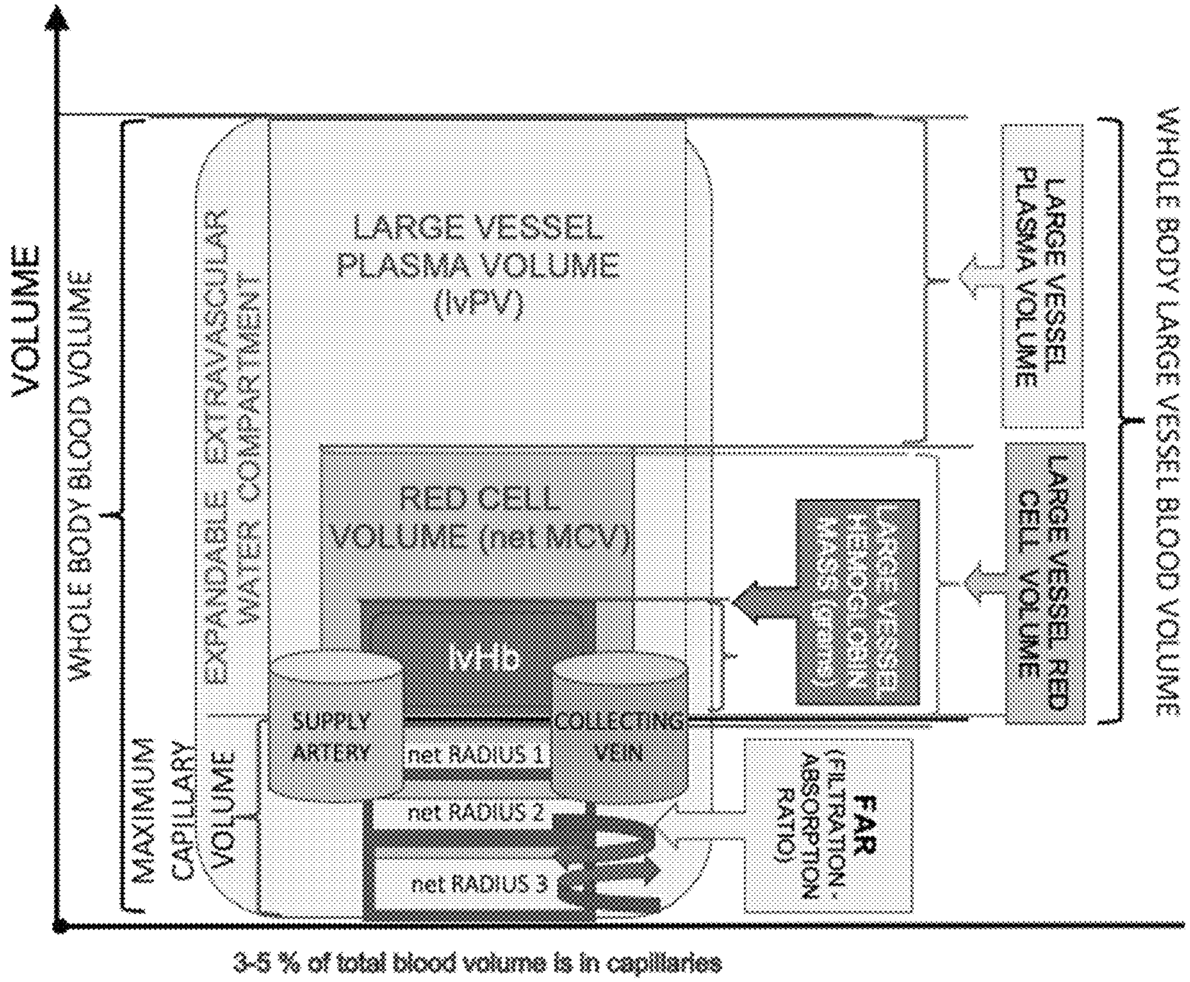
FIG. 28 is a chart indicating a ratio of whole body blood volume to capillary blood volume in accordance with an embodiment of the present disclosure.
Figure 29A:
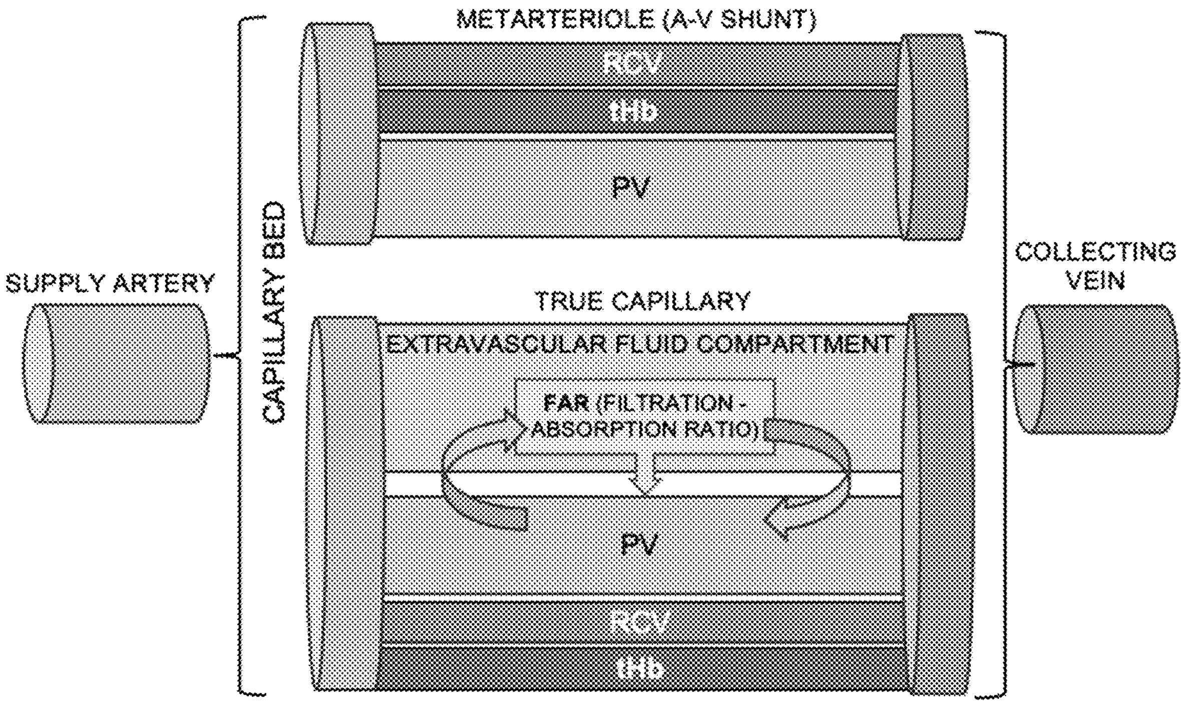
FIG. 29A illustrates fluid filtration-absorption ratio (FAR) in true capillaries in accordance with an embodiment of the present disclosure.
Figure 29B:
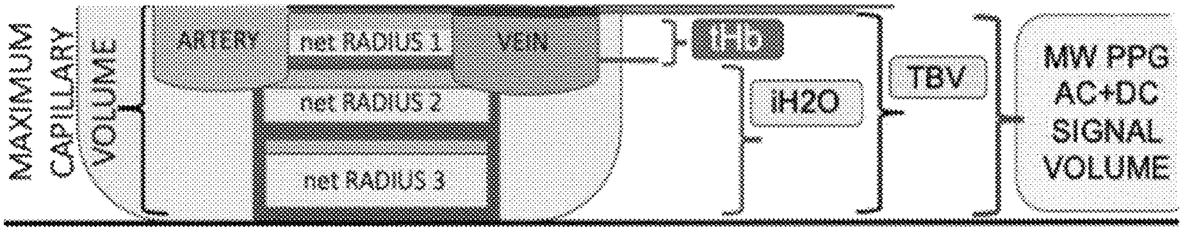
FIG. 29B illustrates the total blood volume (TBV) which refers to the net light absorption by hemoglobin and water in the vicinity of PPG scan.
Figure 29C:
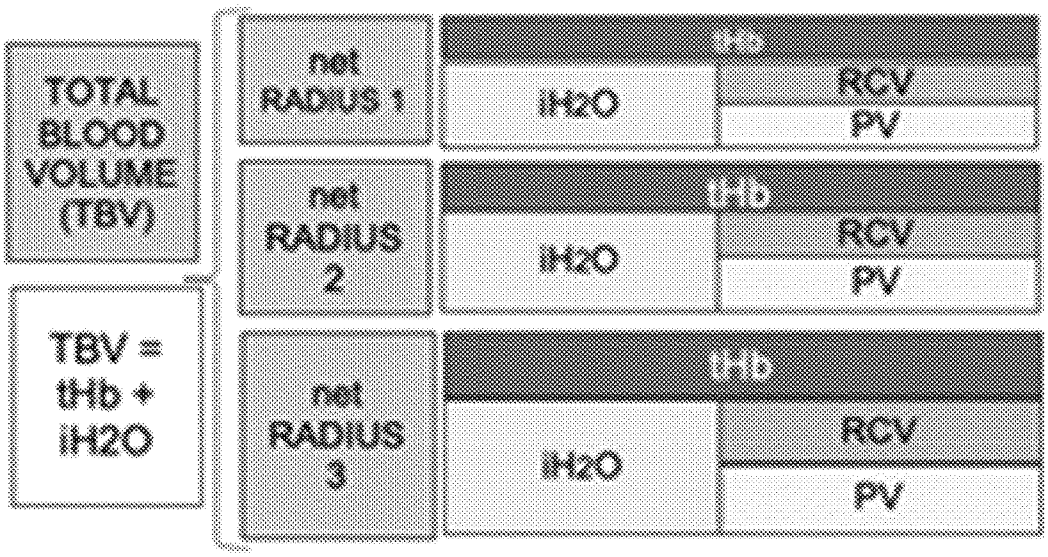
FIG. 29C illustrates TBV dependence on radius patterns of capillaries.
Figure 30A:
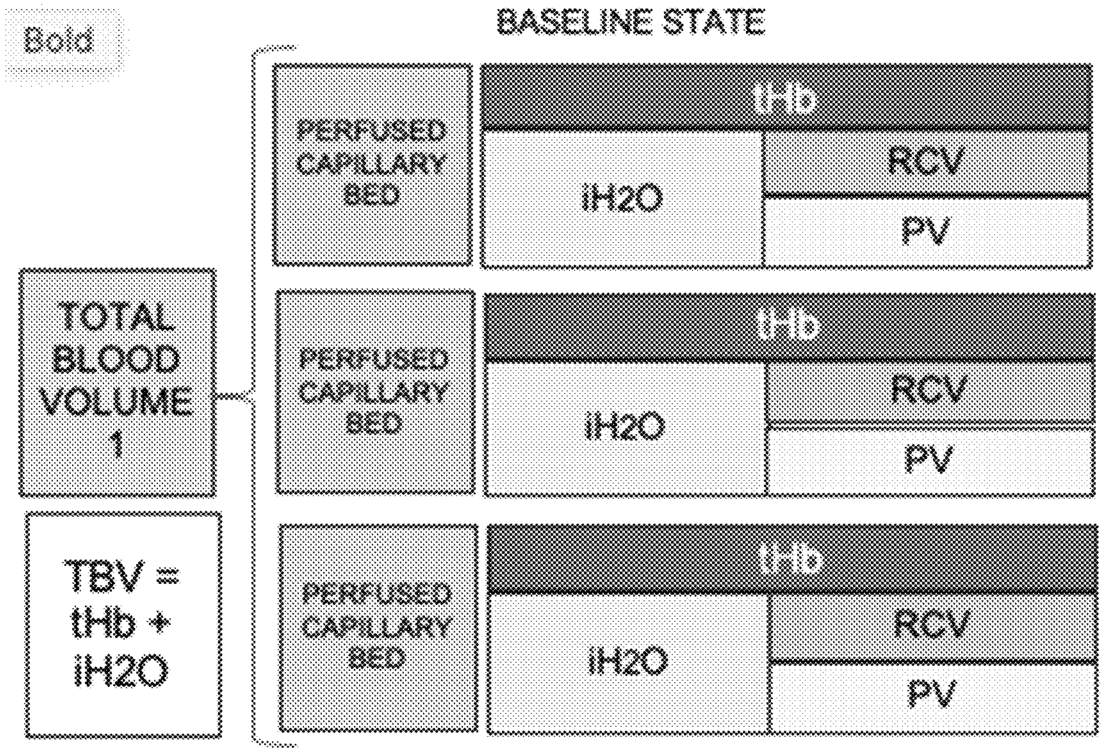
FIGS. 30A-30F illustrates proportional changes in TBV, intravascular water (iH2O) and total hemoglobin tHB) in the scan area under the sensors system in accordance with an embodiment of the present disclosure.
Figure 30B:
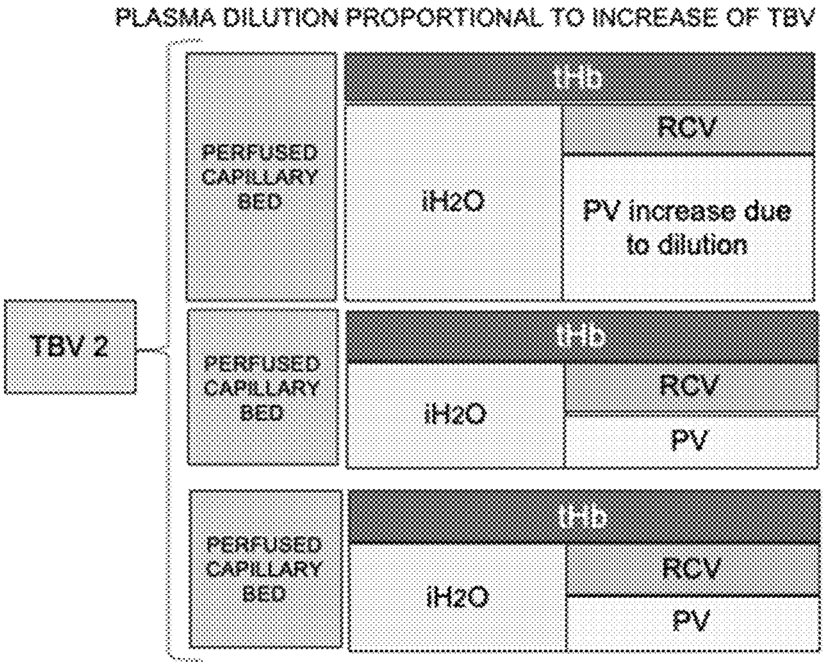
Figure 30C:
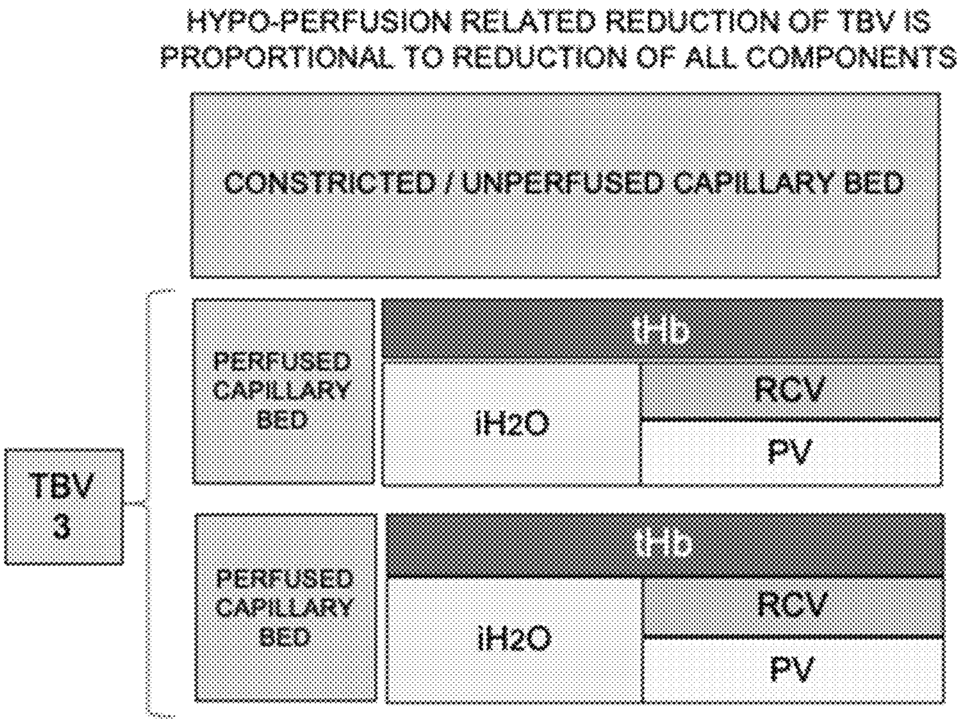
Figure 30D:
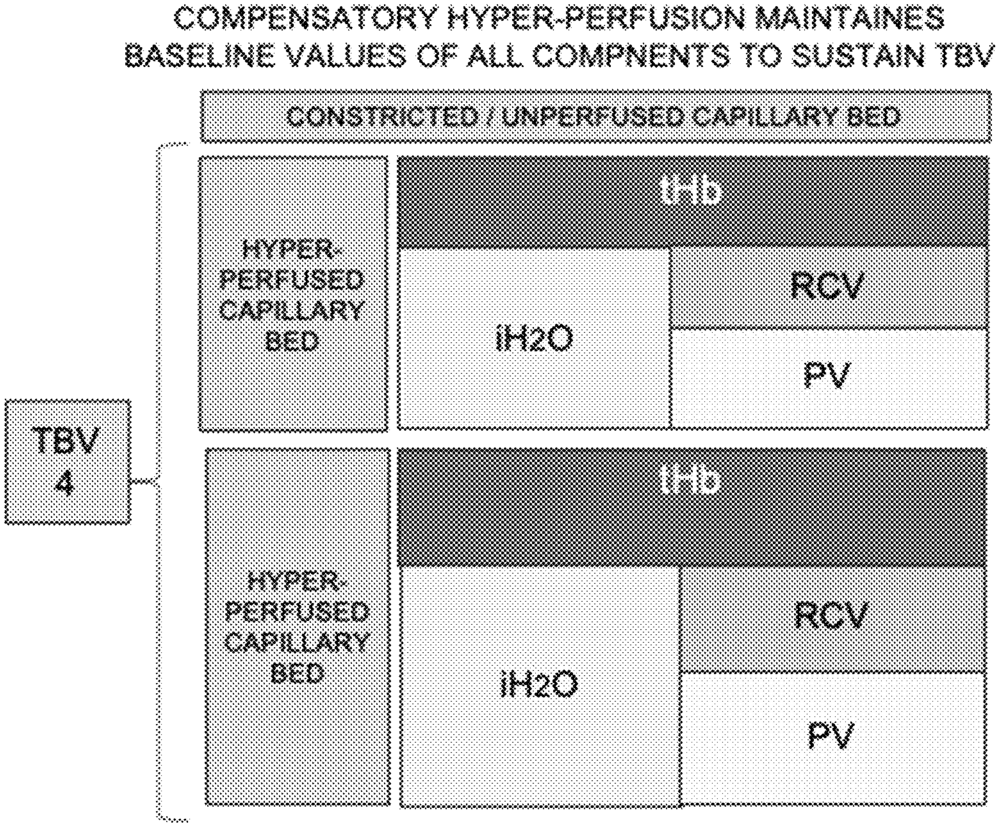
Figure 30E:
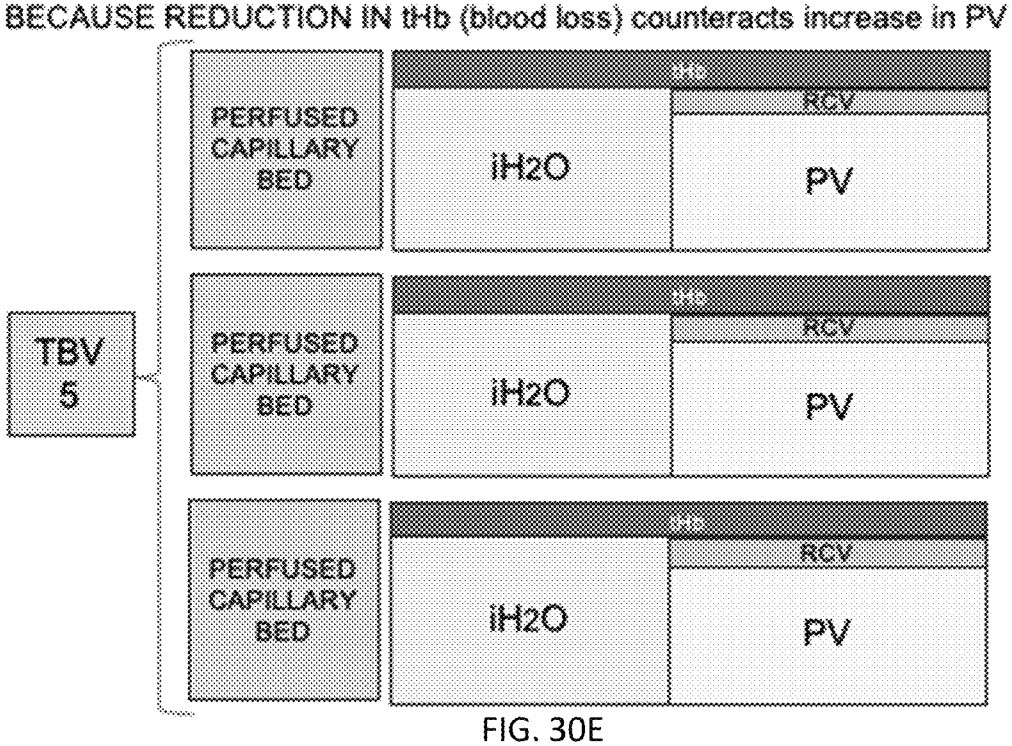
Figure 30F:
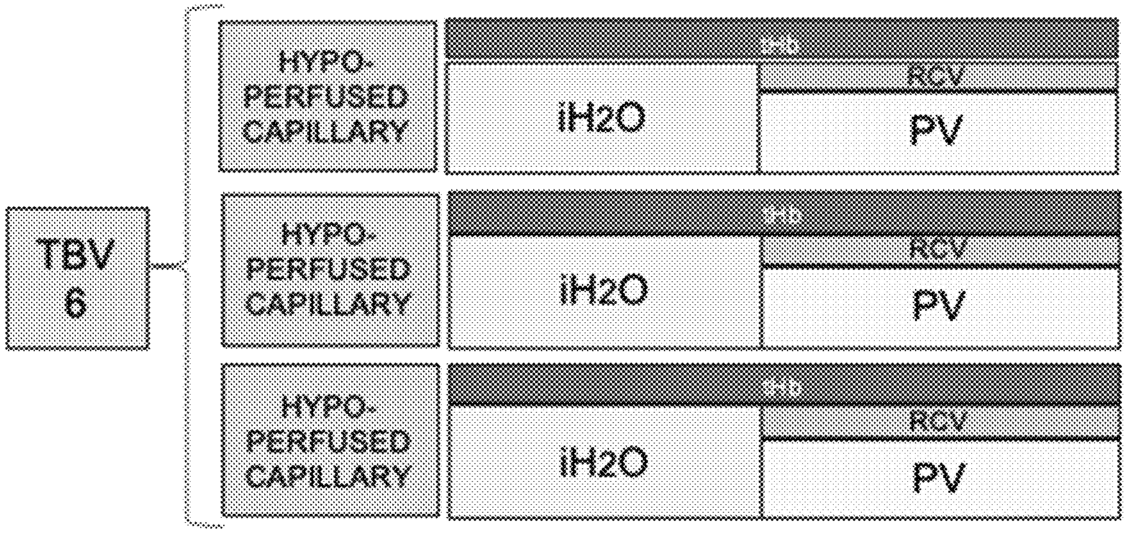
Figure 31:
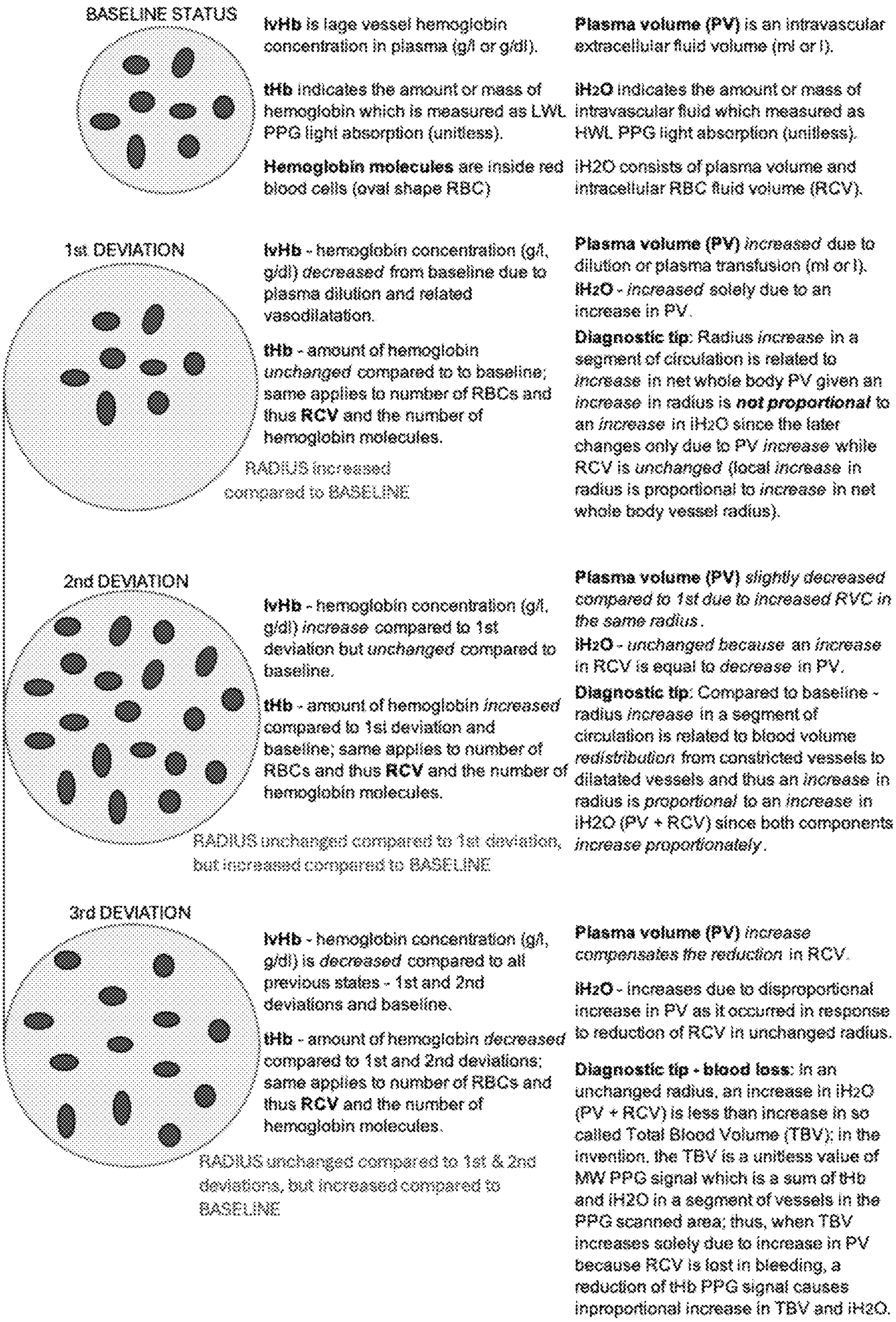
FIG. 31 illustrates exemplary assessment of MW PPG information in a large vessel in accordance with an embodiment of the present disclosure.
Figure 32A:
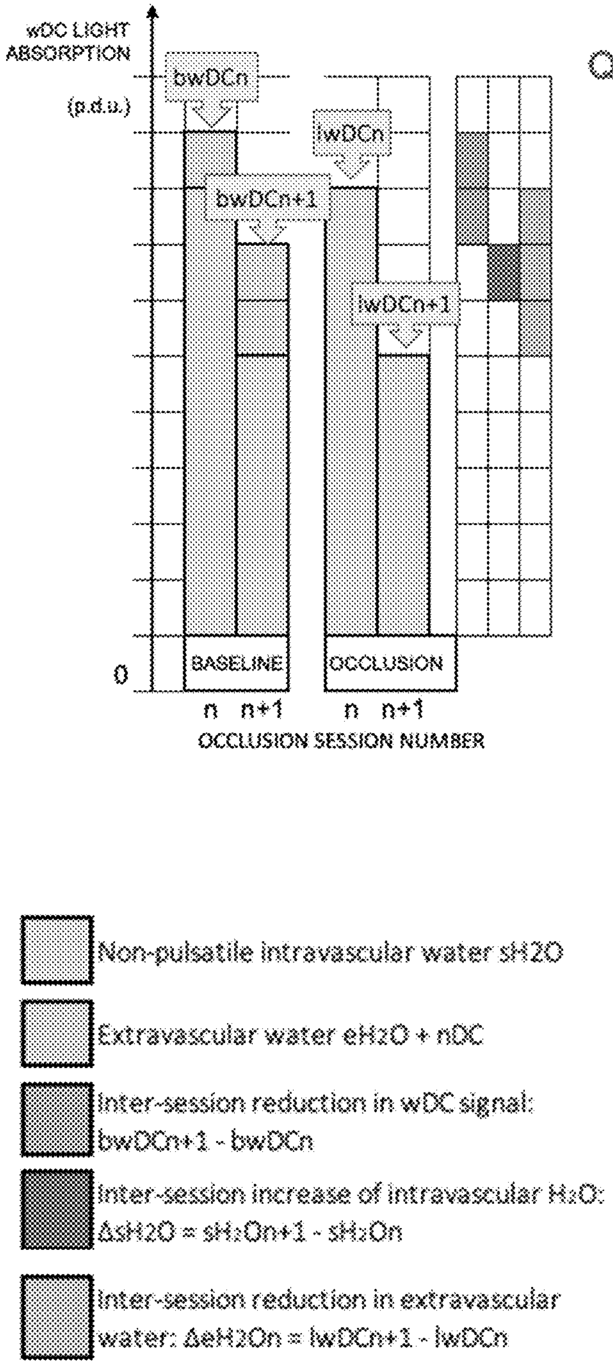
FIG. 32A illustrates phases of cuff inflation to a point of full occlusion and specifically shows HWL DC components measured in two sessions-n and n+1, at baseline (bwDC) and at full occlusion of circulation (lwDC) in accordance with an embodiment of the present disclosure.
Figure 32B:
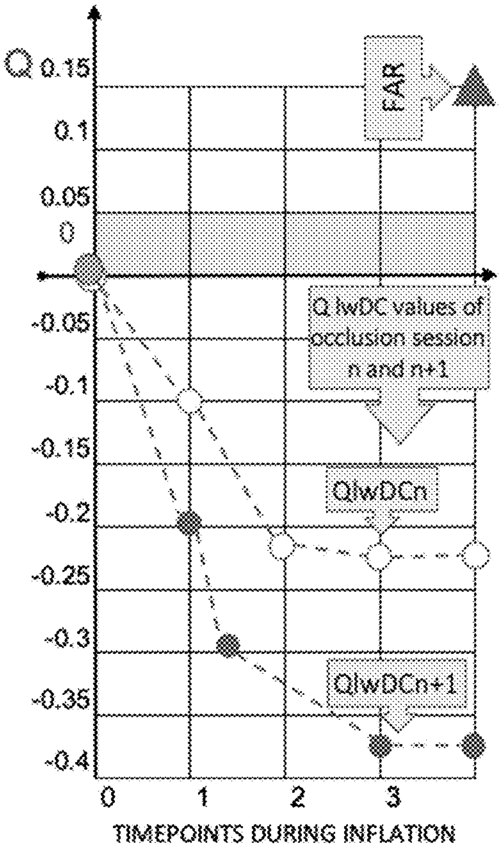
FIG. 32B illustrates a difference (Δ) between fractional changes of lwDC in respect to each session's baseline is an indication of net transcapillary fluid filtration-absorption ratio in accordance with an embodiment of the present disclosure.
Figure 33A:
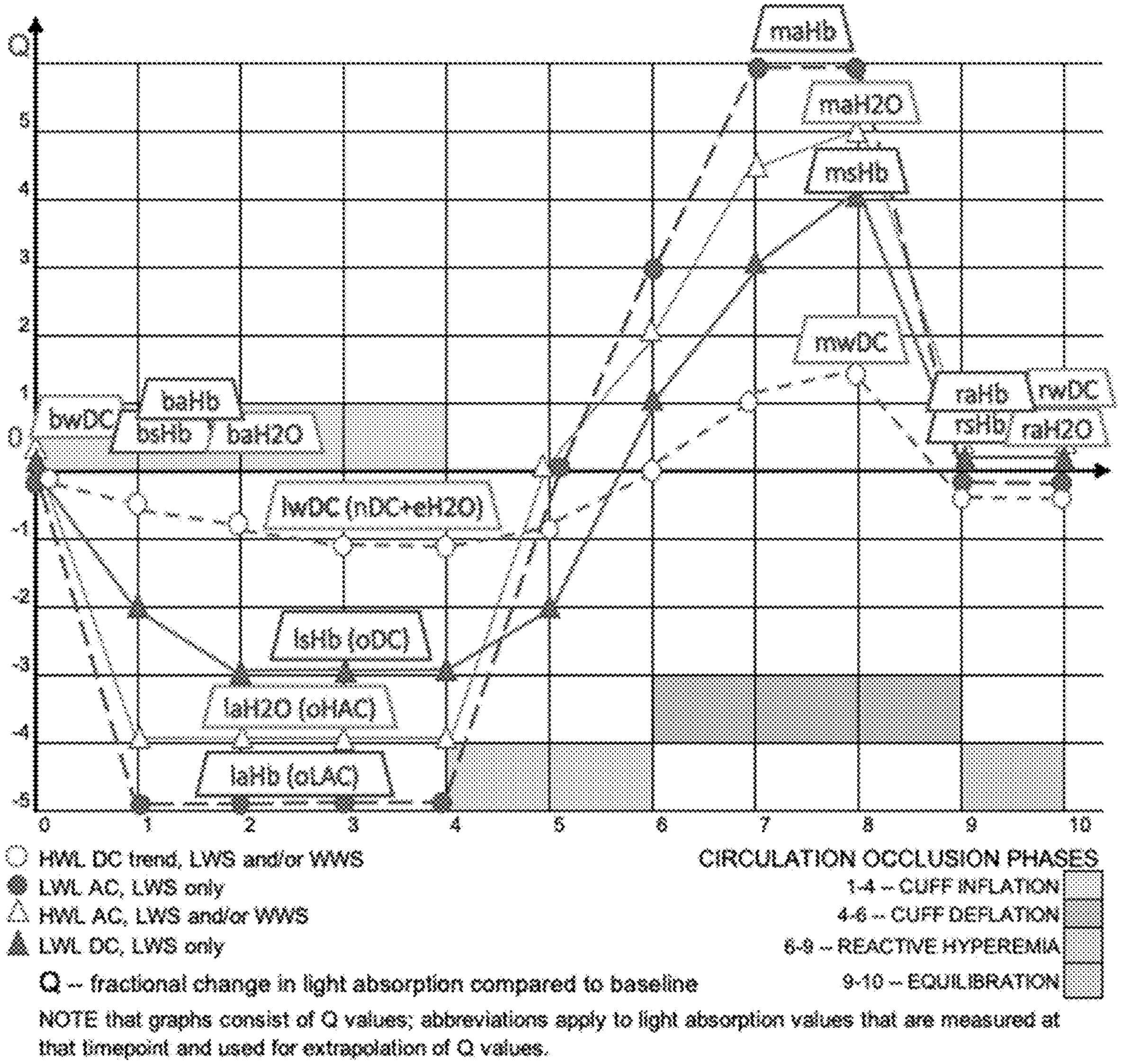
FIG. 33A illustrates four trends in a single occlusion session consisting of fractional changes in light absorption by PPG AC components (aHb and $aH_2O$), and DC components in accordance with an embodiment of the present disclosure.
Figure 33B:
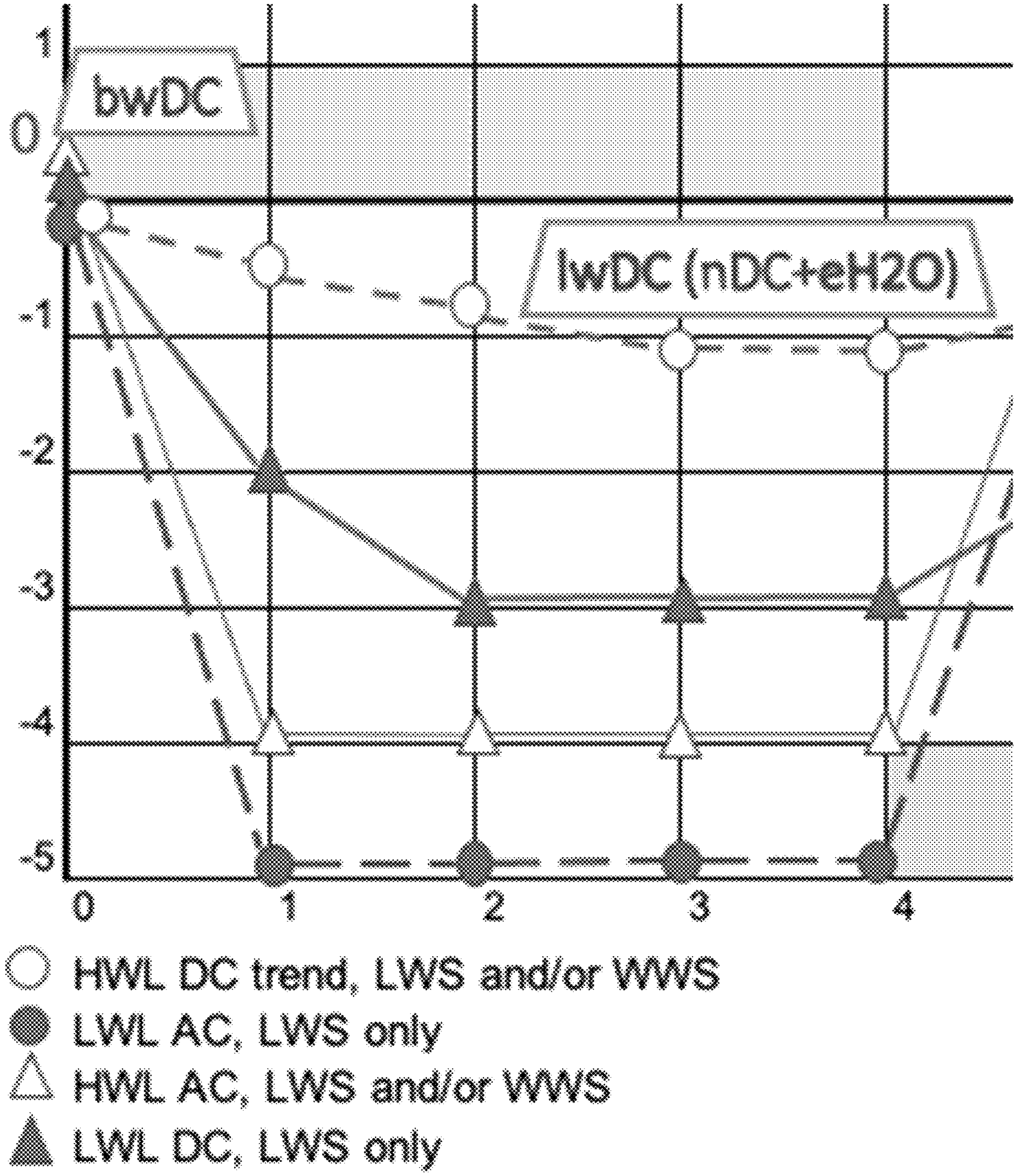
FIGS. 33B-33E shows more detailed views of the graph of FIG. 33A between points 0 and 4 in accordance with an embodiment of the present disclosure.
Figure 33C:
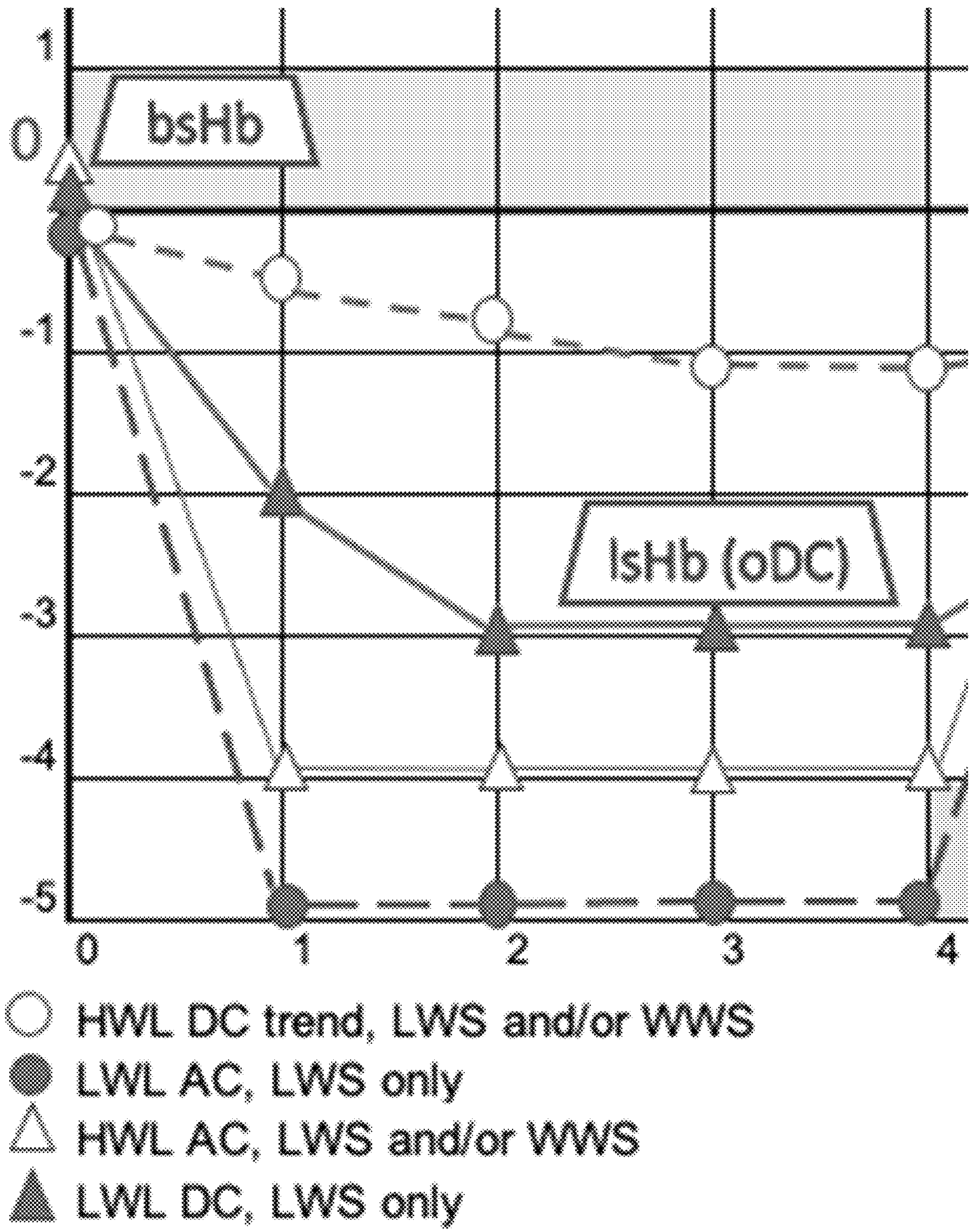
Figure 33D:
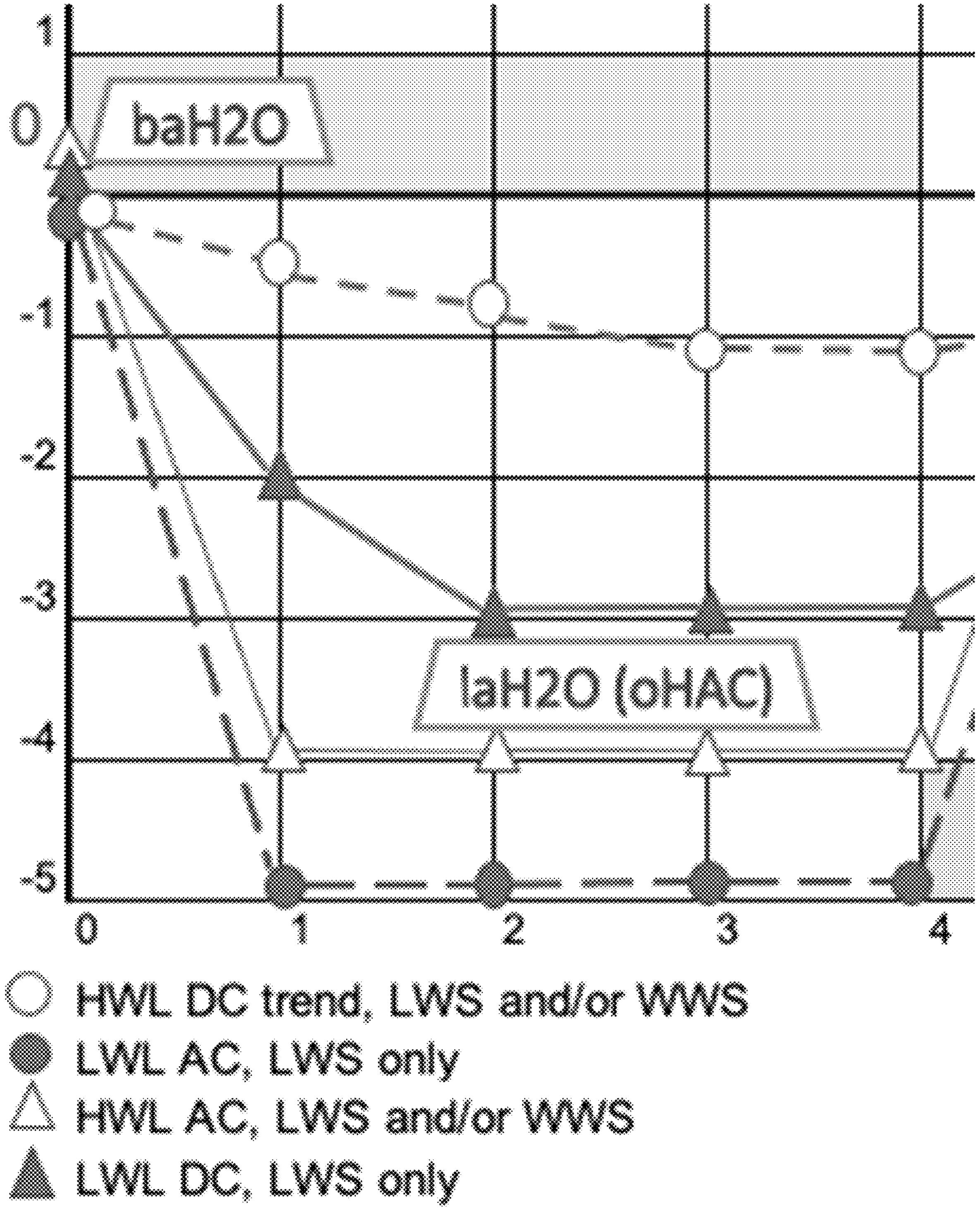
Figure 33E:
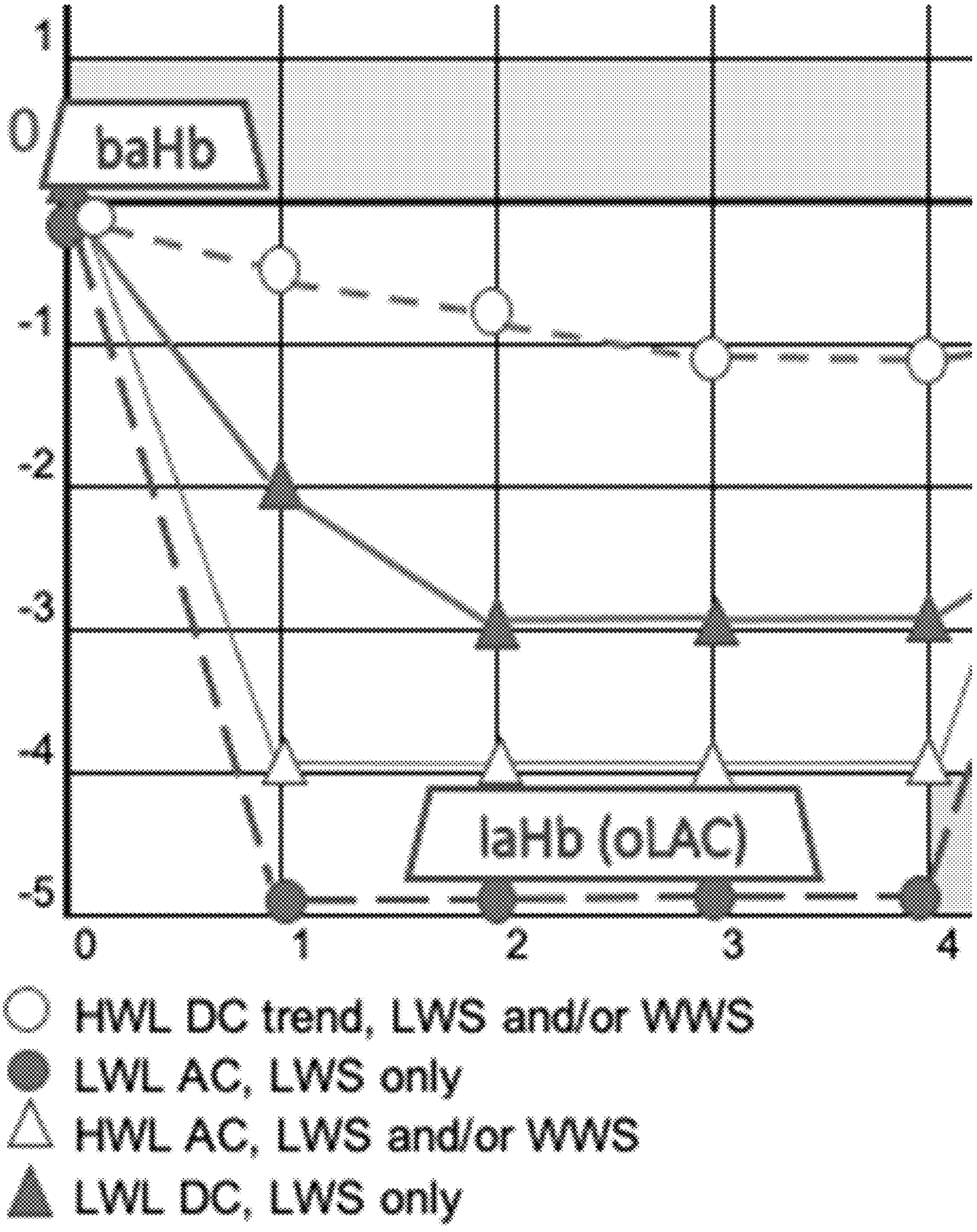
Figure 34:
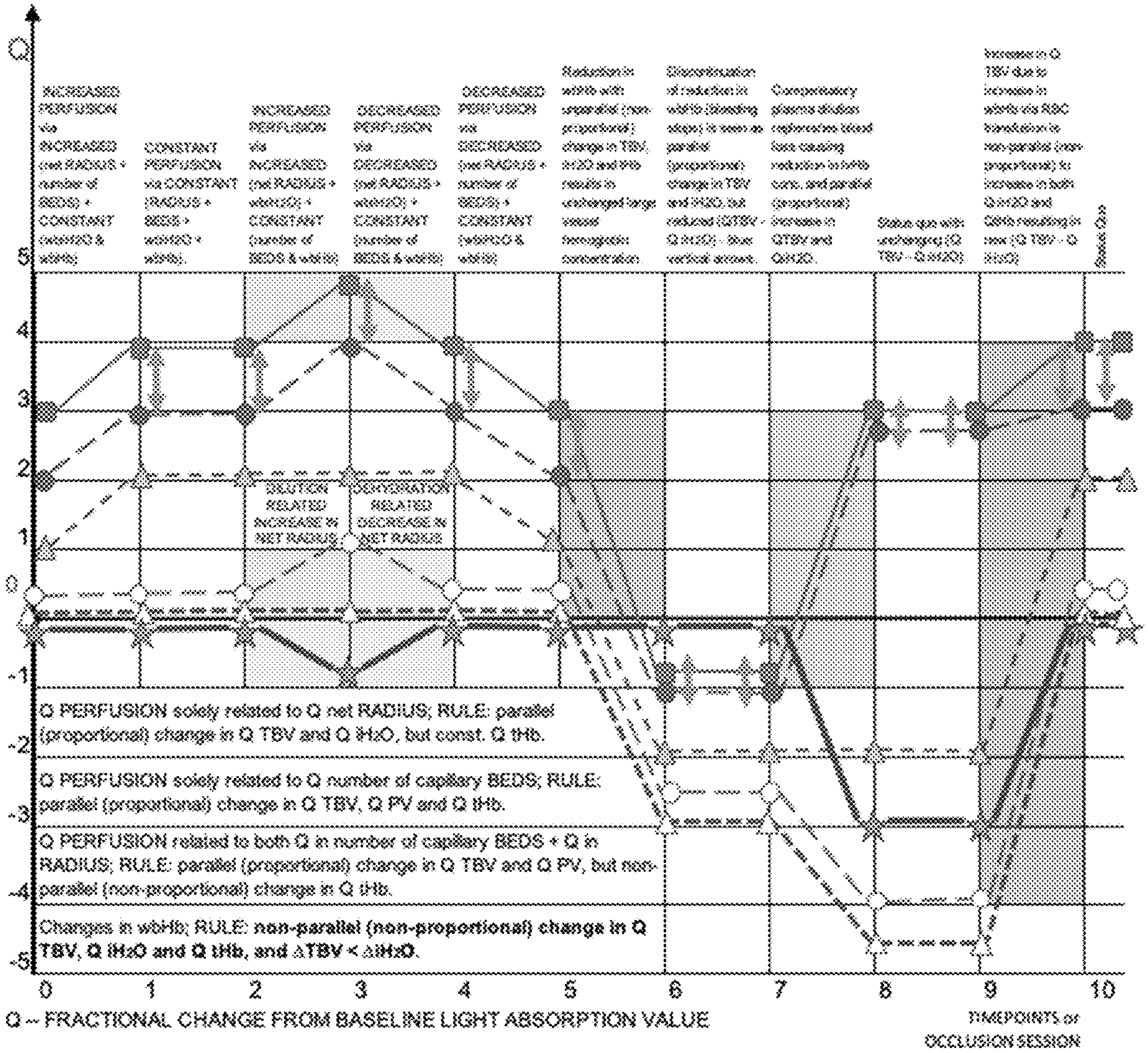
FIG. 34 illustrates diagnostic criteria for plasma dilution and changes in whole body hemoglobin mass where time points indicate PPG measurements in a continuous non-occlusion session or numbers of occlusion sessions in accordance with an embodiment of the present disclosure.
Figure 35:
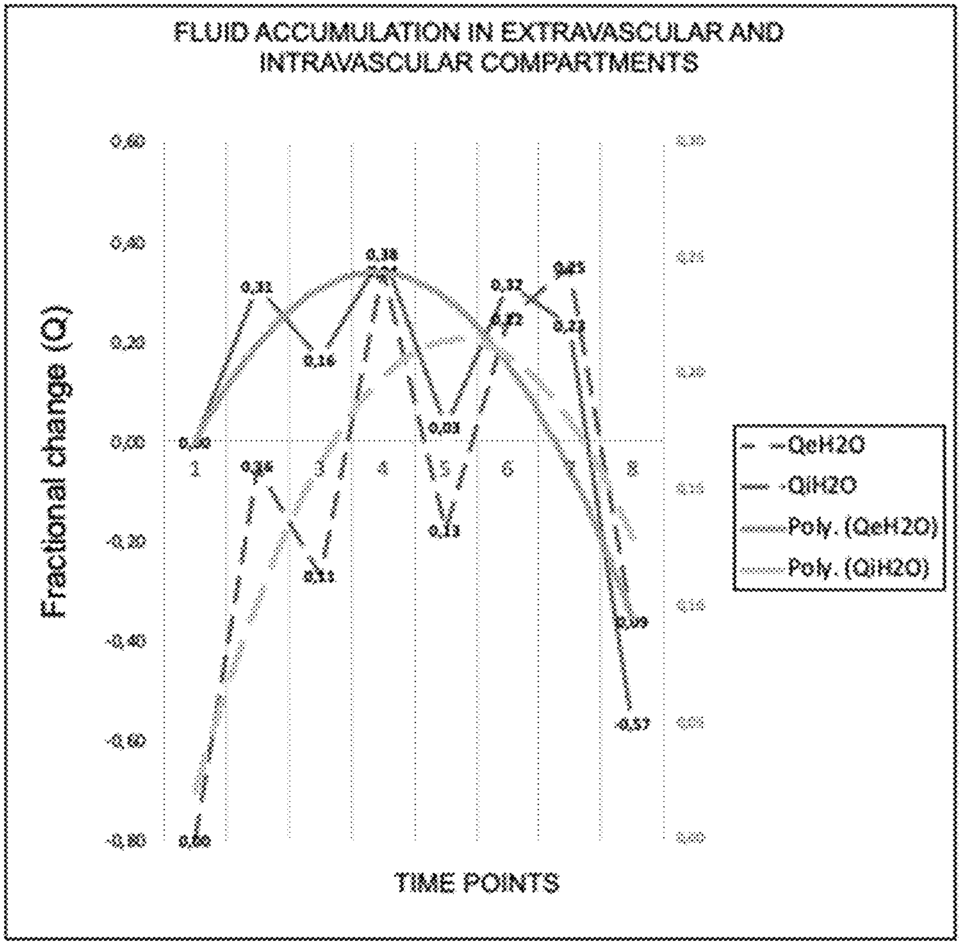
FIGS. 35-36 illustrate trends based on the most relevant variables displayed on the main screen of the invented monitor in accordance with an embodiment of the present disclosure.
Figure 36:
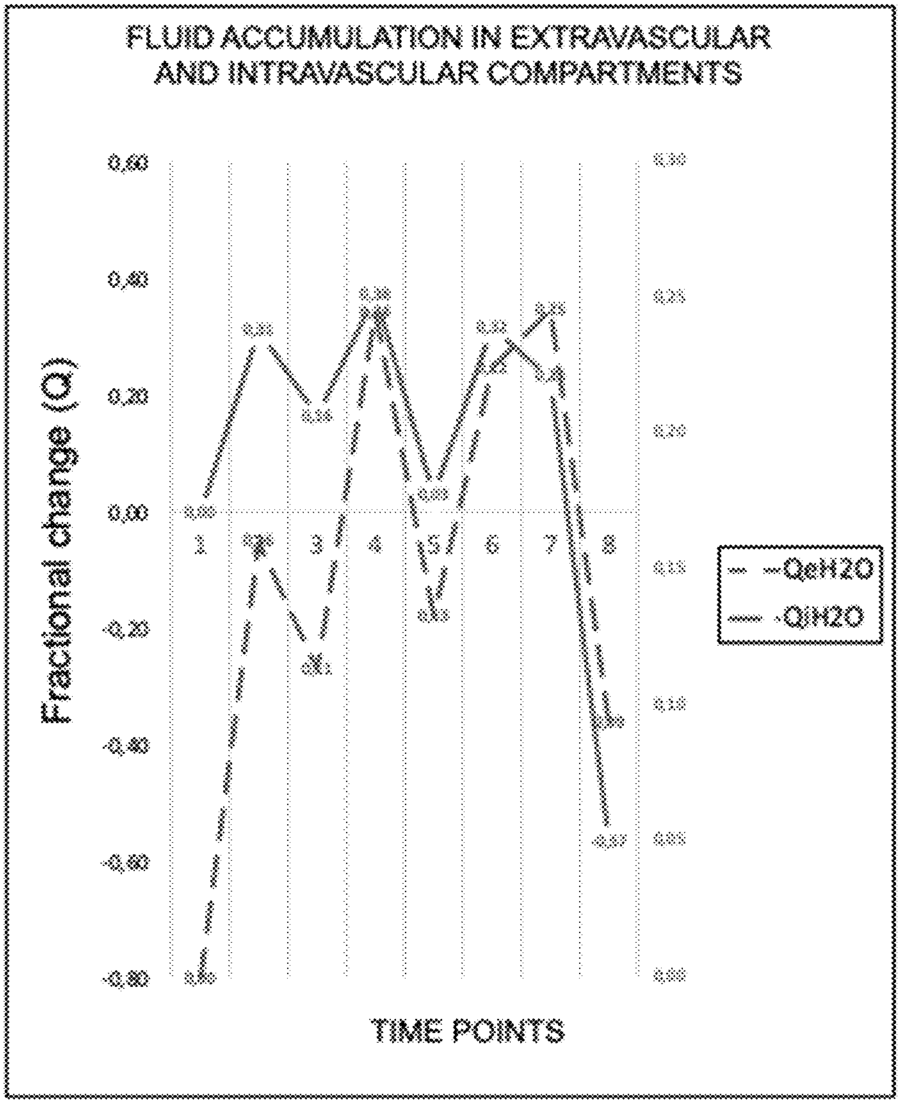
Figure 37A:
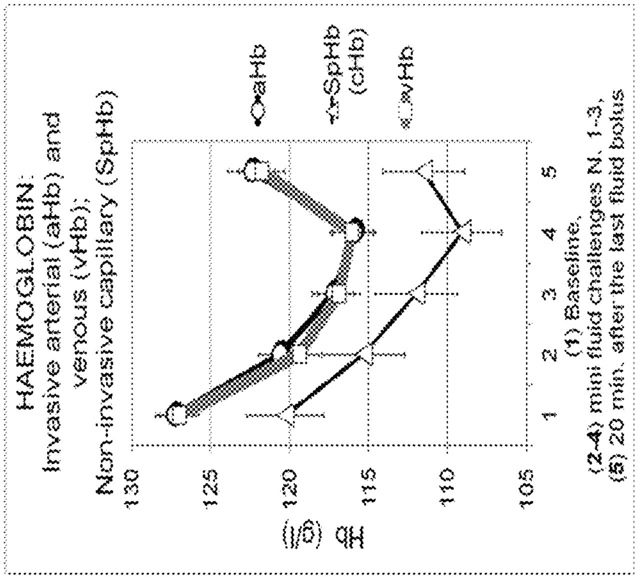
FIG. 37A illustrates arterial, venous and capillary hemoglobin concentration in accordance with an embodiment of the present disclosure.
Figure 37B:
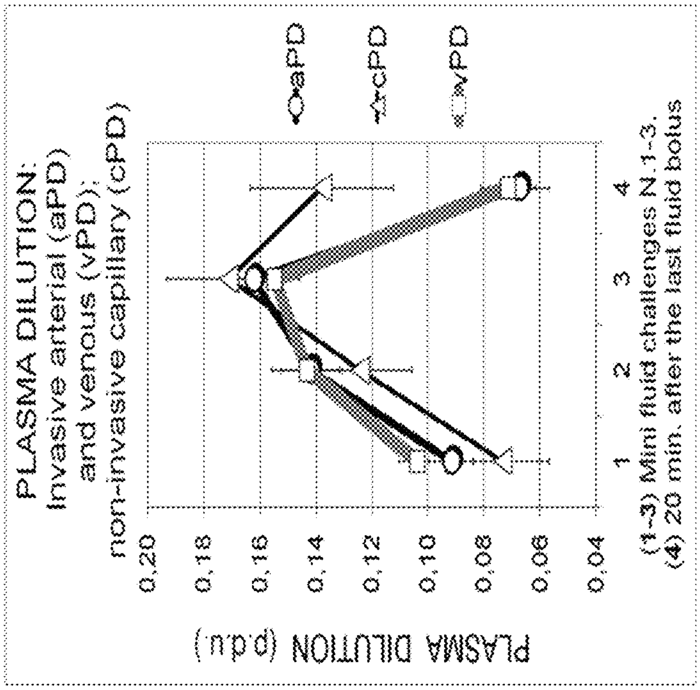
FIG. 37B illustrates arterial, venous and capillary plasma dilution trends in accordance with an embodiment of the present disclosure.
Figure 37C:
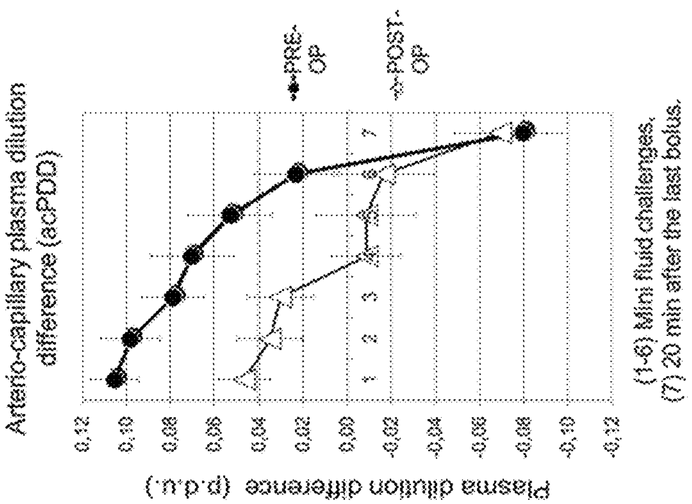
FIG. 37C illustrates arterio-capillary plasma dilution difference in accordance with an embodiment of the present disclosure.
Figure 38:
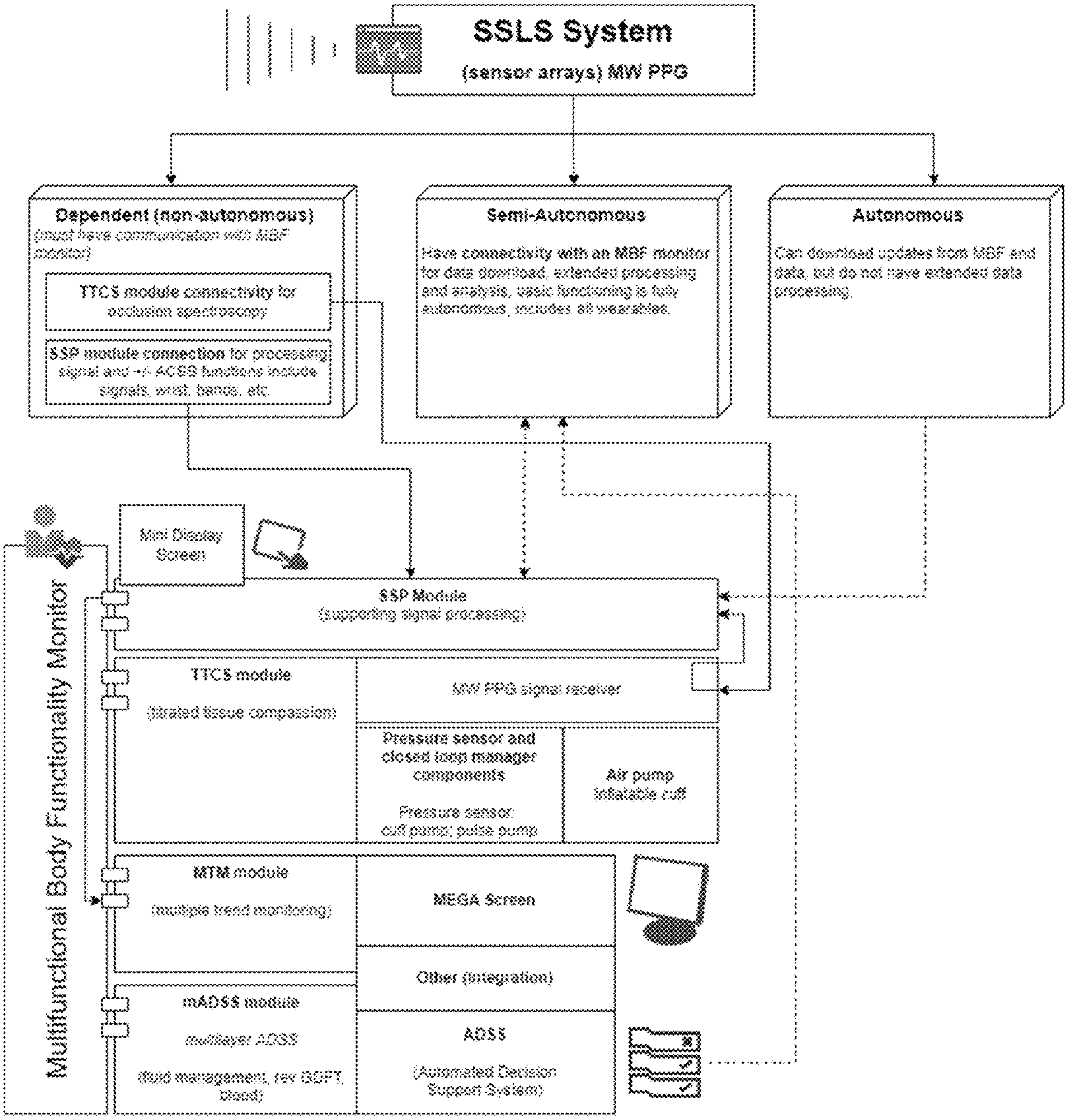
FIG. 38 illustrates an exemplary body function monitoring system in accordance with an embodiment of the present disclosure.
Figure 39A:
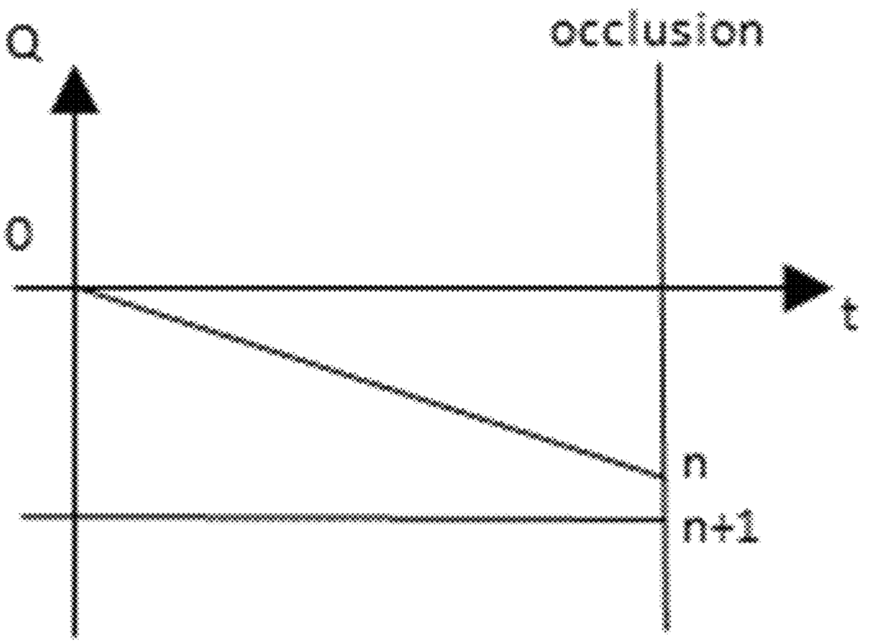
FIGS. 39A-39E illustrate case examples of how iH2O (intravascular) and eH2O (extravascular) measurement may be used to support decisions.
Figure 39B:
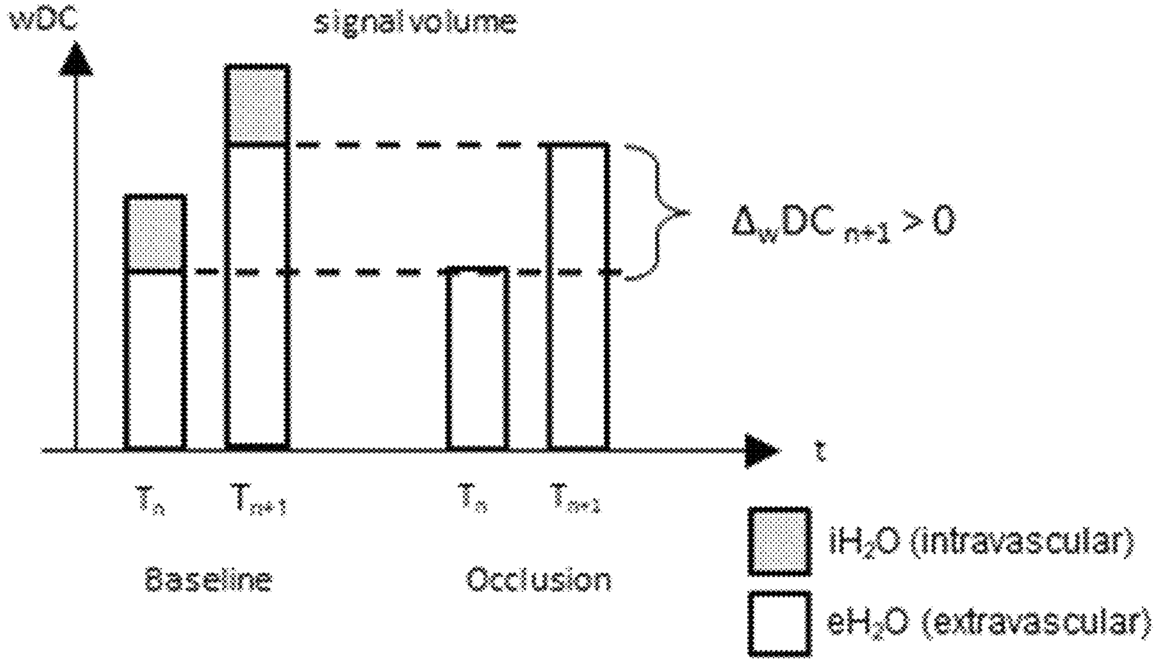
Figure 39C:
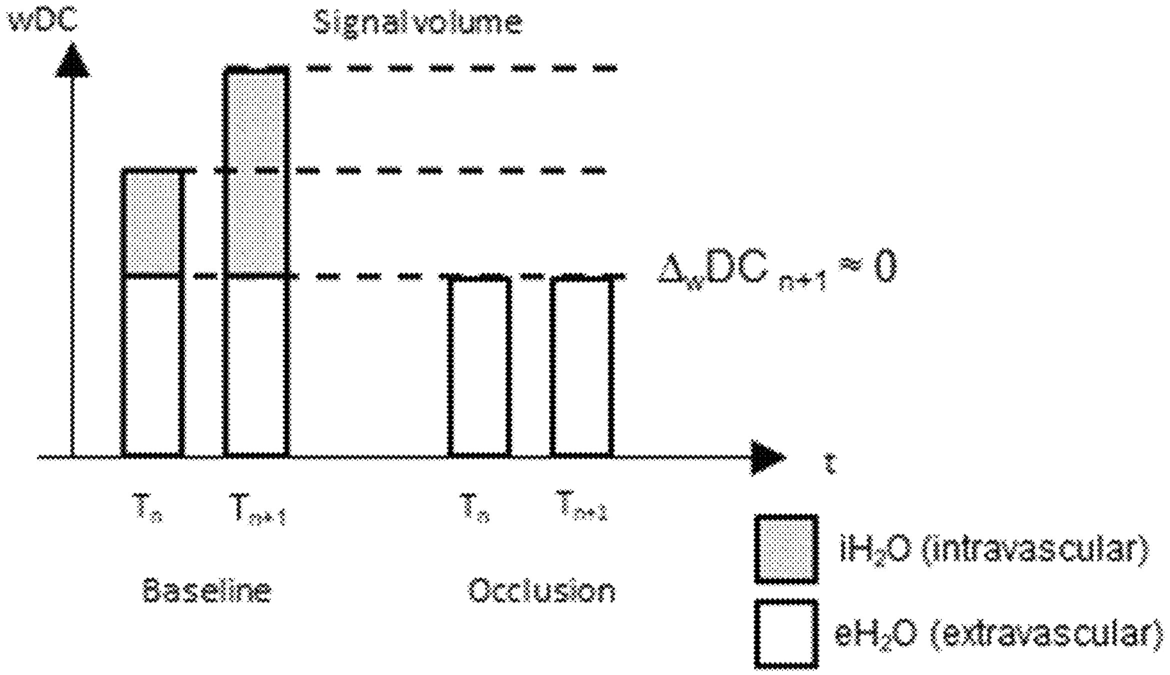
Figure 39D:
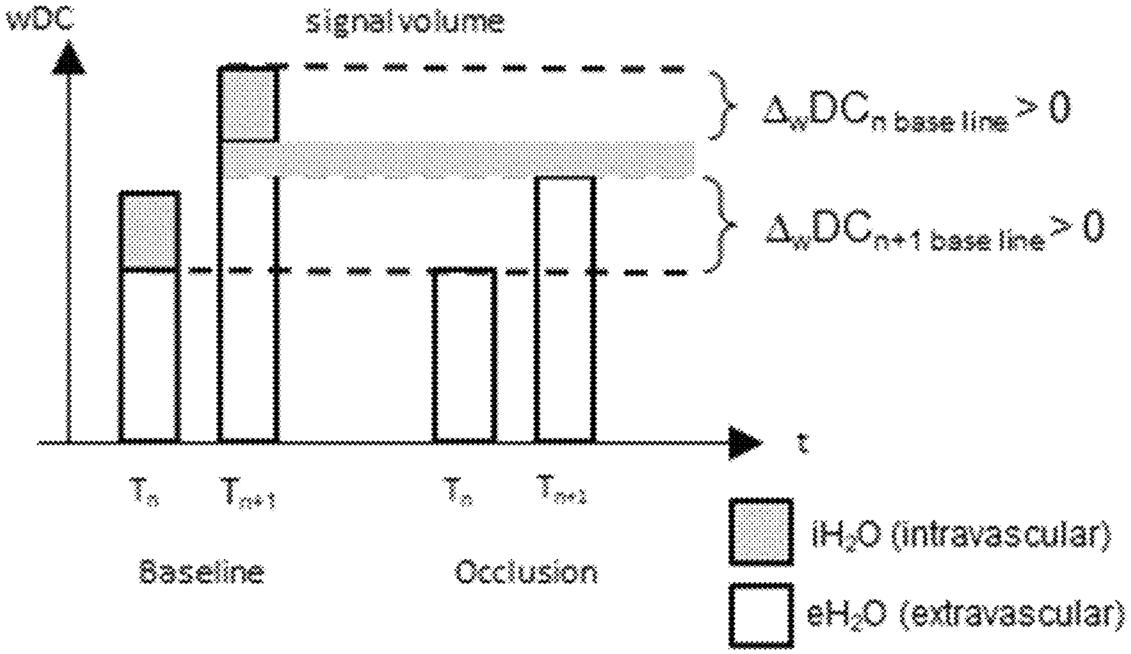
Figure 39E:
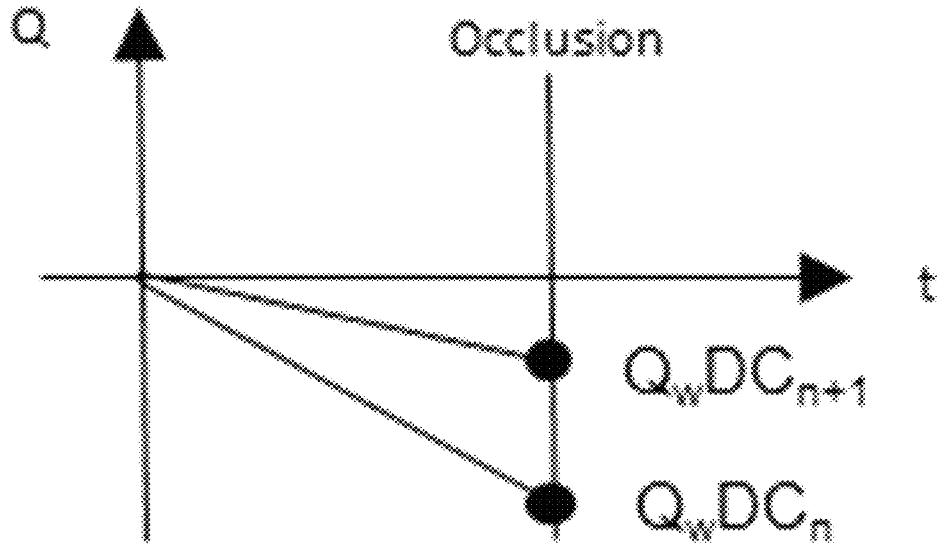
Figure 40A:
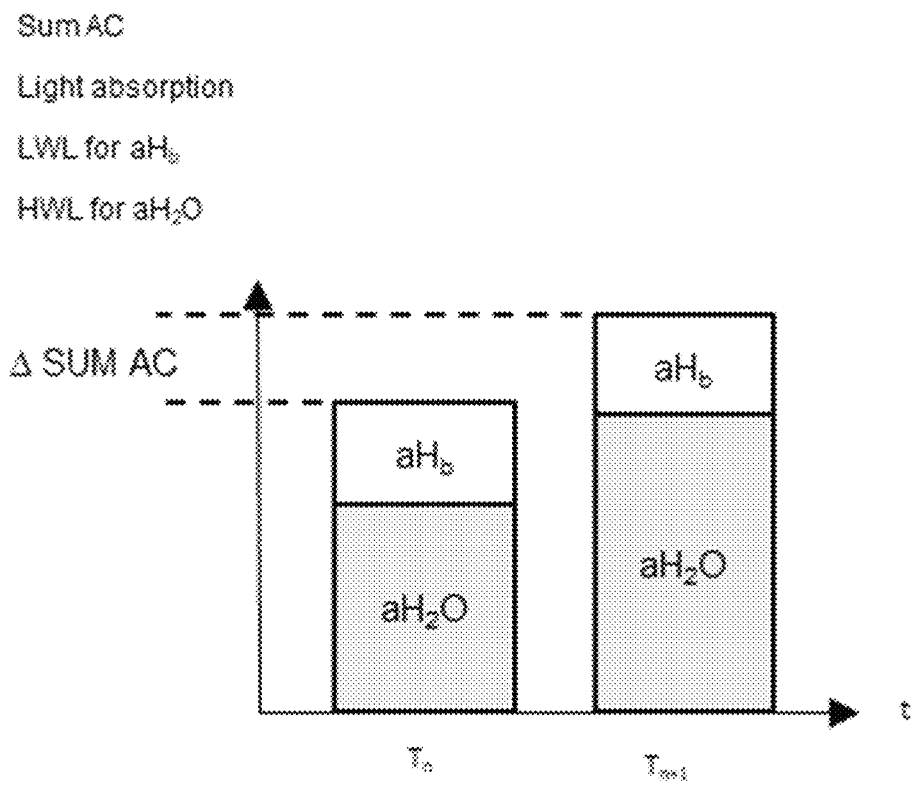
FIGS. 40A-40B illustrate case examples of detection of blood loss in accordance with an embodiment of the present disclosure.
Figure 40B:
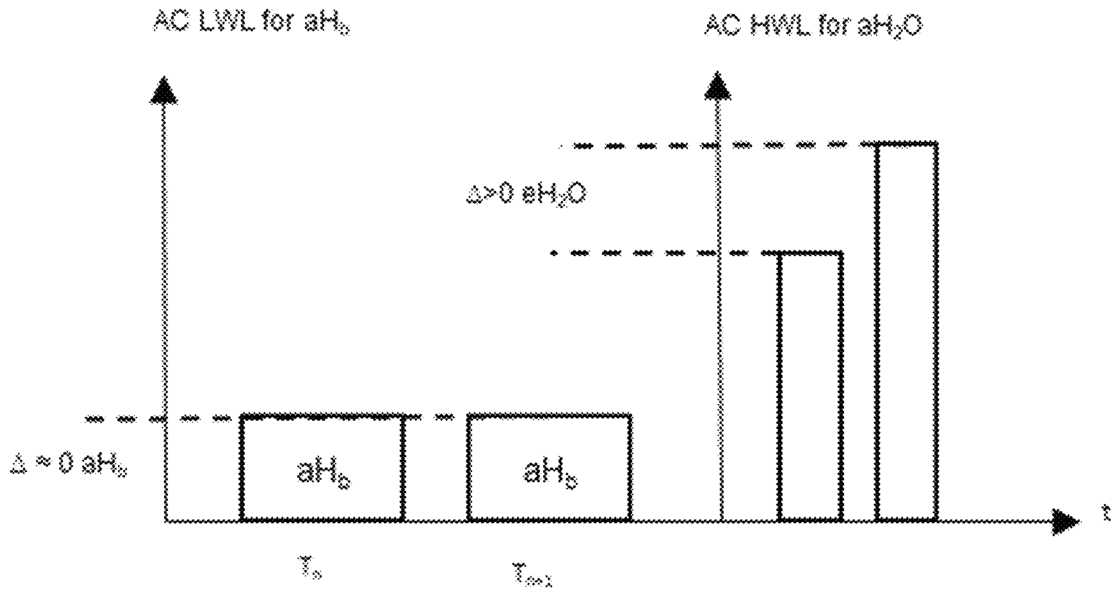
Figure 42A:
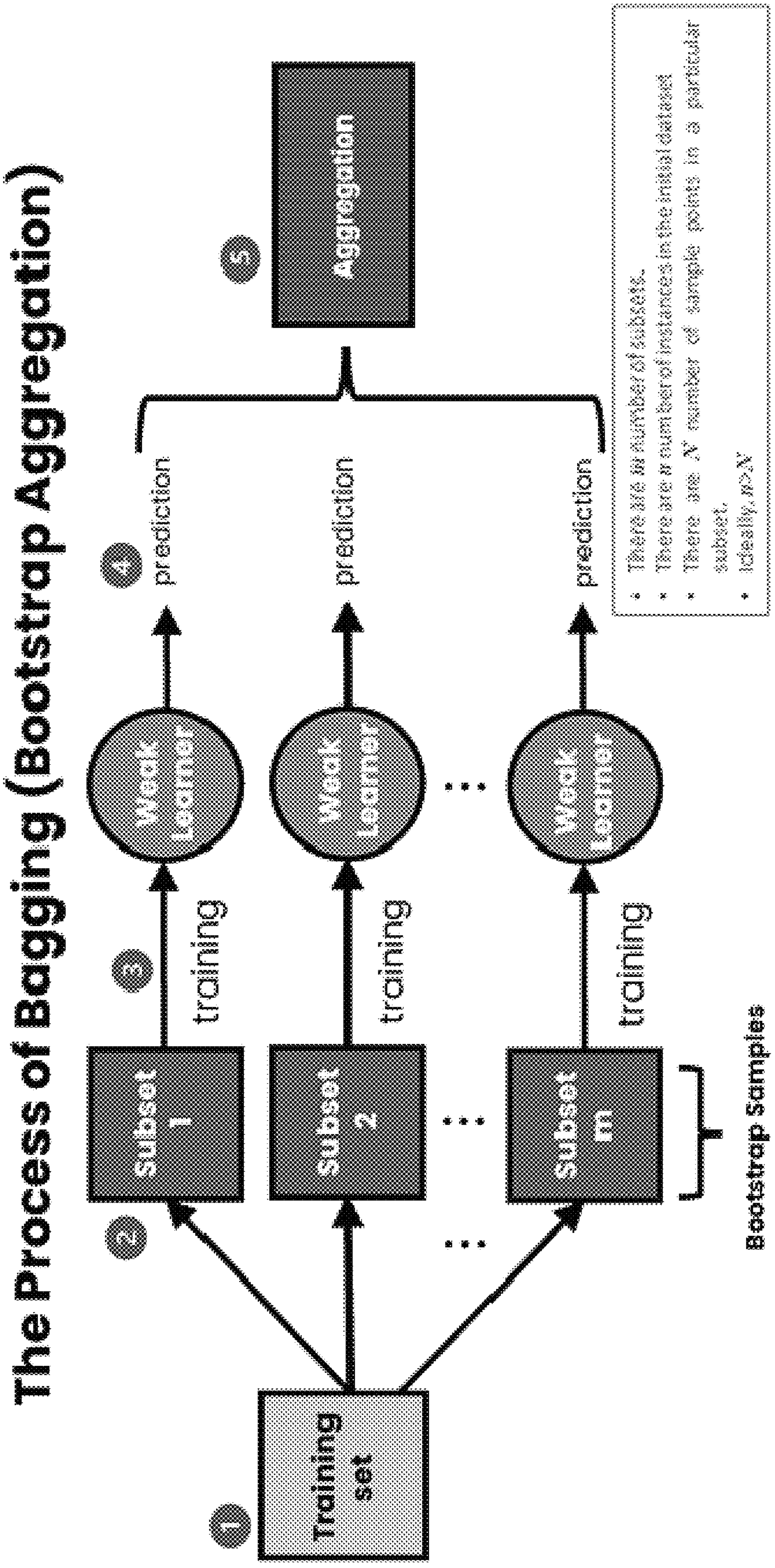
FIGS. 42A-42C illustrate conventional ensemble techniques.
Figure 42B:
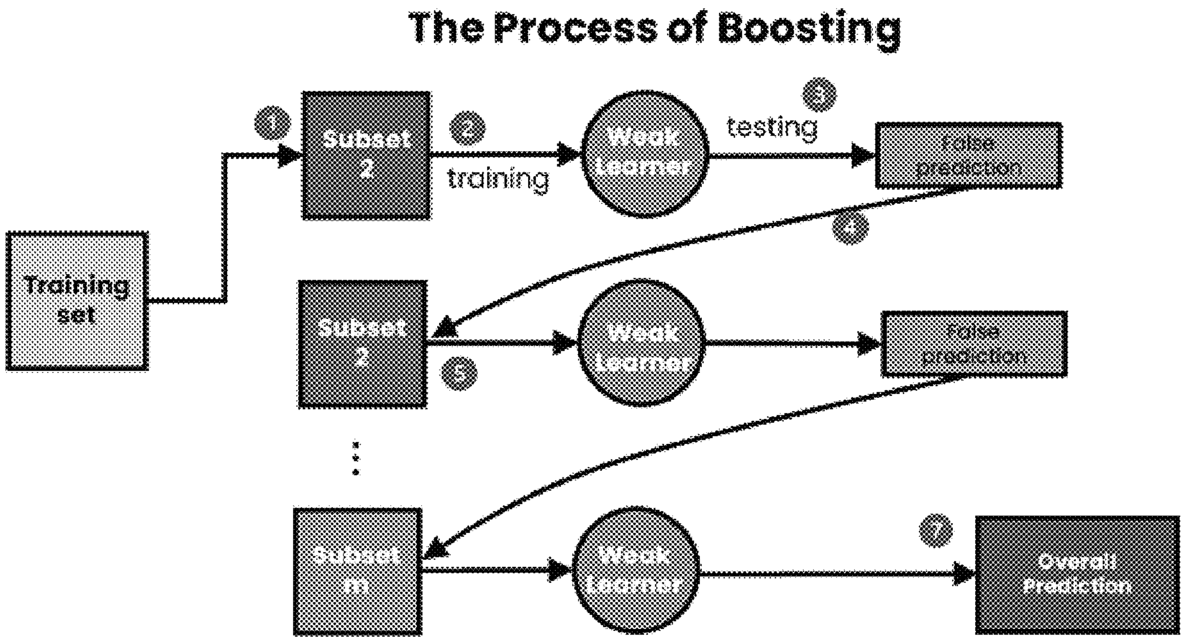
Figure 42C:
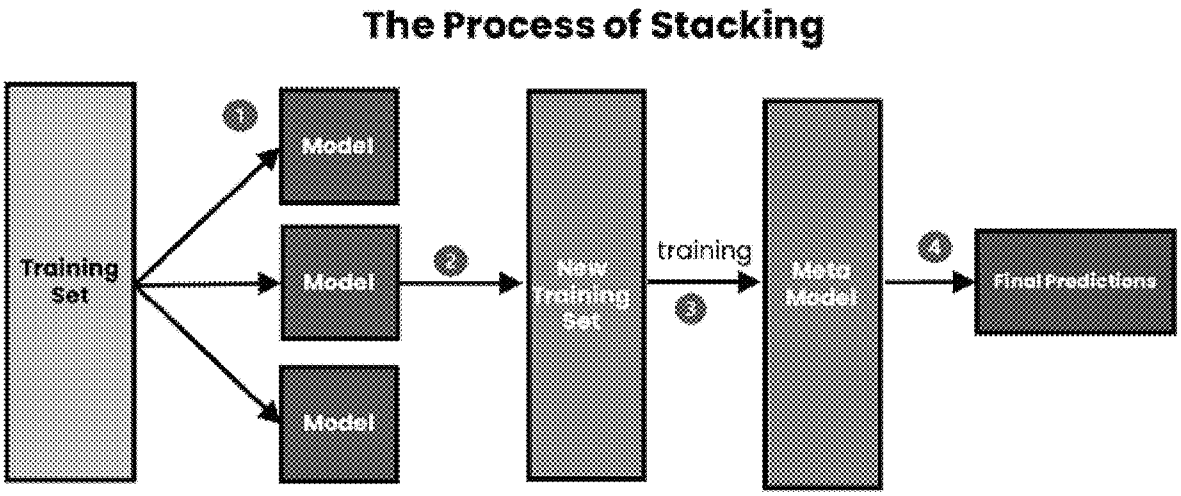

FIG. 18A is another illustration of the anatomy of a hand indicating preferred sites for the placement of a cuff and sensors 102 indicated by the numbered arrows. All these sites are composed of non-compressible tissues such as the synovial sheet indicated by arrows 2 and 3, bone, nerve, tendinea, ligament. Intermediately compressible tissues include skin and other soft tissues, as well as easy compressible structures such as capillaries and veins being the easiest to compress, and arteries being relatively more-hard to compress. Importantly, the invention acknowledges that non-expandable $H_2O$ compartments such as ligaments also absorb HWL light, but this component of $eH_2O$ is constant and thus does not affect assessment of changes in $cH_2O$.

HWL emitting LEDs or LWL emitting LEDs are used.

A DeepNarrow hardware may be used with a TSA or multiple TSAs.

In embodiments, as example of a Scan, the HWL emitting LEDs may be used in the low with scan mode. In a DeepWide Scan the HWL emitting LEDs may be used in the high width scan mode.

Figure 9:
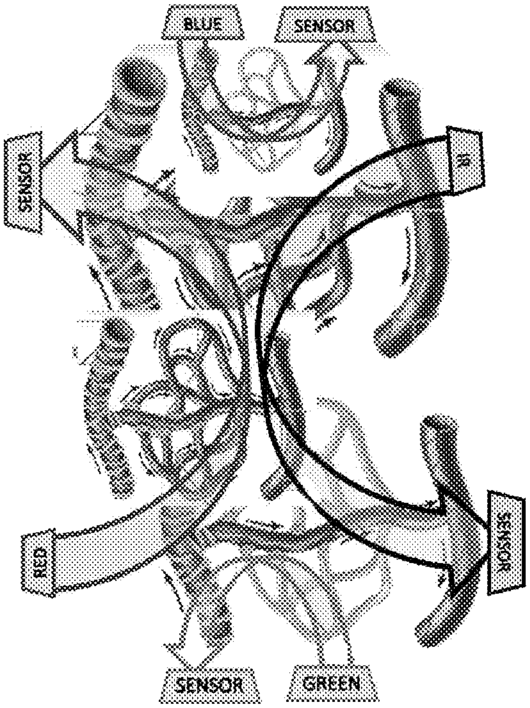
FIGS. 9A and 9C illustrate a swapping-layer sensor system including multiple sensors with different distances between the LWL and HWL LEDs and the corresponding detector where a shallow narrow scan may be provided using short wavelength light *blue and green) and a deep wide scan may be provided using longer wavelengths (IR and red) in accordance with an embodiment of the present disclosure.
FIGS. 9B and 9D illustrate a schematic representation of LED and the detector in a Triplet Array System in accordance with an embodiment of the present disclosure.
Figure 9:
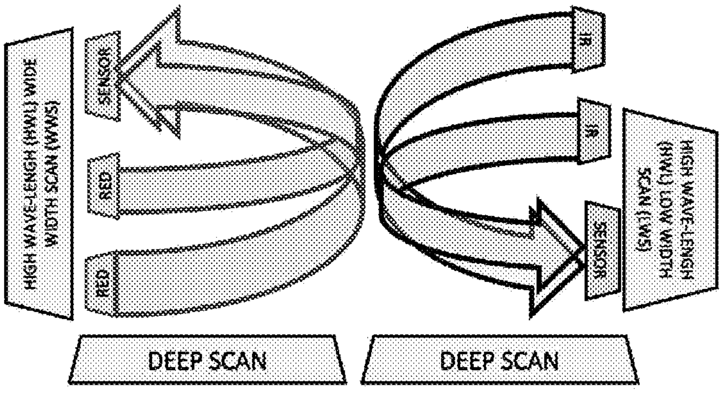
Figure 9:
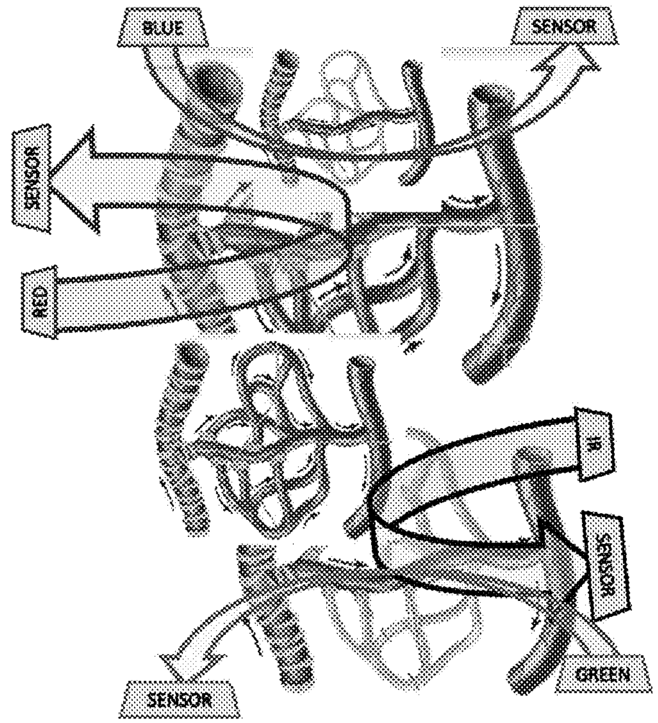
Figure 9:
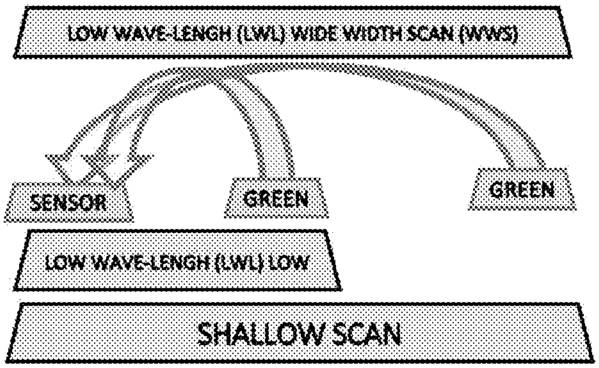

FIG. 9A illustrates a system 100 including multiple sensors 102-1, 102-2, 102-3 and 102-4 that are positioned around an area to scan each including LED's 102L having a desired wavelength and corresponding sensors (detectors) 102D. In FIG. 9B a pair of deep wide scan sensors 102-2 and 102-4 are illustrated which use LEDs 102L that have relatively long wavelengths, such as infrared (IR) and red LEDs and position the sensor (detector) 102 a relatively ling distance from the LEDs. In embodiment, the detector 102D may be embodied using a photoresistor, however aby suitable detector may be used. In FIG. 9C, the sensors are positioned to align with different layers of vessels. FIG. 9D illustrates a pair of sensors 102-1 and 102-3 that provide a shallow narrow scan using LEDs, blue and green LEDs, for example, with a relatively small wavelength and detectors 102D positioned relatively close to the LEDs. FIGS. 9A to 9D show sensor 102-1, 102-2, 102-3 and 102-4 as a flat surface array of sensors (FSAS).

The LWL of the light projected by the LED and the relatively long distance from LED to detector scans relatively wide and deep tissues. The invention deploys measuring light absorption by $H_2O$ using relatively long waves, and both short and long distances between LEDs and detectors. Relatively short waves are used in the invented sensor systems 100 with shorter waves and distances between the LED and detector for measuring light absorption by Hb. All types of sensor systems are installed in sensor arrays with an aim to optimize the signal quality and obtain optimal sensitivity to $H_2O$ and Hb.

In embodiments, the closure and opening of capillary sphincters may change light absorption in the capillary bed and challenge clinical interpretation of PPG measurements provided by sensor 102. The system 100 addressed these drawbacks by using sensor arrays with different characteristics and innovative interpretation.

The following is a more detailed discussion of models generally discussed above. The following definitions are used with respect to this additional discussion:

(1) Acceptable-physiologically acceptable value which is not life-threatening; the range of acceptable values consists of safe and unsafe ranges.

(2) Unsafe-physiologically acceptable value which is poorly tolerated by the body.

(3) Safe-physiologically acceptable value (normal) which is well tolerated by the body.

In embodiments, according to the revised Homeostatic Blood State (revHBS) method of the present disclosure, the PD and PV have maximal acceptable values ($PD_{max}$ and $PV_{max}$) at minimal acceptable hematocrit ($Hct_{min}$) about 15%, PD and PV have minimal acceptable values ($PD_{min}$ and $PV_{min}$) at maximal acceptable hematocrit $Hct_{max}$ about 60%.

In embodiments, wbBV has minimal acceptable value ($BV_{min}$) at minimal acceptable hematocrit $Hct_{min}$ about 15%, wbBV has maximal acceptable value ($BV_{max}$) at maximal acceptable hematocrit ($Hct_{max}$) about 60%.

In embodiments, PD fluctuations are maximal where ideal (normal) blood volume (IBV) and ideal (normal) plasma volume (IPV) are maintained at Hct in the middle of acceptable Hct range—about 40%-referred to as hematocrit of Perfect Match ($Hct_{PM}$). It was referred to as hematocrit of Ideal Total Match ($Hct_{ITM}$) by Homeostatic Blood States (HBS) method, which is reached and detected based on the Volume Loading Test (VLT).

In embodiments, the case and UI simulations include HBS Nomogram based on empiric estimates.

In embodiments, the $Hct_{min}$ is 13.3%, the $Hct_{PM}$ is 40%, the $Hct_{max}$ is 60%.

In embodiments, these features apply to a specific (optimized) combination of whole body RCM, BV, PV and PD: oHct, oBV, oPV and oPD—the RCM specific optimized Hct, wbBV, PV and PD accordingly.

In embodiments, individual oHct specific maximal acceptable plasma dehydration is referred to as dehydrated plasma dilution (dPD), and the limit for maximal acceptable plasma over-hydration is referred to as excessive plasma dilution (ePD); the related hematocrits are referred to as dHct and eHct, accordingly.

In embodiments, the wbBV and wbPV which are associated with dPD are referred to as dehydrated blood volume (dBV) and dehydrated plasma volume (dPV), accordingly In embodiments, oPD is the maximal limit of normal (safe) PD range from dPD to oPD which is consistent with normal plasma hydration status; ideally, oPD is an indication of optimised extravascular fluid volume (oEFV) which is the highest limit of normal (safe) extravascular fluid volume, referred to as highest normal tissue hydration status.

In embodiments, the wbBV and wbPV which are associated with ePD are referred to as eBV and ePV In embodiments, dPD is an indication of depleted extravascular fluid volume (dEFV) which is the lowest safe extravascular volume, an indication of lowest normal tissue hydration status-life threatening dehydration.

In embodiments, ePD is an indication of excessive extravascular fluid volume (eEFV) which is the highest safe extravascular volume, an indication of highest normal tissue hydration status consistent with life threatening edema.

In embodiments, oEFV is the maximal limit of normal (safe) $eH_2O$ range which is consistent with normal tissue hydration status.

In embodiments, a safe range of wbBV, wbPV and wbPD is from dBV to oBV, and from dPV to oPV, and from dPD to oPD; limits of normal plasma hydration-"normo-hydrating PD fluctuation" range. Circadian rhythm related fluctuations occur within this range provided there are no health conditions that predispose to persistent fluid overload, e.g. heart failure, kidney injury.

In embodiments, unsafe ranges of wbBV, wbPV and wbPD is from oBV to eBV, and from oPV to ePV, and from oPD to ePD; limits of excessive plasma hydration-"over-hydrating PD fluctuation" range; circadian rhythm related fluctuations occur within this range due to health conditions that predispose to persistent fluid overload, e.g. heart failure, kidney injury.

In embodiments, the period of homeostatic counteraction to fluid entering circulation is referred to as equilibration period. Homeostatic counteraction implies fluid extravasation which is net effect of fluid elimination and shift into tissues (interstitium).

In embodiments, equilibrated hematocrit (EQ_Hct) is wbHct after equilibration which implies net effect of fluid distribution and elimination on wbPD.

In embodiments, equilibrated plasma dilution (EQ_PD) is wbPD after equilibration In embodiments, quantity of water is referred to as water amount (p.d.u.), and quantity of hemoglobin is referred to as hemoglobin mass (p.d.u.). These terms refer to the quantity of media which is saturated with photons from the passing light rather than quantity of media. Changes in light attenuation are used as approximation of changes in saturated quantity of media, which is context sensitive. The terms "water" and "hemoglobin" are used accordingly.

In embodiments, Depth of Scan (DOS) is a function of an attenuation coefficient which is a measure of the light loss from the combined effects of scattering and absorption over a unit length of travel in light attenuating medium on the path from LED to sensor in PPG.

In embodiments, estimated values of non-measurable variables are calculated using equations disclosed in the following sections. In embodiments, these equations are referred to as the Spectrophotometric Signal Processing (SSP) math model.

A corresponds to light attenuation and reflects the net effect of light absorption and scattering which is estimated as a difference between the energy of LED-emitted light (EL) and energy sensed by the light detector 102D or sensor; where A is a sum of AC and DC components in PPG measurements with specific wavelength:

$$(1)\quad A = EL - DL = \mathrm{AC} + \mathrm{DC} \qquad [1]$$

where EL is LED-emitted light, DL is LD-detected or sensor-sensed incoming light (energy), AC is PPG AC component (procedure defined unit, p.d.u) and DC is PPG DC component (p.d.u) at specific wavelength.

AC and DC components indicate attenuation A but not the reflected or transmitted light (energy) which is sensed by sensor 102*d*. A is not an indication of the quantity of media, but an indication of context-sensitive quantity of absorbent which is saturated with photons from a passing beam of light. V represents the quantity or amount of absorbent media and is not measurable or estimable.

While Hb and $H_2O$ contribute to attenuation, the technique deploys two wavelength (WL) spectra which are individually determined by calibration including: LWL spectrum which is the spectrum where net advance in attenuation by expandable media is predominantly dependent on Hb, and HWL spectrum which is the spectrum where net advance in attenuation by expandable media is predominantly dependent on amount of $H_2O$.

ΔV and fractional change in V (QV) relate to a change in amount and are estimated as change in attenuation as indicated below:

$$\Delta V \cong \Delta A \qquad [2]$$

$$QV \cong QA \qquad [3]$$

where Δ is change (p.d.u.) and Q is fractional change (dimensionless).

Aside from specificity to quantity which is saturated with photons, attenuation by $H_2O$ and Hb are not used for comparing changes in their quantities due to different units of measurement (grams for Hb, and liters for $H_2O$), and thus ΔA estimates are not used for comparison of changes in amount of $H_2O$ and Hb.

In embodiments, the absolute A in attenuation are not directly comparable, the relative changes (how much A increases or decreases with changes in quantities given the WL and measurement area are unchanged) are comparable, preferably with proper normalization In embodiments, fractional changes of attenuation by hemoglobin (QhA) and water (QwA) are used for comparison of changes in their amount over time or due to changes in WL, the site of measurement, the DOS, etc., In embodiments, the technique used is based on monitoring QA, and thus an unchanging amount of non-expandable media has no relevant impact on estimated changes in expandable media which includes water and hemoglobin.

In embodiments, a Beam of Light (BOL) model serves as theoretical background for estimating changes in Hb and iH2O and $eH_2O$ in a living tissue based on WL-specific fractional changes in light attenuation over time.

Figure 44A:
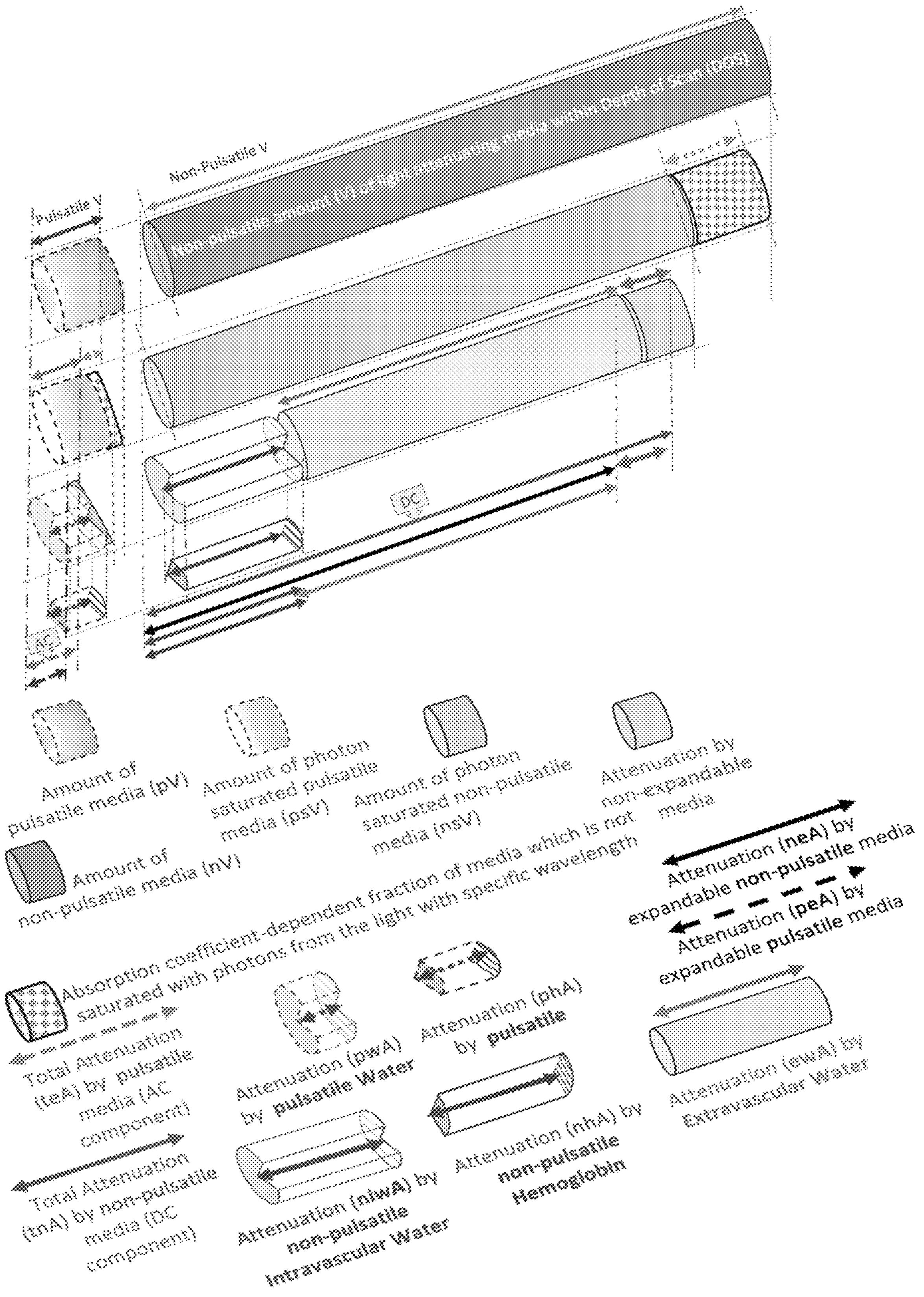
FIG. 44A illustrates a representation of net amount of pulsatile and non-pulsatile media within the path of a beam of light through tissue where depending on wavelength specific light attenuation features some fraction of absorbent's amount V is not saturated with photons from a passing light in accordance with an embodiment of the present disclosure.
Figure 44B:
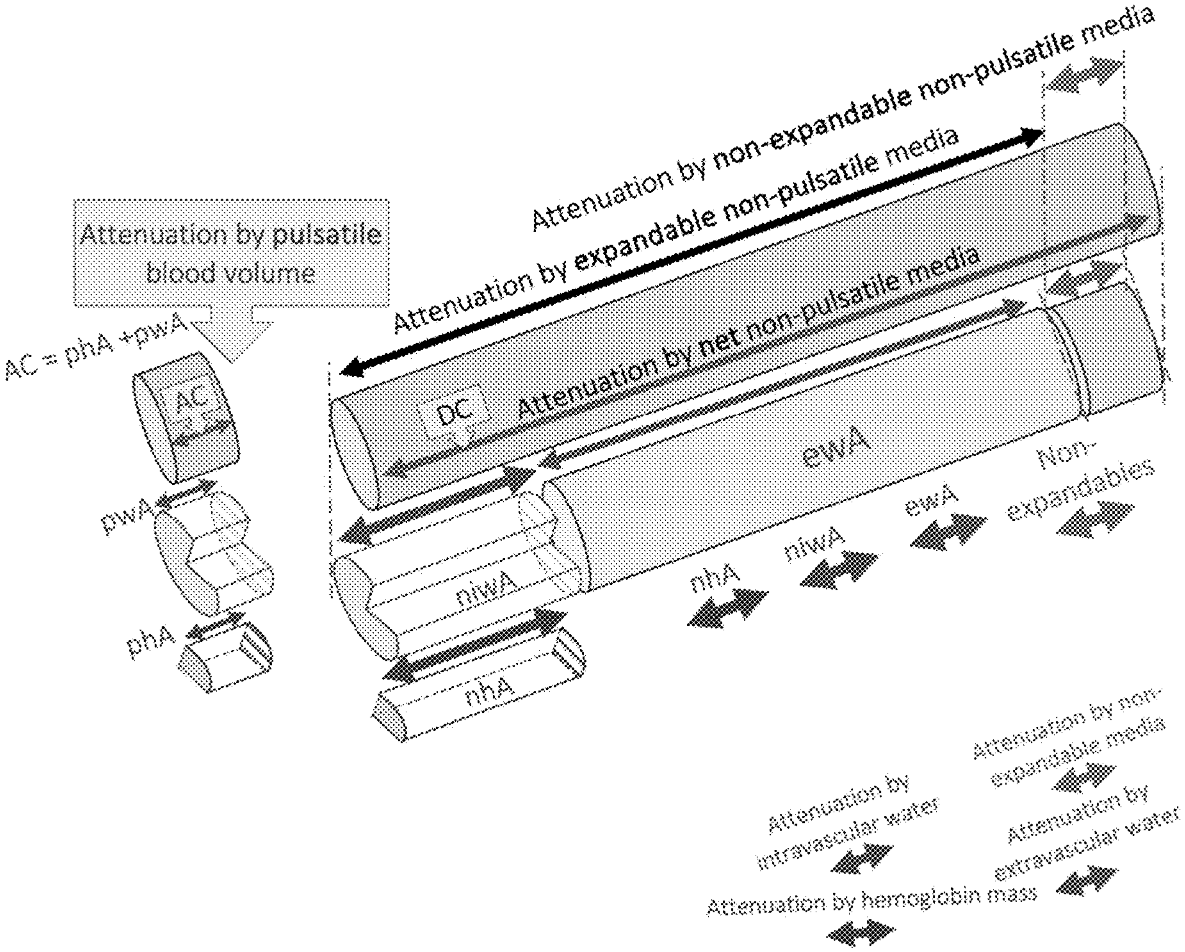
FIG. 44B illustrates attenuation by non-expandable media in an AC component which is nearly constant in short term, and thus does not affect estimates of changes in AC component over time for a given wavelength. Same applies to net amount of media (V) within DOS, and amount of photon non-saturated fraction of V, and their impact on attenuation in accordance with an embodiment of the present disclosure.

FIGS. 44A-44B depict arbitrary relationship between net amount (V) of media within an arbitrary beam of light, as well as photon-saturated and non-saturated, expandable and non-expandable, pulsatile and non-pulsatile components, and their contribution to light attenuation measured as AC and DC components.

Figure 45A:
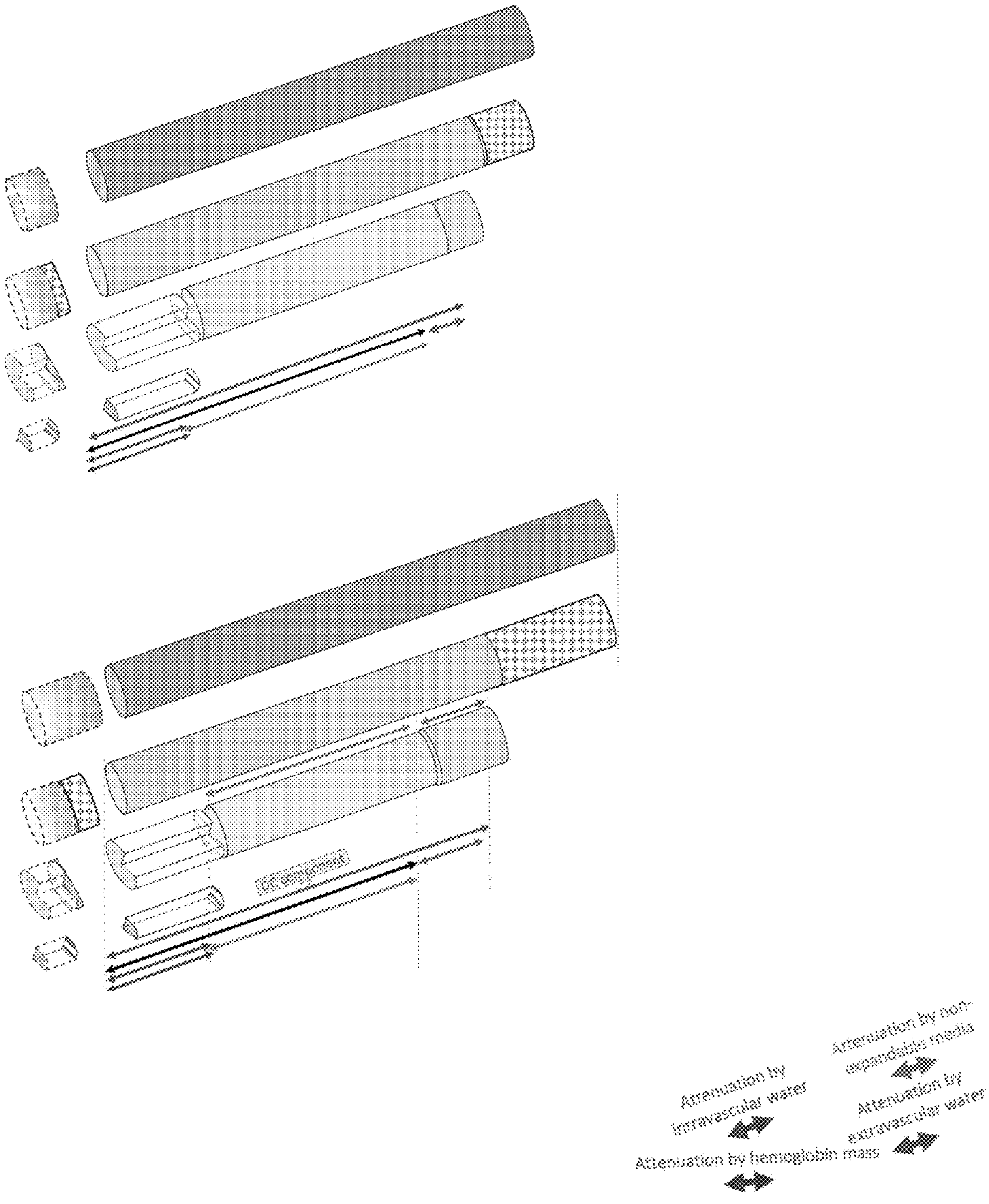
FIG. 45A-C illustrates arbitrary patterns of relationships between relevant variables which are used in analyzing PPG signals and their interpretation in accordance with embodiments of the present disclosure.
Figure 45B:
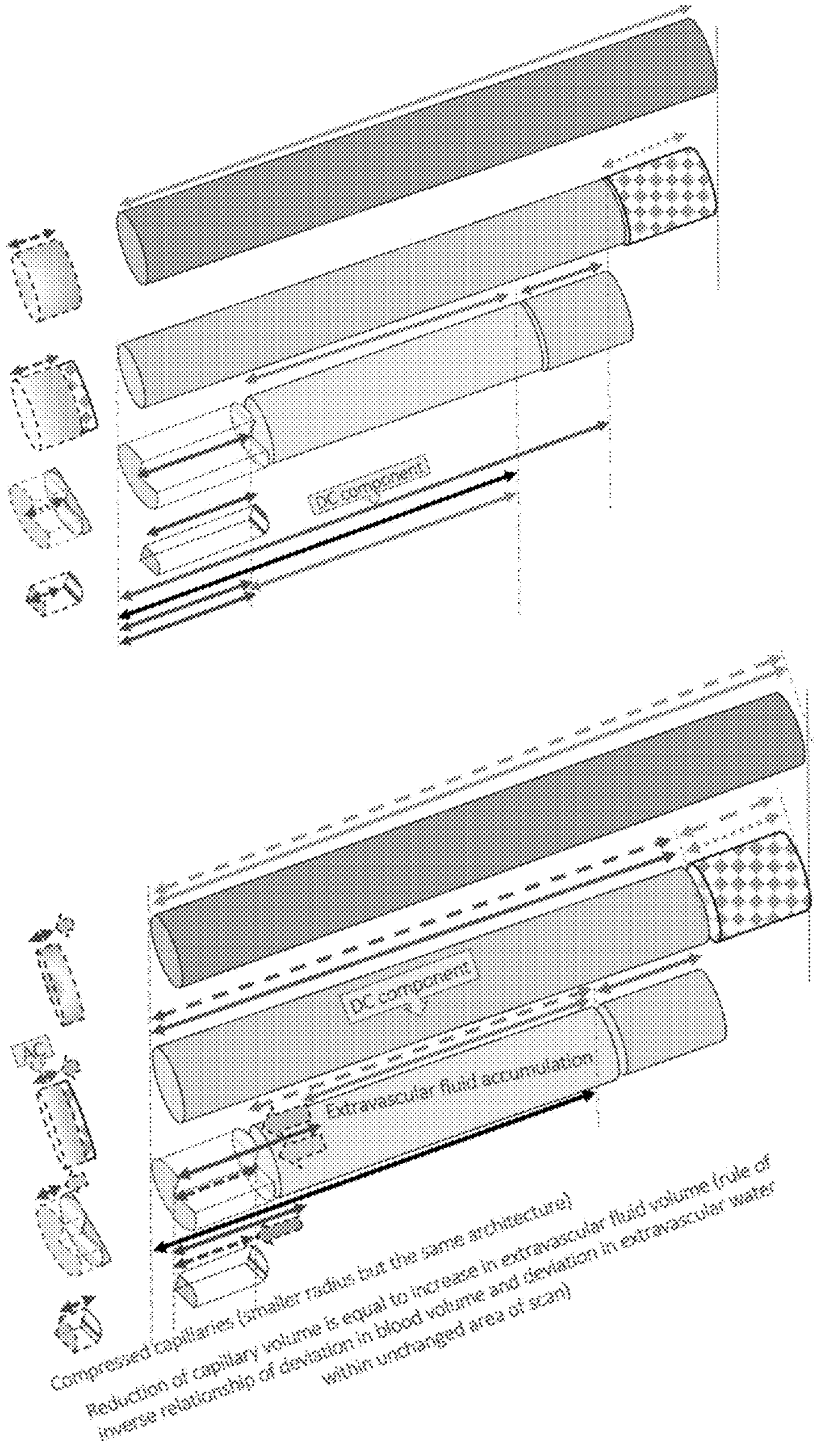
Figure 45C:
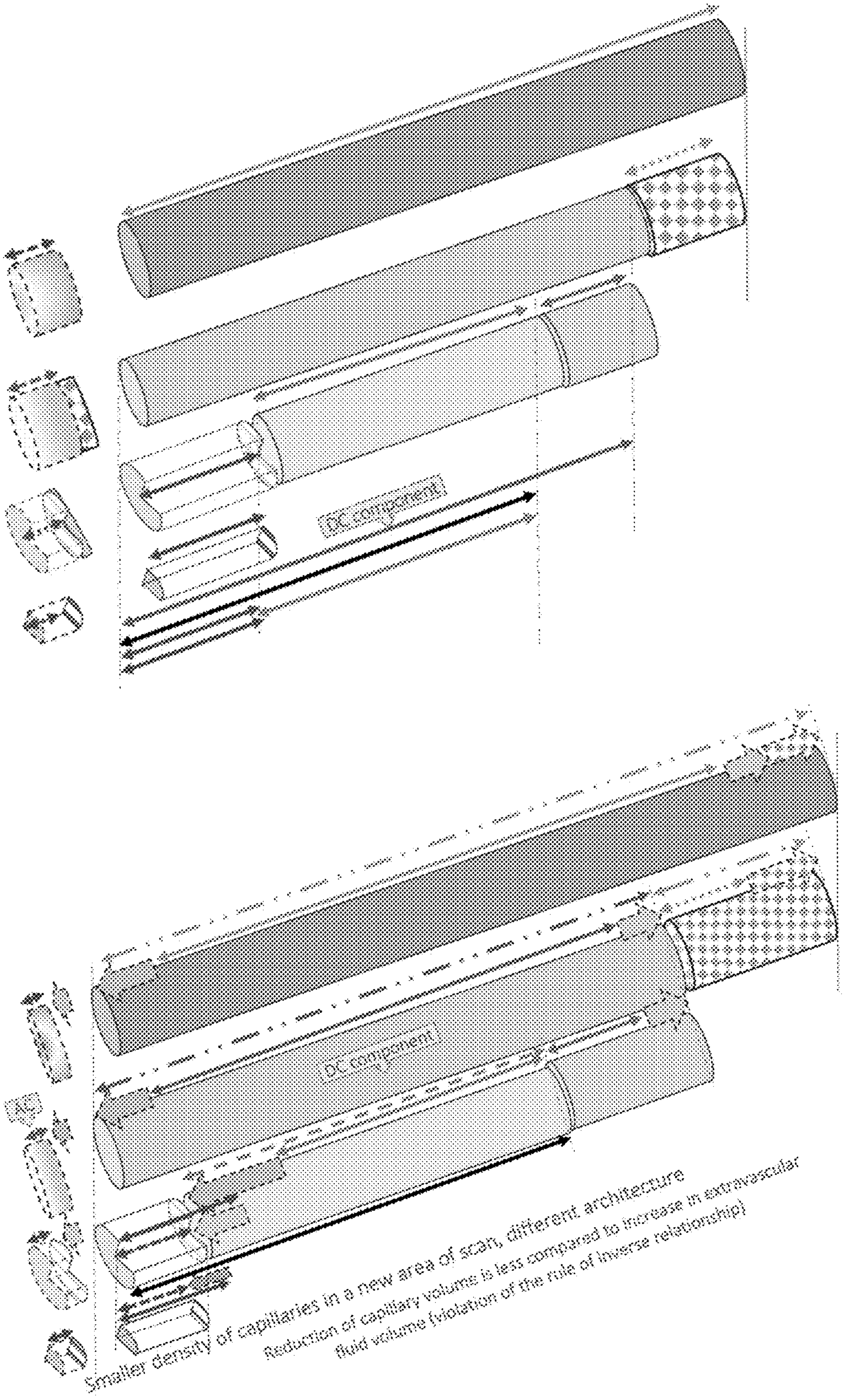

FIG. 45A-45C depict patterns of relationship between relevant variables which are used for analyzing PPG signals and to interpret them.

Figure 46:
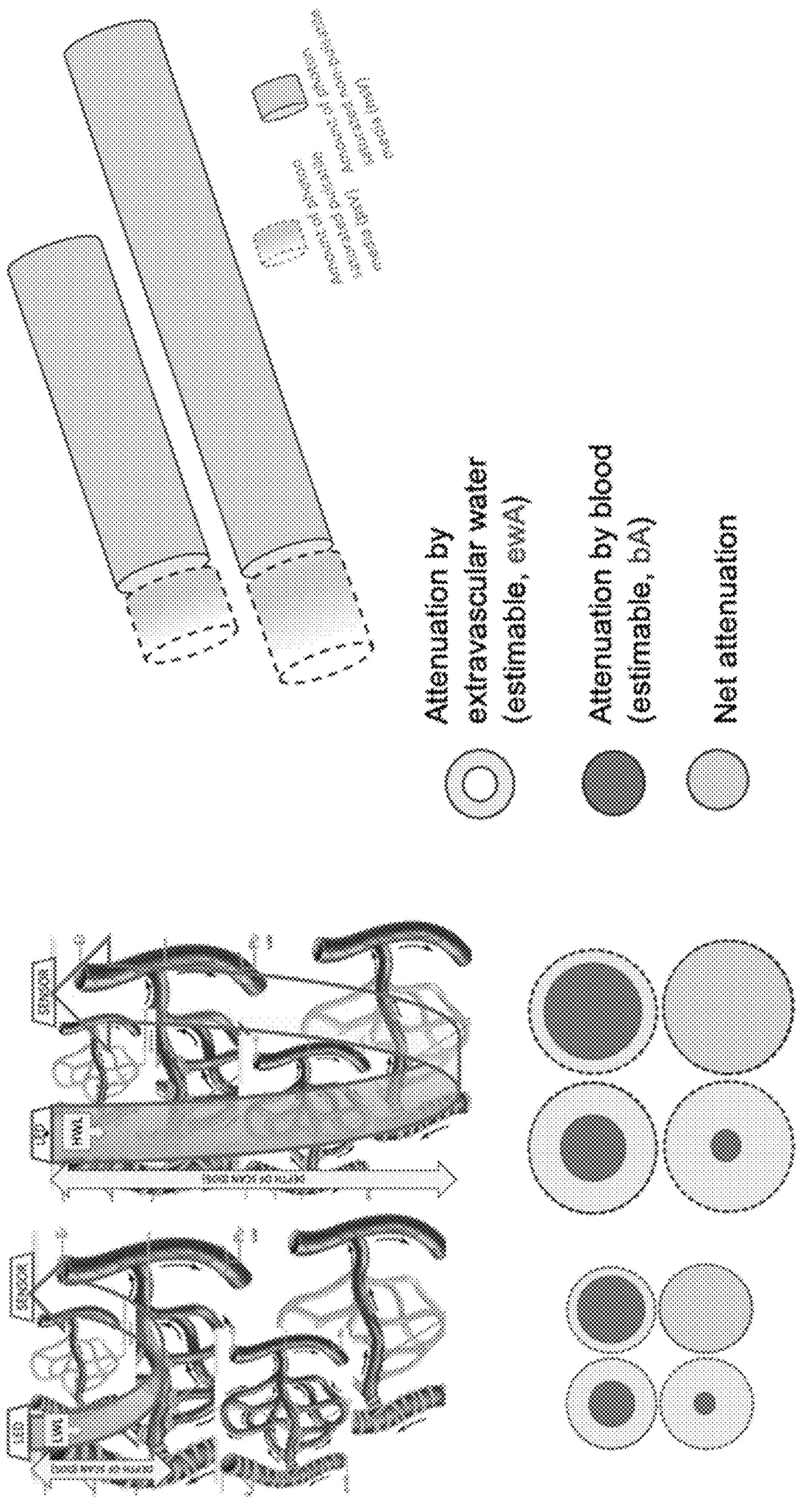
FIG. 46 illustrates differences in attenuation by blood and water where attenuation by blood is based on attenuation by hemoglobin and intravascular water while attenuation by water includes attenuation by plasma water and intracellular water inside red cells and attenuation by extravascular water includes interstitial water, intracellular water inside tissue cells and lymph inside lymphatic capillaries where a ratio between attenuation by blood and extravascular water is the same but PPG signal are different as indicated by different radiuses of circles where net amount of tissues saturated with photons in the path of a beam of light is indicated by the volume inside the green "tubes" while the different sized circles represent different volumes of green tubes in accordance with an embodiment of the present disclosure.
Figure 47:
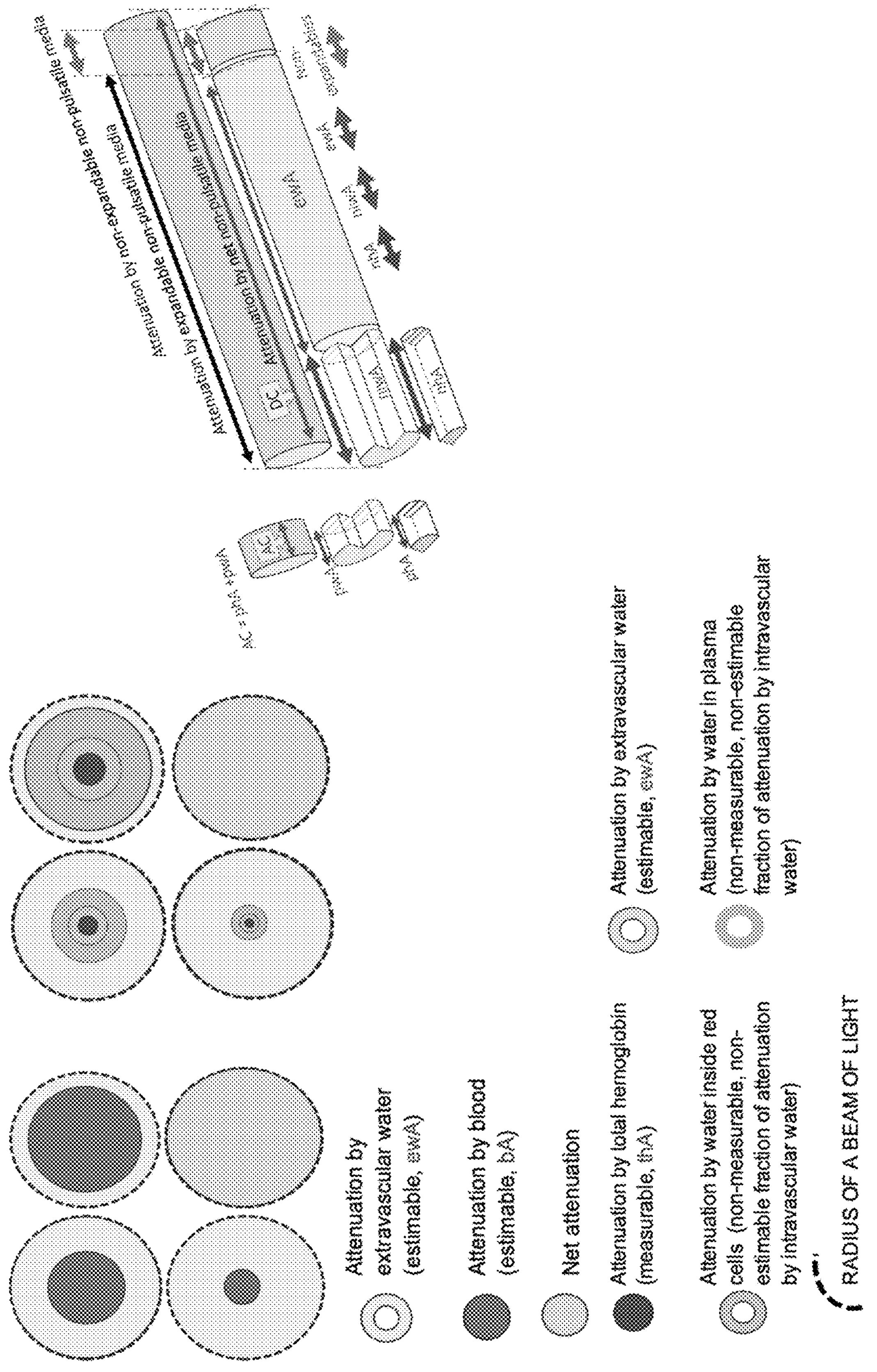
FIG. 47 illustrates attenuation based on water and blood (hemoglobin) in exemplary vessels indicating the inverse relationship between attenuation by blood and extravascular water within an arbitrary beam of light provided that the segment of tissue, the wavelength and the sensor system are unchanged in accordance with an embodiment of the present disclosure.
Figure 51:
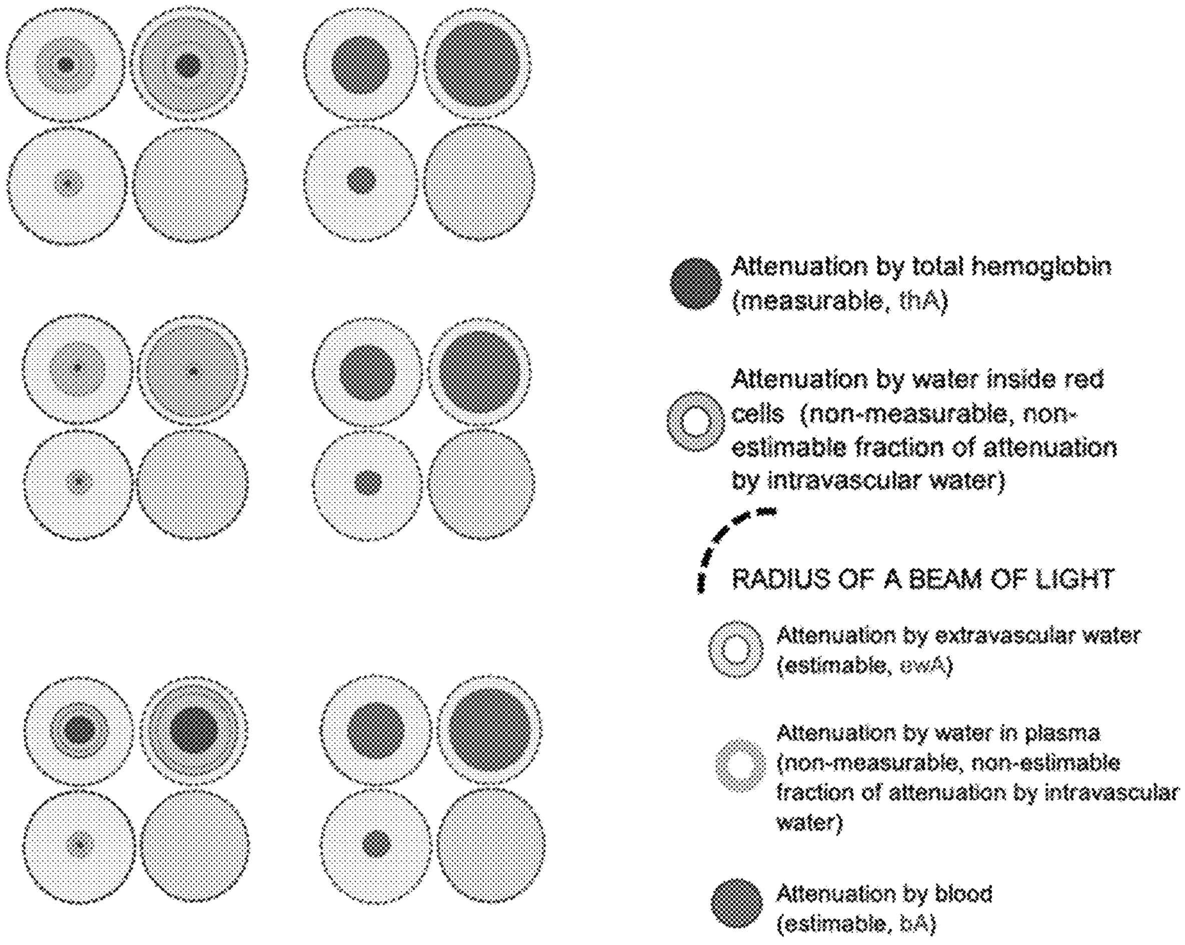
FIG. 51 illustrates examples of hemodilution patterns during changes in tissue perfusion in accordance with an embodiment of the present disclosure.

FIGS. 46, 47 and 51 depict arbitrary relationships between light attenuation by expandable media within an arbitrary beam of light. The relationship between net light attenuation, and attenuation by blood and extravascular water complies with the Rule of Inverse Relationship and can be expressed as below:

$$tA = ewA + tbA = ewA + tiwA + thA \quad [4]$$

where tA is net attenuation (illustrated as area within a ring; (FIGS. 46-47), ewA is attenuation by extravascular water, tbA is attenuation by total blood (amount/volume), tiwA us attenuation by total intravascular water and thA is attenuation by total hemoglobin, and the inverse relationship between ewA and tbA is embodied as hyperbolic curve such that as one variable approaches zero, the other approaches infinity (FIG. 51) and shifts within a parabolic curve are due to changes in tissue perfusion which changes the ratio between bA and ewA.

In embodiments, attenuation by pulsatile blood (pbA) and/or non-pulsatile (nbA) may be used as follows:

$$pA = ewA + pwA + phA = ewA + pbA \quad [5]$$

where pA is net pulsatile light attenuation in a constant segment of tissues, ewA which is attenuation by extravascular water, pwA which is attenuation by pulsatile water, phA which is attenuation by pulsatile hemoglobin, pbA which is attenuation by pulsatile blood (amount/volume), and/or $$nA = ewA + niwA + nhA = ewA + nbA \quad [6]$$

where nA is net non-pulsatile light attenuation in a constant segment of tissues, ewA which is attenuation by extravascular water, niwA which is attenuation by non-pulsatile intravascular water, nhA which is attenuation by non-pulsatile hemoglobin, pbA which is attenuation by pulsatile blood.

Figure 48:
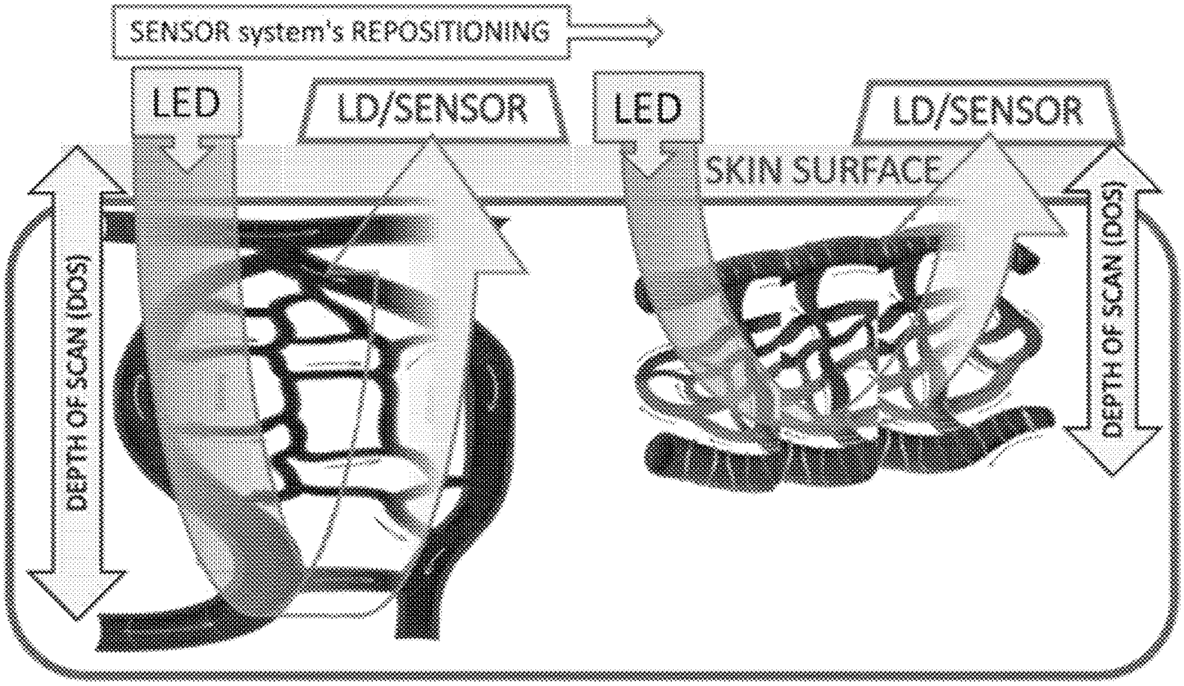
FIG. 48 illustrates an unpredictable change in same wavelength light penetration and attenuation when a sensor is relocated or the direction of the beam of light has changed which may result in different architecture of capillary beds in the path of light in accordance with an embodiment of the present disclosure.

In embodiments, when WL and DOS are constant, but the segment of tissue within a beam is unstable, e.g. due to repositioning of a sensor (FIG. 48) it is recognized as vertical-horizontal shift of the parabolic curve; when the area within a beam stabilizes, the perfusion change related shifts are seen as shifts along a new parabolic curve (FIG. 49) and this model may be used in sensor relocation detection technique.

In embodiments, attenuation by non-expandable media is ignored in the above equations because invention is based on analyzing changes in attenuation over time, and these changes are predominantly caused by changes in attenuation by expandable media as described below.

Figure 50:
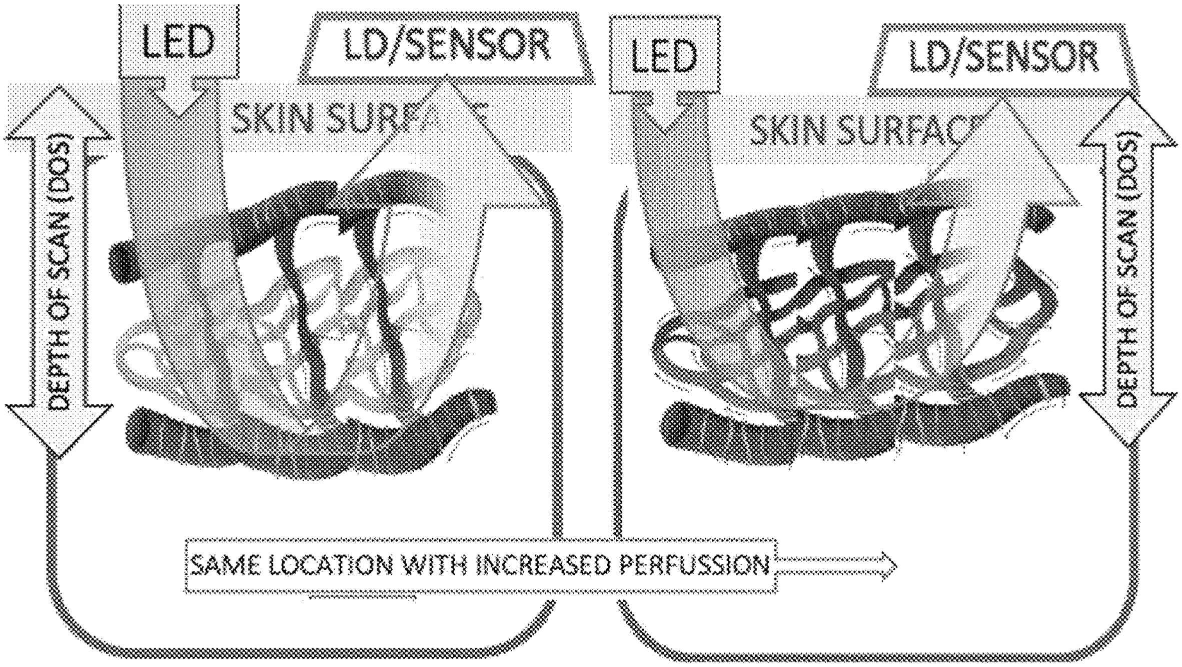
FIG. 50 illustrates changes in perfusion and related light attenuation due to capillary vasoconstriction and increased attenuation by extravascular water due to reduced net radius of capillaries within a path of a beam of light in accordance with an embodiment of the present disclosure.

In embodiments, assessment of hemodilution related changes in perfusion (FIGS. 50, 51) require discrimination between attenuation by hemoglobin and water, as well as between intravascular and extravascular water and a sensor calibration technique may be applied for this purpose.

Attenuation by non-expandable media is ignored in the above equations because the system 100 is based on analyzing changes in attenuation over time, and these changes are predominantly caused by changes in attenuation by expandable media as described below.

Assessment of hemodilution related changes in perfusion (FIG. 50, 51) require discrimination between attenuation by Hb and $H_2O$, as well as between $iH_2O$ and $eH_2O$ and the system 100 deploys a sensor calibration technique for this purpose. Sensor systems calibration implies method for determining WL (nm) which is predominantly attenuated by hemoglobin compared to water (labeled as LWL), and the WL which is predominantly attenuated by water compared to hemoglobin (labeled as HWL).

Figure 52A:
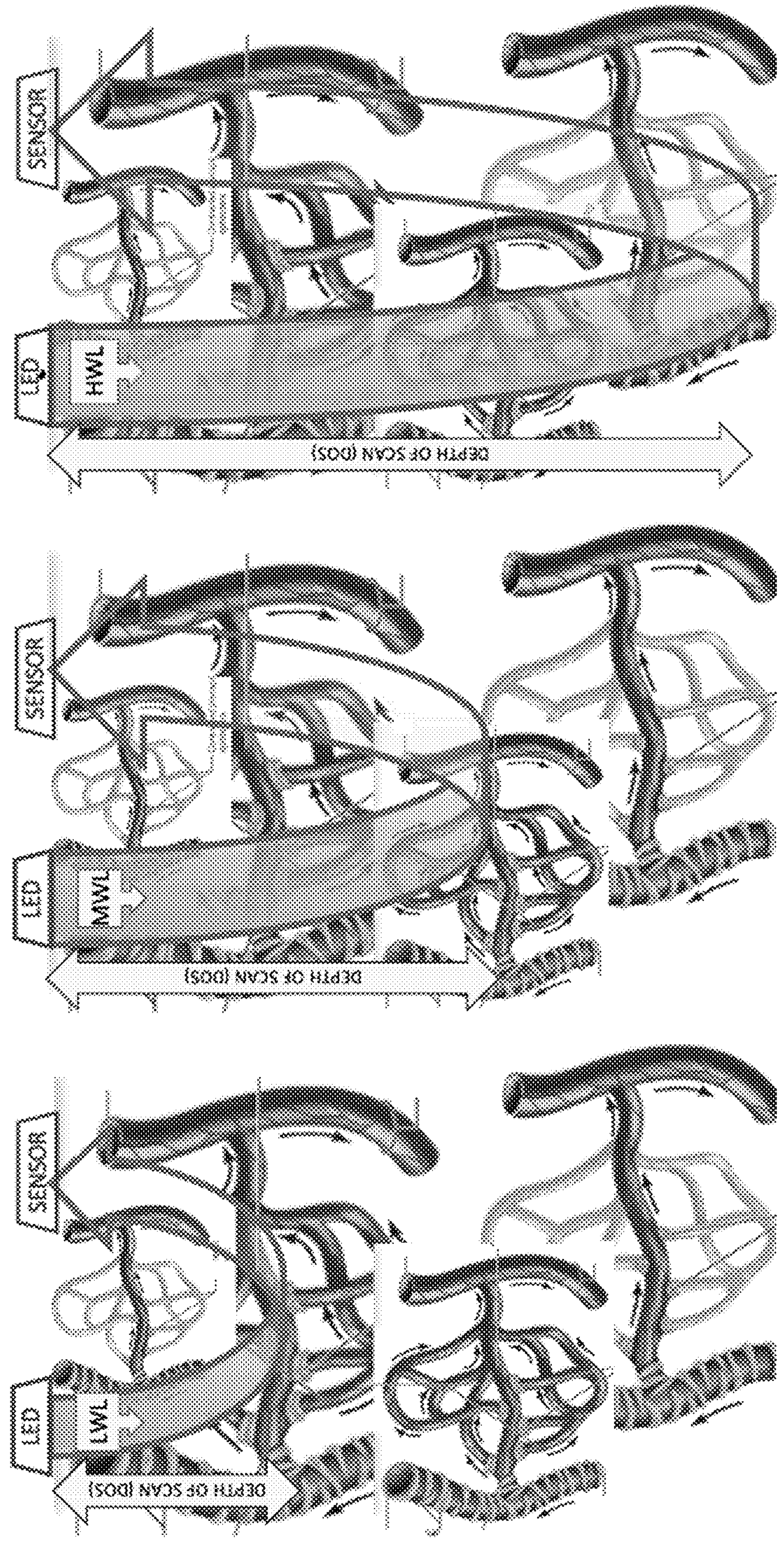
FIGS. 52A-52D illustrate relationships between attenuation (A) by water and hemoglobin depending on wavelength (WL) and depth of scan (DOS) in accordance with an embodiment of the present disclosure.
Figure 52B:
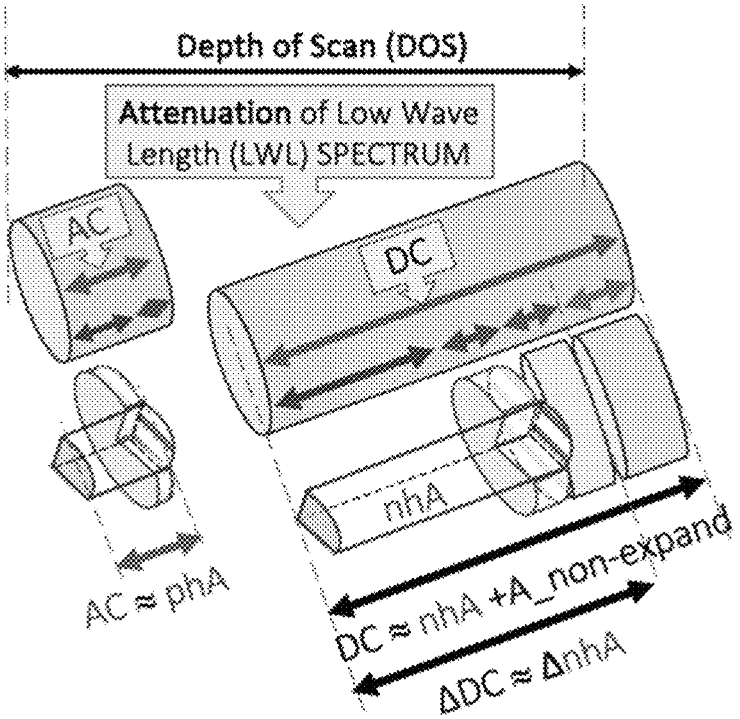
Figure 52C:
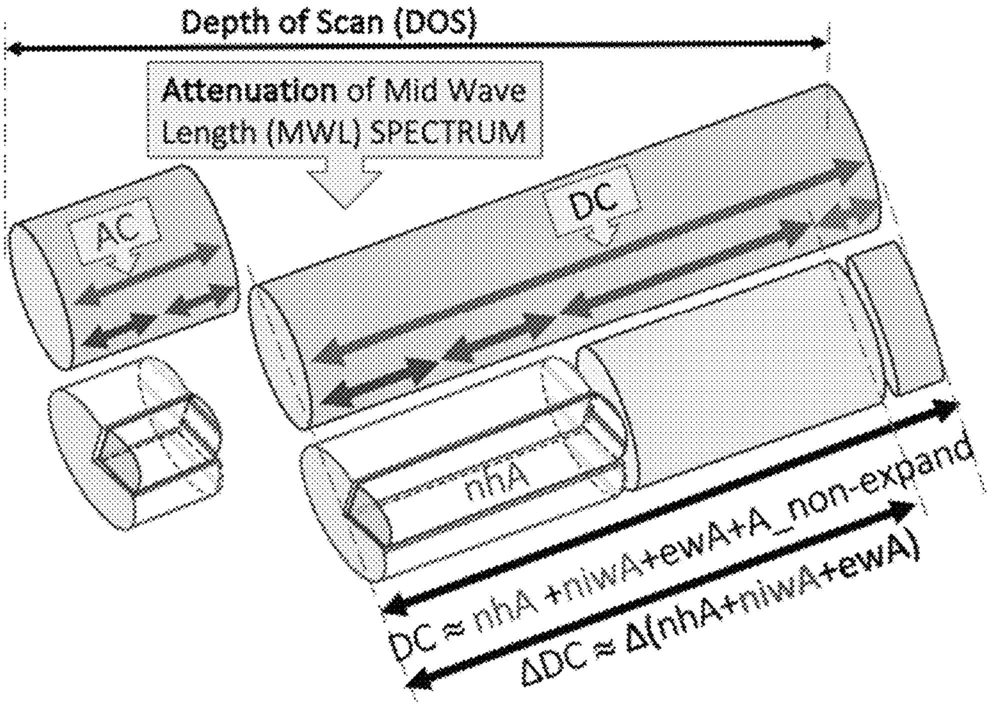
Figure 52D:
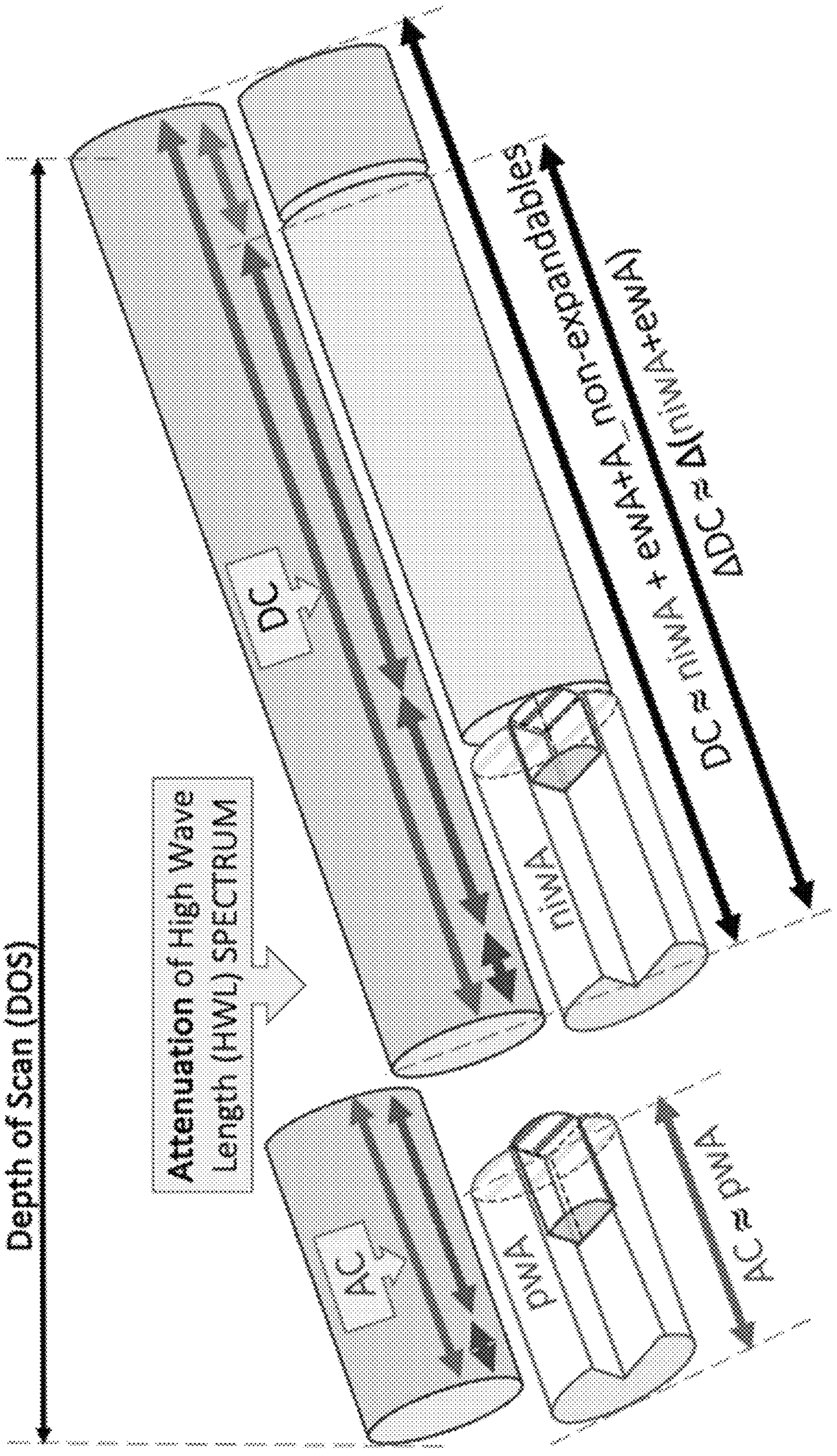

As can be seen in FIG. 52A, DOS increases during step-wise increase in WL. In embodiments, the related step-wise changes in AC and DC are due to changes in WL-dependent light attenuation features of media, also depth related amounts of media, changes in capillary density and architecture, ratio $iH_2O$ to $eH_2O$, as well as amounts of non-expandable media as indicated in FIG. 52D.

Changes in attenuation (AA) by $H_2O$ and Hb may be an indication of changes in their amounts are not comparable due to different units of measurement, thus, fractional change in attenuation (QA) by hemoglobin (QhA) and by water (QwA) are used by the model for comparison of changes in their amounts as indicate in FIG. 53.

Light absorption efficacy (LAE) indicates inter-WL-step ability of a medium to advance light attenuation with increasing WL, e.g.:

$$LAE = QAn + 8 = (An + 8 - An + 7)/An + 7 \quad [7]$$

where WLs are labelled as n, n+1, n+3 and so on, and LAE refers to either pulsatile variables including pulsatile hemoglobin, where:

$$phLAE = QphAn \quad [8]$$

and $$\text{pulsatile water} - pwLAE = QpwAn \quad [9]$$

and/or non-pulsatile variables:

non-pulsatile hemoglobin may be expressed as:

$$nhLAE = QnhAn \quad [10]$$

and non-pulsatile intravascular water may be expressed as:

$$niwLAE = QniwAn \quad [11]$$

or the sum of pulsatile and non-pulsatile variables which may be referred to as total hemoglobin (thLAE) which may be expressed as:

$$thLAE = phLAE + nhLAE \quad [12]$$

and total intravascular water (tiwLAE) may be expressed as:

$$tiwLAE = pwLAE + niwLAE \quad [13]$$

In embodiments, LAE indicates inter-WL-step ability of a medium to advance light attenuation with increasing WL, e.g.:

$$LAE = QAn + 8 = (An + 8 - An + 7)/An + 7 \quad [7]$$

where WLs are labelled as n, n+1, n+3 and so on, and LAE refers to pulsatile variables including pulsatile hemoglobin, where:

$$phLAE = QphAn \quad [8]$$

and $$\text{pulsatile water} - pwLAE = QpwAn \quad [9]$$

and/or non-pulsatile variables:

non-pulsatile hemoglobin may be expressed as:

$$nhLAE = QnhAn \quad [10]$$

and non-pulsatile intravascular water may be expressed as:

$$niwLAE = QniwAn \quad [11]$$

or the sum of pulsatile and non-pulsatile variables which may be referred to as light absorption efficacy of total hemoglobin (thLAE) which may be expressed as:

$$thLAE = phLAE + nhLAE \quad [12]$$

and light absorption efficacy of total intravascular water (tiwLAE) may be expressed as:

$$tiwLAE = pwLAE + niwLAE \quad [13]$$

Figure 53A:
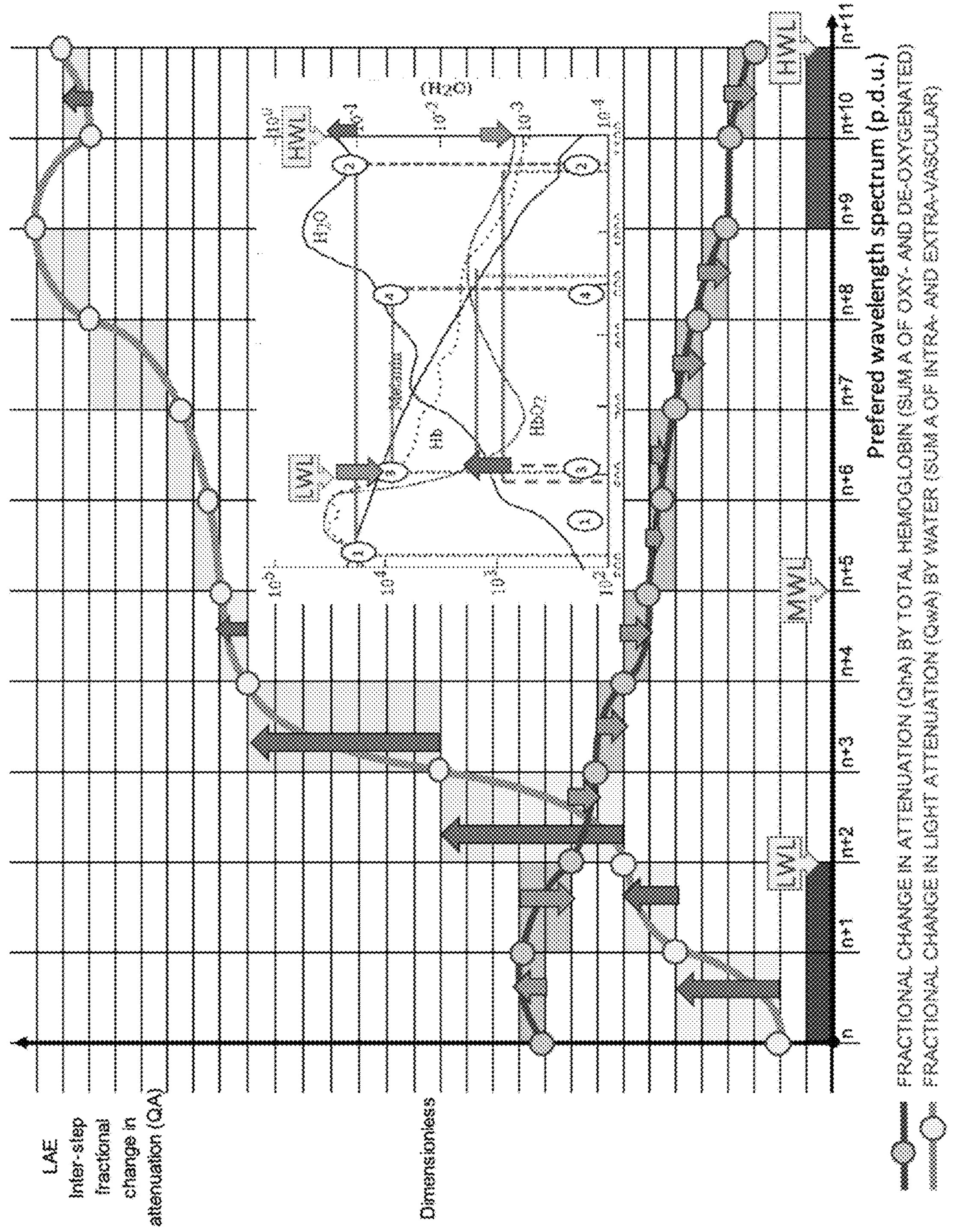
FIG. 53A illustrates a chart showing fractional changes in attenuation by hemoglobin and by water in accordance with an embodiment of the present disclosure.
Figure 53B:
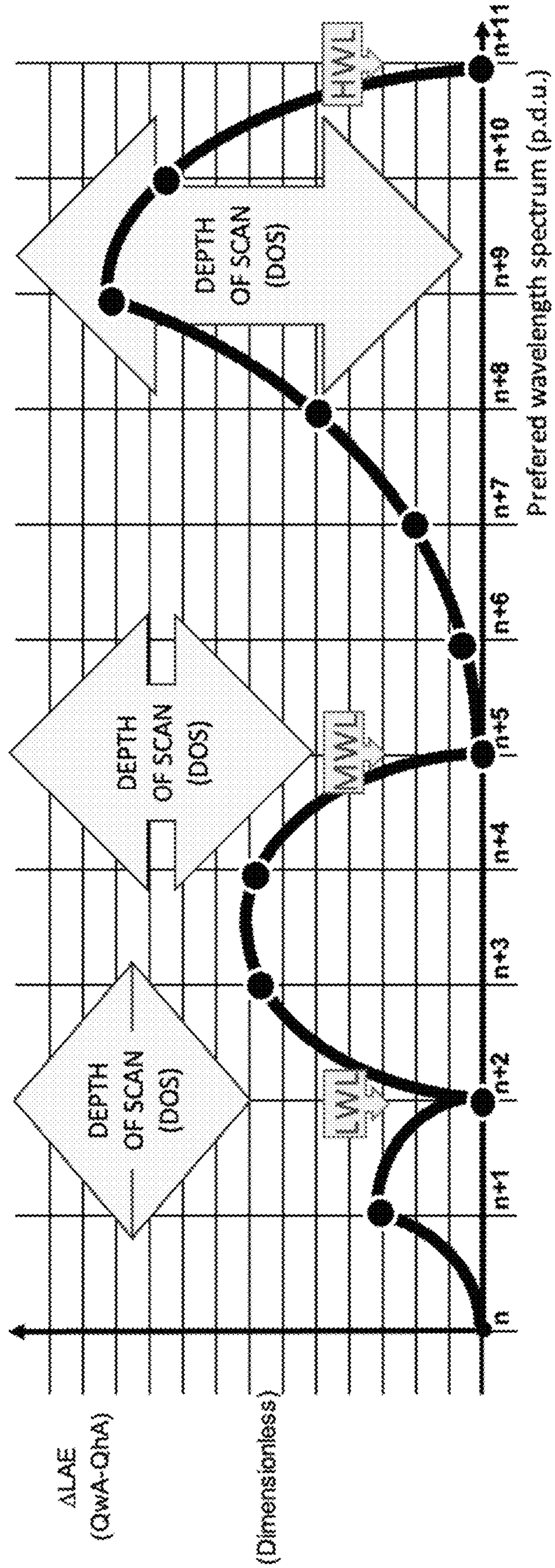
FIG. 53 B us a chart indicating changes in light attenuation efficacy for different wavelengths as part of a calibration process in accordance with an embodiment of the present disclosure.

In embodiments, LAE trends include any of above described pairs of LAEs of $H_2O$ and LAEs of Hb and may intersect only once per legally allowed WL spectrum of as can be seen in FIG. 53A that WL is labeled as LWL and at that WL, there is an inverse relationship between LAE of Hb and LAE of $iH_2O$. LAE trends intersect at different WL compared to WL at the intersection of absorption coefficient trends. The inverse relationship between LAEs occurs with several relevant WLs (see FIG. 53B). The term LWL relates to the spectrum where net advance in attenuation by expandable media is predominantly dependent on Hb. The term HWL relates to HWL which is the spectrum where net advance in attenuation by expandable media is predominantly dependent on amount of $H_2O$ and are not limited to particular ranges. The inverse relationship between attenuation by relevant media at LWL indicates that attenuation by $H_2O$ will become dominant over attenuation by Hb with further increase in WL. WLs in the direction of shorter WL are used for estimation of changes in attenuation by Hb and the inverse relationship between attenuation by relevant media at HWL indicates that attenuation by $H_2O$ has become dominant over attenuation by Hb. WLs in the direction of shorter WLs are used for estimation of changes in attenuation by $H_2O$ including $iH_2O$ and/or $eH_2O$. The inverse relationship at MWL indicates that progressive increase in attenuation by $H_2O$ compared to Hb has stalled, and thus net attenuation is equally sensitive to changes in both $H_2O$ and Hb. This WL may be used for specific applications such as estimates of hemoglobin concentration (Hbc).

In embodiments, a ΔLAE trend determines individual, case-specific and context-sensitive WLs referred to as LWL, MWL and HWL: these are WLs where ΔLAE=0 as in FIG. 11B. In embodiments, based on the model, net light attenuation including AC and/or DC components at every WL step, and estimates LAE as step-wise fractional change in AC and/or DC. In embodiments, the minimized LAE=0 may be used as alternative to the model-depicted (ΔLAE=0) WLs (nm) (FIG. 11*b*) for determining optimal LWL and HWL (nm).

In embodiments, sensors 102D may be calibrated. In embodiments, each array of sensors 102 may include an operator/developer and a preferred number of LEDs with the same WL (nm). As individual array deployed WL is within legally allowed spectrum for PPG applications in humans. In embodiments, parallel arrays use stepwise increasing wavelengths where each wavelength step aims for minimal feasible difference of wavelength from adjacent arrays. Parallel arrays are feasibly close to each other and arrays have light protective shields that are most feasible for a case-specific application. In embodiments, arrays are placed and secured on skin or other positions suitable for sensor contact with organ(s).

In embodiments, each array is activated separately during calibration and sensors (detectors) 102D within arrays are activated one at a time for the operator-preferred duration and number of activations. Parallel sensor arrays are activated in an operator-preferred sequence.

In embodiments, a dedicated PPG signal processing device may be used to record PPG signals—AC and/or DC—for each array. After the arrays are activated, an automated processing of the recorded AC and DC components, and analysis of data is performed. In embodiments, based on AC and/or DC components (p.d.u.) measured by adjacent sensors in parallel arrays, the LAE, which indicates inter-WL-step ability of absorbent media to advance light attenuation with increasing WL, is estimated in accordance with the following:

$$LAE = QAn + 8 = (An + 8 - An + 7)/An + 7 \quad [14]$$

where WLs are labelled as n, n+1, n+3 and so on, and Minimized LAE values-LAE=0—are used as alternative to the background model-depicted ΔLAE=0 points (FIG. 11B) for determining optimal LWL and HWL (nm), because the plateau of net attenuation approximates equal opposite values of QhA and QwA as shown by downward and upward arrows within the frames in FIG. 11A.

In embodiments, the most sensitive and informative group of sensors from parallel arrays may be selected for use in monitoring after calibration is complete. In embodiments, options for selecting sensors, e.g. "triplets", from parallel arrays for continuous PPG measurements after calibration may include:

(1) selecting one sensor sensitive to LWL and one sensitive to HWL which are closest to each other;

(2) selecting one sensor sensitive to LWL and one sensitive to HWL which are most informative, regardless of distance, (3) selecting more than two sensors based on signal qualities and informativeness with possible use of mean value of AC and/or DC from a group that uses MWL and a group that uses HWL for analysis of changes in attenuation by hemoglobin and water, accordingly.

Calibration provides information about PPG signal quality and sensitivity (ability to detect LWL and HWL), and signal analysis may provide guidance on sensor relocation to other sites when: (1) minimized LAE values cannot be reliably determined, (2) there is inverse trend of AC component, (3) the AC wave is negative.

Figure 54:
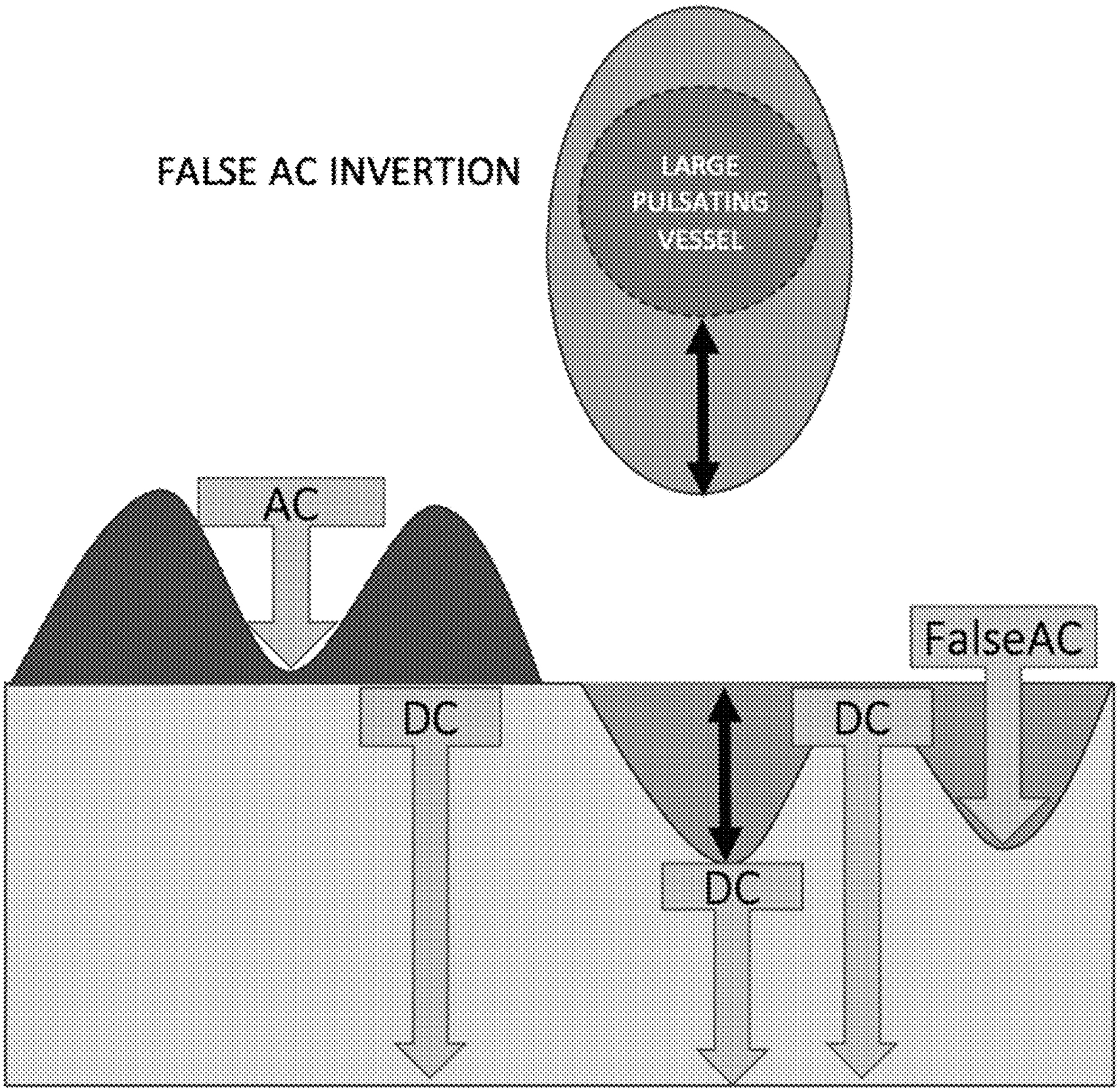
FIG. 54 illustrates an inverted AC waveform that may be caused by pulsation of nearby larger vessel that mechanically compresses capillary beds which results in disappearance of pulsation in capillaries and reduction of the DC component during that time which appears to be an inverted AC component in accordance with an embodiment of the present disclosure.

In embodiments, a negative AC wave may be caused by pulsation of nearby larger vessel(s), the pulsation of which mechanically compresses capillary beds in the path of a beam of light and causes disappearance of pulsation in capillaries, and thus reduction of DC signals during the pulse appears as inverted AC component as can be seen in FIG. 54.

Figure 43A:
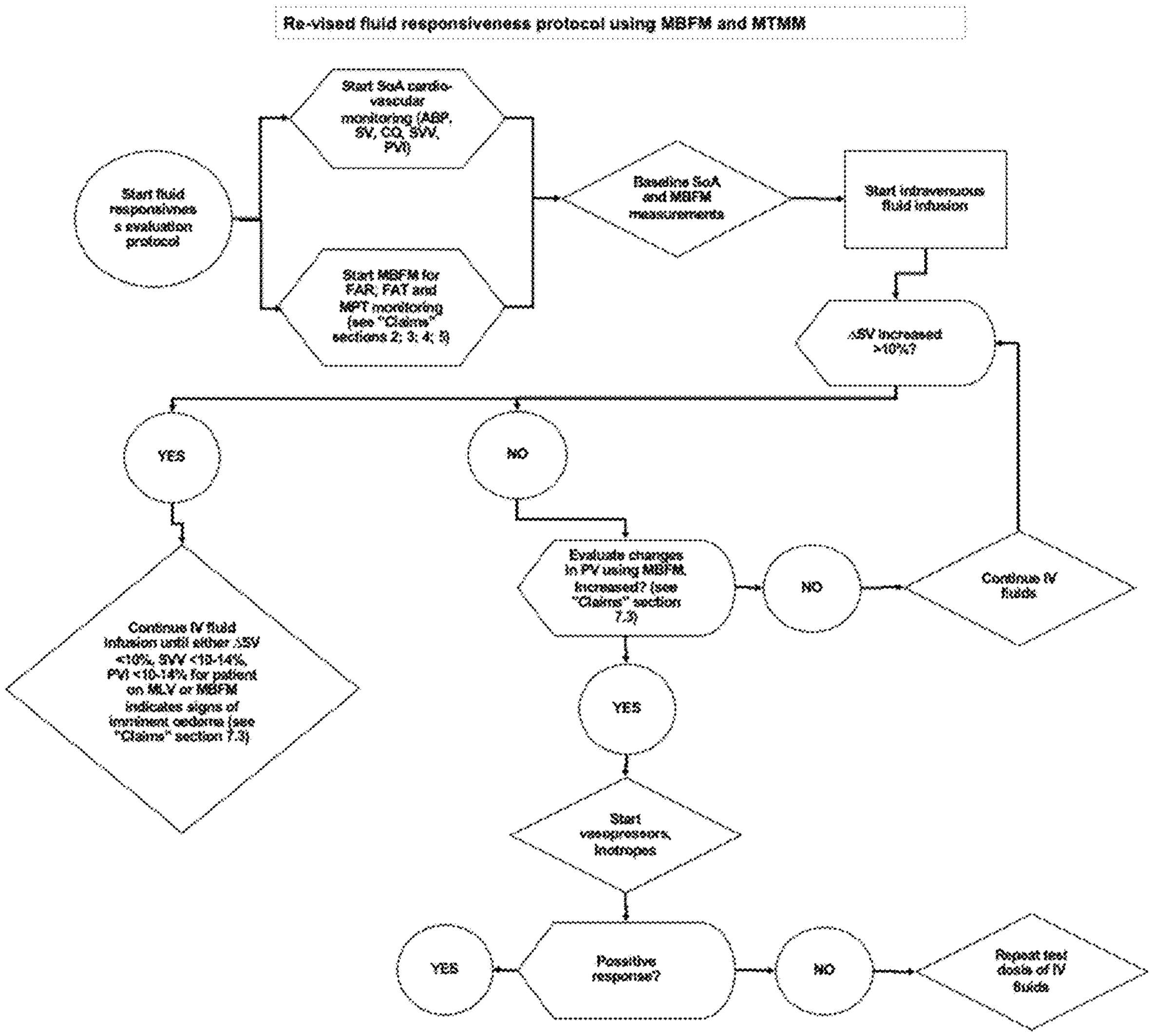
FIG. 43A illustrates an exemplary fluid responsiveness protocol using the system of the present disclosure.

In embodiments, an SSP model may be implemented. In embodiments, the DC component indicates net attenuation by non-expandable and expandable non-pulsatile media as indicated in FIGS. 43A and 44 where the DC component may be expressed as follows:

$$DC = nwA + nhA \cong \text{HWL\_DC} + \text{LWL\_DC} \quad [15]$$

where nwA corresponds to non-pulsatile water and is net attenuation by non-pulsatile intravascular plus extravascular water in HWL spectrum also referred to as HWL_DC and nhA corresponds to non-pulsatile hemoglobin and is attenuation by non-pulsatile hemoglobin mass in LWL spectrum, also referred to as LWL DC.

and $$nwA = niwA + ewA \cong \text{HWL\_DC} \quad [16]$$

where nwA corresponds to attenuation by non-pulsatile water, ewA corresponds to attenuation by extravascular water, and niwA corresponds to attenuation by non-pulsatile intravascular water, and ewA is attenuation by non-pulsatile extravascular water;

and the niwA calculation uses:

$$niwA = nawA + nvwA + cwA \quad [17]$$

where nwA corresponds to attenuation by non-pulsatile water, nawA corresponds to attenuation by non-pulsatile arterial water, nvwA corresponds to attenuation by non-pulsatile venous water, cwA c corresponds to attenuation by capillary water.

In embodiments, the equation for determine attenuation by non-pulsatile hemoglobin (nhA) follows:

$$nhA = nahA + nvhA + chA \,\square\, \text{LWL\_DC} \quad [18]$$

where nhA corresponds to attenuation by non-pulsatile hemoglobin mass in LWL spectrum, also referred to as LWL_DC, nahA corresponds to attenuation by non-pulsatile arterial hemoglobin, nvhA corresponds to attenuation by non-pulsatile venous hemoglobin and chA corresponds to attenuation by capillary hemoglobin.

In embodiments, the AC component indicates net attenuation by non-expandable and expandable pulsatile media. Here, this term is treated differently than discussed above in that it is not an approximation of net quantity of media but of the fraction which is saturated as indicated in FIG. 44. The AC component may be expressed as indicated below:

$$AC = pwA + phA \cong \text{HWL\_AC} + \text{LWL\_AC} \quad [19]$$

where pwA relates to pulsatile water and corresponds to net attenuation by pulsatile intravascular water (includes attenuation by pulsatile water in metateriolae and true capillaries) in HWL spectrum also referred to as HWL_AC (similarity to arterial water $aH_2O$), and phA related to pulsatile hemoglobin and corresponds to attenuation by pulsatile hemoglobin (includes attenuation by pulsatile hemoglobin in metaterioles and true capillaries) in the LWL spectrum, also referred to as LWL_AC.

In embodiments, attenuation by net Hb is measurable and may be expressed as follows:

$$thA = nhA + phA \cong \text{LWL\_DC} + \text{LWL\_AC} \quad [20]$$

where thA is attenuation by total hemoglobin mass, nhA is attenuation by non-pulsatile hemoglobin (DC signal with LWL), and phA is attenuation by pulsatile hemoglobin (AC signal with LWL).

In embodiments, processing the PPG data after sensor calibration allows for estimation of values. For example attenuation by net intravascular water may be estimated based on the below:

$$tiwA = niwA + pwA = niwA + \text{HWL\_AC} \quad [21]$$

where tiwA is attenuation by total intravascular water, niwA is non-measurable attenuation by non-pulsatile intravascular water, pwA is measurable attenuation by pulsatile intravascular water (pwA □HWL_AC, which is the AC component with HWL)

Further, attenuation by non-pulsatile intravascular water may be estimated based on the below:

$$niwA = \text{HWL\_DC} - ewA \quad [22]$$

where niwA—is non-measurable attenuation by non-pulsatile intravascular water, HWL_DC, which is DC component with HWL, and attenuation by non-pulsatile extravascular water ewA is measurable by using COT technique or.

Circulation Obstruction Technique (COT) which implies measurement in exsanguinated tissues, and ewA is equal to DC component with HWL (ewA≈HWL_DC), or estimable during unobstructed blood circulation under the sensors according to the below:

$$ewA = nwA - niwA = nwA - nhA \times pwA/phA \quad [23]$$

where nwA is attenuation by non-pulsatile water (measurable), niwA-non-pulsatile intravascular water (estimable), nhA is non-pulsatile hemoglobin (measurable), pwA is attenuation by pulsatile water (measurable), phA is attenuation by pulsatile hemoglobin (measurable).

Hemodilution (HD) in pulsatile and non-pulsatile blood is approximately indicated by:

$$nHD \cong pHD = phA/pwA = nhA/niwA \text{ and} \quad [24]$$

$$niwA = nhA/pHD = nhA \times pwA/phA \quad [25]$$

where nHD is non-pulsatile hemodilution (estimable), pHD is pulsatile hemodilution (measurable), and the other values are set forth above.

Attenuation by pulsatile and non-pulsatile blood may also be estimated in accordance with the below:

$$bA \cong thA + tiwA = phA + nhA + pwA + niwA \quad [26]$$

where thA is attenuation by total hemoglobin (measurable), tiwA is attenuation by total intravascular water (estimable), phA is attenuation by pulsatile hemoglobin (measurable), nhA is attenuation by non-pulsatile hemoglobin (measurable), pwA-attenuation by pulsatile water (measurable), and niwA-attenuation by non-pulsatile intravascular water (estimable).

Since V of non-expandable media is constant, a fractional change in A (QA) indicates a change in V of expandable media. Trends may then be determined based on:

(1) Inter-session change, which is the variable's shift between two sessions, where a "session" refers to the data point when the measured or estimable variable is put into trend according to case specifics and user's preferences, (2) Trending change which is a shift between baseline (1st session) and the selected session.

An example of inter-session fractional change of attenuation (QA) is represented below:

$$QAn + 8 = (An + 8 - An + 7)/An + 7 \quad [27]$$

where n+7 is the preceding session, and n+8 is the consecutive session.

An example of Q-trend which is for monitoring changes in respect to baseline is represented below:

$$QAn + 5 = (An + 5 - An)/An \quad [28]$$

where n is the 1st session (baseline), and (n+5) is the 5th session; the Qn+1, Qn+2, Qn+3 and so on are used as Q-trend variables.

Note: The above approach is applied to any measurable or estimable variable, and is used for monitoring their trends as changes over time.

Figure 49:
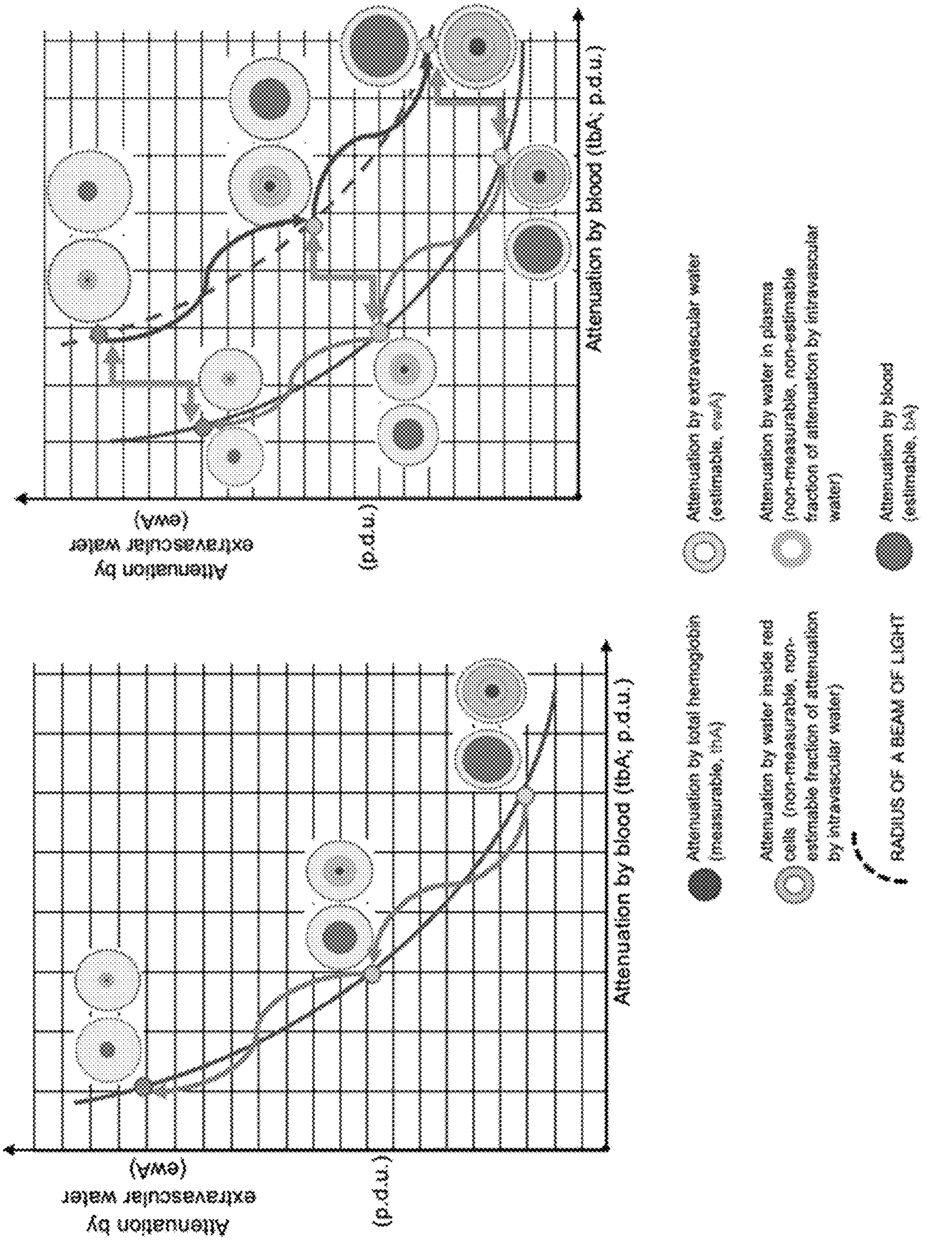
FIG. 49 illustrates exemplary shifts along a parabolic curve for assessment of perfusion and relocation of a sensor where shifts along the curve indicate perfusion changes in the same tissue and shifting between curves indicates a shift in the sensor system in accordance with an embodiment of the present disclosure.

When the sensor system 100 is repositioned, either intentionally or accidentally, movement is recognized as a vertical-horizontal shift of the parabolic curve. When the measurements in a new area stabilize, the perfusion change related shifts are seen as shifts along a new parabolic curve as indicated in FIG. 49. During a gap in time between the detection of repositioning and restart of entering new data, the extrapolated trends may be generated by AI based on previously recorded trends. In embodiments, the operator/user may be notified about this process, In embodiments, a maximal safe gap may be preset or determined by the system.

Figure 55:
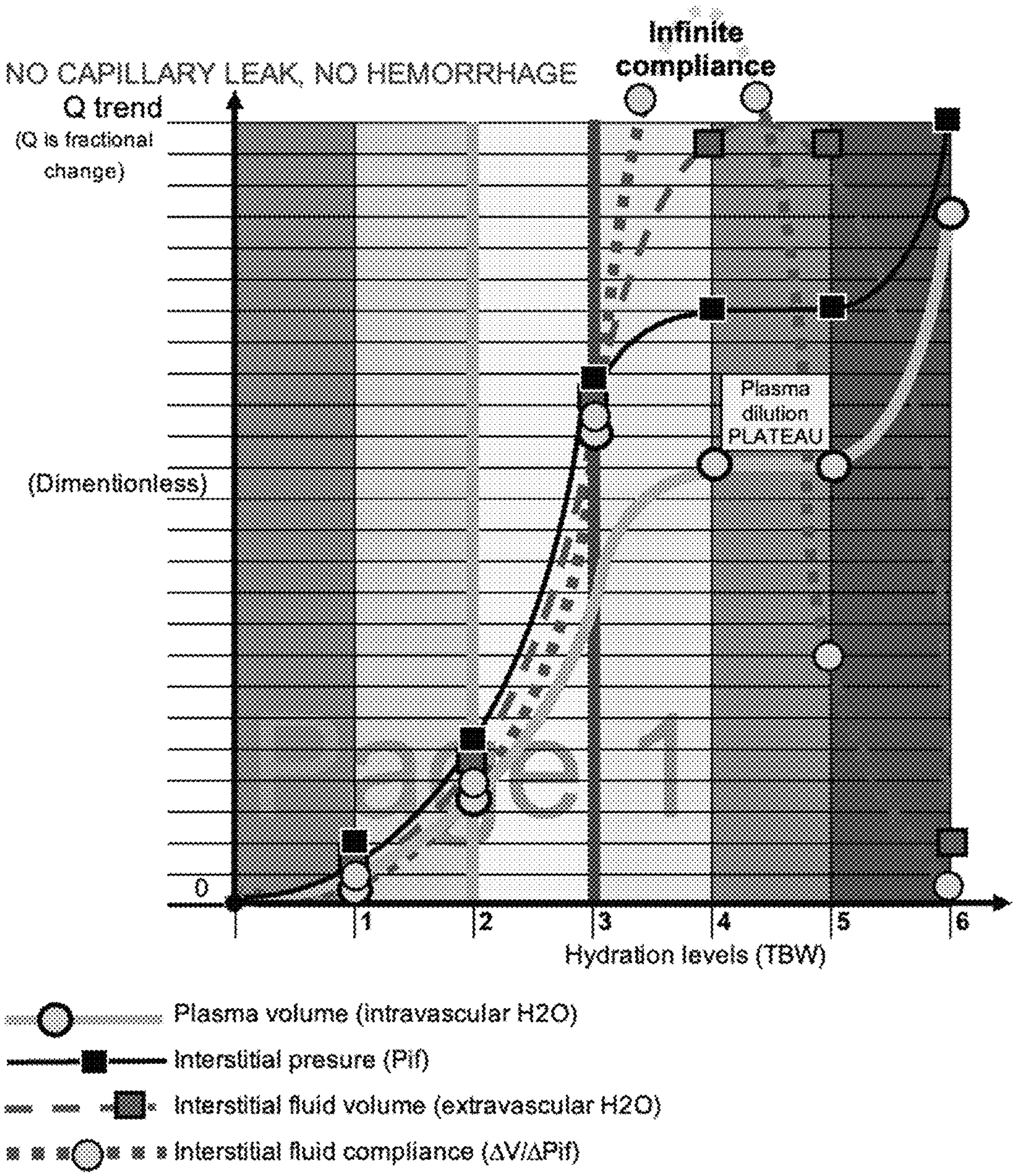
FIG. 55 illustrates a relationship between changes in variables that are used as indication of changes in intravascular and extravascular fluid accumulation at specific tissue hydration levels that is taken into consideration by a model for estimation of hydration levels in accordance with an embodiment of the present invention.
Figure 56:
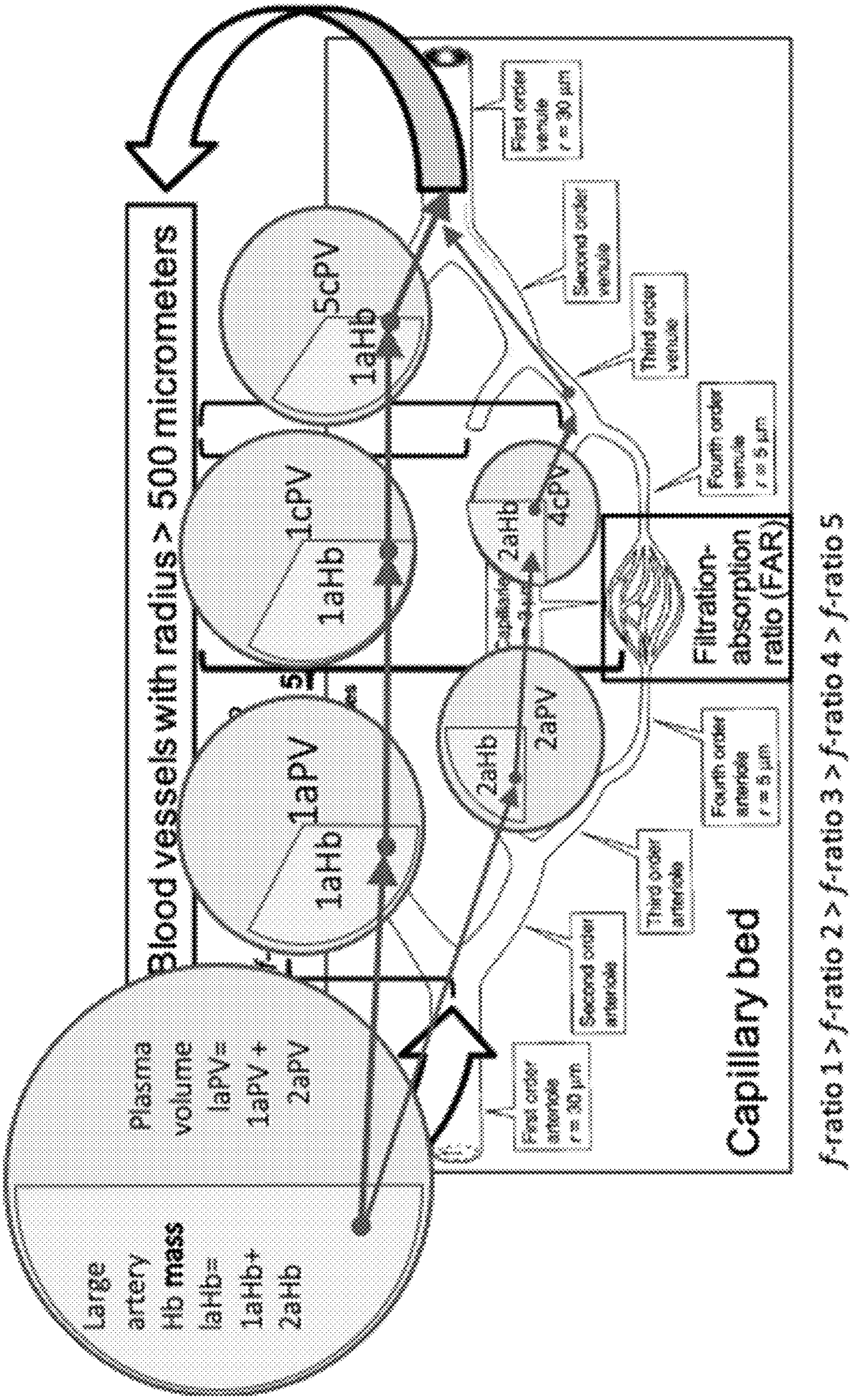
FIG. 56 illustrates the Fahraeus effect on difference in hematocrit between large vessels and capillaries in embodiments of the present invention.

A model for estimation of hydration levels based on relationships between changes in plasma dilution-PD (water is diluting plasma, not hemoglobin) and fractional changes in extravascular water (QewA) may be used. The model may take into consideration the relationship between changes in variables that are used as indication of changes in intravascular and extravascular fluid accumulation at specific tissue hydration levels (FIG. 55). Hydration levels are related to threshold states between necessary (beneficial) and detrimental fluid levels, and thus are used to provide alerts about imminent deteriorations. The system 100 of the present disclosure uses estimation of plasma dilution (PD), and hemodilution by accounting for f-ratio which is the Fahraeus effect related hematocrit (Hct) difference between blood vessels with different radiuses (FIG. 14), and the OLA math model and the below calculations.

U.S. Patent Application Publication No. 2011070210 filed Aug. 16, 2010 as a divisional of application Ser. No. 11/514,667 filed on Sep. 1, 2006 entitled SYSTEMS AND METHODS FOR HOMEOSTATIC BLOOD STATES discloses a mathematical model for determining HBS trends. The system of the present application improves on this disclosure and deploys additional mathematical models and avoids the need for fluid challenges such as used in VLT, and enables reliable discrimination between the extravasation of fluid via fluid elimination systems and via the shift into extravascular space (tissues), as well as detection of changes in RCM due to hemorrhage or transfusion, as well as imminent deteriorations in hydration status, intra- and extravascularly.

In addition to its inherent role in reflecting oxygen carrying capacity, Hct is one of the five major factors that affect plasma viscosity and red blood cell (RBC) function. In physiology textbooks and laboratory investigation handbooks, the highest critical Hct value is considered being 60% and the lowest below 15% (TAB. 1). Ideal plasma viscosity is when Hct is about 40%.

The BV consists of red cell mass (RCM) and PV. Under existing art, there are several methods for mathematical estimation of IBV, and IPV. If homeostasis unconditionally prioritized IBV, there would be dangerously abnormal PD when RCM is either low or high. If IBV was maintained with low RCM, the PV would be expanded to abnormally high PD which causes dilutional coagulopathy and other dangerous adverse effects. If IBV was maintained with high RCM, the PV would be depleted to abnormally low PD (plasma concentration) which causes deterioration of viscosity, aggregation of red blood cells, thrombosis and other adverse effects.

If homeostasis unconditionally prioritized IPV, there would be dangerously abnormal BV when RCM is either low or high. If IPV was maintained with low RCM, the BV would be reduced to abnormally low volume, hypovolemia and other adverse effects. If IPV was maintained with high RCM, the BV would be increased to abnormally high BV, hypervolemia, edema and other adverse effects.

According to the improved HBS method of the present disclosure, there is a balanced adaptation of BV and PV to changes in RCM so that neither BV, nor PV overcomes physiologically acceptable (acceptable, later in the text) limits. The acceptable limits of BV, PV and PD are not established. However, limits of acceptable Hct can be used as an indication of acceptable PD. The SoA range of acceptable Hct is from 60% to about 15%. Thus, acceptable limits of BV and PV are consistent with PD at these critical Hct values.

Figure 57:
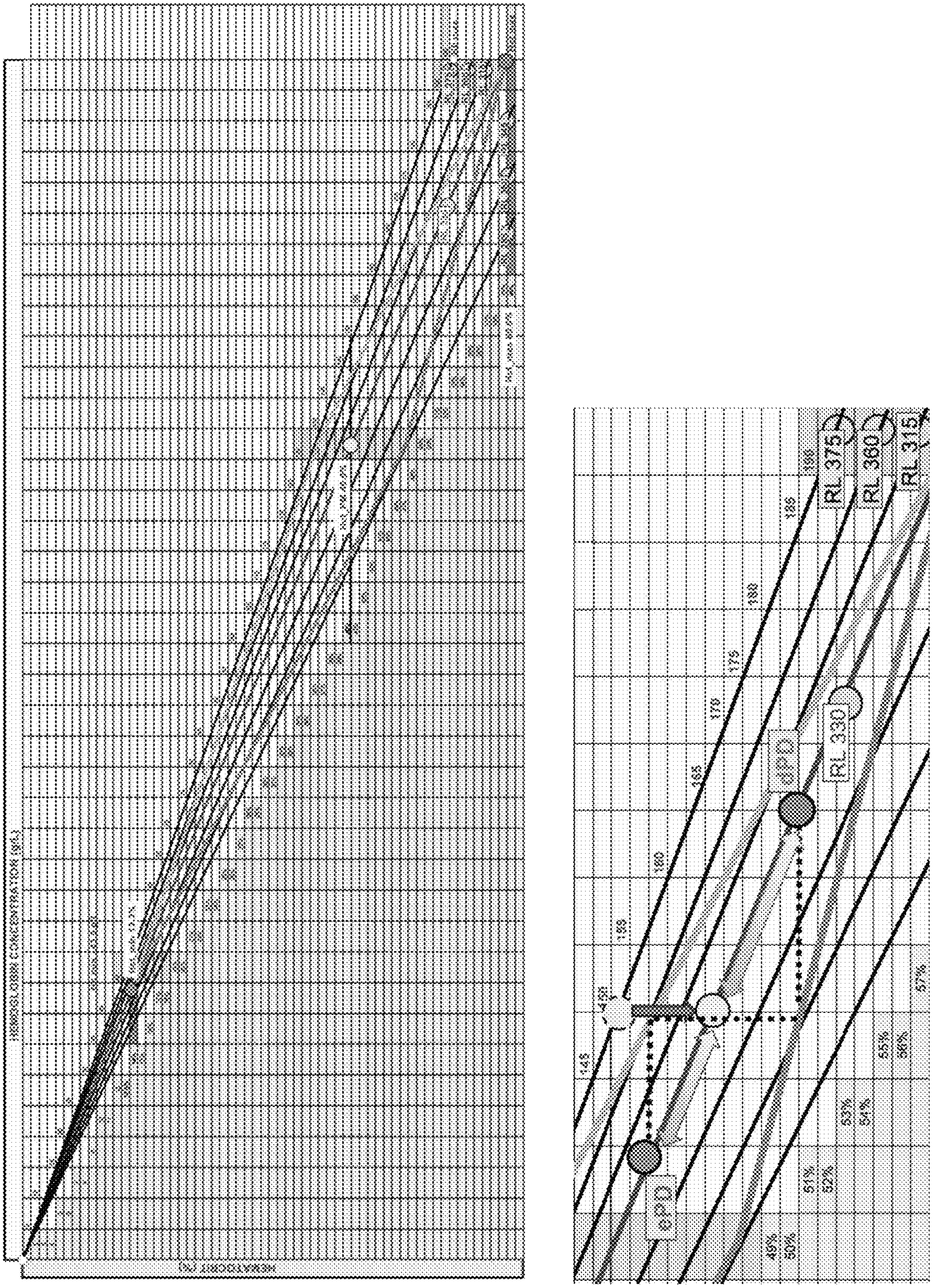
FIG. 57 illustrates an exemplary HBS Nomogram including radiating lines related to mean cell hemoglobin concentration with hemoglobin concentration on the X axis and Hct on the Y axis in accordance with an embodiment of the present disclosure.

The PD and PV have $PD_{max}$ and $PV_{max}$ at $Hct_{min}$ about 15%. The BV has $BV_{min}$ at $Hct_{min}$ about 15%, and $BV_{max}$ at $Hct_{max}$ about 60%. The PD and PV have $PD_{min}$ and $PV_{min}$ at $Hct_{max}$ 60%. Since BV and PV are already maximally deviated from IBV and IPV, there are no acceptable fluctuations in PD at Hct about 15% and 60% (FIG. 57).

The method discussed in U.S. Patent Application Publication No. 2011070210 includes a mathematical model for simulating the RCM specific amplitude of acceptable BV and PV fluctuations which depend on the selected values of $Hct_{min}$ and/or $Hct_{max}$ and/or $Hct_{PM}$, originally referred to as $Hct_{ITM}$, which is presumably reached and detected based on Volume Loading Test (VLT) that has limited clinical feasibility. Since BV and PV deviations from IBV and IPV at $Hct_{min}$ and $Hct_{max}$ are considered as acceptable, they are applied to define acceptable limits of BV and PV deviations due to changes in PD at Hct values between $Hct_{min}$ and $Hct_{max}$. The limits of PD fluctuation are thus maximal at Hct which is about the middle of the acceptable Hct range where IBV and IPV are maintained. This Het is referred to as hematocrit of Perfect Match ($Hct_{PM}$). Since these features apply to a specific (optimized, later in the text) combination of RCM, BV, PV and PD, the RCM specific Hct, BV, PV and PD are referred to as optimised—oHct, oBV, oPV and oPD.

Figure 58:
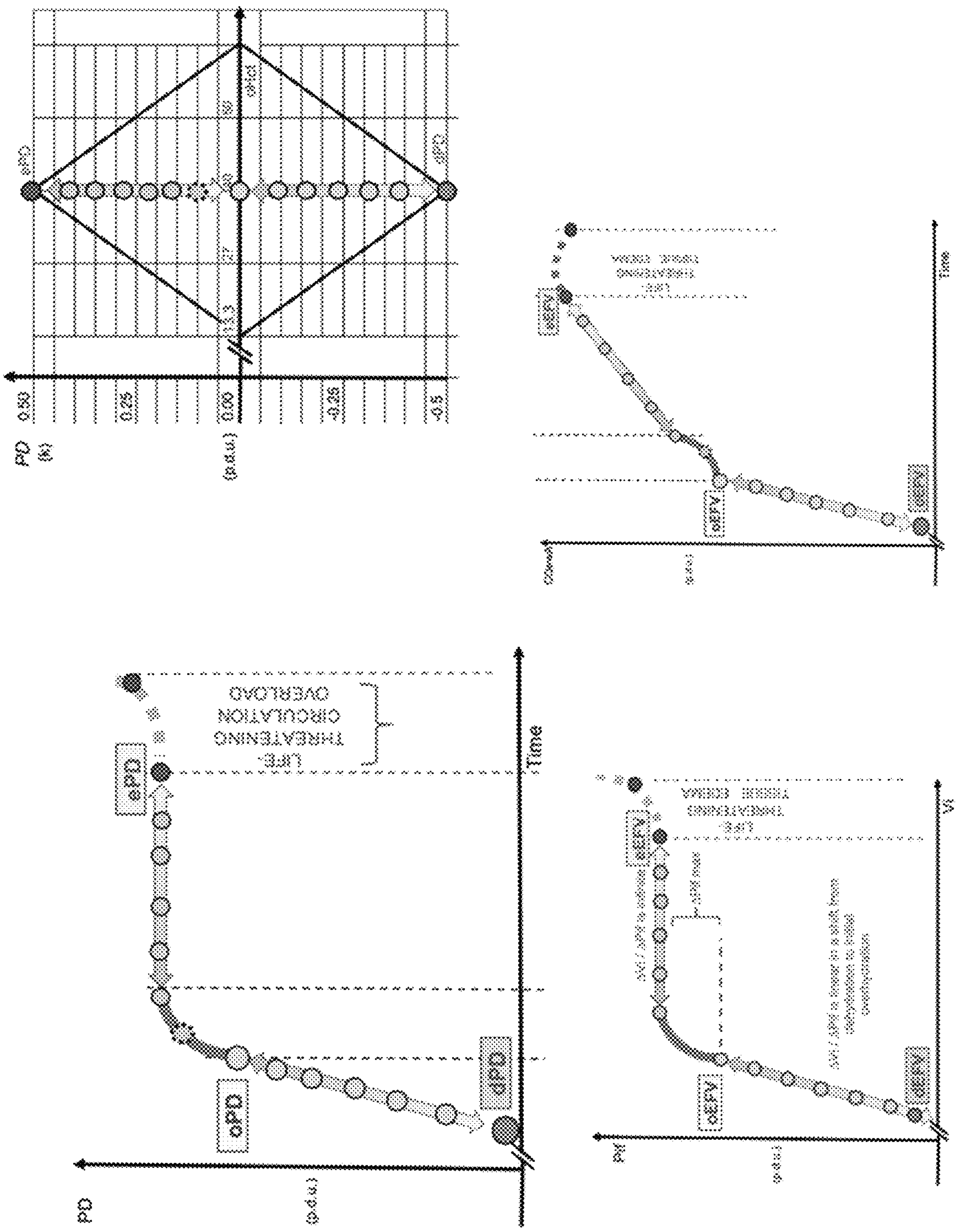
FIG. 58 illustrates examples of conceptual context-sensitive relationship between large vessel plasma dilution, interstitial compliance and changes in extravascular fluid volume where optimized hemocrit is 40% in accordance with an embodiment of the present disclosure.

According to this method, the acceptable deviations from oPD are when either BV or PV reach the 0.5k deviation from IBV or IPV. The constant k is calculated using the empirical values of HctPM and oHctmax or oHctmin, e.g. Constant k is 0.29 IBV when oHctPM is 40.0% and oHctmax is 60.0% and oHctmin is 13.3% (FIGS. 57-59) while k is 0.25 IBV when $oHct_{PM}$ is 37.5% and $oHct_{min}$ is 14.4%. Since ideal plasma viscosity is when Hct is about 40%, it suits to be considered as $Hct_{PM}$. Thus, for the explanation of revHBS technique, the Constant k=0.29 IBV, the $oHct_{PM}$ 40.0%, the $oHct_{max}$ 60.0% and the $oHct_{min}$ 13.3% are deployed.

oPD stays along the oHct range from $oHct_{min}$ 13.3% to $oHct_{max}$ 60% maintain increasing BV and PV deviations in respect to IBV and IPV when oHct shifts bi-directionally from $oHct_{PM}$. The oHct specific limit of maximal acceptable plasma dehydration is referred to as dehydrated plasma dilution (dPD), and oHct specific limit for maximal acceptable plasma over-hydration is referred to as excessive plasma dilution (ePD).

Figure 59:
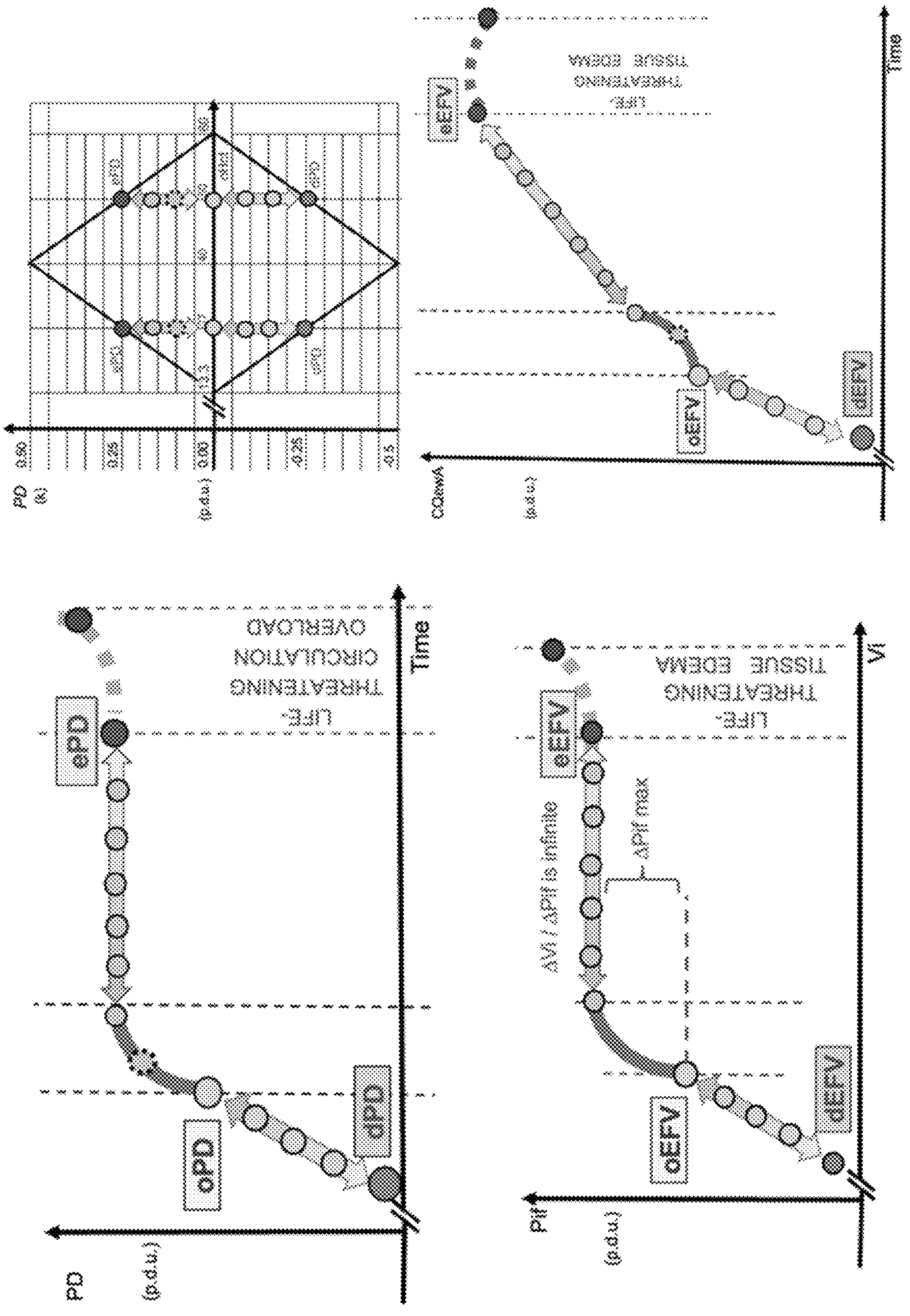
FIG. 59 illustrates examples of conceptual context-sensitive relationship between large vessel plasma dilution, interstitial compliance and changes in extravascular fluid volume where optimized hemocrit is 27% and 50% in accordance with an embodiment of the present disclosure.

The BV and PV associated with dPD are referred to as dehydrated blood volume (dBV) and dehydrated plasma volume (dPV), accordingly. Hematocrit is referred to as dehydrated-dHct. The BV and PV which are associated with ePD are referred to as excess-hydrated-eBV and ePV (FIG. 59). Hematocrit is referred to excess-hydrated-eHct. The oPD is the highest normal (safe, later in the text) PD which is an indication of highest normal plasma hydration status. The range between the RCM specific dPD and oPD is associated with the range of safe plasma hydration states. The circadian PD fluctuations in health occur within this range.

The range from oPD to ePD is referred to as abnormal (unsafe, later in the text) since it is related to excessive intravascular and potentially extravascular fluid accumulation (FIGS. 58-69). The homeostatic counteraction against a shift from oPD to ePD is explained by the possibility that, during evolution, the human body was mostly exposed to the lack of water rather than its abundance. Thus, a range from oPD to ePD is associated with risk of circulation overload and edema (increase in total body water). Homeostasis counteracts increase in PD over oPD by increasing fluid extravasation which is the net effect of elimination and shift into tissues. Fluid "drainage" from circulation into derma is the first line of immediate defense against intravascular fluid overload, and muscles get involved, if necessary, later. Elimination systems are activated with delay.

The improved HBS method (revHBS) of the present disclosure uses terms such as RCM specific optimized variables-oBV, oPV, oHct-which can be used interchangeably with terms homeostatic target values tBV, tPV and tHct, accordingly.

In embodiments, UI simulations may include a HBS Nomogram based on empiric estimates for minimal acceptable hematocrit (Hctmin) of 13.3%, hematocrit of Perfect Match (HctPM) of 40%, and maximal acceptable hematocrit (Hctmax) of 60%.

Figure 60:
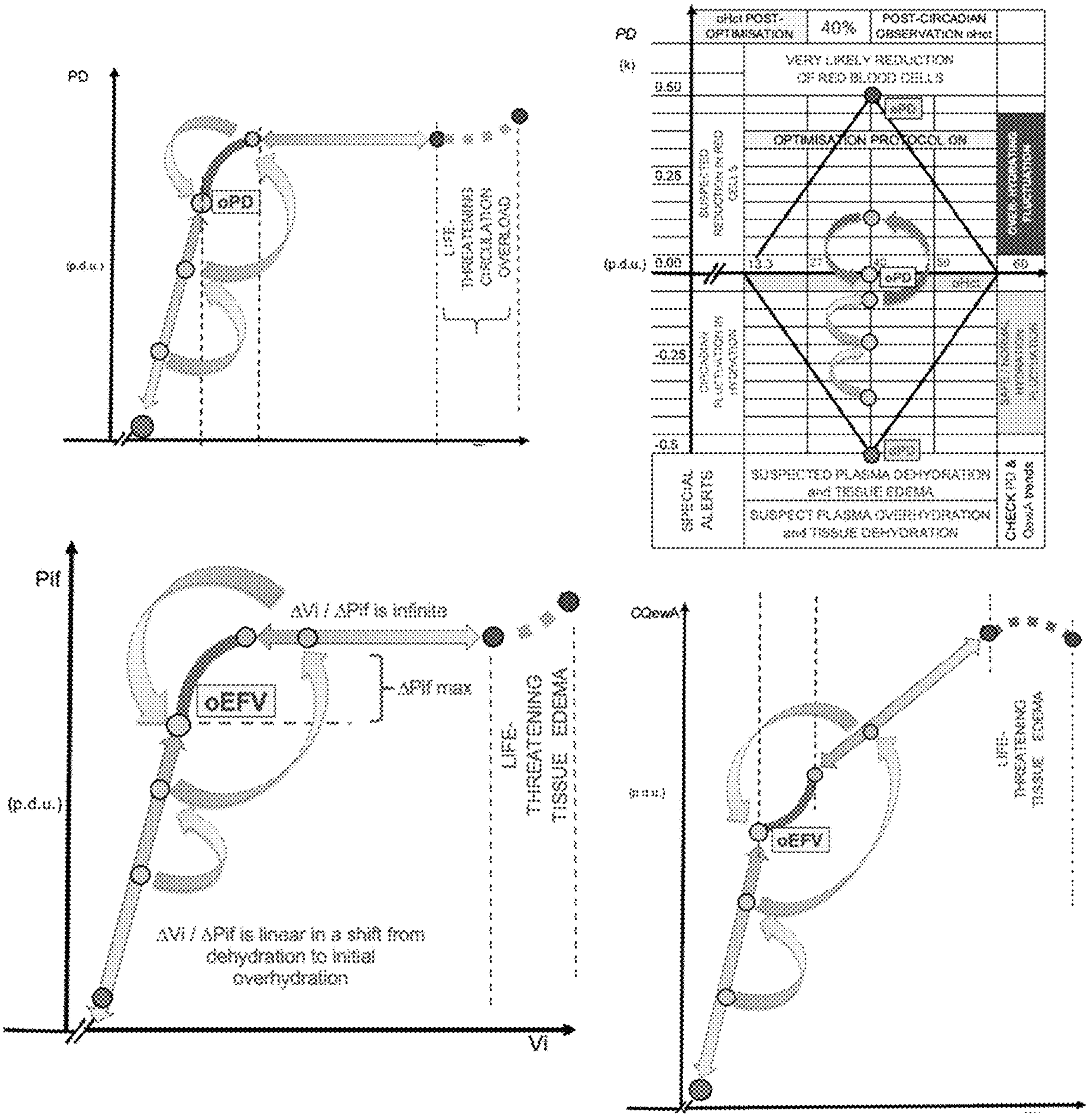
FIG. 60 illustrates examples of conceptual context-sensitive relationship between large vessel plasma dilution, interstitial compliance and changes in extravascular fluid volume during fluid administration which optimizes plasma and tissue hydration status in accordance with an embodiment of the present disclosure.
Figure 61:
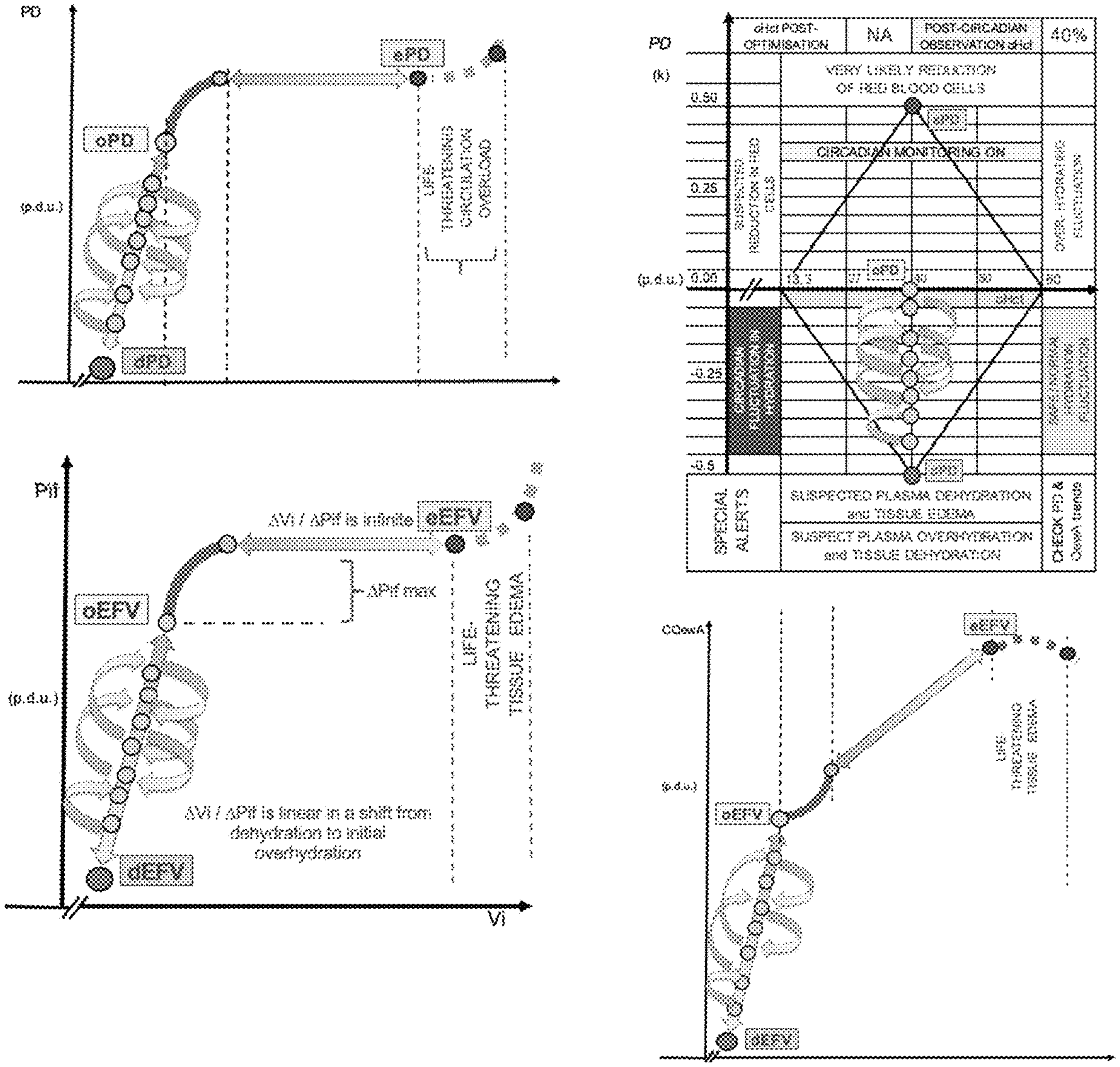
FIG. 61 illustrates examples of conceptual context-sensitive relationship between large vessel plasma dilution, interstitial compliance and changes in extravascular fluid volume during circadian rhythm related changes in variable (24 hours) in accordance with an embodiment of the present disclosure.
Figure 62A:
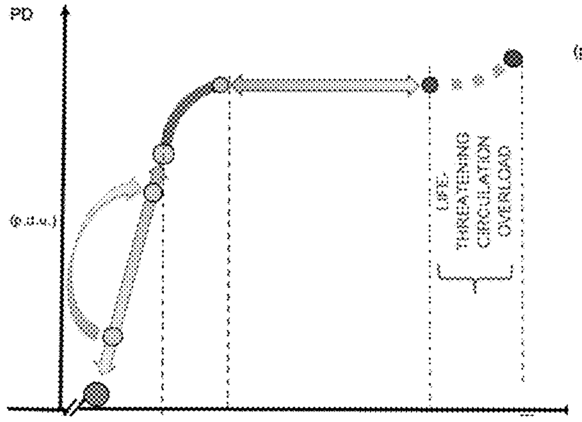
FIGS. 62A-62D illustrate examples of conceptual context-sensitive relationship between large vessel plasma dilution, interstitial compliance and changes in extravascular fluid volume during rehydration when plasma us more dehydrated compared to tissues in accordance with an embodiment of the present disclosure.
Figure 62B:
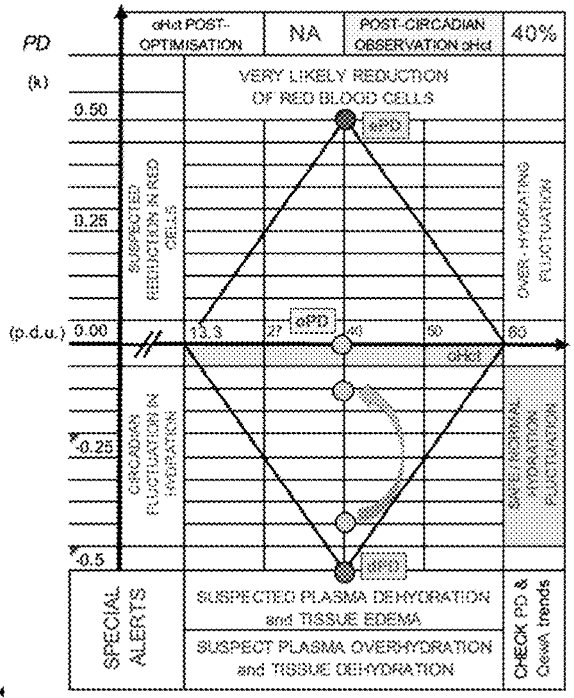
Figure 62C:
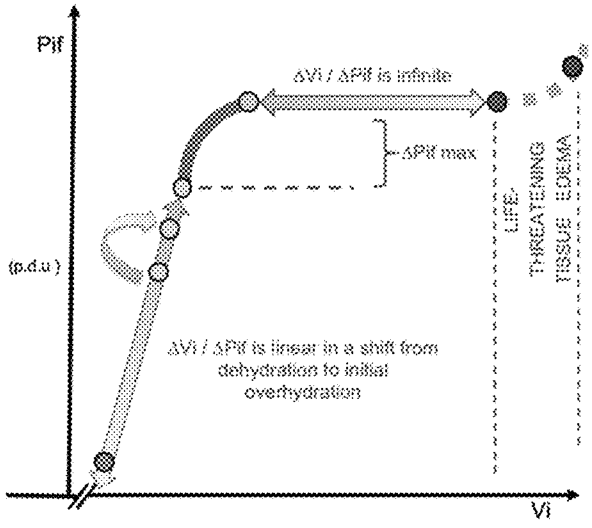
Figure 62D:
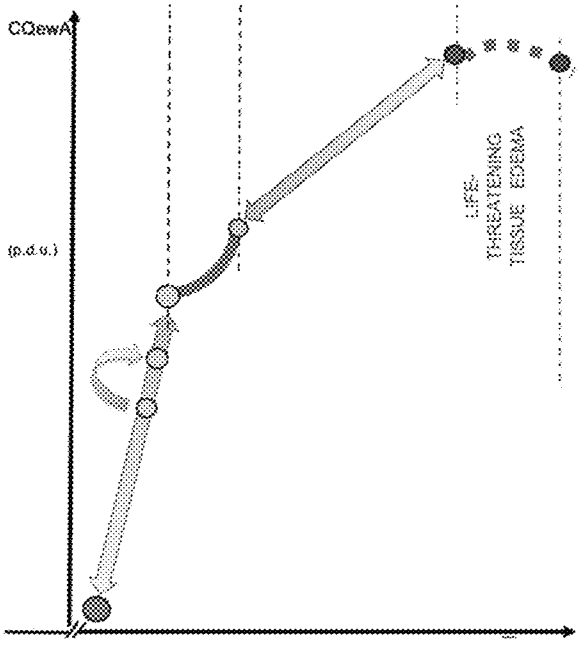
Figure 63A:
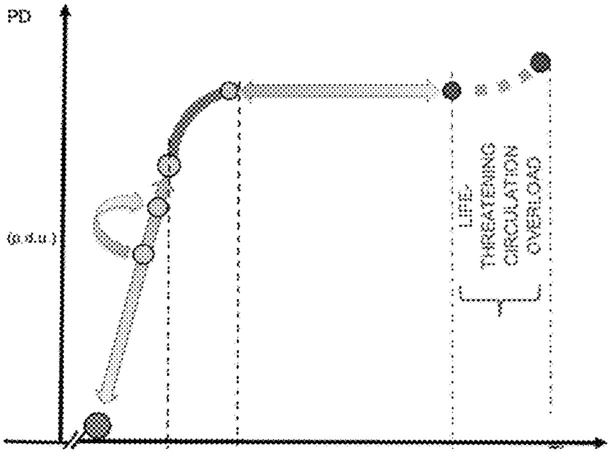
FIGS. 63A-63D illustrate examples of conceptual context-sensitive relationship between large vessel plasma dilution, interstitial compliance and changes in extravascular fluid volume during edema formation due to excessive fluid administration
Figure 63B:
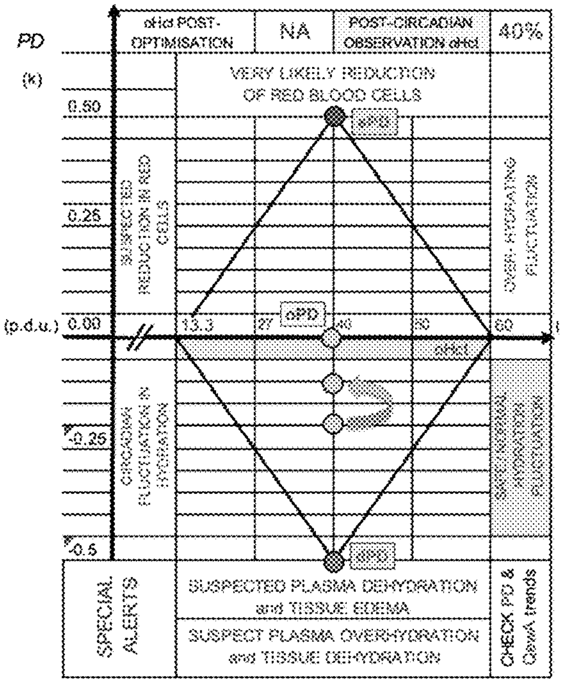
Figure 63C:
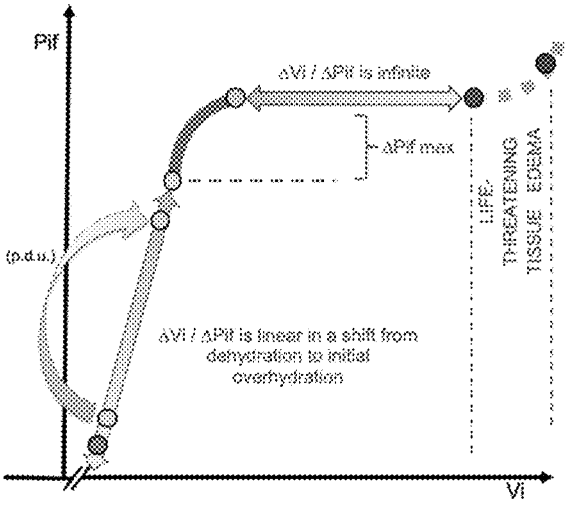
Figure 63D:
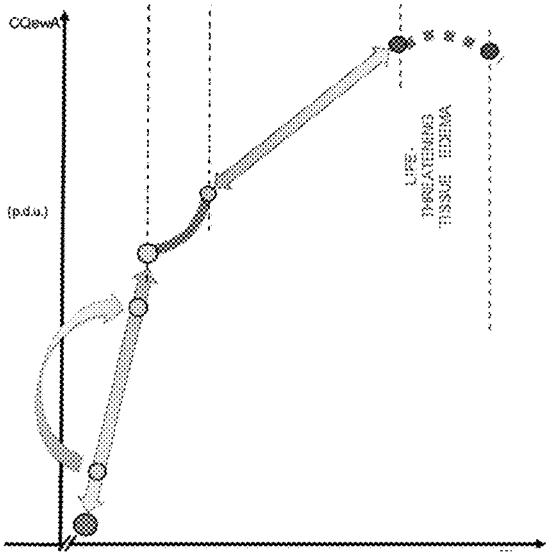
Figure 64:
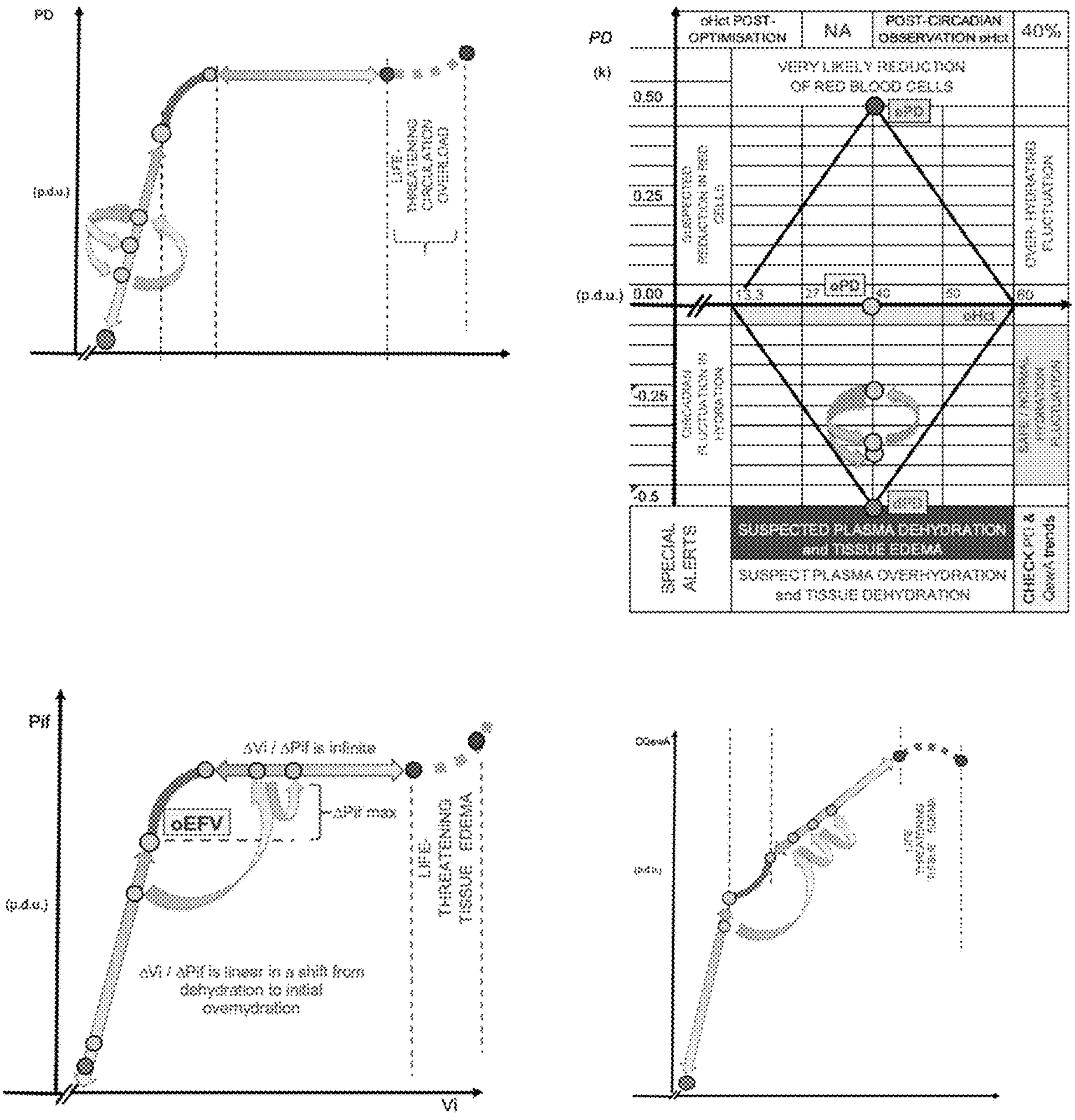
FIG. 64 illustrates examples of conceptual context-sensitive relationship between large vessel plasma dilution, interstitial compliance and changes in extravascular fluid volume during fluid administration and capillary leak, e.g. in sepsis, in accordance with an embodiment of the present disclosure.
Figure 65:
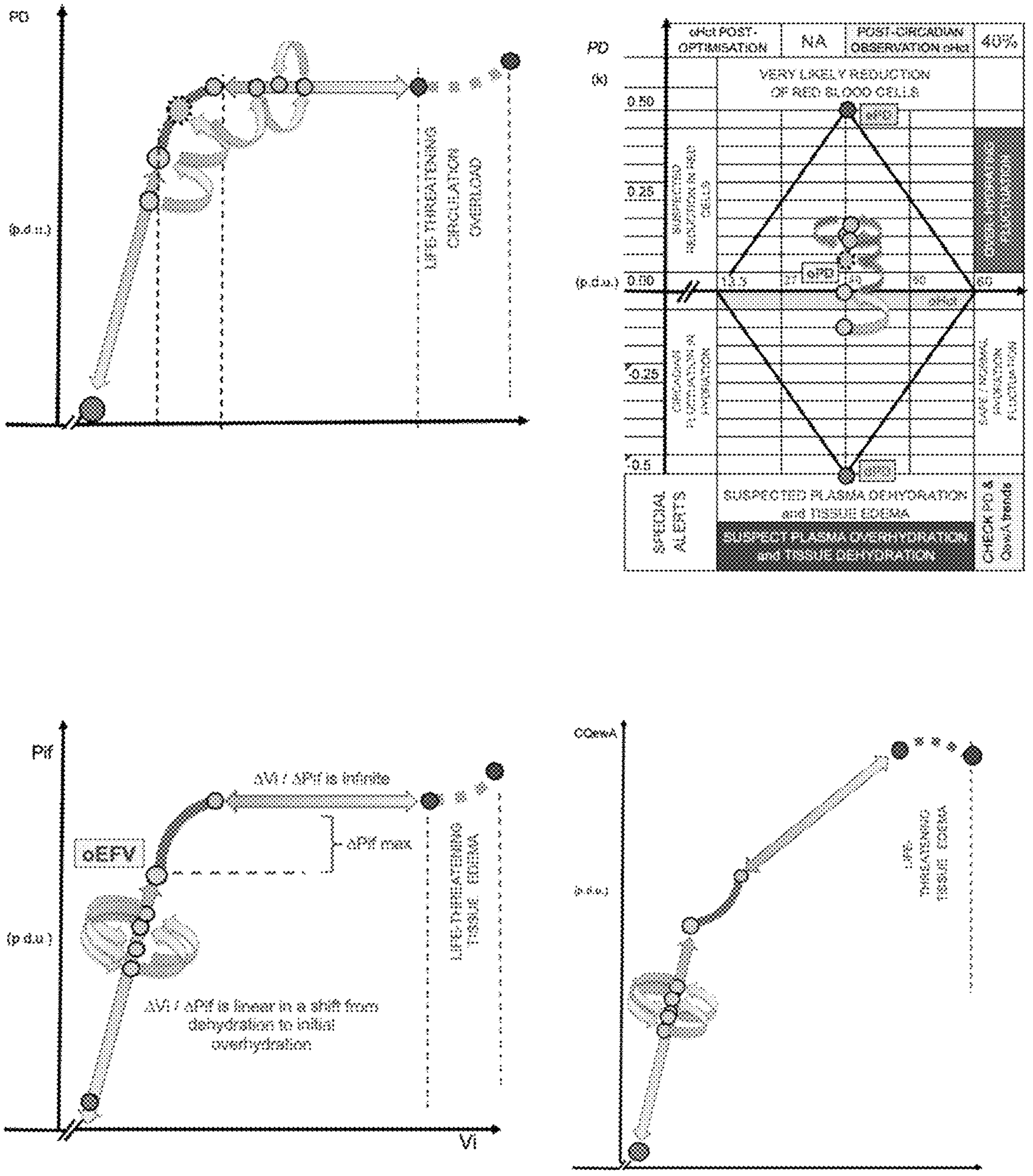
FIG. 65 illustrates examples of conceptual context-sensitive relationship between large vessel plasma dilution, interstitial compliance and changes in extravascular fluid volume during preferential fluid accumulation in circulation, e.g. in conditions with plasma hyperosmotality in accordance with an embodiment of the present disclosure.
Figure 66A:
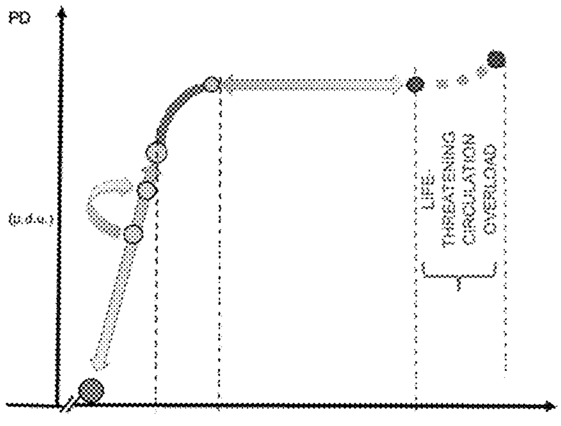
FIG. 66A-66D illustrates examples of conceptual context-sensitive relationship between large vessel plasma dilution, interstitial compliance and changes in extravascular fluid volume during fluid restriction and/or removal in accordance with an embodiment of the present disclosure.
Figure 66B:
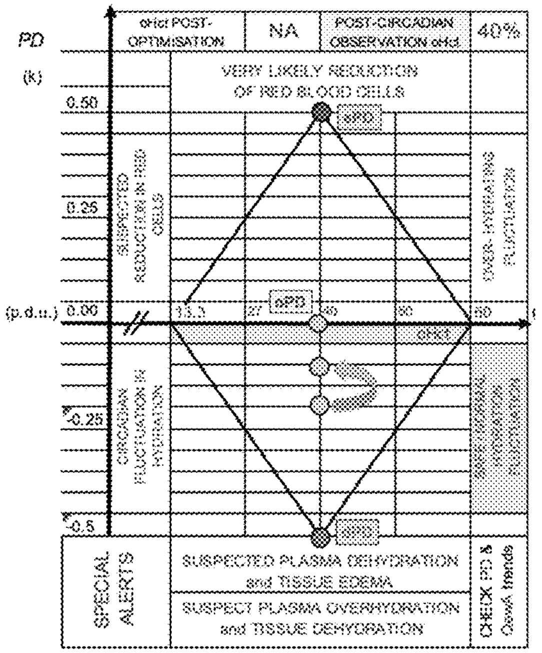
Figure 66C:
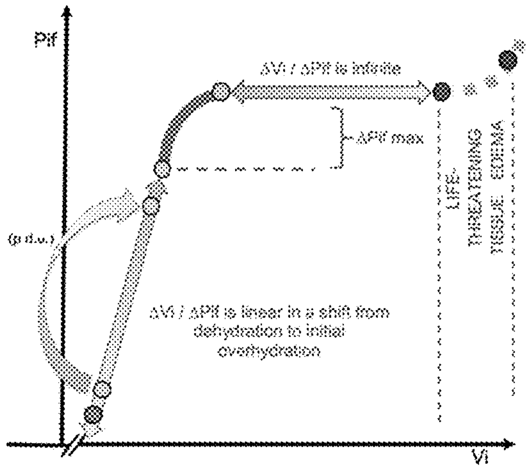
Figure 66D:
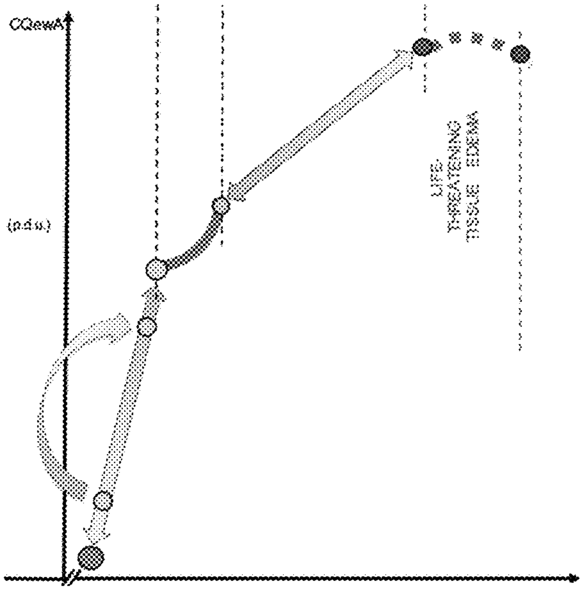

Fluid is distributed between intravascular and extravascular fluid spaces depending on their expansion by fluids (hydration status). Plasma dehydration may co-exist with tissue edema, and vice versa. Thus, when fluid is entering circulation in states of plasma and/or interstitial dehydration, there is no homeostatic counteraction since it is a necessary fluid. According to the system and method of the present disclosure fluid is proportionally distributed between blood and tissues, as reflected by good correlation between the PD and interstitial accumulation of water in tissues (QewA). Conceptual context-sensitive relationship between large vessel PD, (indication of intravascular fluid accumulation), interstitial compliance in skin and muscles and changes in extravascular fluid volume (QewA) may be used in the present method and system. However, fluid is retained more significantly in circulation when plasma is dehydrated more than tissues. Meanwhile, fluid tends to shift into interstitial more than being retained in circulation when tissues are dehydrated more than plasma (FIGS. 59-61).

Since there is poor relationship between intravascular and extravascular hydration status, the fluid distribution and accumulation in both compartments have to be evaluated by measuring fluid levels specifically in each compartment. Large vessel plasma dilution (lvPD) is continuously and noninvasively measured by SoA technologies. It is used for monitoring fluid levels in plasma provided RCM is unchanging. Meanwhile, monitoring interstitial fluid levels requires measuring changes in extravascular fluid, e.g. extravascular water (QewA). In addition to monitoring fluid distribution, trend analysis of PD and QewA (fractional changes over time) are used for detecting existing or imminent deterioration of hydration status, fluid underload or overload, specifically in circulation and/or in tissues, as well as discriminating between the change in PD due to change in hydration status and changes in PD due to change in RCM, e.g. due to hemorrhage.

The extravasation of fluid which enters circulation (digestion or intravenous infusion) is part of a non-stop process of fluid intake, elimination, distribution and re-distribution. The time required to assess the hemodiluting effect of ingested fluid and its distribution can vary based on several factors, including the type and volume of fluid ingested, individual physiology, and the method of assessment. The following timelines are used:

(1) Initial effects: within 15-30 minutes after ingestion, change in PD and eH2O compared to pre-fluid ingestion PD and eH2O is an indication of initial hydrating effect as fluid distribution has begun;

(2) Peak effects: the change in PD and QewAO compared to estimates of initial effects are estimated 1 and 2 hours post-ingestion, when the fluid is most uniformly distributed;

(3) Return to baseline: depending on the volume and type of fluid, it may take several hours (3-4 hours or more) to return to pre-fluid ingestion level provided no more fluid is taken.

According to the revHBS method of the present disclosure, the circadian rhythm related PD fluctuations in health occur within a range from dPD to oPD (FIGS. 49-61). The counteraction against getting into the range from oPD to ePD is related to the probability that during evolution the body was challenged by the lack of water rather than abundance. Thus, a range of PD from oPD to ePD is related to progressive circulation overload and tissue edema (increase in total body water).

Circadian cycle-related fluctuations in PD are influenced by physiological processes that follow a 24-hour cycle. Key factors include:

(1) Fluid Intake Patterns: People have varying fluid intake throughout the day, which can affect blood volume and hemodilution. Increased fluid intake during the day may lead to more pronounced hemodilution in the afternoon and evening.

(2) Hormonal Influences: Hormones such as aldosterone and vasopressin (ADH) exhibit circadian rhythms, impacting fluid retention and distribution. Higher levels of these hormones during certain times can promote fluid retention, potentially reducing hemodilution.

(3) Activity Levels: Physical activity tends to vary throughout the day, influencing blood flow and plasma volume. Increased activity can enhance circulation and may lead to temporary changes in hemodilution status.

(4) Metabolic Rate: The metabolic rate typically peaks in the late afternoon to early evening, which may also affect fluid dynamics and hemodilution as the body processes nutrients and fluids consumed during the day.

(5) Sleep-Wake Cycle: During sleep, there is a decrease in fluid intake and a potential increase in urine production due to hormonal changes, which can affect blood volume and concentration upon waking.

(6) Individual Variability: According to the SoA, the estimated average amplitude of Hct fluctuation is about 5%, but the amplitude of PD varies widely based on the context and individual circumstances. Individual differences, such as age, gender, and health status, can also influence the amplitude of these fluctuations. For example, athletes may experience more pronounced fluctuations due to their training and hydration practices.

Assessment of acute extravasation of intravenously infused crystalloid solutions is performed after equilibration period of 5 min (immediate equilibration) and 20-30 min (acute equilibration) after the end of infusion. It is applicable in fluid protocols that imply fluid challenges, a short and rapid infusion followed by equilibration period. Ideally, as a result of homeostatic counteraction to fluid infusion which overcomes oPD level, the PD after acute equilibration is at the level of oPD. Since PD after acute equilibration may not be consistent with oPD, the PD after equilibration is referred to as equilibrated plasma dilution (EQ_PD) which is consistent with equilibrated hematocrit (EQ_Hct)

According to the improved HBS method, ideally (provided there is good correlation between fluid accumulation in plasma and tissues) intravascular hydration is in perfect balance with extravascular hydration status. If so, intravascular fluid accumulation may be theoretically estimated based on PD trends. Ideally, the oPD is an indication of optimized extravascular fluid volume (oEFV) which is the highest normal (safe, later in the text) extravascular fluid volume (EFV), referred to as highest normal interstitial hydration status (FIGS. 49-61). Ideally, the dPD is an indication of dehydrated extravascular fluid volume (dEFV) which is the lowest safe EFV, referred to as lowest normal interstitial hydration status consistent with life threatening dehydration. Ideally, the ePD is an indication of excess-hydrated extravascular fluid volume (eEFV) which is the highest safe EFV, referred to as highest normal interstitial hydration status consistent with life threatening edema. Since ideal relationship between PD and EFV (FIGS. 49-61) is not warranted, the reliable evaluation of changes in EFV deploys the current invention technique for measuring changes in extravascular water (ΔeH2O). Ideally, during rehydration and initial overhydration, as well as during dehydration of plasma and tissues, there is good correlation between PD and QewA. The range between dPD and oPD corresponds to the range between the oEFV and the dEFV (FIGS. 49-61).

If interstitial fluid volume increases over oEFV level in skin and muscles, the interstitial fluid compliance starts increasing and eventually becomes infinite what allows translocation of fluid from overloaded circulation into tissues without any relevant counter-pressure. In such scenario, the PD increase slows while extravascular accumulation increases as indicated by the QewArend. It occurs temporarily when, e.g. short fluid infusion related PD overcomes oPD limit, and thus fluid is drained into derma shortly after infusion facilitating return of PD to oPD level. Relevant edema does not occur due to autoregulation of interstitial fluid volume, as well as fluid elimination from circulation which allows the transcapillary reflux of excessive tissue fluid without causing the PD increase over oPD level (FIGS. 49-61).

Circadian cycle related fluctuation in PD is between dPD and oPD, and fluctuation in extravascular fluid volume (QewA) is between dEFV and oEFV provided there are no conditions that predispose to fluid accumulation, e.g. heart failure and kidney injury (FIGS. 49-61).

If fluid overload in circulation increases further, the trend of slightly increasing PD over the oPD is associated with significantly increasing ΔeH2O, and edema formation. If fluid overload in circulation increases even further, the trend of slowly increasing PD is associated with the slower than before increase in ΔeH2O trend, and edema formation in derma since fluid accumulation in muscles becomes relevant. At this point, the interstitial fluid compliance in derma starts decreasing. The PD value is in the middle of the range between oPD and ePD. Eventually, life threatening fluid overload in circulation and tissues presents as good correlation between increase in PD and ΔeH2O. The PD value approaches the ePD level (FIGS. 49-61). However, such a balanced fluid distribution requires intact autoregulation, integrity of capillary barrier, cardiovascular function and elimination. Thus, assessment of extravascular fluid accumulation cannot rely on evaluation of PD.

According to the revHBS method, evaluation of actual accumulation of intravascular and extravascular fluid deploys assessment of correlation between estimated PD and QewA trends based on the measurement of both PD and eH2O.

The above described interpretation of correlation between trends applies. Additionally, interpretation of PD and QewA under circumstances when the correlation is poor or none is provided. Correlation is lost in conditions such as heart failure, kidney injury, capillary leak and many other (FIGS. 49-61). When PD is stable or slowly increasing or decreasing within the safe range between dPD and oPD (limits of normal plasma hydration-normal plasma hydration fluctuation range) (FIGS. 49-61). While QewA is significantly increasing suggests capillary leak and edema formation, e.g. in sepsis and while QewA is significantly increasing suggests rehydration when tissues are more dehydrated compared to plasma. While QewA is significantly decreasing, suggests capillary refill due to osmotic drive and/or hypovolemia and/or plasma dehydration and/or diuretic administration and/or edema resorption (e.g. after rescue phase of fluid therapy), and/or during renal replacement therapy (RRT). Ideally, during RRT, capillary refill and fluid elimination by RRT is equal to the reduction in eH2O; thus, PD stays stable while $eH_2O$ significantly decreases. This may be used for guiding the RRT settings with an aim to avoid hemodynamic deterioration during the procedure (FIGS. 49-61).

Refilling of the vascular space through absorption of interstitial fluid by micro vessels is a crucial mechanism for maintaining hemodynamic stability during hemodialysis (HD) and allowing excess fluid to be removed from body tissues. The rate of vascular refilling depends on the imbalance between the Starling forces acting across the capillary walls as well as on their hydraulic conductivity and total surface area. Various approaches have been proposed to assess the vascular refilling process during HD, including the so-called refilling coefficient (Kr) that describes the rate of vascular refilling per changes in plasma oncotic pressure, assuming that other Starling forces and the flow of lymph remain constant during HD. The Kr decrease during HD is attributed to a HD-induced decrease in the whole-body capillary hydraulic conductivity (LpS). However, studies reveal that Kr is not a good marker of LpS and should not be used to guide fluid removal or to assess the fluid status.

When PD is stable or slowly increasing or slowly decreasing within the unsafe range between oPD and ePD (limits of excessive plasma hydration-over-hydrating PD fluctuation range): while ΔeH2O is significantly decreasing suggests fluid overload in both intravascular and extravascular spaces, as well as capillary refill due to diuretic administration, and/or edema resorption (e.g. after rescue phase of fluid therapy), lymphatic drainage, and/or inadequate RRT, etc.

According to the revHBS method, evaluation of hydration status and its changes based solely on a QewA trend in derma implies fitting its trend patterns to the SoA patterns of interstitial fluid compliance in skin and muscles (FIGS. 49-61).

According to the revHBS method, the decrease in RCM (e.g. hemorrhage) presents with significant and rapid increase in PD over the oPD level and moving towards and even above the ePD level without a corresponding increase in QewA or especially a significant decrease in QewA. The increase in RCM (e.g. blood transfusion) presents with a reverse trends with significant and rapid decrease in PD towards the dPD level and/or below it without a corresponding decrease in QewA or especially a significant increase in QewA. (FIGS. 19-61).

Figure 67:
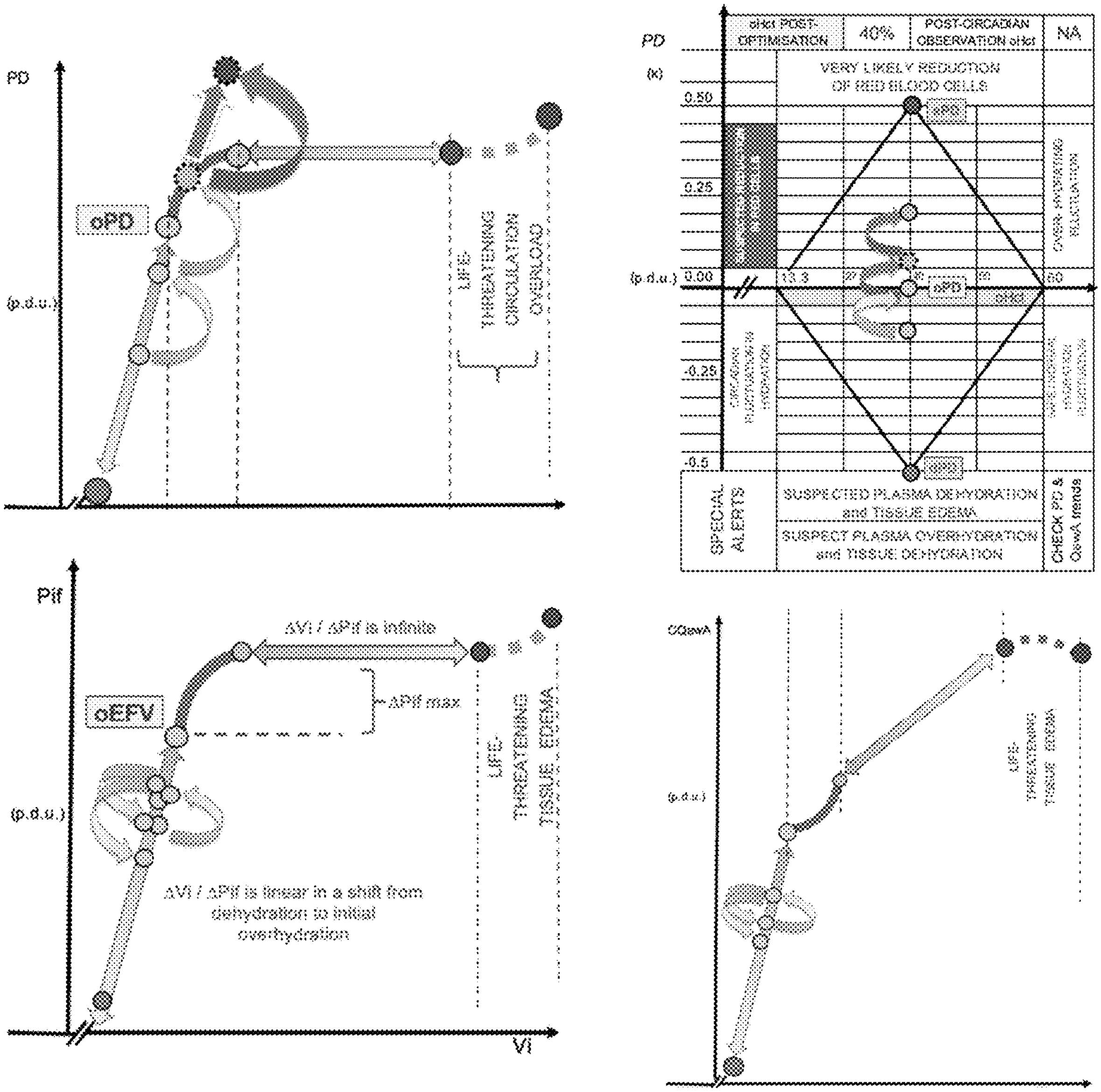
FIG. 67 illustrates examples of conceptual context-sensitive relationship between large vessel plasma dilution, interstitial compliance and changes in extravascular fluid volume during suspected red cell loss, e.g, hemorrhage or blood donation in accordance with an embodiment of the present disclosure.
Figure 68:
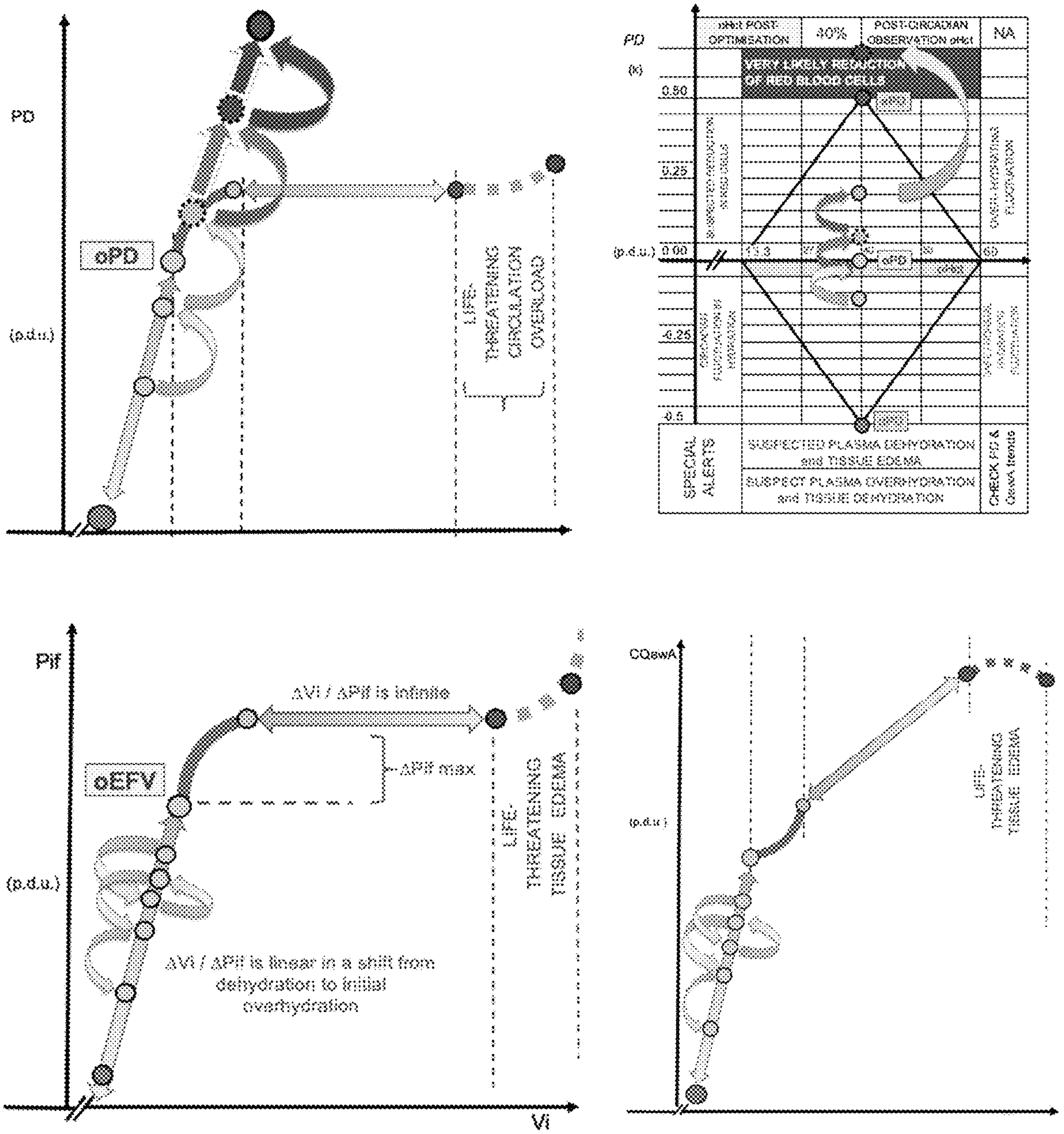
FIG. 68 illustrates examples of conceptual context-sensitive relationship between large vessel plasma dilution, interstitial compliance and changes in extravascular fluid volume during very likely red cell loss, e.g, hemorrhage or blood donation in accordance with an embodiment of the present disclosure.
Figure 69:
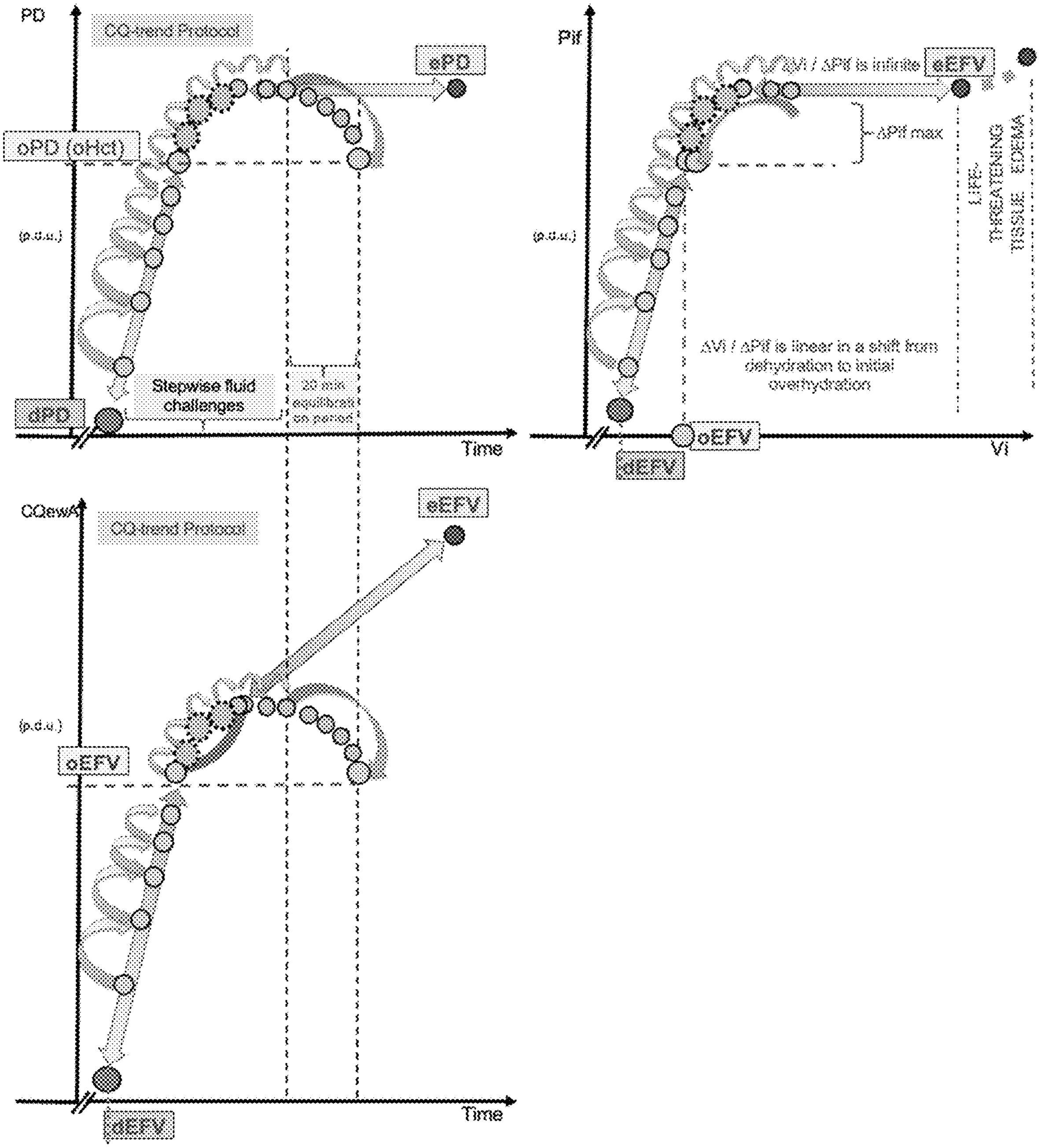
FIG. 69 illustrates examples of conceptual context-sensitive relationship between large vessel plasma dilution, interstitial compliance and changes in extravascular fluid volume during PD and Hct Optimization using goal direct fluid challenges in accordance with an embodiment of the present disclosure.

The conventional Nomogram includes radiating lines (RL) which indicate mean cell hemoglobin concentration (MCHC); hemoglobin concentration (Hb) is in axis X, and Hct in axis Y (FIG. 67, lower table). Typically, normal large vessel hemoglobin concentration (lvHb) is 135 to 17.5 g/L for men, and 120 to 155 g/L for woman. The highest physiologically acceptable lvHb is around 180 to 200 g/L. Levels above this range can be associated with various conditions, such as Polycythemia vera, a blood disorder that leads to an increased production of red blood cells, Chronic hypoxia often seen in individuals living at high altitudes or those with chronic lung diseases. While some athletes may achieve higher levels due to adaptations from training at high altitudes, levels consistently above 200 g/L lead to dangerously increased blood viscosity. Maximal Hb in the SoA HBS Nomogram is 200 g/L.

The preferred conventional method for estimating IBV is Nadler's formula which estimates IBV based on a person's body surface area (BSA). For men, this estimate is provided as below:

$$\text{Blood Volume (mL)} = 0.366 \times BSA(\text{m}^2)3/2 + 0.054 \times \text{weight (kg)}$$

For women, the estimate is defined by the below:

$$\text{Blood Volume (mL)} = 0.356 \times BSA(\text{m}^2)3/2 + 0.033 \times \text{weight (kg)}$$

In embodiments, Body Surface Area (BSA) is estimated using the Du Bois formula:

$$BSA(\text{m}^2) = 0.007184 \times \text{weight(kg)}0.425 \times \text{height(cm)}0.725$$

IPV is calculated by SoA methodology as follows:

$$IPV = IBV(1 - oHctPM)$$

where IPV is ideal/normal plasma volume, IBV is ideal/normal blood volume and oHctPM is optimised hematocrit at the Perfect Match.

Optimised hematocrit (oHct) value specific RCM is estimated using the the HBS method's equation:

$$RCMn = Cn\ (IBV + IPV\ (1 - oHctn) - 1))oHctn$$

where RCMn is red cell mass inherent to oHct value n, Cn is coefficient C, which is inherent to oHct value n, IBV is ideal blood volume, IPV is ideal plasma volume and oHct is optimised hematocrit value n and Coefficient C is inherent to oHct value and n estimated using the HBS method's equation:

$$C_n = \left((IBV + IPV)/(2 - oHct_n)\right)/\left(IBV + IPV/(1 - oHct_n)\right)$$

where Cn is Coefficient C inherent to target Hct value n, IBV-ideal blood volume, IPV is ideal plasma volume, oHct is optimised hematocrit value n.

Or:

$$C_n = ((IBV + IBV(1 - HctPM))\,(2 - oHctn) - 1)/\left(IBV + IBV(1 - Hct_{PM})(1 - oHct_n) - 1)\right)$$

where Cn is coefficient inherent to oHct value n, IBV is ideal blood volume, $Hct_{PM}$ is optimised hematocrit at the Perfect Match, and oHct is optimised hematocrit value n.

Optimised blood volume (oBV) may be estimated using the patented HBS method's equation:

$$oBV_n = 0.5\,(IBV + IPV + RCM_n)$$

where oBVn is optimised blood volume when oHct value is "n", IBV ideal blood volume, IPV ideal plasma volume and RCMn is the oHct value "n" specific red cell mass.

Optimised plasma volume (oPV) is estimated using the patented HBS method's equation:

$$oPV_n = oBV(1 - oHct_n)$$

The oHct specific maximal acceptable plasma hydration origin deviation in plasma volume (APV) (MAD). Equations are applicable when $oHct=Hct_{PM}$ and $oHct<Hct_{PM}$. Maximal acceptable plasma over-hydration volume for a given oHct is a volume of ePVD positive deviation from oPV based on the equation:

$$ePVD_n = IPV + 0.5\,k - oPV_n$$

where ePVn is maximal acceptable PV over-dilution inherent to $oHct_n<Hct_{PM}$, IPV is ideal plasma volume, k is constant k, $oPV_n$ is optimised plasma volume at $oHct_n<Hct_{PM}$.

$$ePV = oPV + ePVD$$

Maximal acceptable dehydration volume for a given oHct is a volume of negative dPV deviation from oPV:

$$dPVD_n = oBV_n - IBV + 0.5\,k$$

where $dPV_n$ is maximal acceptable plasma dehydration inherent to $oHct_n<Hct_{PM}$, $oBV_n$ is optimised blood volume inherent to $oHctn<Hct_{PM}$, IBV is ideal blood volume and k is constant k.

Maximal acceptable plasma over-hydration volume for a given oHct is a volume of positive ePV deviation from oPV:

$$ePVD_m = IBV + 0.5\,k - oBV_m$$

where $ePV_m$ is maximal acceptable plasma over-dilution inherent to $oHctm>Hct_{PM}$, IBV-ideal blood volume, k constant k and $oBV_m$ is optimised blood volume at $oHctm>Hct_{PM}$.

Maximal acceptable plasma dehydration volume for a given oHct is a volume of negative dPV deviation from oPV:

$$dPVD_m = oPV_m - IPV + 0.5\,k$$

where $dPV_m$ is maximal acceptable plasma dehydration volume inherent to $oHctm>Hct_{PM}$, $oPV_m$ optimised plasma volume at $oHct_m>Hct_{PM}$, IPV is ideal plasma volume and k is constant k.

Constant k is calculated as following:

$$k = IPV + RCM_{max} - IBV = IBV(1 - Hct_{PM}) + RCM_{max} - IBV$$

where k is constant k, IPV is ideal plasma volume, IBV is ideal blood volume, $Hct_{PM}$ hematocrit of perfect match, $RCM_{min}$ is red cell mass at minimal acceptable hematocrit ($Hct_{min}$).

Alternatively $$k = IBV - RCM_{min} - IPV = IBV - RCM_{min} - IBV(1 - Hct_{PM})$$

where k is constant k, IBV is ideal blood volume, IPV is ideal plasma volume, $Hct_{PM}$ is hematocrit of perfect match, and $RCM_{max}$ is red cell mass at maximal acceptable hematocrit ($Hct_{max}$).

In general, Hct is lower in capillaries depending on their radius due to the Fahraeus effect. In general, Capillary Hct (cHct) is ½ to ⅓ of large vessel hematocrit (lvHct). For example, experimental data provides an f-ratio of 0.35 to 0.8 for the ratio of "tissue hematocrit"/lvHct in liver and kidney. Hct may be a calculated value (percentage or dimensionless fraction) which is a ratio RCM to BV. The system 100 does not provide estimation of RCM directly from PPG data, however, a threefold conversion commonly used under existing art may be used:

a.

$$Hct = 3\,Hb\,(\%)$$

where Hb (hemoglobin concentration) is measured in (g/dl), or b.

$$Hct = 0.3\, Hb\, (\%)$$

where Hb is measured in (g/l).

or c.

$$Hct = 100 * Hb/MCHC\, (\%)$$

where d.

$$Hb = 100 * Hbm/BV\, (\mathrm{g/l})$$

where Hct is hematocrit (%), Hb is hemoglobin concentration in (g/l), MCHC is average normal value of mean cell hemoglobin concentration–330 (g/l). Hbm is hemoglobin mass (g) and BV is the blood volume (L).

e.

$$MCHC = 100 * Hb/Hct$$

where Hb is hemoglobin concentration in (g/l), Hct is hematocrit (%).

The mean normal MCHC value (mMCHC) is around 330 (g/L). The MCHC is equal in large vessels and capillaries.

In embodiments, the mean normal MCHC value (mMCHC) is around 330 (g/L). The MCHC is equal in large vessels and capillaries.

The system 100 uses data processing utilizing unique variables as set forth below:

thA-light attenuation (p.d.u.) by total hemoglobin (mass) as indication of net capillary hemoglobin mass (measurable by invented technique), tiwA-light attenuation (p.d.u.) by net intravascular water as indication of the amount of capillary water ($cH_2O$) (measurable by invented technique), ewA-light attenuation (p.d.u.) by extravascular water as indication of the amount of extravascular water ($eH_2O$) (measurable by invented technique), cHb—capillary hemoglobin concentration (p.d.u.) (estimated by invented technique), cHct-capillary hematocrit (%) (estimated by invented technique), plvHct-predicted large vessel hematocrit (%) (estimated by invented technique), plvHb-predicted (estimated) large vessel hemoglobin concentration (g/L).

The method and system of the present disclosure utilizes unique mathematical formulas to determine the variables used.

Estimating plvHct-predicted (estimated) large vessel hematocrit (%) using the following equation:

$$plvHct = cHct/f{-}ratio = 1000 * thA/(mMCHC * tiwA)$$

where cHet is capillary hematocrit, thA is net capillary hemoglobin mass, tiwA is total intravascular water; depending on availability, alternative variables-pulsatile hemoglobin mass (phA) and amount of pulsatile water (pwA), or or non-pulsatile hemoglobin mass (nhA) and non-pulsatile water (nwA) can be used; mMCHC is mean normal MCHC value which is around 330 (g/L), and f-ratio is the arbitrary f-cell ratio of 0.3

Estimating plvHb-predicted (estimated) large vessel hemoglobin concentration (g/L):

$$plvHb = 0.01 * plvHct * mMCHC$$

where plvHct is predicted (estimated) large vessel hematocrit, and mMCHC is mean normal MCHC value which is around 330 (g/L).

In embodiments, fractional changes in light attenuation by expandable media (QA) indicates change in V of expandable media. The QA trends include Inter-session (fractional) change in A where the term "session" refers to the time-point when the measured or estimable A of a relevant variable is obtained. Every session implies measuring a variable for one minute, and at the end of it an average A value is derived after filtering errors, eliminating outliers, and Spectrophotometric Signal Processing (SSP) is completed. Equations apply to any static variables used in the invented data processing and monitoring changes over time. One variable is used in these equations, e.g. fractional change in extravascular water (Q_ewA) deploys estimated ewA value. Only trends of PD, a special kind of QA trend, consists of variable—the PD-which are estimated by different equation because it uses Hb and Hct.

Generating a QA-trend including fractional changes in extravascular water (QewA) over time, and a special kind of QA-trend which includes predicted large vessel plasma dilution (plvPD) changes over time, and or actual large vessel plasma dilution (lvPD) changes over time provided external SoA data is available.

Figure 70:
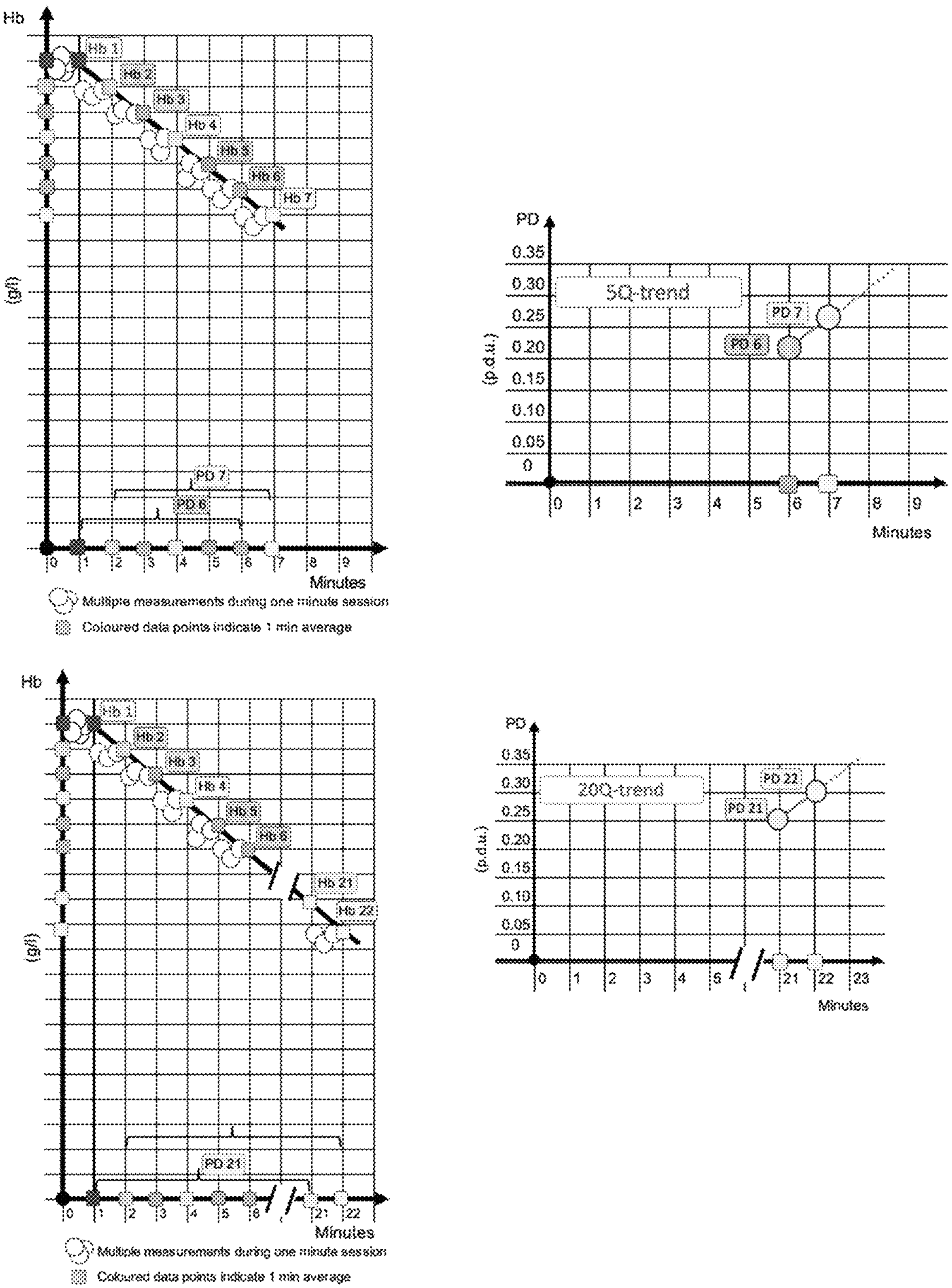
FIG. 70 illustrates three default types of QA trends relating to immediated intercession changes, acute intercession change and continuous Q-trend in accordance with an embodiment of the present disclosure.
Figure 71:
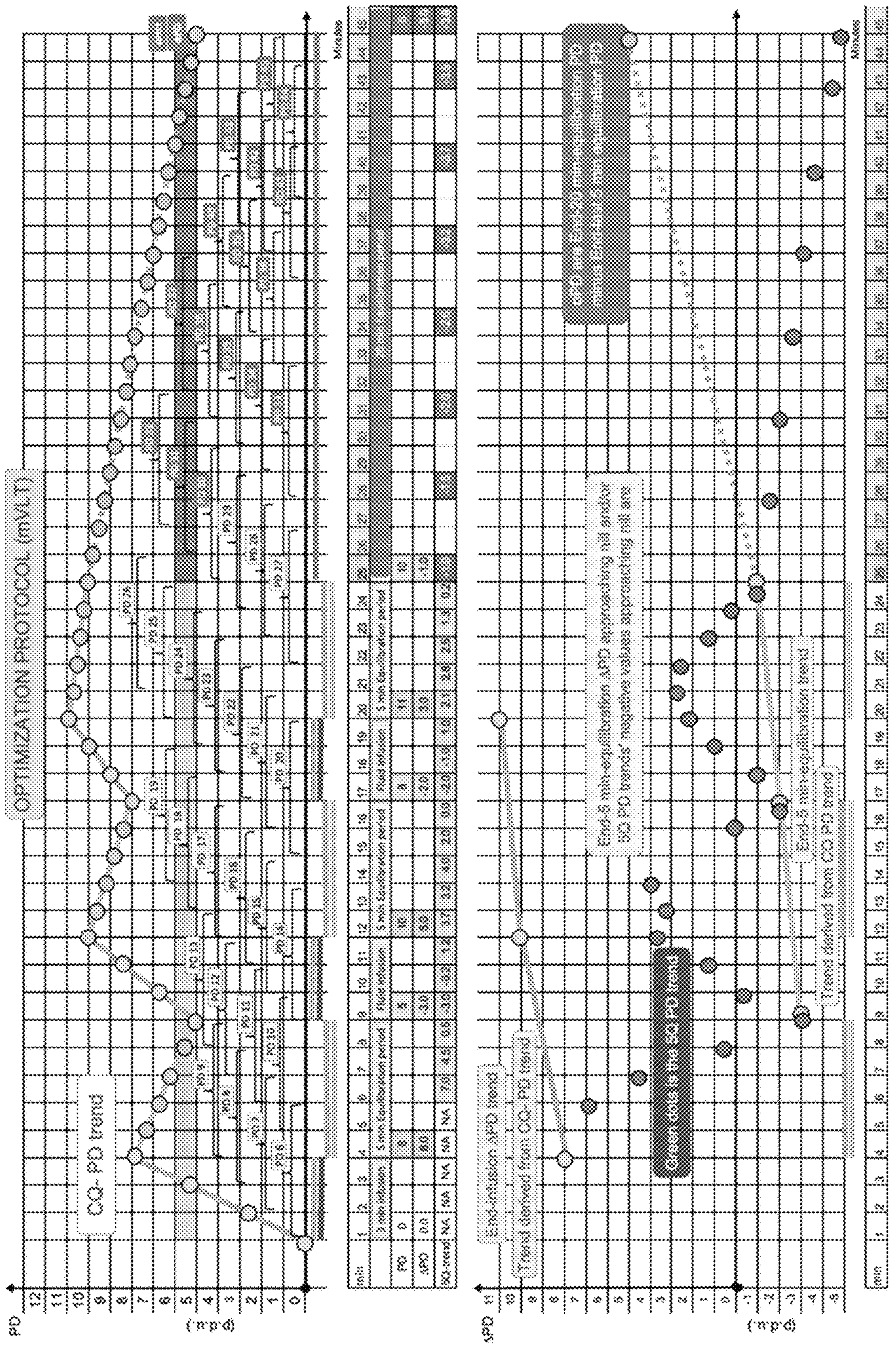
FIG. 71 illustrates an exemplary optimization protocol in which the relationship between the continuous and 5 minute trend is illustrated.
Figure 73A:
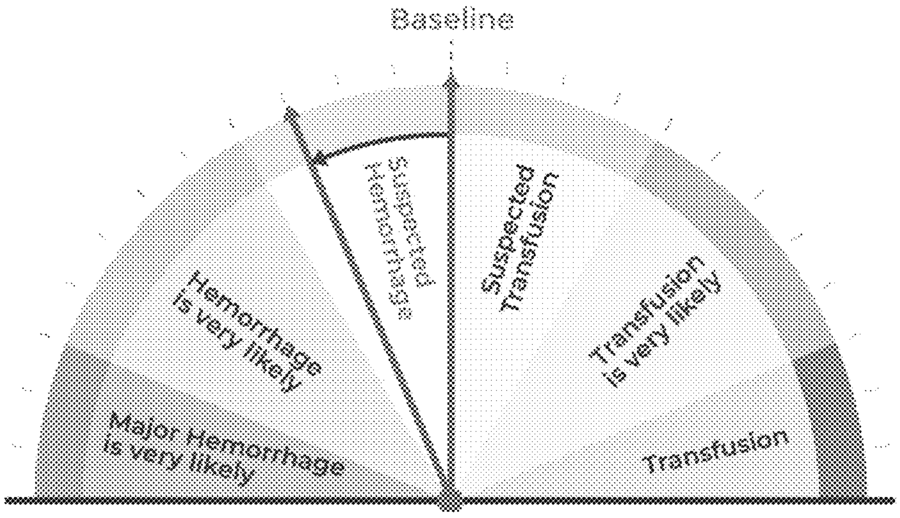
FIG. 73A-73B illustrates an example of RCm and body hydration monitorin using a non-medical device in accordance with an embodiment of the present disclosure.
Figure 73B:
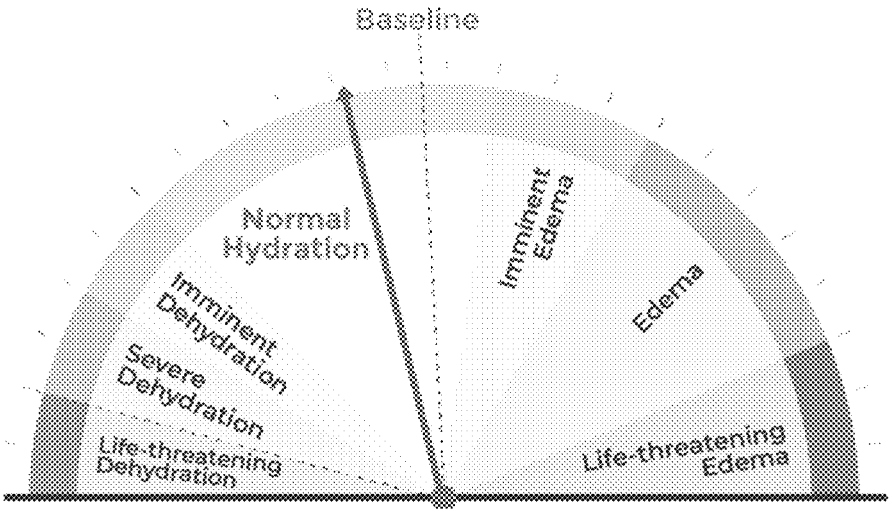

There are three default types of QA trends (trend examples are solely for illustration of time-points, and thus trends are arbitrary indicating linear relationship):

a. 5Q-trend is an Immediate Inter-session change which is the difference in plvPD between sessions separated by 5 min (Higher-Order Finite difference), e.g. between session n.1 and session n.6, session n.2 and session n.7, and so on; thus, the 5Q-trend begins with $plvPD_6$ value which is 6 min after the start of measurements; all consecutive plvPD values appear every minute; every plvPD value in the trend indicates a change in variable during the last 5 minutes, e.g.:

$$QA_6 = (A_6 - A_1)/A_1$$

where $QA_6$ is a fractional change in variable, e.g. in extravascular water (ewA) amount, during a 5 min period from the end of session n.1 to the end of session n.6 (FIG. 70).

b. 20Q-trend is an Acute Inter-session change is the plvPD between sessions that are separated by 20 min (Higher-Order Finite difference), e.g. between session n.1 and session n.21, session n.2 and session n.22, and so on; thus, the 20Q-trend begins with $plvPD_{21}$ value which is 21 min after the start of measurements; all consecutive plvPD values appear every minute; every plvPD value indicates plvPD during the last 20 minutes, e.g.:

$$QA_{21}=(A_{21}-A_1)/A_1$$

where QAn is fractional change in variable, e.g. in extravascular water (ewA) amount, during a 20 min period from the end of session n.1 to the end of session n.21 (FIG. 70).

c. CQ-trend is a Continuous Q-trend and includes a Finite difference-a difference between plvPD in baseline ($1^{st}$) session and every session thereafter: The CQ-trend begins with $plvPD_2$ value which is 2 min after the start of measurements; all consecutive plvPD values appear every minute; every plvPD value in the trend indicates plvPD from baseline; the baseline is reset after every repositioning of sensors, and the CQ-trend continues without interruption as AI generates a predicted trend during the repositioning related interruption in measurement:

$$QA_2=(A_2-A_1)/A_1$$

where $A_1$ is the first or baseline session n.1, and $A_2$ is the second session; the CQ-trend begins with QA value which is 2 min after the start of measurements; all consecutive QA values appear every minute; every QA value in the trend indicates a change in variable, e.g. in extravascular water (ewA) amount, compared to baseline; the baseline is reset after every repositioning of sensors, and the CQ-trend continues without interruption as AI generates a predicted trend during the repositioning related interruption in measurement.

The QA-trend consisting of changes in extravascular water (QewA) is used for AI-assisted fitting to the patterns of QewA for interpretation of changes in hydration status as described by the improved HBS method (FIGS. 58-69). The plvHet is used to find the best fit value of oHct in Table 2; the plvHct may ideally be consistent with oHct if it is obtained after optimisation protocols such as mVLT; if not, the plvHet is considered as approximation of oHct if it is the minimal plvHct value observed during observation of Hct (and PD) fluctuation due to Circadian rhythm.

Estimation of plasma dilution as an indication of changes in plvHb and plvHet is used in a special kind of QA trend:

a. 5Q-PD trend is Immediate Inter-session change is plvPD between sessions separated by 5 min, e.g. session n.1 and session n.6, session n.2 and session n.7, and so on; thus, the 5Q-trend begins with $plvPD_6$ value which is 6 min after the start of measurements; all consecutive plvPD values appear every minute; every plvPD value in the trend indicates a change in variable during the last 5 minutes.

b. 20Q-PD trend is Acute Inter-session change is the plvPD between sessions that are separated by 20 min, e.g. session n.1 and session n.21, session n.2 and session n.22, and so on; thus, the 20Q-trend begins with $plvPD_{21}$ value which is 21 min after the start of measurements; all consecutive plvPD values appear every minute; every plvPD value in the trend indicates plvPD during the last 20 minutes.

c. CQ-PD trend is a Continuous Q-trend consisting of plvPD between baseline ($1^{st}$) session and every session thereafter: The CQ-trend begins with $plvPD_2$ value which is 2 min after the start of measurements; all consecutive plvPD values appear every minute; every plvPD value in the trend indicates plvPD from baseline; the baseline is reset after every repositioning of sensors, and the CQ-trend continues without interruption as AI generates a predicted trend during the repositioning related interruption in measurement.

2. The plvPD estimate:

$$plvPD_i=\left(plvHb_n-plvHb_i^{-1}-1\right)\cdot(1-plvHct)^{-1}$$

where $plvPD_i$ is predicted large vessel plasma dilution estimated in a session which is after i number of minutes from the previous session, $plvHb_n$ is the predicted large vessel hemoglobin concentration value in previous session which serves as baseline, and plvHct is the predicted large vessel hematocrit value in previous session which serves as baseline.

NOTE that same PD estimation is used with external SoA techniques-provided data of lvHb and lvHct.

In embodiments, the system and method of the present disclosure use non-invasive AI-assisted spectrophotometric technologies and techniques to monitor, detect and provide aid in addressing hydration in a user' body.

In embodiments, the system may monitor one or more of: whole body hemoglobin, mass, fluid accumulation in tissue, fluid accumulation in circulation, blood supply to organs and transcapillary fluid shift.

In embodiments, the monitoring may allow for detection of one or more of fluid hypoperfusion of tissues, blood loss and changes in hemoglobin mass, imminent or present severe deteriorations in hydration including dehydration and edema, deterioration of organ perfusion (microcirculation)

In embodiments, the method and system of the resent disclosure may be used in a variety of applications including perioperative and intensive care unit monitoring, non-clinical health monitoring and Space Medicine to name a few.

In embodiments, AI-assisted advanced processing of MW PPG signals allows novel monitoring of fluid and their distribution in the body to prevent inadequate oral fluid consumption and intravenous infusion, as well as detection of imminent edema and occult hemorrhage.

In embodiments, the system and method of the present disclosure offers the advantage of using non-invasive multiwavelength (MW) photoplethysmography (PPG) and AI analysis of the PPG signal to monitor hydration in the user's body. The method and system utilize real-time data processing of the PPG signal to provide such monitoring.

In embodiments, the monitoring provides several advantages. For example, as noted above, early detection of occult bleeding may be is lifesaving, especially in postoperative periods, and in individuals with an increased risk of internal hemorrhage, for example, those taking blood thinners (anticoagulants). Assessment of fluid requirements in terms of tissue hydration status is crucial for adequate oral fluid consumption in everyday life and clinical settings, as well as for administration of intravenous fluid therapy and prevention of adverse effects such as edema or dehydration. Further, detection of imminent edema may be lifesaving as it may allow for intervention to prevent or limit harm.

In embodiments, detection of imminent circulation overload (hypervolemia) may also be lifesaving as it allows for initiation of preventive measures. Similarly, monitoring blood supple to organs (perfusion of microcirculation) ay avoid damage as well. In embodiments, early detection of hypoperfusion is crucially important for the timely interventions to prevent life-threatening deterioration of blood supply to organs (microcirculation) due to hypoxia.

The monitoring of transcapillary fluid shift may be important for monitoring distribution of fluids and medication to tissues and is also important for monitoring treatment in microgravity environment during space exploration missions.

In embodiments, the method and system of the present application may be implemented in a variety of technology to offer versatile applications across a wide range of consumer and healthcare settings (medical and non-medical grade), bringing new possibilities for real-time health monitoring and management.

In embodiments, in a perioperative or intensive care unit application, assessment of fluid requirements and titration of fluid management measures may be provided. In addition, evaluation of a response to fluid therapy and cardiovascular medication may also be possible. In embodiments, assessment of fluid accumulation and the ability to provide alerts about imminent deteriorations is critical. In embodiments, the method and system may also be used to optimize fluid removal measures, e.g. diuretics or hemodialysis. More generally, the method and system monitoring changes in whole body hemoglobin mass and may be used to evaluate microcirculation and transcapillary shifts.

In embodiments, the system and method may be used to provide self-monitoring of hydration status, fluid requirements and hemoglobin mass. In embodiments alerts about imminent under- or over-hydration may be provided to a user, or to a health care provided to allow for intervention. In embodiments, the alerts may be used to urge fluid intake or restriction as appropriate. In embodiments, the alerts may provide alerts about dangerous conditions, e.g. edema and occult blood loss or may prompt the user to seek medical assistance.

In embodiments, the method and system may guide fluid management in a microgravity environment where conventional concepts do not apply. Monitoring transcapillary fluid shifts under unpredictable impact of multiple factors during space exploration missions may allow for prevention of harm.

Figure 74A:
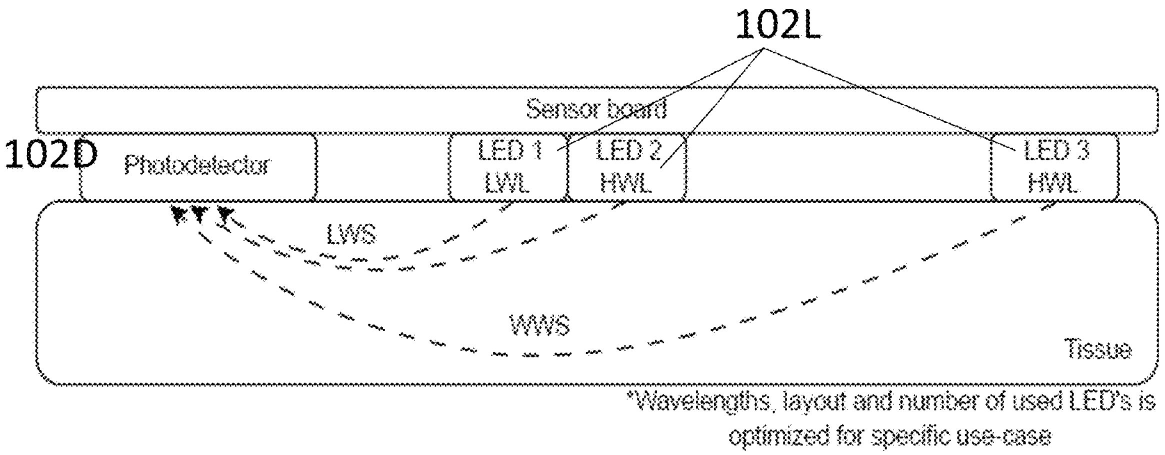
FIG. 74A illustrates an exemplary sensor that may be used to obtain PPG information in accordance with an embodiment of the present disclosure.
Figure 74B:
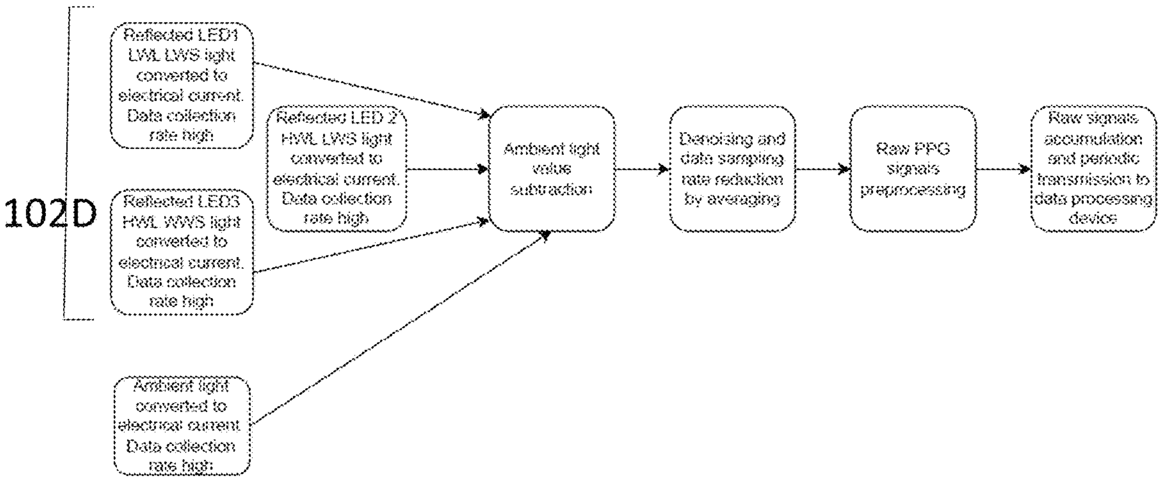
FIG. 74B illustrated an exemplary signal path of PPG information from the sensor to a device for processing in accordance with an embodiment of the present disclosure.

In embodiments, the method and system of the resent disclosure may provide multiple levels of signal processing. In embodiments, raw-level signal processing may be performed on the PPG signal (FIG. 74). In embodiments processing may be provided to allow for reflected light signal acquisition as indicated in FIG. 74A where light from the LEDs 102L passes through the user's body and is detected at the detector 102D. Various hardware and software may be provided along the signal path to provide processing as is generally indicated in FIG. 74B.

Reflected light from the LEDs 102L may be detected by the detector 102D which may provide an electrical signal related thereto. In embodiments, the PPG signal output from the detector 102D may be processed to remove the effect of ambient light. Thereafter, the signal may be cleaned to removed noise. The signal may then undergo preprocessing. As indicated in FIG. 74B, the PPG signal may be accumulated for periodic transfer to a data processing system.

Figure 74C:
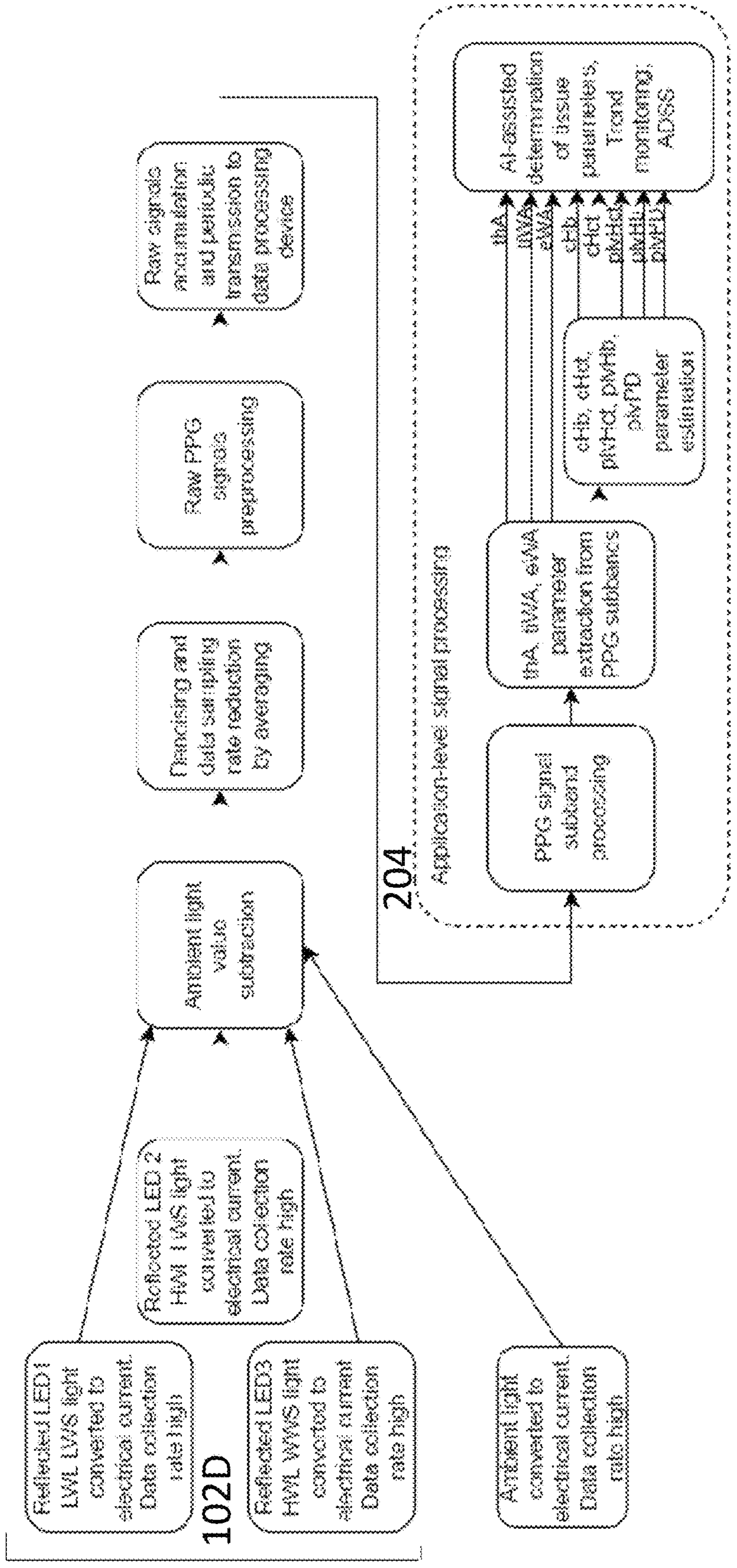
FIG. 74C illustrates an exemplary signal path of the information in accordance with an embodiment of the present disclosure.
Figure 74D:
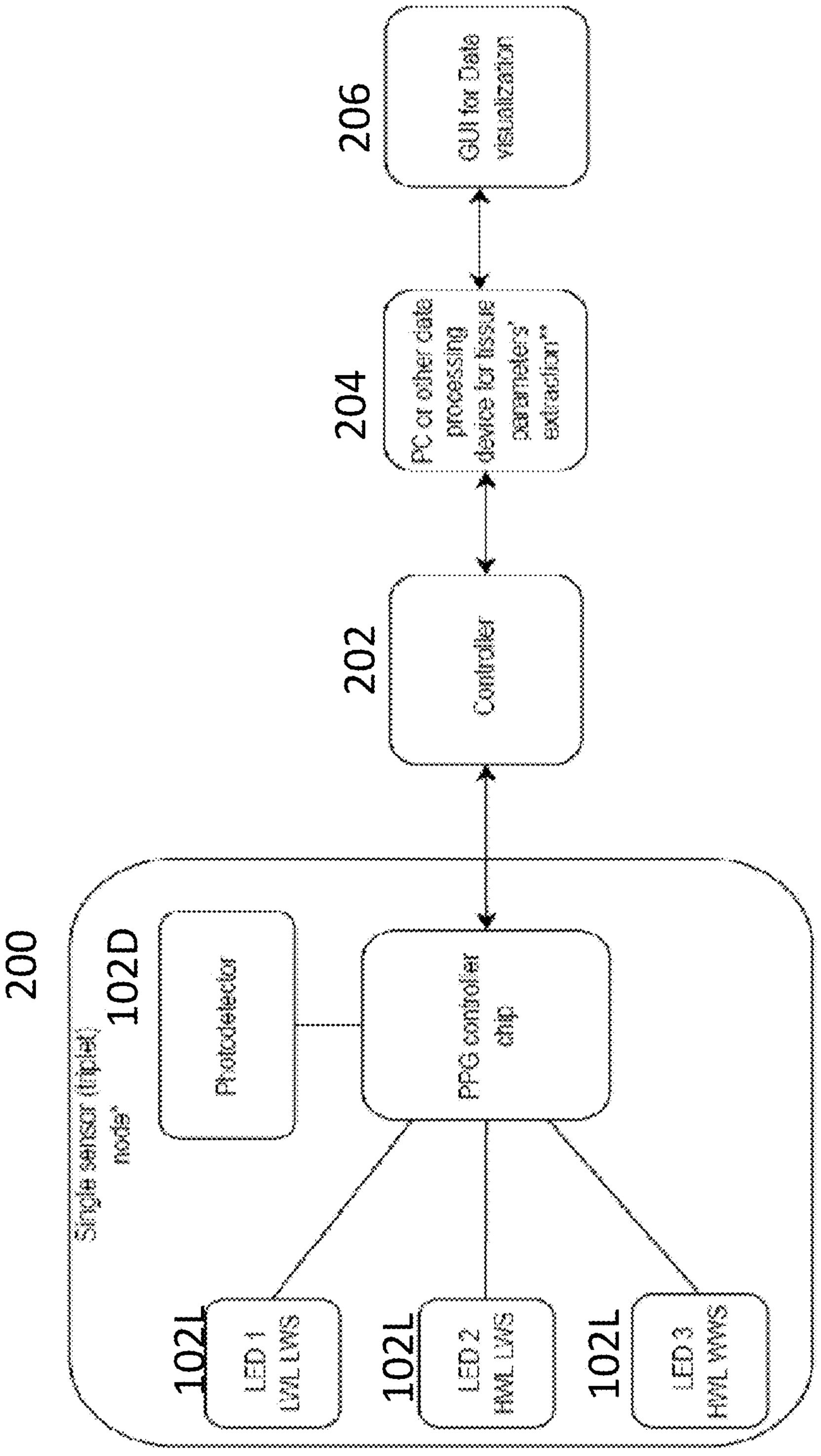
FIG. 74D an exemplary block diagram of a PPG sensor for use in a system in accordance with an embodiment of the present disclosure.

FIG. 74C illustrates the full signal path, where the accumulated PPG signal may be transmitted or otherwise provided to a signal processing element where the PPG information may be received via a PPG sub band. Parameters may be extracted from the received PPG information. In addition, estimable values may be estimated and the estimated values, extracted parameters and PPG information may be passed to an AI assisted determination module. FIG. 74D illustrates an MW PPG apparatus 200 that may be used to provide the PPG information. In embodiment, the apparatus 200 includes multiple LEDs 102L, including both high wavelength and low wavelength versions as well as a detector 102D to detect light that passes through the user's body. As noted above, the amount of light that is detected depends on the amount of light that is absorbed in the user's body b water and Hg. A controller 202 may be used to control emission of light from the LEDs 102L as well as detection via the detector 102D. In embodiments, a data processor 204 may be operably connected to the apparatus 200 to receive the PPW information provided by the detector 102D, as well as the estimated parameters and extracted parameters discussed above and processes them to make decisions regarding the health and treatment of the user. As indicated in FIG. 74D, a user interface 206 may be provided to allow display of the PPG information, extracted. parameters as well as any advice or alerts that may be generated based on the AI aided processing.

Figure 74E:
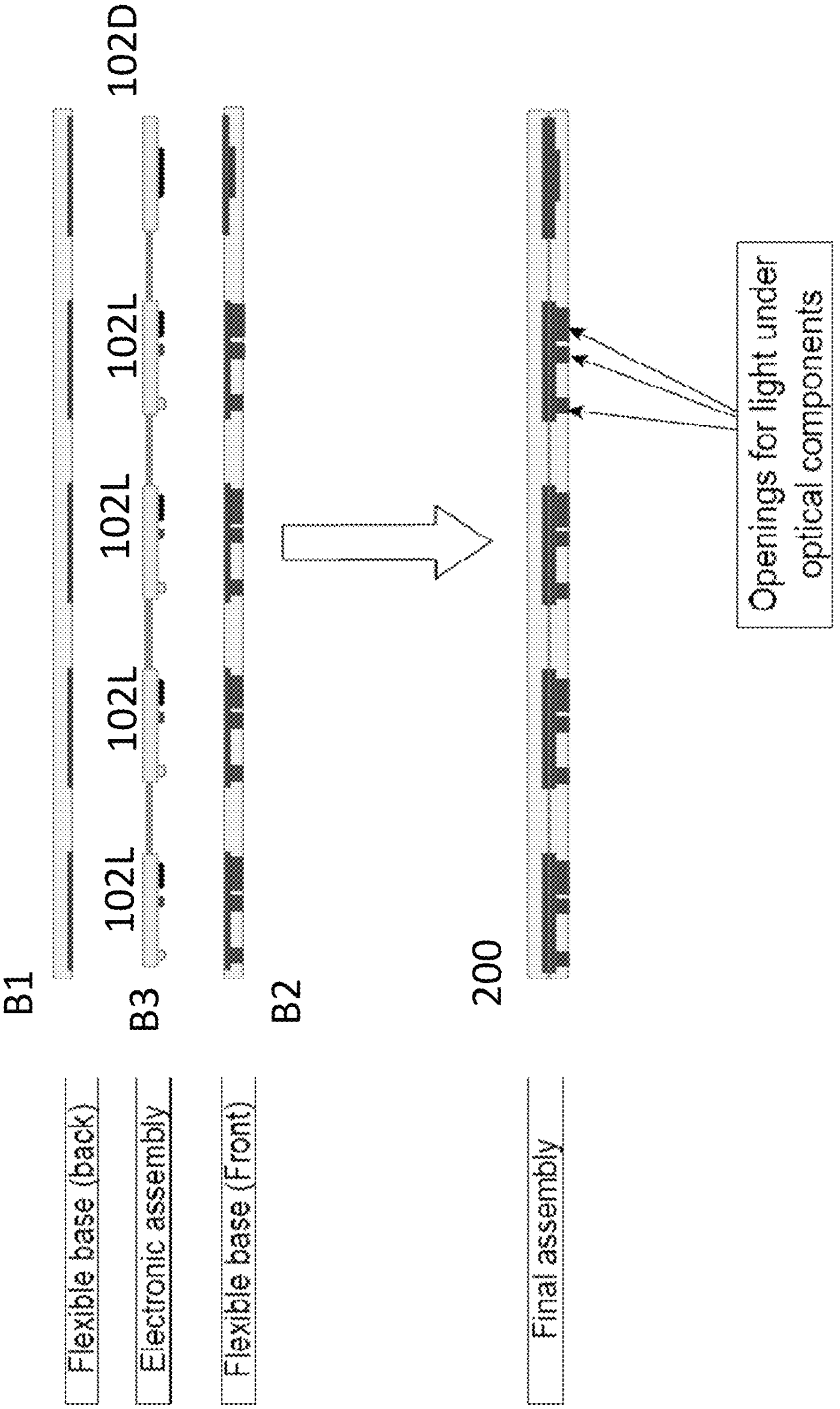
FIG. 74E illustrates an example of a sensor array include multiple PPG sensors mounted in a flexible band for application to a users body in accordance with an embodiment of the present disclosure.

FIG. 74E illustrates a particular implementation of the device 200 in which the LEDs 102L and detector 102D may be integrated into a flexible band B to allow for any desired positioning on the user's body. The band B may include a back B1 and a front B2 with an electronics assembly B3 mounted therebetween. In embodiments, the assembly B3 may include the LEDs 102L and the detector 102D. The band B is configured to wrap around a user's wrist, Leg, hand, finger, or the like, and direct the light toward the user's skin and the detector 102D also facing toward the user's skin.

Figure 74F:
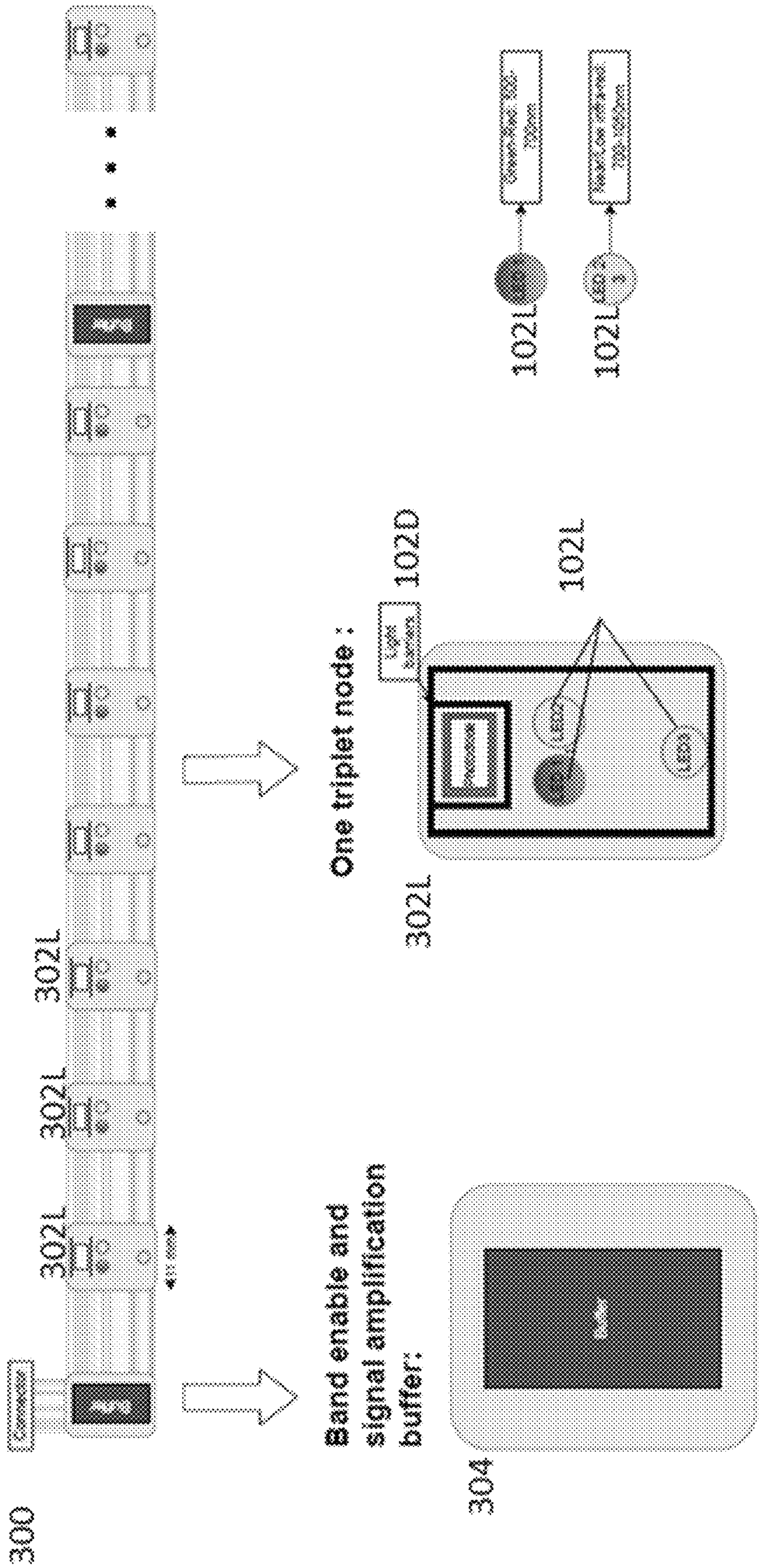
FIG. 74F illustrate a schematic view of the flexible band with detail showing the use of triplet sensor arrays in accordance with an embodiment of the present disclosure.
Figure 74G:
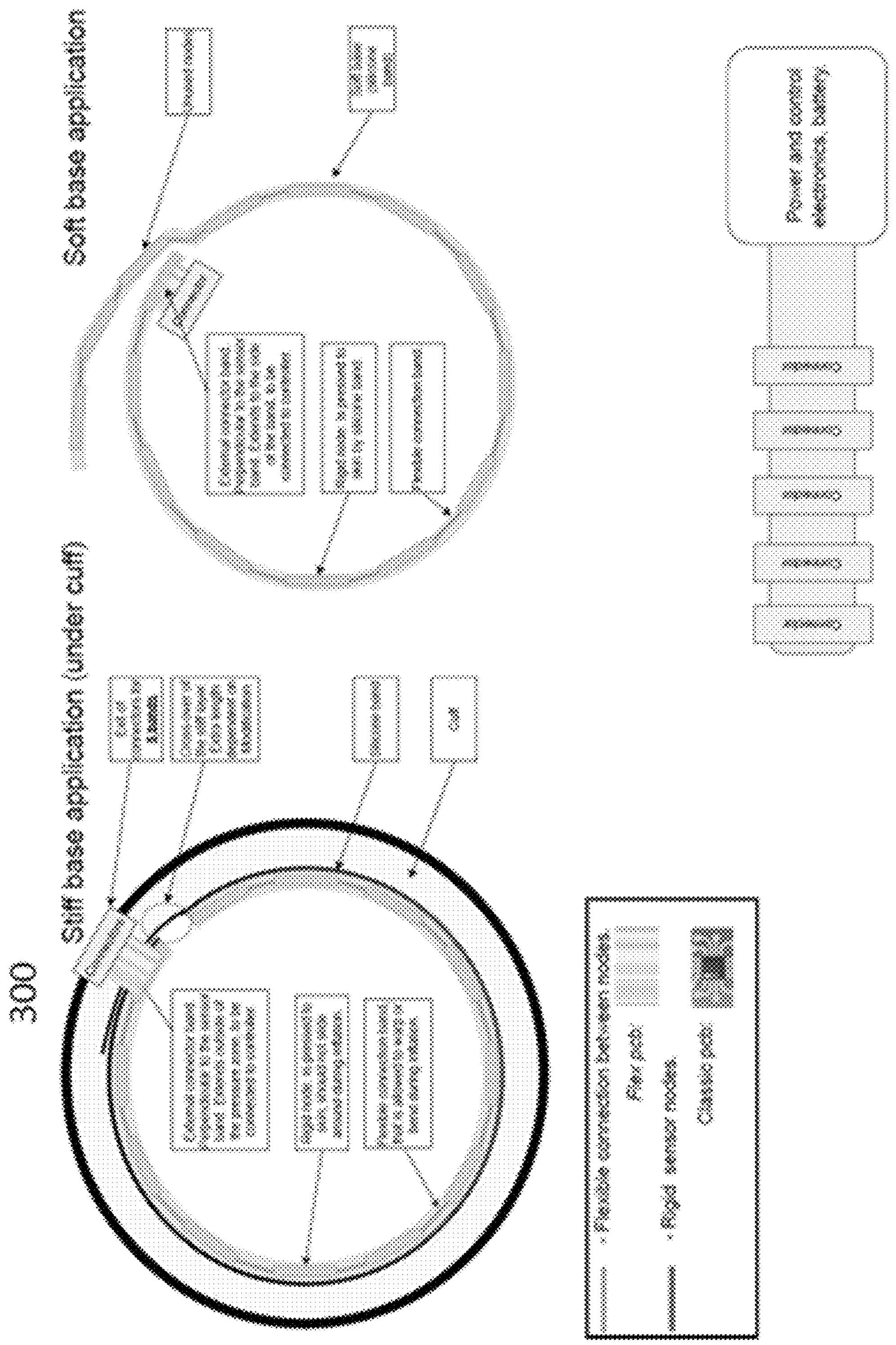
FIG. 74G illustrates the flexible band including the triplet sensor arrays wrapped and suitable for application to a user in accordance with an embodiment of the present disclosure.
Figure 75:
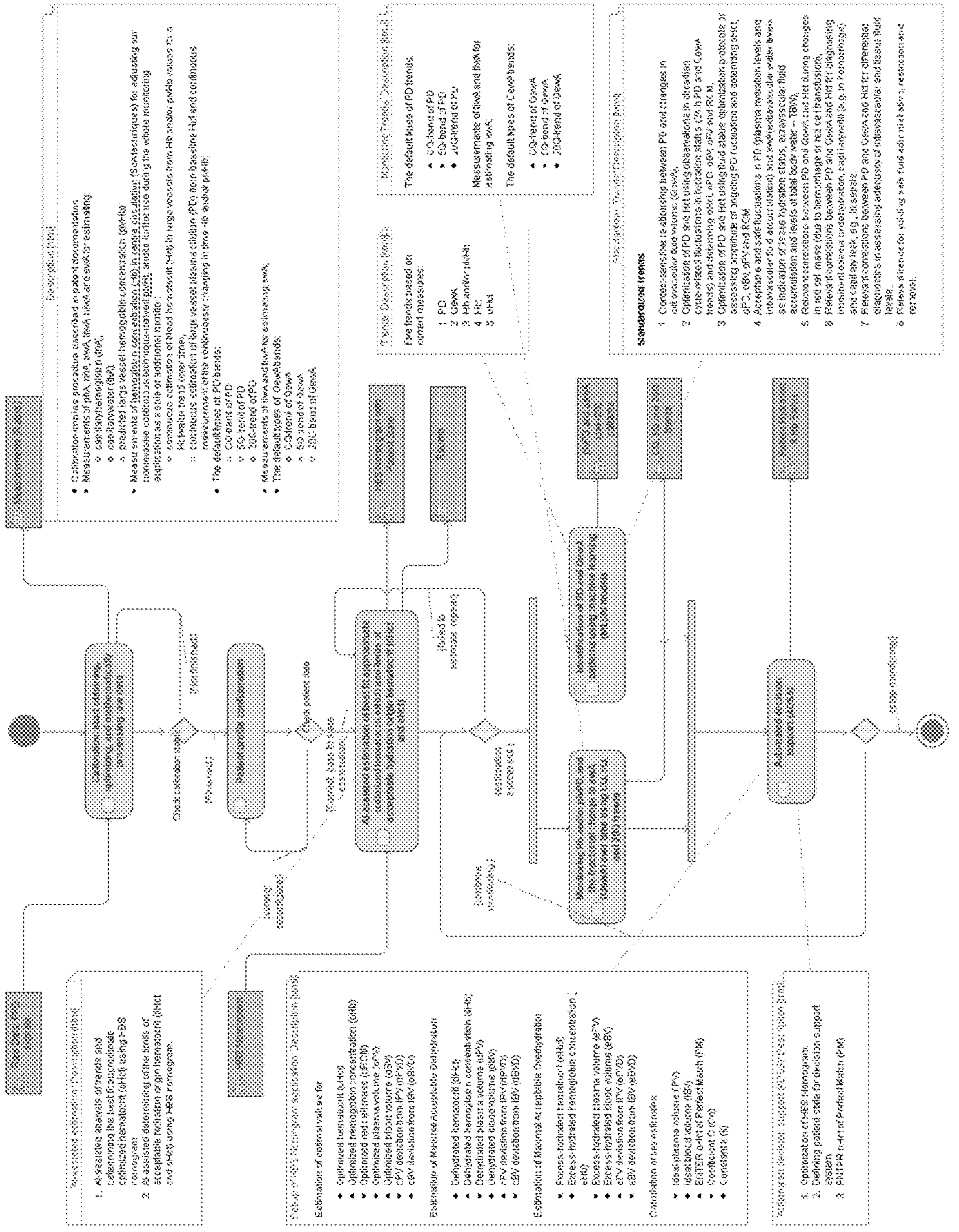
FIG. 75 illustrates an exemplary signal processing chart for a system in accordance with an embodiment of the present application.

FIG. 74F illustrates another embodiment of a MW PPG device 300 utilizing the triplet sensor array 302 discussed above. A plurality of triplet sensor arrays 302 are provided, each of which includes multiple LEDs 102L of different wavelengths as well as a detector 102D, which may be a photoresistor. In embodiments, multiple triplet sensors 302 may be mounted on a flexible band B such that the array of sensors 302 can be secured to the user's body. In embodiments, a power source or batter may be provided on the band to power the triplet sensors 302. In embodiments, a buffer 304 may also be provided on the band as well to allow for gathering and amplifying the PPG data provided by the sensors 302.

In embodiments, the MW PPG device 200, 300 may undergo calibration first. First, measurements of phA, nhA, pwA, tiwA, niwA and ewA (FIG. 43A) may be received for estimating capillary hemoglobin (thA), capillary water (thA), predicted large vessel hemoglobin concentration (plvHb). In embodiments, measurements of hemoglobin concentration Hb in central circulation (using conventional techniques) may be used for adjusting derived plvHb and/or for use during the whole monitoring application as a sole or additional monitor. In embodiments, continuous estimation of blood hematocrit (Hct) in large vessels from Hb and/or plvHb values for a Hct-value trend (over time) may be provided. In embodiments, continuous estimation of large vessel plasma dilution (PD) from baseline Hct and continuous measurement of the continuously changing in time Hb and/or plvHb may be provided using signal processing.

In embodiments, the default types of PD trends include: CQ-trend of PD, 5Q-trend of PD and 20Q-trend of PD. In embodiments the signal processing may result in measuring tiwA and tiwA for estimating ewA. In embodiments, the default types of OewA trends include: CQ-trend of QewA, 5Q-trend of QewA and 20Q-trend of QewA.

In embodiments, patient information including one or more of: body weight, body height, gender and age may by input, via user interface 206, for example.

In embodiments, the signal processing may also include calculating HBS auto data, BSA2, IBV and setting initial parameter for estimates.

In embodiments, AI assistance may be used to provide trend analysis and determination of the best fit for optimized hematocrit (oHct) using HBS Nomogram. Further, AI may be used to determine the limits of acceptable hydration origin hematocrit (dHct and eHct) using HBS nomogram.

In use, continuous monitoring of Hb and or plvPD and change in ewA (QewA) over times uses CQ, 5Q and 20Q trends. Further, the PD and QewA patterns may be identified based on machine learning models trained using data sets based on prior PPG data.

In embodiments, as part of decision support for a medical professional, an HBS Nomogram may be established for a particular application. The patient state is established for the decision support system, which may be provided by a caregiver or determined based on prior results. Thereafter, the following may be determined: oHct, oHb, oRCM, oPV, oBV, and oPV deviation from IPV (oPVD), and oBV deviation from IBV (oBVD).

Further, in embodiments, dehydration parameters may be estimated including estimation of maximal acceptable dehydration: dHct, dHb, dPV, dBV, and dPV deviation from IPV (dPVD), and dBV deviation from IBV (dBVD).

In embodiments overhydration parameters may also be estimated including eHct, eHb, ePV, eBV, and ePV deviation from IPV (ePVD), and eBV deviation from IBV (eBVD).

In embodiments, the following values may be estimated: Ideal plasma volume (IPV). Ideal blood volume (IBV), ENTER oHct which is $Hct_{PM}$, Coefficient C (Cn) and constant k (k).

Figure 76:
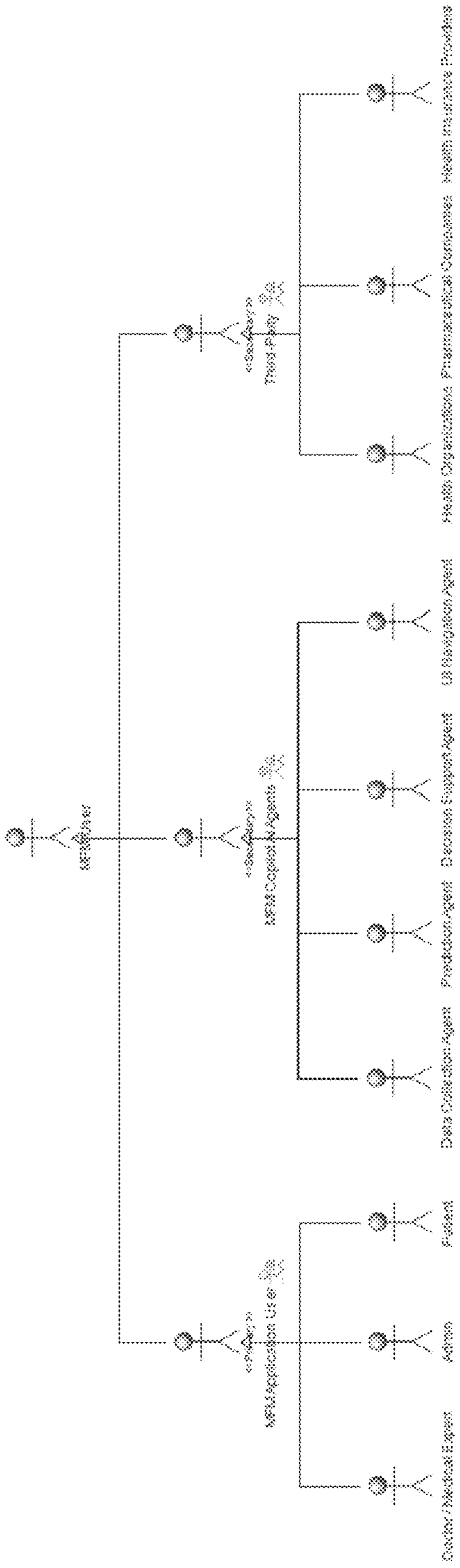
FIG. 76 illustrates an exemplary hierarchy of roles in the system in accordance with an embodiment of the present disclosure.

In embodiments, the method a system of the present disclosure may be implemented via a software application running on a mobile computer device or other computer device. In embodiments, there are three hierarchies of users of the system and method as indicated on FIG. 76. The first group of users includes the application user which may include doctors or medical professionals, administrators and patients. The second group corresponds to copilot AI agents including a data collection agent, a prediction agent, a decision support agent and a User Interface Agent. The third group includes third parties including health organizations, pharmaceutical companies and insurance providers.

Figure 77:
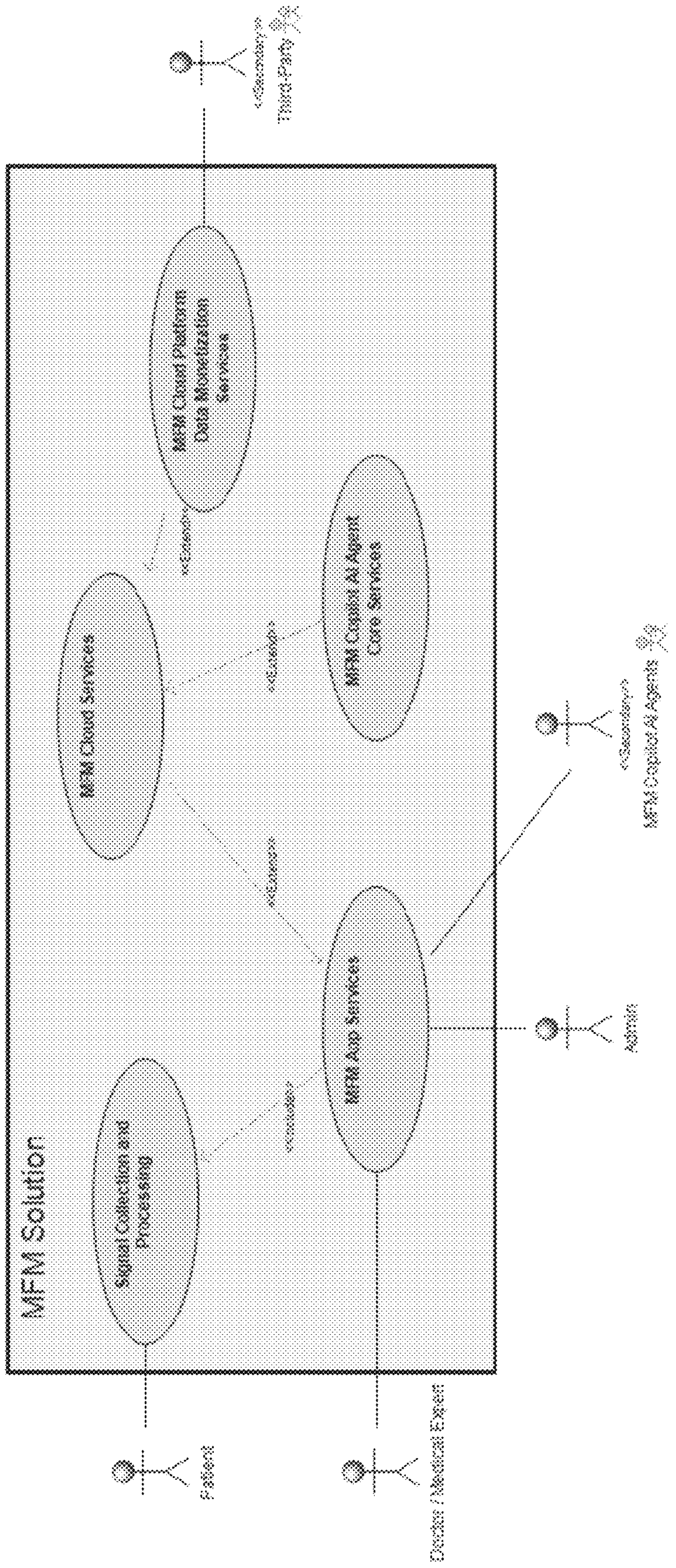
FIG. 77 illustrates an exemplary structure of user scenarios and functional modules used in the system in accordance with an embodiment of the present disclosure.

FIG. 77 illustrates a use case for use of a software application. To collect data and process it, the pressure pump, such as the pump 106 discussed above. Thereafter PPG data may be gathered from the detectors 102D whether paired with individual LEDs 102L or triplet sensor arrays 302 discussed above. As noted above the PPG data is processed at a raw level where it is received from the detectors of sensors and may be subjected to application-level processing for use in the application. The application includes providing ratio analysis relative to the measured values, Q-Trend analysis, monitoring of standard trends to support decision support, clinical decision support, patient profile management, application administration and AI agent management. The software application may be cloud-based or may communicate with the cloud. Cloud services implement via the software application may include as AI agent for clinical decision support, traditional CDSS and Prediction Services, data services, AI prediction and recommendations online services and embedded clinical decision support. In embodiments, a cloud platform may be used which may provide monetization opportunities including data access and licensing, data products and services, enhanced services, value-added offering and data aggregation and analysis services, clinical trials support services, subscription-based model services, data security and compliance services and partnership or collaboration services.

In embodiments, the AI agent core services include data collection AI agent services, prediction AI agent services, clinical decision support AI agent services and User interface navigation AI agent services.

In embodiments, the software application may be implemented via modules which include processor executable code that when executed by a processor perform certain steps and functions. In embodiments the software application includes: a main screen module, a Q-trends Module, a standard trend for decision support module, a CDDS module: HBS Nonograms, a patient profile module, an administrator module and an AI Agent module.

Figure 78:
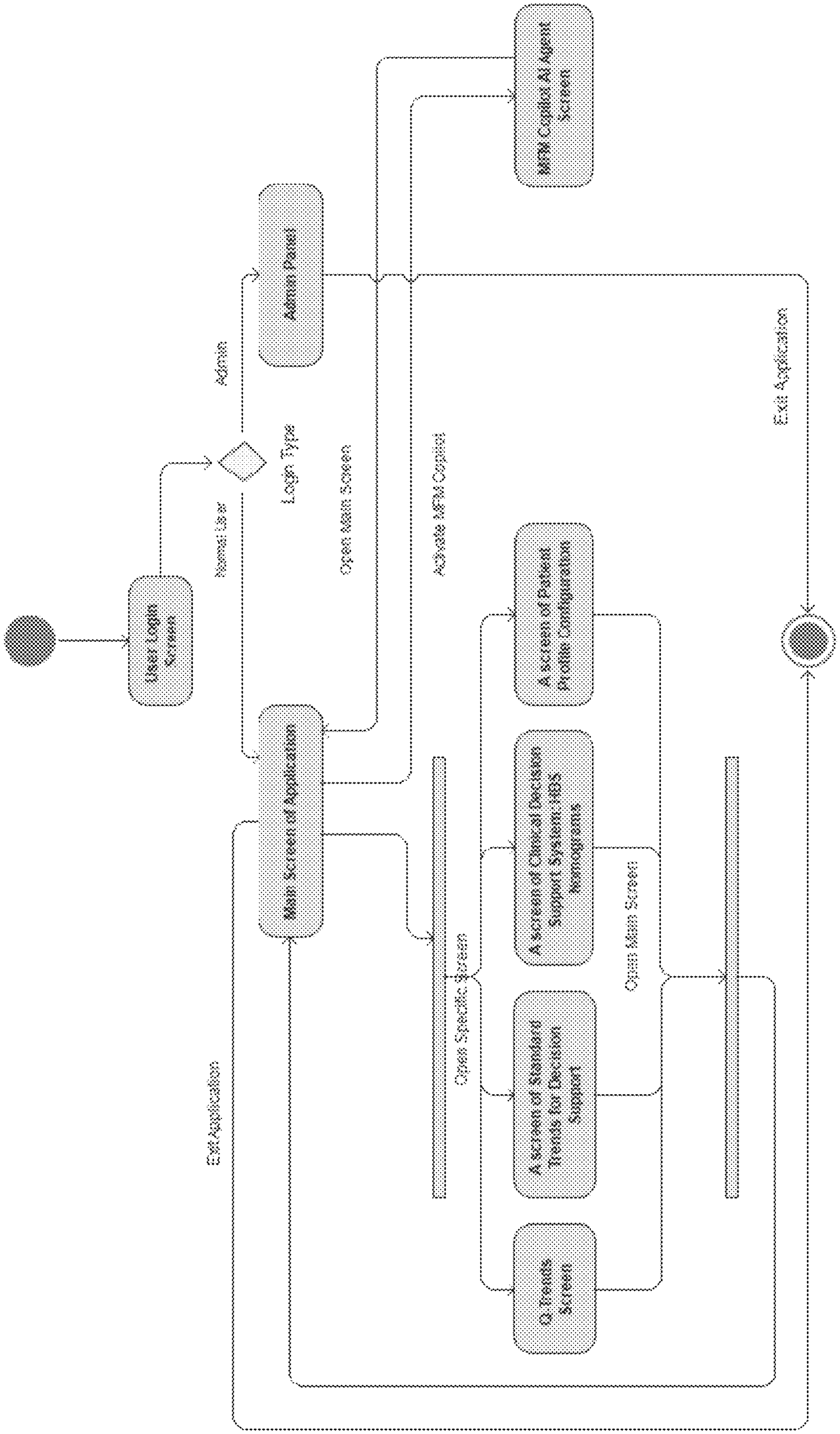
FIG. 78 illustrates an exemplary navigation diagram for a user interface of the system in accordance with an embodiment of the present disclosure.

FIG. 78 illustrates a core navigation module of the software application User Interface (UI) and illustrates primary navigation scenarios. In embodiments, application screens may be adapted to allow for use on a variety of devices. For example, the application may be implemented on or with a Medical Monitoring Device, such as the MG PPG device 100 discussed to ensure compatibility with medical monitoring equipment for real-time patient data tracking. In embodiments the UI may be optimized for use on a mobile electronic device. In embodiments, the software application may be optimized of PC or tablet us in which case screens may be fully functional and provide a comprehensive view of patient data, PPG information as estimates and predictions along with alerts.

Figure 79A:
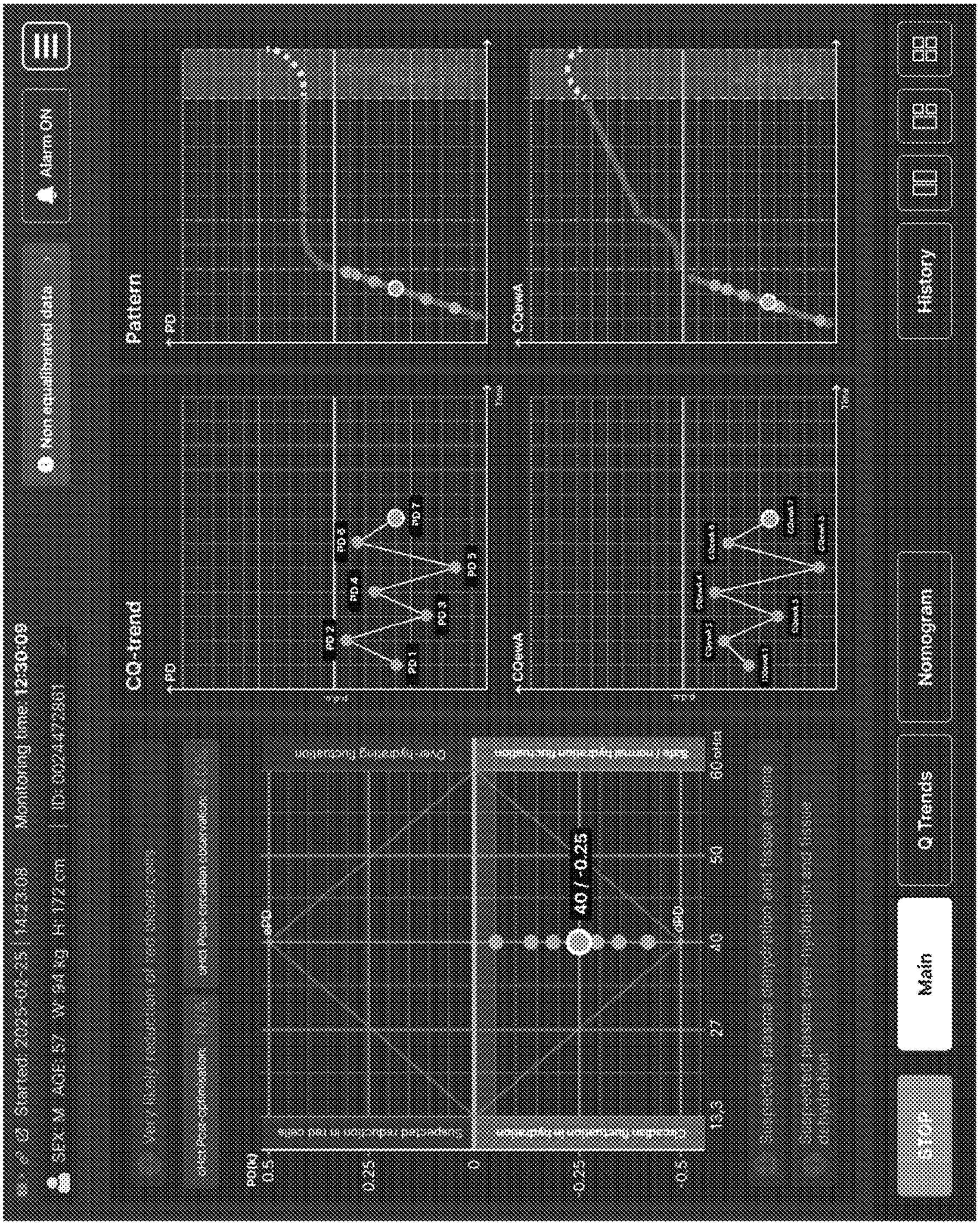
FIG. 79A illustrates an example of a primary trend tracking screen that may be presented to a user during a circadian rhythm related fluctuation.
Figure 79B:
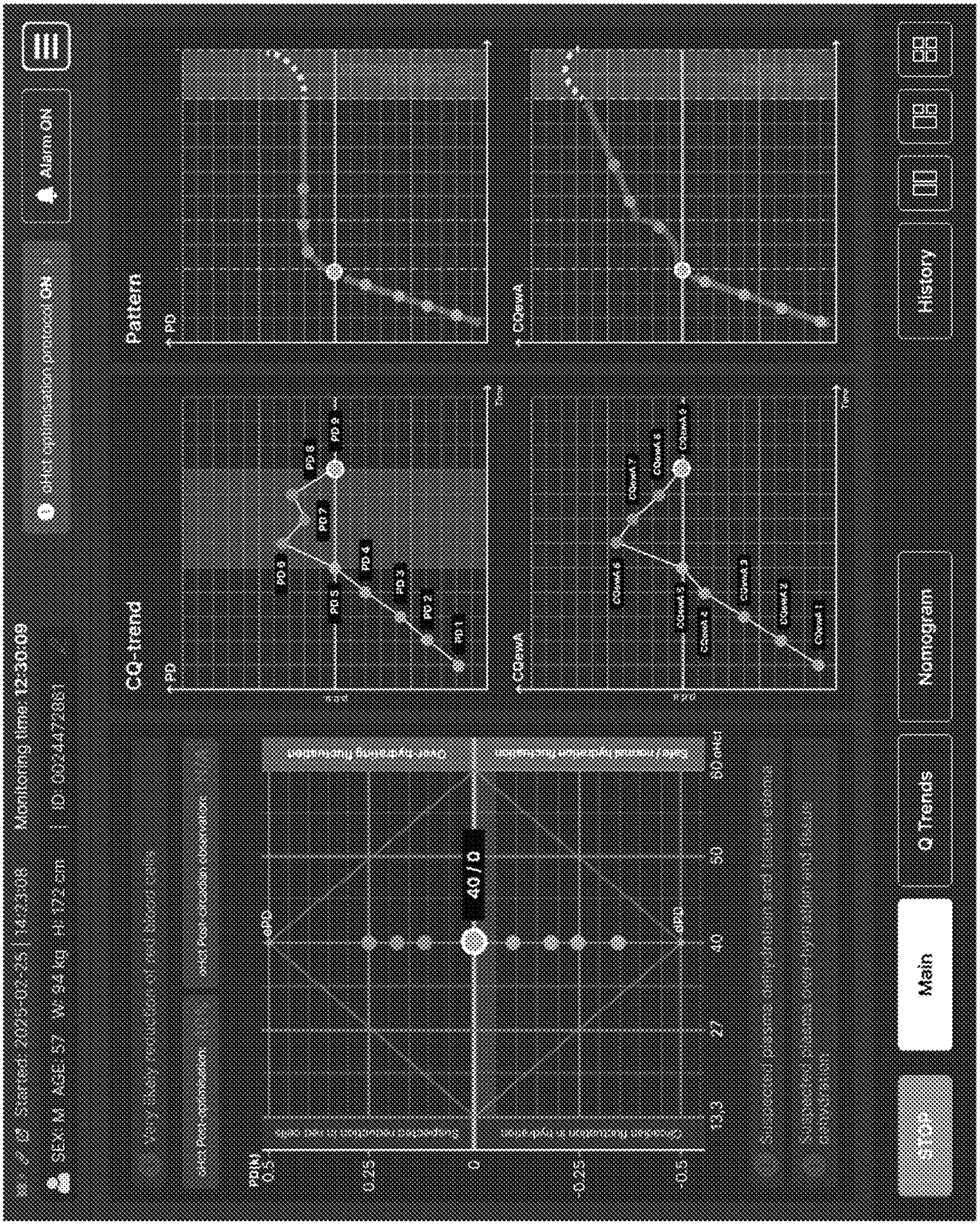
FIG. 79B illustrates an example of a primary trend tracking screen that may be presented to a user during edema formation in accordance with an embodiment of the present disclosure.
Figure 79C:
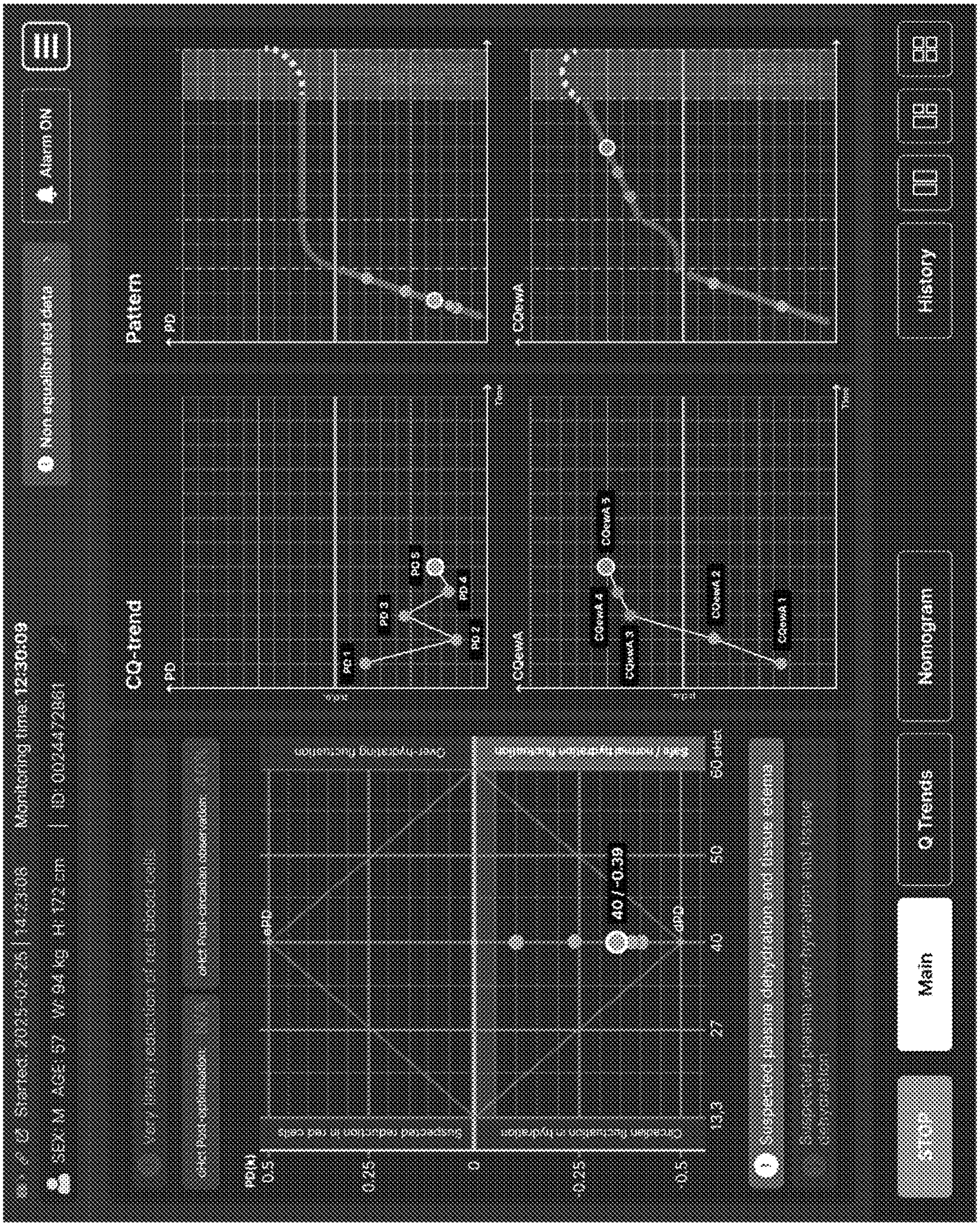
FIG. 79C illustrates an example of a primary trend tracking screen that may be presented to a user during very likely red cell loss in accordance with an embodiment of the present disclosure.
Figure 79D:
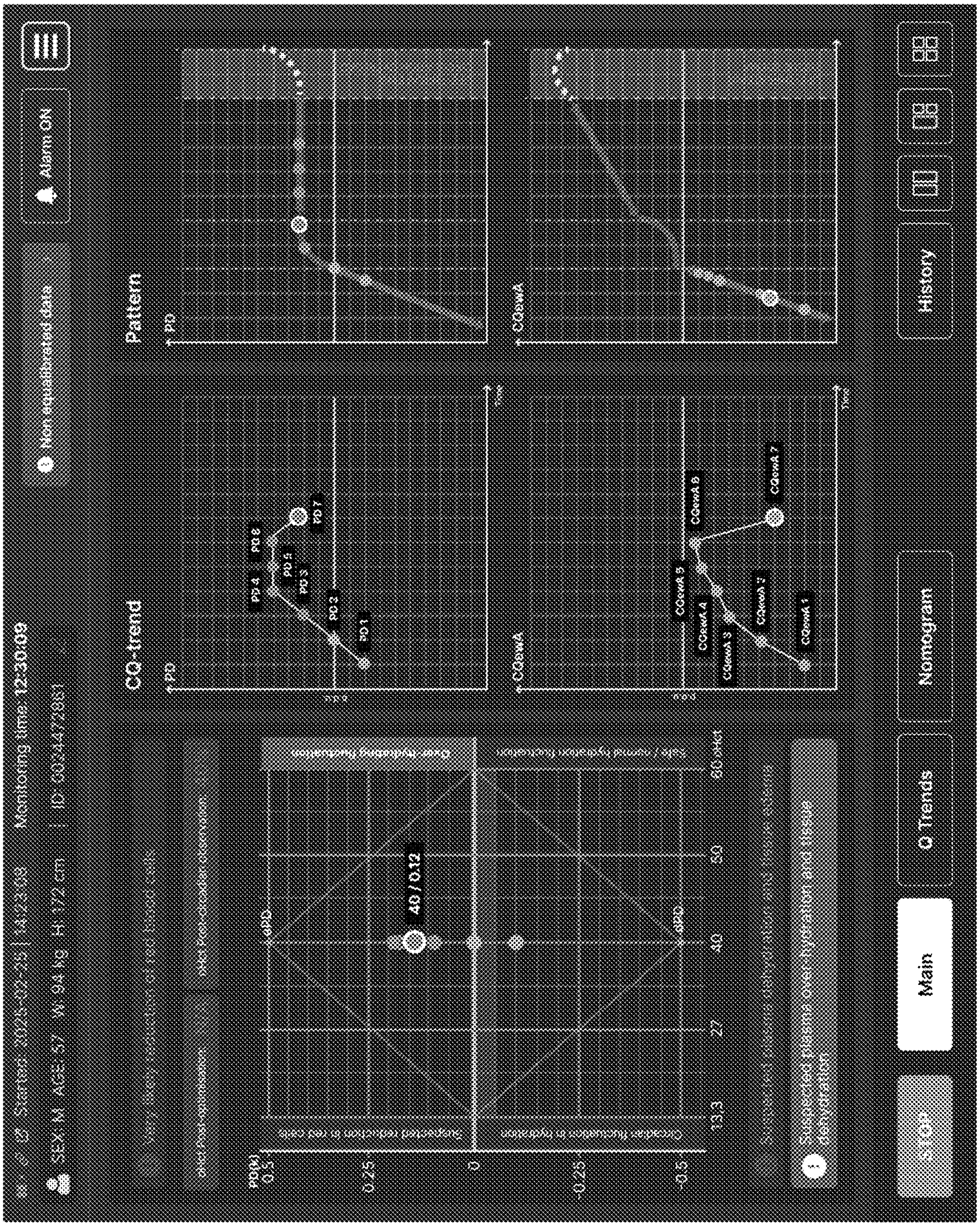
FIG. 79D illustrates an example of a primary trend tracking screen that may be presented to a user during PD and Hct optimization in accordance with an embodiment of the present disclosure.
Figure 79E:
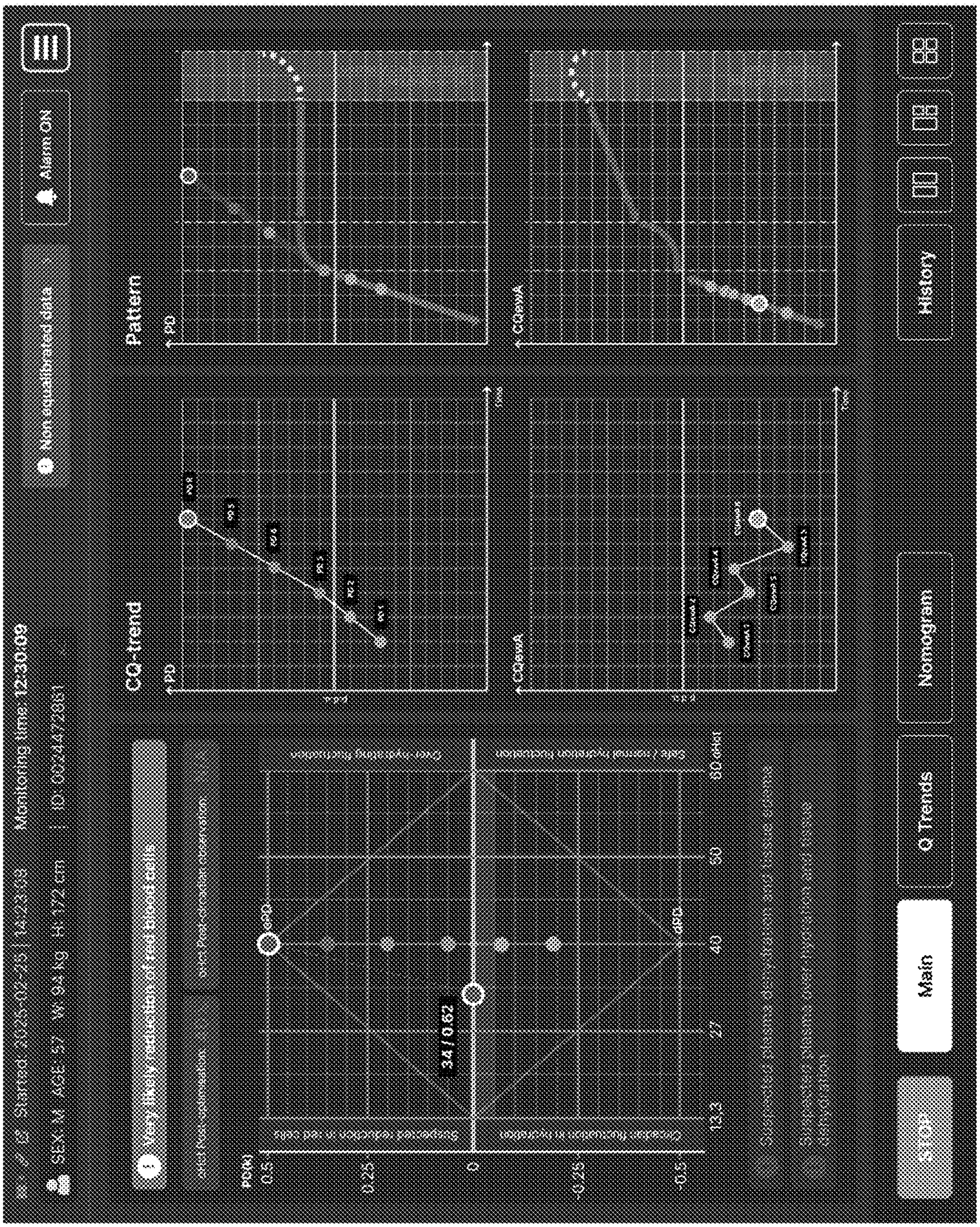
FIG. 79E illustrates an example of a primary trend tracking screen that may be presented to a user during fluid restriction and/or fluid removal in accordance with an embodiment of the present disclosure.
Figure 79F:
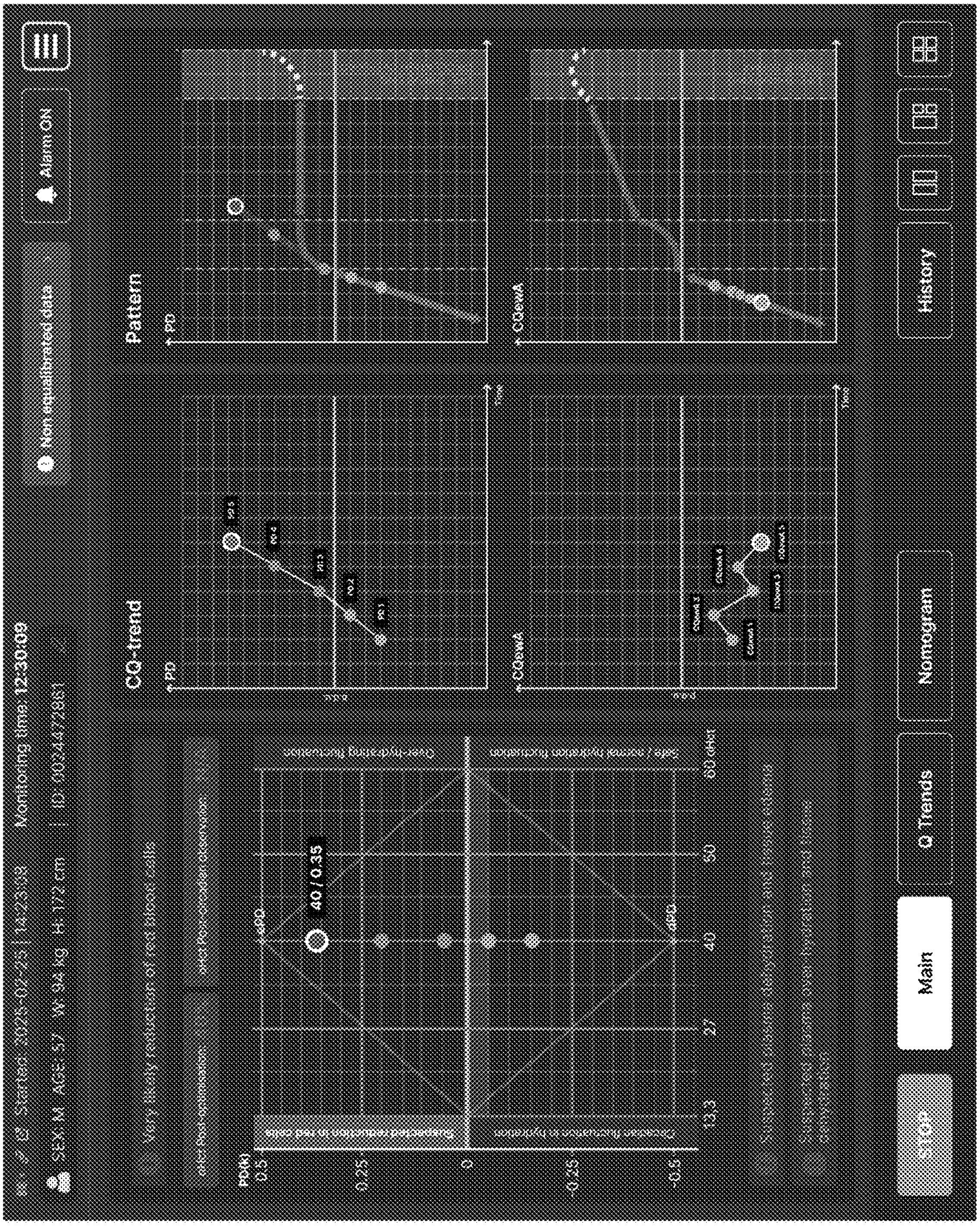
FIG. 79F illustrates an example of a primary trend tracking screen that may be presented to a user during a suspected red-blood cell loss in accordance with an embodiment of the present disclosure.
Figure 80:
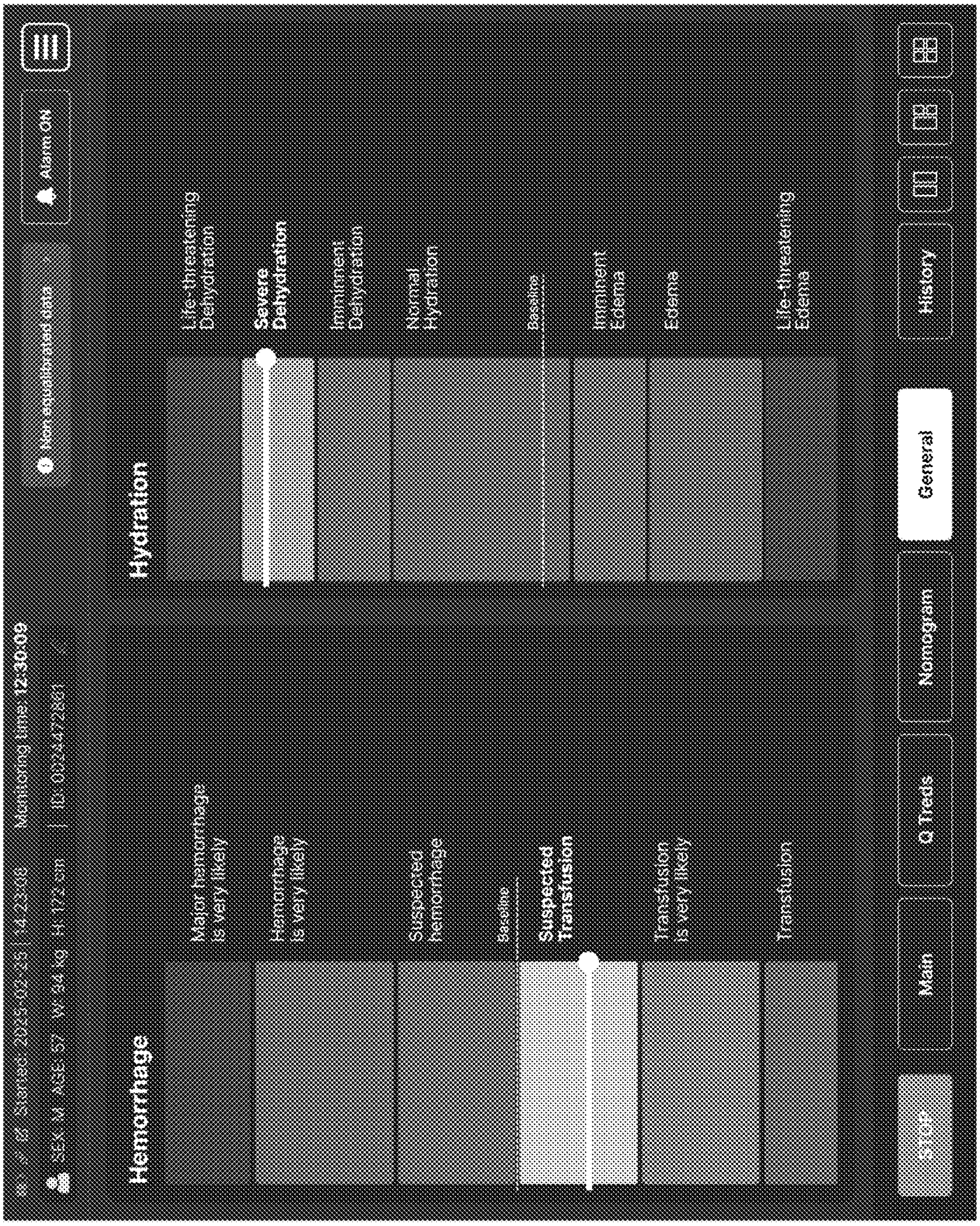
FIG. 80 is an example of a traffic light indicator that may be presented to a user in accordance with an embodiment of the present disclosure.

FIGS. 79-80 illustrate a main screen provided by the software application for visual display on a display of a device associated with the software application which may display PD and oHct dependency as a rhombus shape with all required statuses and measured CQ trends and pattern ratios. It will also reflect the transitions in health states as well as the primary trend and Q-trend.

In embodiments CQ trend diagrams display PD (plasma dilution) and CQewA (changes in extravascular fluid volume) ratios over timer per preconfigures discretization step.

In embodiments, an application using machine learning algorithms fits patient measurements of PD and CQewA to predetermined heath patterns/scenarios (see FIG. 80. The ML algorithm fits PD and CQewA measurements (OF T1, T2 . . . . TN periods) to the pattern indicating the overall patient's health status related to monitored ratios.

Depending on trends and changes in measurements in the monitored scope the application enables alerts on the main screen or display, like "Very likely reduction of red blood cells," "Suspected plasma dehydration and tissue edema"," Suspected plasma over-hydration and tissue dehydration", etc. In combination series. FIG. 79B illustrates the main screen with an alert related to overhydration. FIG. 79C illustrates the main screen with an alert related to reduction of red cells. FIG. 79D shows of transition from a potential problem to a healthy prediction.

Examples of Primary Trend Indicator & CQ-Trend & Pattern in combination screens as can be seen in FIG. 79 which illustrates examples of "traffic light" indicator screens indicating the present status of hydration.

In embodiments, as noted above, the primary trend indicator may show a rhombus shape as the leading and most crucial trend indicator. In embodiments, this indicator should encompass all relevant data, including alerts on detrimental deviations from normal (safe) in red cell mass, plasma dilution and tissue hydration. In embodiments, A rhombus fitting method may be used with respect to the collected data to assess the data distribution and its statistical relevance to follow a rhombus shape (yellow line) for testing the theoretical red cell mass dependent limits of homeostatic plasma dilution. In embodiments, aPD_EQ data sets and cPD_EQ data sets were fit to the rhombus nomogram In embodiments, the "traffic light" indictor provides quick reference to red cell mass and hydration levels. The traffic light structure ensures these indicators are prominently displayed for immediate visibility.

As noted above the main screen quickly provides current Hb, plvHb, Hct, PD and hydration status (including total body water level based on PD and QewA trend patterns). In embodiments, the focus will be to display the most recent or last 2-5 measurement periods—measured health status or ratio transition. The main screen will preferably void showing the entire history of point movements on this screen.

In embodiments there may be an option to view detailed trends (5Q; 20Q; CQ) on a separate section or screen and to provide the ability to select and view trends. In embodiments, all three trends (5Q; 20Q; CQ) along with PD and QewA trends may be shown or available. In embodiments, the user may select either PD or QewA trends. The main scree should include options to navigate to other screens.

Figure 81:
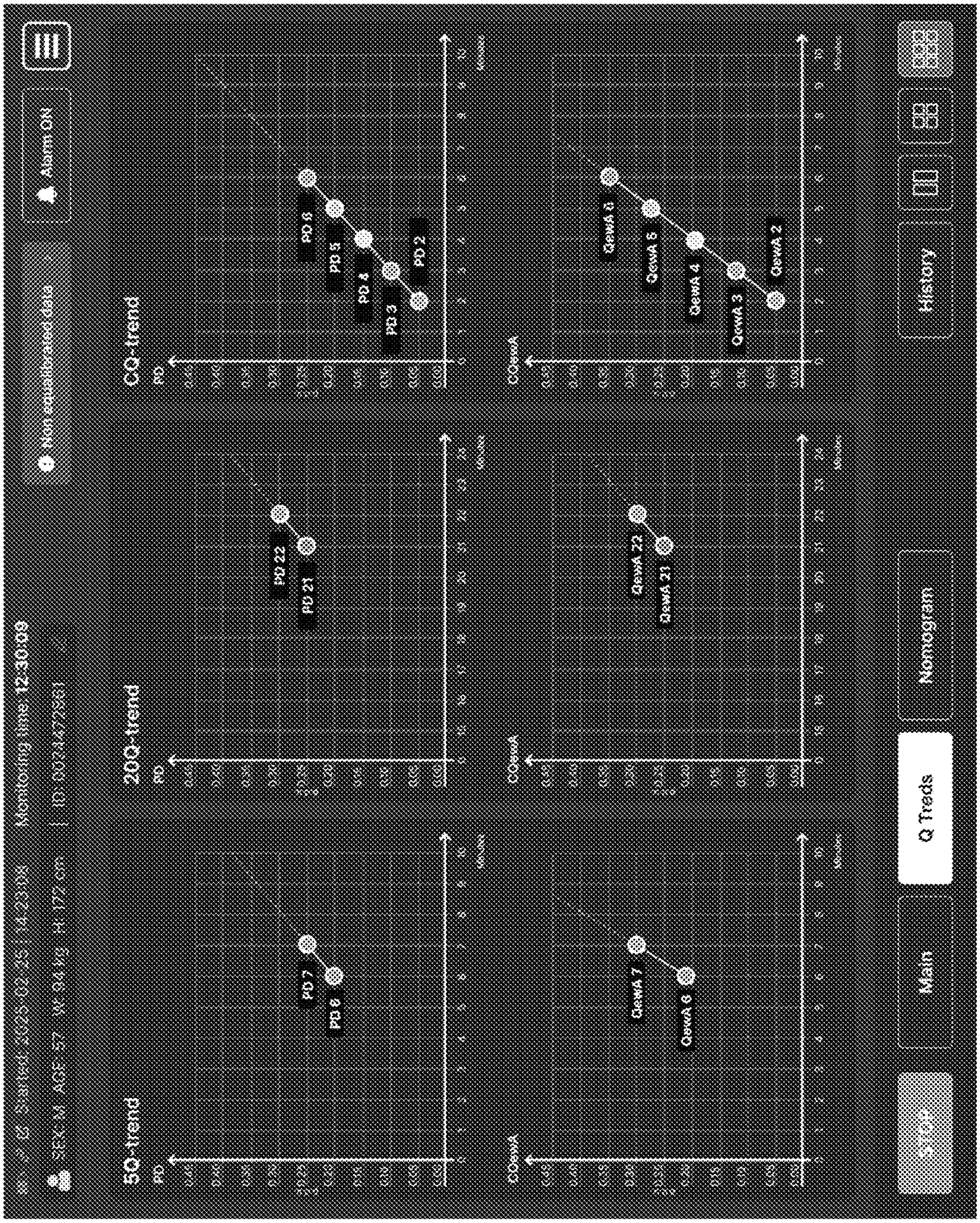
FIG. 81 illustrates example of Q-Trend screens that may be presented to in accordance with an embodiment of the present disclosure.

In embodiments, the Q-Trends screen (FIG. 81) allows users to view and select various trends (Q5, Q20, QC, PD, QewA). An example of the Q-Trends screen is shown in FIG. 81 which allows the ability to view all three trends (5Q; 20Q; CQ) for both PD and QewA or to allow the user to select either PD or QewA trends. The Q-trends display further provides the possibility to configure the default layout of Q-Trends, which may be stored and repeated in the next session as a default.

In embodiments, AI agents in the background will constantly monitor the situation and based on it, will provide recommendations to refocus or change the configuration of the Q-Trends screen to ensure the most relevant information is displayed in the context of patient health status.

In embodiments, a standard trend for decision support screen displays two trends (PD and Delta $eH_2O$) and provides access to a Clinical Decision Support System (CDSS) with eight standardized patterns (however fewer or additional patterns may be used). The AI agent may use machine learning to analyse trends, notify matches, and predict short-term, average, and long-term trends, offering explanations and educational descriptions for each pattern. FIGS. 58-69 illustrate exemplary patterns.

In embodiments, five trends may be established based on current measures including trends for: PD, QewA, Hb and/or plvHb, Hct and oHct.

In embodiments, the CDSS us accessible to allow viewing all prepared standardized patterns based on clinical condition. In embodiments, eight standardized patterns may be available, however, fewer or additional patterns may be used. In embodiments, all possible selections may be displayed in one window using small icons, each accompanied by a single indicative sentence.

In embodiments, the trends indicate context-sensitive relationships between PD and changes in extravascular water (QewA). In embodiments, optimization of PD and Hct using observations in circadian cycle-related fluctuations in hydration status (24 h PD and QewA trends) and determining oHct, oPD, oBV, oPV and RCM may be accomplished. In embodiments, optimization of PD and Hct using fluid status optimization protocols or assessing amplitude of ongoing PD fluctuation and determining oHct, oPD, oBV, oPV and RCM may be implemented. Acceptable and safe fluctuations in PD (plasma hydration levels and intravascular fluid accumulation) and ewA (extravascular water levels as indication of tissue hydration status, extravascular fluid accumulation and levels of total body water) may be reflected in the patterns. In embodiments, relevant correlations between PD and QewA and Hct during changes in red cell mass (due to hemorrhage or red cell transfusion) may be represented in the patterns.

In embodiments, relevant correlations between PD and QewA and Hct for diagnosing imminent edema or dehydration, capillary refill (e.g. in hemorrhage) and capillary leak, e.g., in sepsis may be reflected in the patterns.

Further, relevant correlations between PD and QewA and Hct for differential diagnostics in assessing adequacy of intravascular and tissue fluid levels may be reflected in the patterns.

In embodiments, relevant trends for guiding safe fluid administration, restriction and removal may be reflected in the patterns.

In embodiments, each pattern will have a more detailed description, serving as an educational tool like current medical monitors.

In all AI agent modes, a machine learning (artificial intelligence) algorithm will always be active, analysing the current trend. Upon detecting a match with one of the eight patterns, however fewer or additional patterns may be used, it may indicate this on the main screen by providing a notification. Activating the notification will open the standard trends window, allowing the medical professional to assess the patient's condition.

In prediction mode, the AI agent may predict standardized trends: short-term (up to 1 hour), average (up to 3 hours) and long-term (up to 6 hours) and additional trend duration combinations can be applicable. Prediction may be indicated in a separate section. In copilot mode, the AI agent may provide the possibility to explain standardized trends and their predicted transition.

Figure 82A:
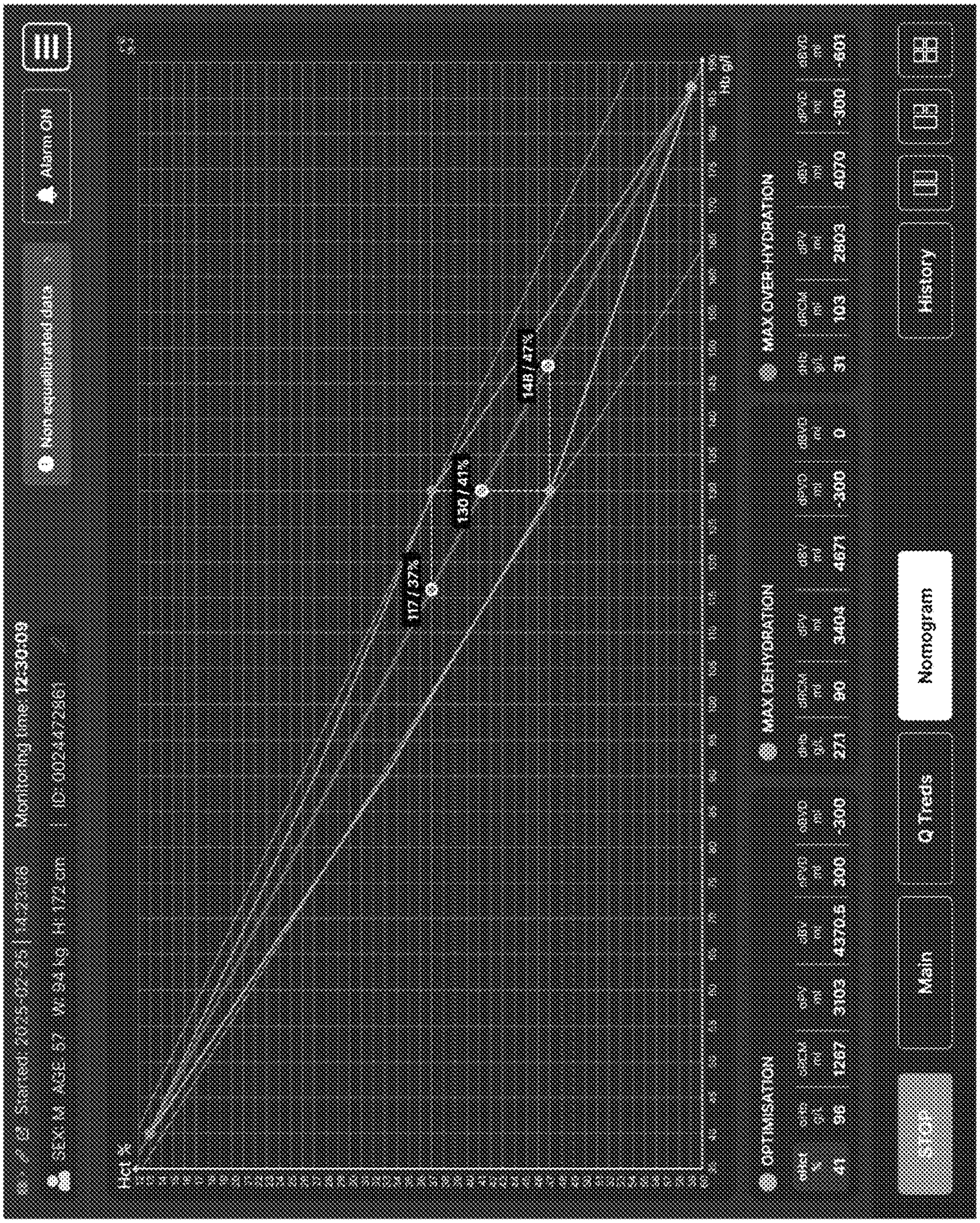
Figure 82B:
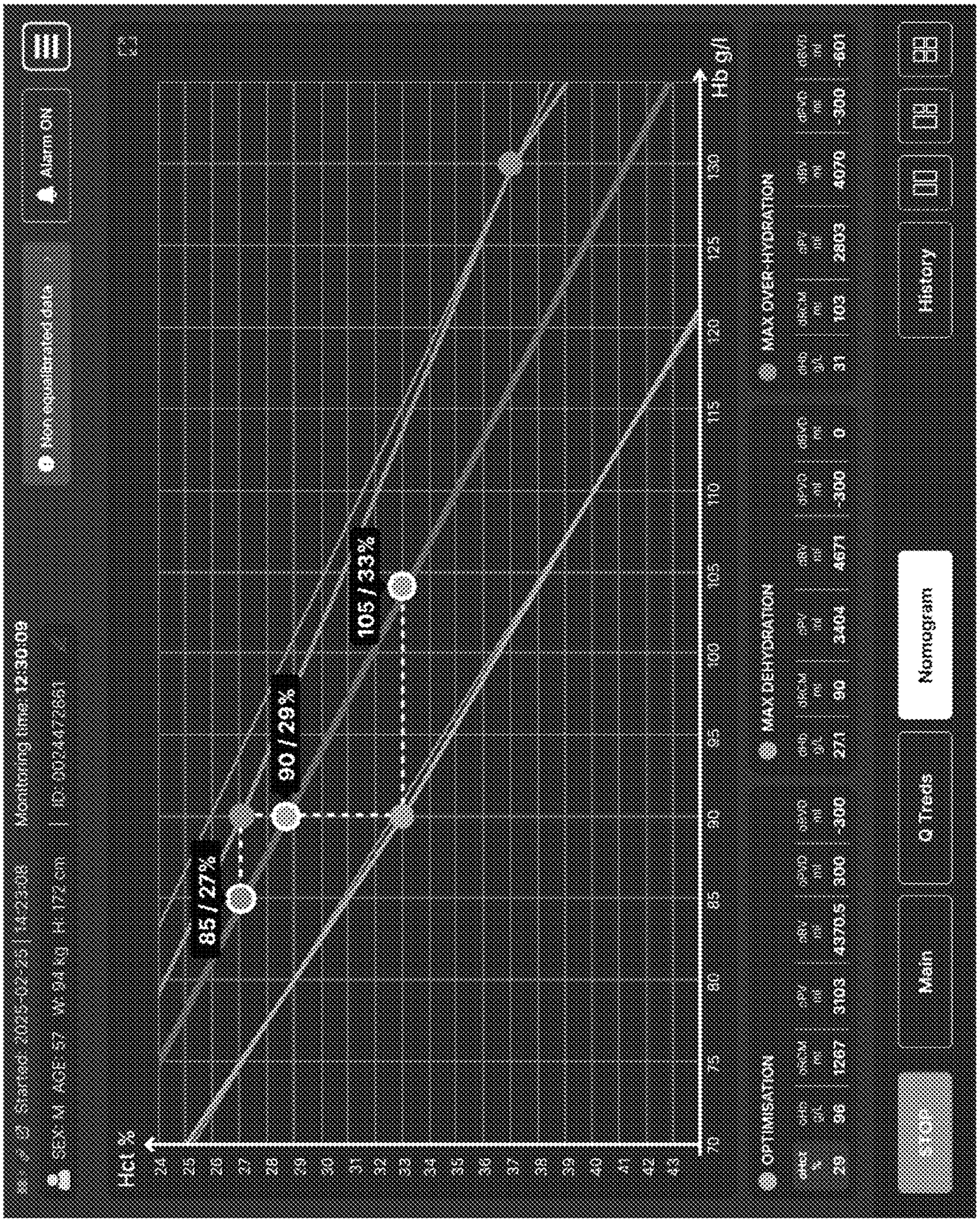
Figure 82C:
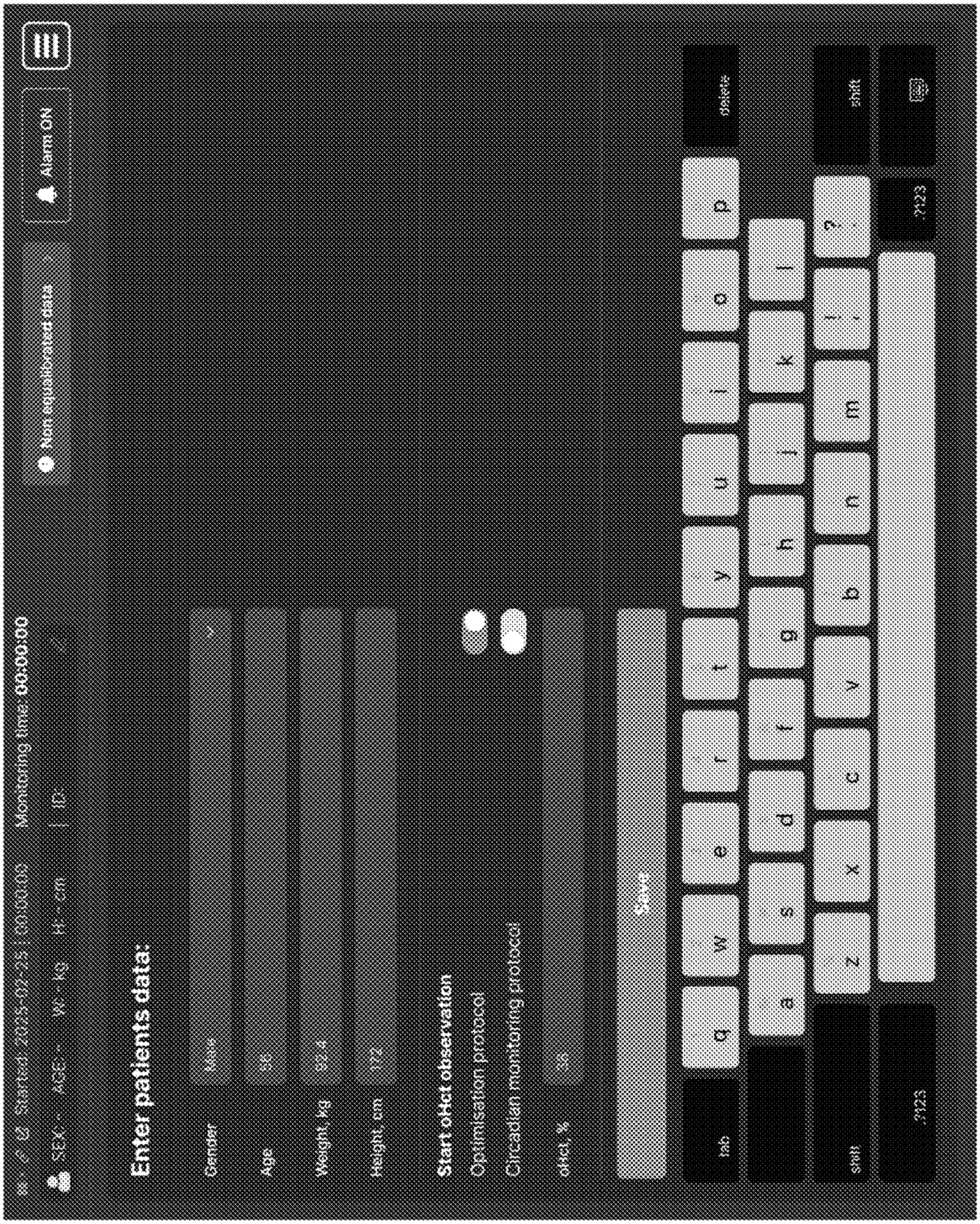

In embodiments, the CDSS screen for HBS Nomograms (FIG. 82-82A) displays two HBS nomograms, including optimization and a non-standard rhombus, with real-time measurement indicators. AI agents predict HBS nomogram statuses for short-term, average-term, and long-term periods, providing recommendations and support in various modes to assist medical personnel in decision-making.

As noted above, the primary trend will be a rhombus, a snapshot of the overall measurement view, showing only the part based on the current measurement status. In embodiments, the AI agent may provide an option to call up the full rhombus diagram on a separate screen and allow the user to access the full nomogram with zoom-in and zoom-out capabilities on a separate screen.

In embodiments, AI agents will predict HBS nomogram statuses/movements for: short-term prediction (up to 1 hour), average-term prediction (up to 3 hours) and long-term prediction (up to 6 hours) and additional trend duration combinations ay be applicable. In embodiments, predictions will be displayed on 2xHBS Nomogram+ for each time frame by highlighting its predicted status.

In embodiments, the transition of health states and ratios by selected prediction range (short-term, average-term, long-term) may be visible. In embodiments, AI agents may provide recommendations for medical personnel, such as:

1. Normal mode-medical experts manage all. AI provides no suggestions or recommendations. A classical CDSS system is enabled.
2. Predicted mode-medical experts manage all, but AI agents predict the future health status of a monitored patient and provide this information for guidance. A classical CDSS system is enabled but augmented with future predictions.
3. Copilot mode. Provide the option to switch to copilot mode. This mode will automatically display the application screen and information most relevant for decision support, considering the context of the current health status. AI agents will recommend actions based on classical CDSS system decision rules in this mode with the option to generate new decision paths.

Figure 83:
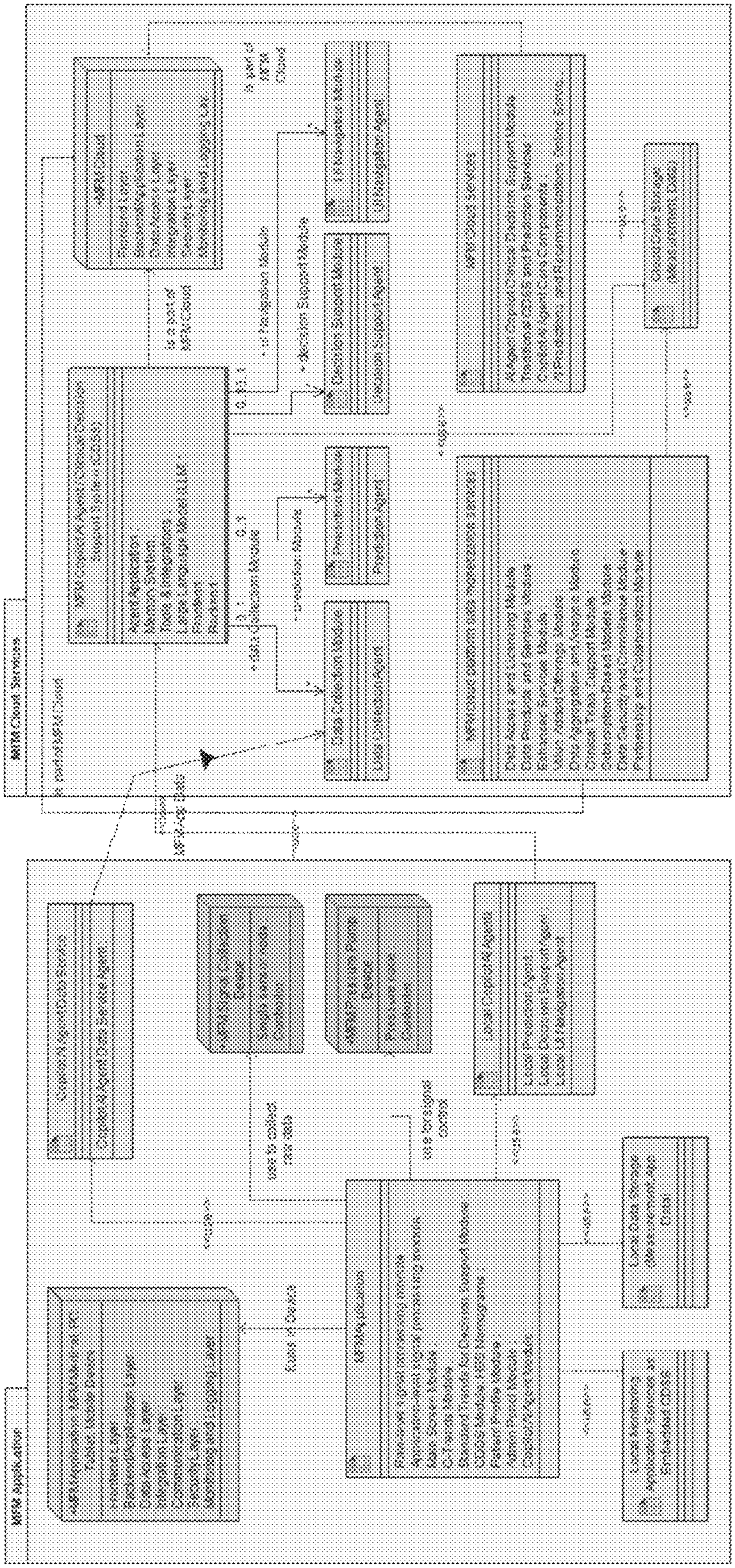

In embodiments, the software application may begin by asking will ask for the patient's profile details by popping a notification on the main screen. The system may use average default values if a medical personal do not set it. FIG. 83 illustrates an example of a patient profile configuration. In embodiments, the patient may provide their information including: weight, height, age, add and gender.

In embodiments, body surface area (BSA) may be automatically calculated based on the patient profile information. In addition, the IBV may also be automatically calculated.

In embodiments, initial parameters (like oHct, %) for key estimates may be set based on the entered patient data. In an oHct observation mode, the system will automatically optimize and estimate the optimal profile of patients and measure circadian rhythm or parameters changes.

In embodiments, a Admin Panel may provide comprehensive management capabilities across various domains, including patient profiles, trends, nomograms, AI predictions, and user accounts and features an Admin Dashboard for key metrics and notifications and configurable settings.

In embodiments, the Admin Dashboard displays key metrics and statistics (e.g., active trends and alerts), provides quick access to recent activities and notifications. Summary cards show counts, measurements, trends, and alerts and an Activity Feed should list recent actions and updates. Notifications should display essential alerts and messages on application status.

In embodiments, the admin dashboard may be used to manage patient profiles, including adding, editing, and deleting patient information. The dashboard may display a searchable and sortable list of patients and show detailed information for a selected patient. It may provide a form for entering or updating patient data (e.g., name, date of birth, gender, body weight, body height).

In embodiments, patient information may be exported for processing. In embodiments, the dashboard may be used to manage trends, including viewing and configuring trend data. In embodiments, the dashboard may be used to display a searchable and sortable list of trends and detailed information for a selected trend and to allow configuration of trend display settings (e.g., Q5, Q20, QC).

In embodiments, HBS nomograms may be managed including viewing and configuring nomogram data, displaying a searchable and sortable list of nomograms, showing detailed information for a selected nomogram and allowing configuration of nomogram display settings.

In embodiments, AI predictions and the CDSS services may be managed. The dashboard allows for a display of AI prediction services and a list of CDSS services and allows configuration of AI and CDSS settings.

In embodiments, the dashboard may manage user accounts, including adding, editing, and deleting users, displaying a searchable and sortable list of users, showing detailed information for a selected user and proving a form for entering or updating user data (e.g., username, role, permissions).

In embodiments, the dashboard may configure application settings and preferences, configure general application settings (e.g., theme, language) and security settings (e.g., password policies, access controls) as well as notification preferences.

In embodiments, the dashboard allows for viewing of settings of reports based on patient data, trends, and AI predictions, displays a list of available reports, shows detailed information for a selected report and provided report configuration options (e.g., date range, parameter ranges).

In embodiments, an AI agent screen predicts hemorrhage and hydration statuses for short-term, average-term, and long-term periods, displaying these predictions on traffic light indicators. It offers recommendations and support based on CDSS rules, with interaction modes including normal, predicted, and copilot modes. It supports continuous learning and various information-sharing forms like on-screen, voice, and text chat.

In embodiments, AI agents will predict hemorrhage and hydration statuses for the following time frames: Short-term prediction (1 hour), Average-term prediction (3 hours) and Long-term prediction (6 hours) and additional trend duration combinations may be applicable. In embodiments, predictions will be displayed on traffic light indicators for each time frame. Further, the AI agent screen may display the transition of health states and ratios by selected prediction range (short-term, average-term, long-term).

In embodiments, AI agents will provide recommendations and support for medical personnel, such as: (1) suggest which parameters or application screens could be activated to evaluate patient status more precisely, and (2) give hints on actions based on CDSS decision rules.

In embodiments, normally, medical experts manage all aspects of the application. In prediction mode medical experts manage all aspects, but AI agents predict the future health status of a monitored patient and provide this information for guidance. In embodiments, a classical CDSS system is enabled but augmented with future predictions.

In embodiments, in copilot mode, the AI agent may: automatically display the application screen and information most relevant for decision support, considering the context of the current health status and AI agents will recommend actions based on classical CDSS system decision rules, with the option to generate new decision paths.

In embodiments, the AI agent and Clinical Decision Support Module may constantly learn and improve its decision paths based on collected data (patient measures and medical expert actions) and patient health outcomes. This module provides predictions, augments current diagrams and data with predicted data and shows prediction alerts, writes recommendations and explains ratios and health transition status. In embodiments, the module may allow voice communication to allow medical experts to talk with the AI agent to get guidance, navigate application functionality, and ask for decision support in spoken language. The module preferably allows for switching between traditional on-screen, voice communication, and free-form dialog text chat modes should be possible.

In embodiments, the cloud services provide a comprehensive and secure platform for hosting AI Agent Core applications and components. Cloud services provide scalable computing resources to handle varying workloads and ensures continuous access to AI agent services and data. The cloud services secure data transfer and storage and adheres to healthcare regulations for data privacy and security.

In embodiments, an AI Agent Copilot Clinical Decision Support Module may allow access online to the cloud services and provides advanced decision support and predictive analytics.

In embodiments, the CCDS module may be embedded into the monitoring application and offers traditional clinical decision support and prediction services without requiring constant cloud connectivity but can periodically be updated with improvements.

In embodiments, the AI agent components may be hosted on the cloud services which ensures scalability and availability for healthcare professionals.

In embodiments, Temp Local Measurements Data Storage may allow for temporary storage of all measurement data locally within the device and application to allow real-time data tracking and immediate access.

Cloud Measurements Data Storage allows for periodic transfers of stored measurement data to the cloud which ensures data consistency and availability for analysis and reporting.

In embodiments, AI predictions and recommendations may be accessible via the cloud services to provide real-time insights and guidance based on collected data using Multiple Interaction Modes.

As noted above, alerts and predictions may also be provided visually via the main monitor.

In embodiments, the cloud Platform Data Services include modules for data access, licensing, and custom reporting. Predictive analytics and personalized medicine enhance patient outcomes and operational efficiency. Value-added offerings bundle insights into healthcare services, while data aggregation supports population health management. Subscription-based models provide access to AI predictions and continuous updates, ensuring data security and compliance. Partnerships with technology providers and cloud services enhance data capabilities.

In embodiments, the platform may manage access to anonymized patient data for external entities (e.g., research institutions and pharmaceutical companies).

In embodiments, the platform may handle licensing agreements and provide data to healthcare providers, insurers, and other stakeholders.

In embodiments, the platform may generate and deliver customized reports based on collected data.

In embodiments, the platform may offer predictive analytics services to healthcare providers for improved patient outcomes and operational efficiency.

In embodiments, the platform may provide enhanced services. In embodiments, the enhanced services may include developing personalized treatment plans and wellness recommendations using patient data, optimizing internal processes and service delivery based on data insights.

In embodiments, the platform may provide value-added offerings which may include bundling data-driven insights with existing healthcare services to create comprehensive solutions, developing selling advanced decision support tools utilizing AI predictions and recommendations.

In embodiments, the application may provide aggregate data to identify health trends and patterns for public health organizations. The application may stratify patient risk levels and provide valuable information to insurers and healthcare providers. The application may also provide data to support clinical trials and drug development.

In embodiments, AI services may be offered on a subscription basis to provide AI-driven predictions and recommendations.

As noted above, the system and method provide regular updates and improvements to traditional CDSS and prediction services using the AI agents which are trained and retrained based on prior data from the system and method.

In embodiments, advanced encryption and data security services may be used to protect data. In embodiments, consulting services may be offered to help organizations adhere to data privacy regulations.

In embodiments, the architecture of the system utilizing the software application can be seen in FIG. 83. In embodiments, the Frontend Layer displays patient data and trends, adapting to various screen sizes. The Backend/Application Layer manages interactions and provides core functionalities. The Data Access Layer handles the storage and retrieval of information.

In embodiments, the Integration Layer uses APIs for communication between components. In embodiments, the communication protocols may be used. The Communication Layer supports real-time updates and interactions, while the Security Layer ensures secure access. Monitoring and Logging tracks performance and record events.

Various screens display patient data, trends, and decision-support information. Interactive elements for user input and data visualization. Ensure the application adapts to various screen sizes (medical monitoring devices, mobile, PC, tablet).

The Backend/Applicant Layer manages user interactions and screen updates and provides core functionalities like predictions, decision support, and data calculations.

The Data Access Layer handles data storage and retrieval for patient information, trends, nomograms, etc.

The Integration Layer uses an API to facilitate communication between different system components and external services.

The Communication Layer provides real-time communication to enable instant data updates and interactions. Voice and Text Communication may be available to support spoken and written interactions with the AI agent.

Authentication and Authorization ensure secure access to the application. Further, interactions are tracked and a log record is maintained.

The AI agent should predict hemorrhage and hydration statuses for varying time periods including: 1 hour, 3 hours, and 6 hours and additional trend duration combinations may be applicable. Predictions will be displayed on traffic light indicators as short-term (up to 1 hour), average (up to 3 hours), and long-term (up to 6 hours) and additional trend duration combinations, like 12 hours m 24 hours, etc.

Similarly, transition of health states and ratios may be selected for prediction in the following range: short-term (up to 1 hour), average (up to 3 hours), and long-term (up to 6 hours) and additional trend duration combinations.

AI agents on any application screen may provide recommendations/support on actions for medical personnel, such as:

1. Suggest which parameters or application screens could be activated to evaluate patient status more precisely.
2. Giving hints/recommendations on actions based on Clinical Decision Support System (CDSS) decision rules.

On any screen, there should be a possibility to go into normal, predicted, or copilot mode. In normal mode, medical experts manage all activity based on information provided by the MW PGG data and AI provides no suggestions or recommendations (a classical CDSS system). In predicted mode, medical experts manage all, but AI agents predict the future health status of a monitored patient and provide this information for guidance. In copilot mode, automatically displays/selects the application screen and information most relevant for decision support, considering the context of the current health status. AI agents should recommend actions based on classical CDSS system decision rules in this mode with the option to generate new decision paths.

The AI agent Copilot Clinical Decision Support module will constantly learn and improve its decision paths based on collected data (patient measures and medical expert actions) and patient health outcomes which may be used as training state to train and improve machine learning algorithms at use in the module.

Switching to AI agent Copilot interaction modes should be possible and traditional on-screen, voice communication, and free-from-dialog text chat may be used. The copilot AI Agent should support multiple information-sharing forms: traditional on-screen, voice communication, free-from dialog, and text chat:

In embodiments, the AI agent Copilot Clinical Decision Support module may be part of the cloud services and accessible online. Traditional CDSS and prediction services should be available as a local component embedded into the monitoring application.

In embodiments, the AI agent Core includes: a memory system; tools and integrations and a large language model (LLM) (or other suitable machine learning or AI option).

Figure 84:
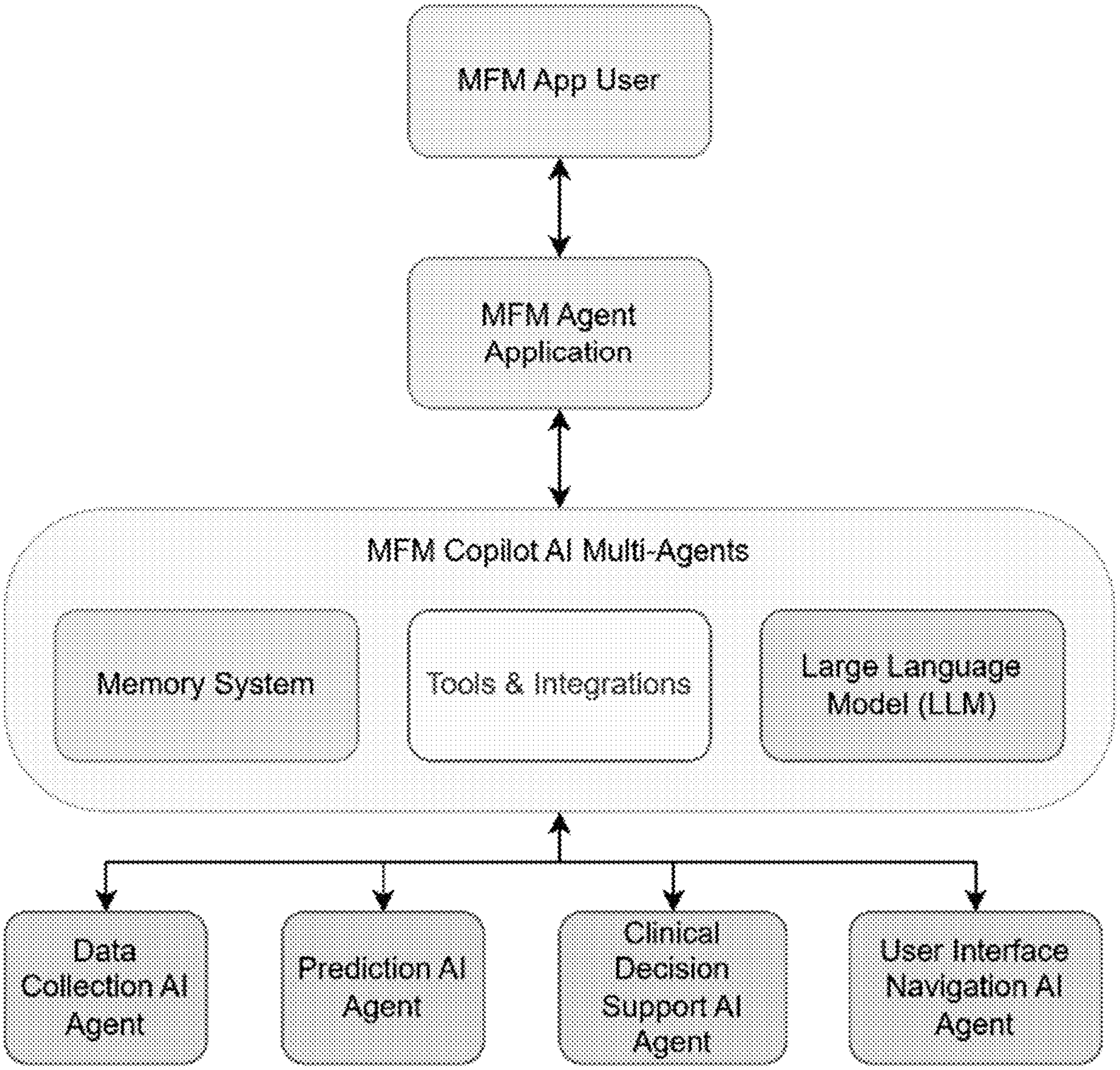

FIG. 84 illustrates the Copilot AI Agent Core module architecture. The Copilot AI Agent core components should be part of cloud services and accessible online. A Copilot AI Agent data service agent should be a local component embedded into the monitoring application. It should temporarily store all measurement data locally in the device and application and periodically transfer it to the cloud.

The Agent Application is the user-facing part of the AI agent and provides the interface through which users interact with the agent and may include:

1. Chatbots. Text-based interfaces for medical expert support or information retrieval.
2. Voice Assistants. Voice-activated interfaces for hands-free interaction with applications.
3. APIs. Programmatic interfaces that allow other software to interact with the agent.

The Memory System maintains context and improve the agent's performance. It includes:

1. Short-term Memory. Stores recent interactions to maintain context within a session.
2. Long-term Memory. Retains information over multiple sessions to personalize user experiences and improve responses based on past interactions.
3. Knowledge Base. A repository of structured and unstructured data that the agent can reference to provide accurate and relevant information.

Tools & Integrations enable the AI agent to perform various tasks by connecting with application services.

The Large Language Model (LLM) is the core of the AI agent's intelligence. It processes natural language inputs and generates appropriate responses. Key features include:

1. Natural Language Understanding (NLU). Interprets user inputs to understand intent and context.
2. Natural Language Generation (NLG). Generates coherent and contextually appropriate responses.
3. Training and Fine-tuning. The model is trained in vast amounts of data and will be fine-tuned for specific application tasks.

In embodiments, the Data Collection Module collects real time date to provide as inputs to the machine learning algorithms. This data may be collected using the system 100 or the sensors 102, 302. The prediction module makes predictions regarding health status based on the collected data using the AI modules which may be trained using training data as discussed above. The Decision Support Module provides recommendations based on the predictions. The UI provides for display of predictions and recommendations.

The AI prediction modules are developed and trained to provide short-term (up to 1 hour), average-term (up to 3 hours), and long-term (up to 6 hours) and additional trend duration combinations and predictions of monitored ratios, however, these time periods may be modified. Predictions may include predictions of standardized trends.

In embodiments, the CDSS may integrate classical CDSS rules. A recommendation engine may provide recommendations based on the AI predictions and the CDSS rules. In embodiments, a continuing learning mechanism may be provided to continue training of the AI to improve decision paths based in collected data.

In embodiments, the User Interface Navigation Module may operate in different modes. In normal mode, the medical experts manage all aspect of the system and AI provides not suggestions. In embodiments, in a predicted moder, AI predicts future health status and provides guidance, but the medical professional makes all decisions. In copilot mode. The AI automatically displays relevant information and recommends actions.

In embodiments, the software application may be a cross-platform software and hardware solution designed for non-invasive, continuous, real-time monitoring, evaluation, and recommendation of human hydration status. The application implements a system operable on iOS and Android operating systems, a smartwatch application operable on Apple Watch and Wear OS platforms, and a back-end algorithmic engine performing personalized hydration analytics. In embodiments, the software application may be implements on any mobile electronic device and may be used on a laptop, PC or server device.

A hydration monitoring system 100 includes at least one wearable sensor (or sensor array) and a companion mobile application or other software element, configured to provide continuous real-time hydration status classification and recommendations based on personalized data.

A method of initiating personalized hydration may be implemented to provide a baseline during a 24-hour continuous physiological data acquisition protocol.

A hydration state classification schema may include multiple gradated levels (at least seven in a preferred embodiment) that are algorithmically derived from real-time sensor data and historic baseline patterns.

A context-sensitive smart alert system uses trend analysis and user context (time, activity, intake) to initiate preemptive notifications regarding hydration.

Figure 85:
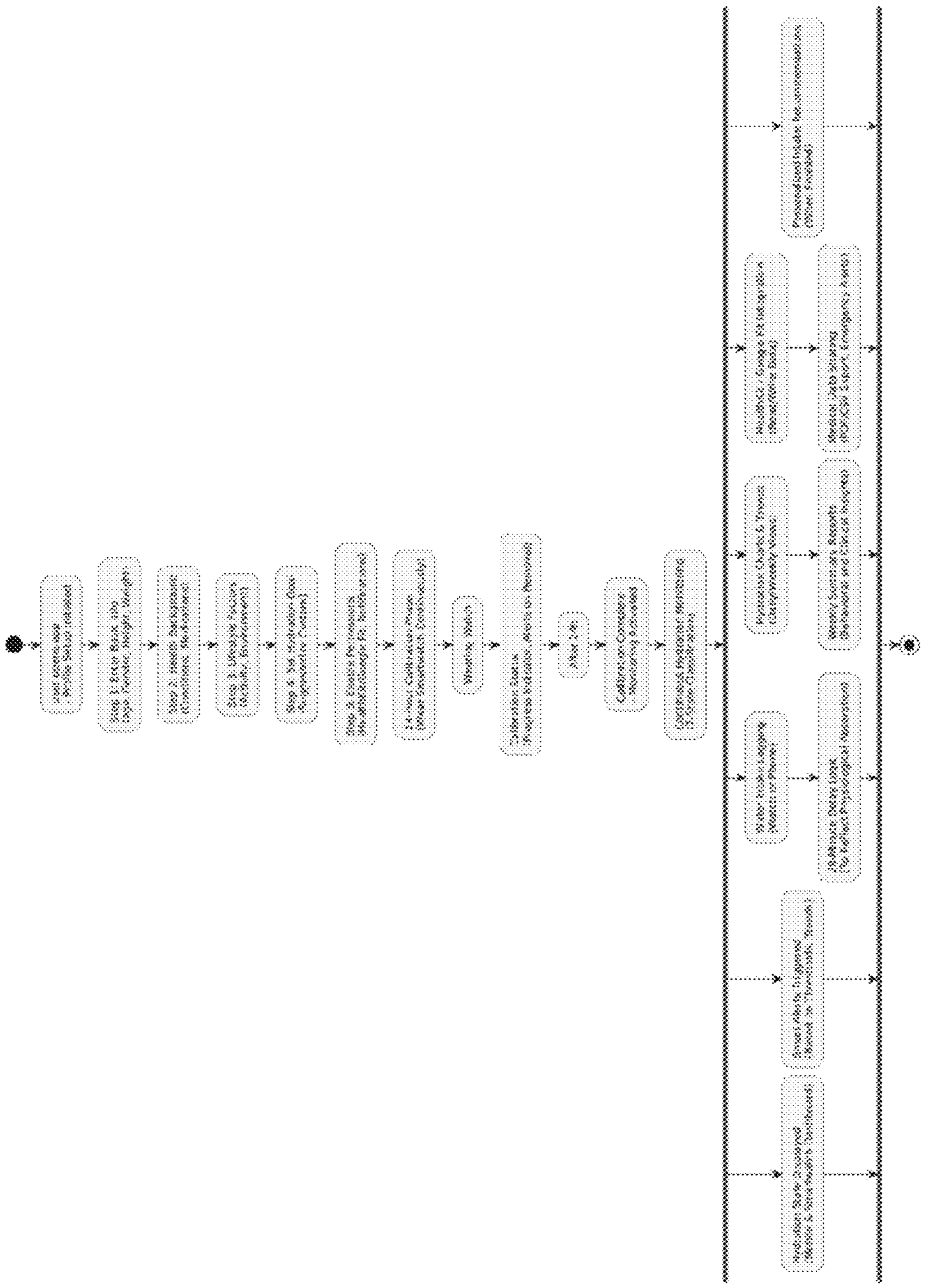

FIG. 85 illustrates an exemplary workflow for the software application that ensures accurate, personalized, and real-time hydration monitoring and is divided into six modules.

Figure 86:
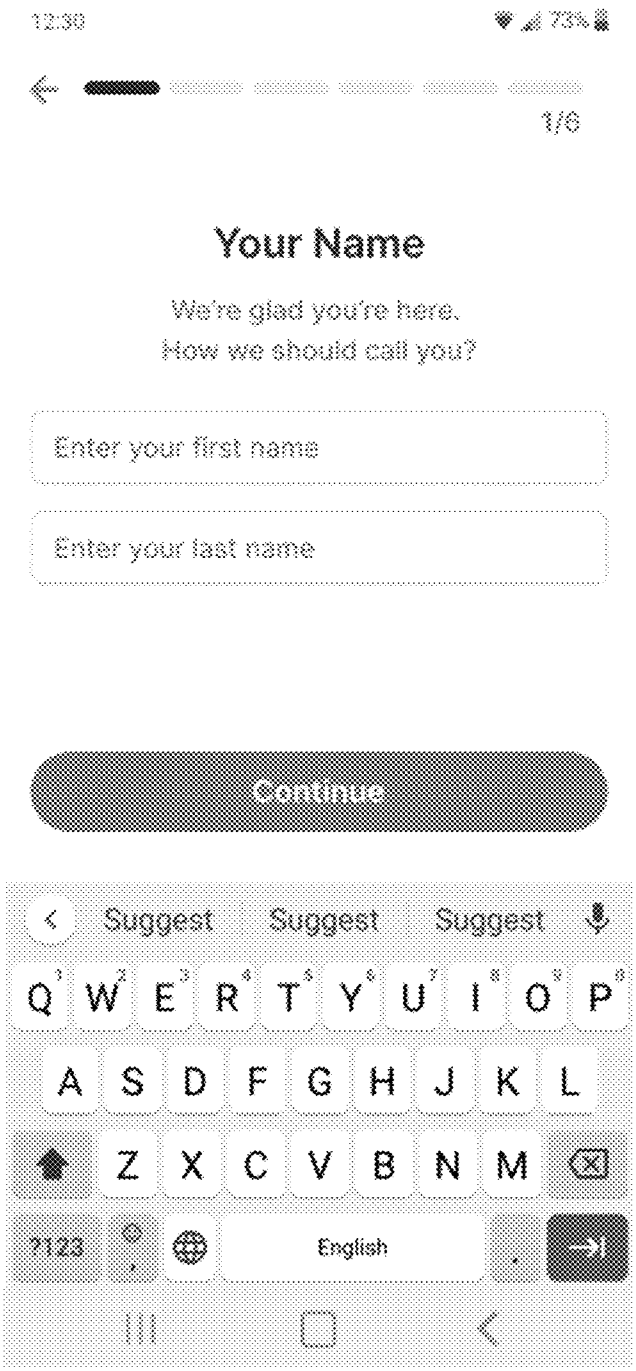

Upon first use, the application initiates a guided onboarding sequence that collects critical user information necessary for hydration modelling including the patient information discuss above as indicated in FIG. 86.

In embodiments a declaration of medical conditions may also be requested and provided by the patient or a caregiver. In embodiments, lifestyle variable regarding activity levels may also be requested and provide. In addition, the patient may be asked to authorize access to their information.

Figure 87:
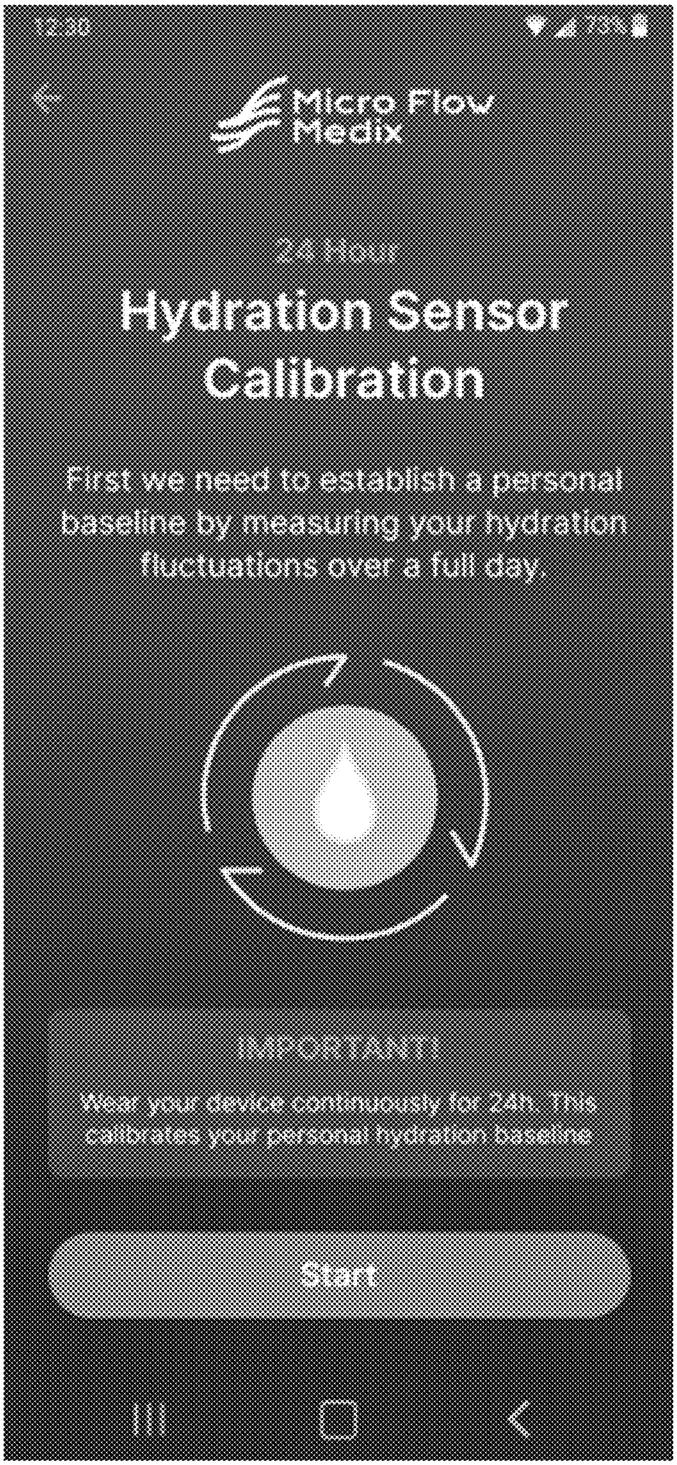
Figure 88:
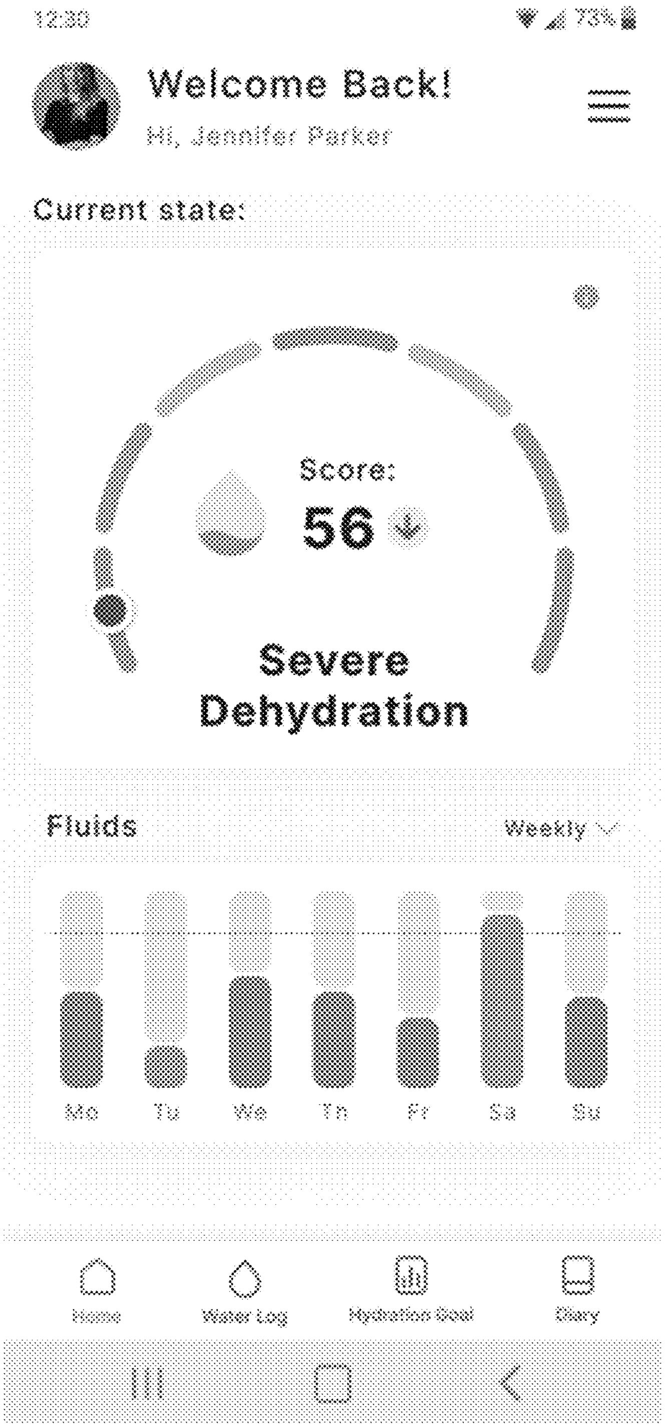

In embodiments, following onboarding, the user is prompted to wear a compatible smartwatch or other wearable sensor or sensor array for a continuous 24-hour period. During this time, the system collects raw physiological signals to establish a personalized hydration baseline. In embodiments, calibration incudes tracking and alerts in case of signal interruption. Once calibration is complete, real-time monitoring may proceed as indicated in FIG. 87.

Once calibrated, the system performs continuous, passive hydration analysis using integrated biosensors. Key components include:

1. Classification of hydration status into one of seven defined states (e.g., Suboptimal, Optimal, Edema).
2. Presentation of the current state and hydration score through mobile and smartwatch dashboards.
3. Real-time triggering of smart alerts based on thresholds and trend analysis.
4. Logging of fluid intake via smartwatch or mobile interface.

When enabled, the system provides individualized recommendations on fluid intake volumes and timing. An internal delay mechanism (approximately 20 minutes) is applied post-intake to account for physiological fluid absorption, reducing premature alerts and improving recommendation accuracy.

Figure 89:
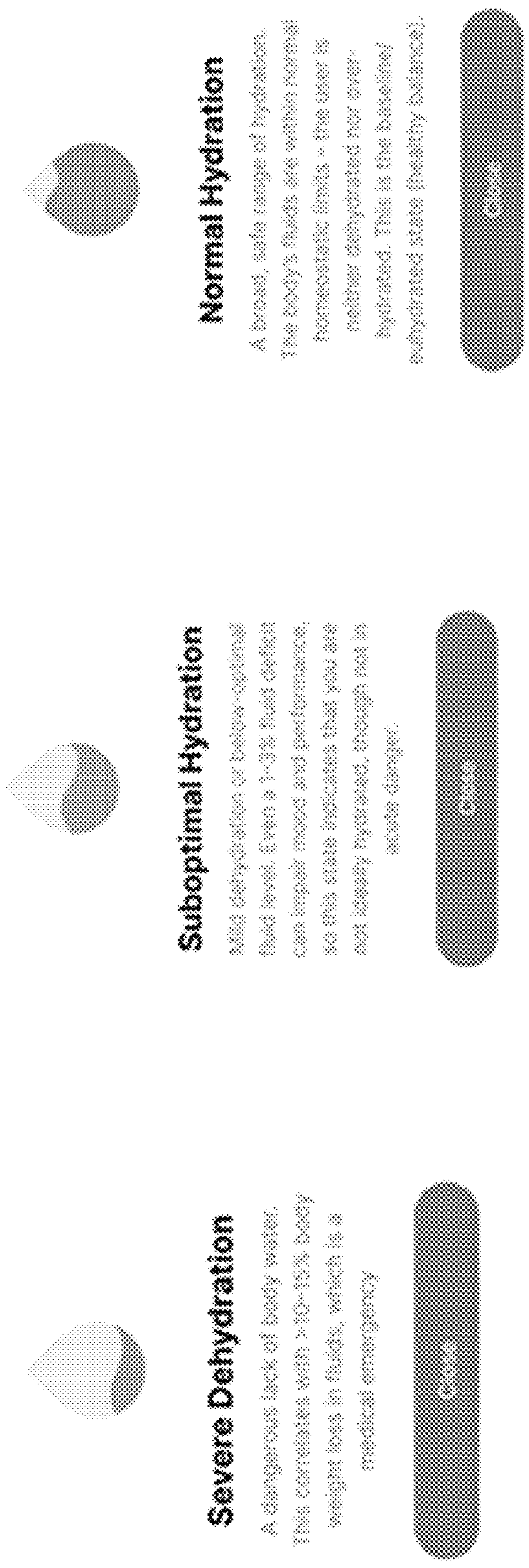

Hydration data is visualized through daily and weekly trend charts on a main monitor. Examples are illustrated in FIG. 89, for example. In embodiments, the user may receive automated weekly summary reports containing behavioral insights and clinical observations.

In embodiments, the system may synchronize with other health or fitness platforms such as Apple HealthKit or Google Fit. Reports may be generated in any desired format for storage or export.

The system deploys trend-sensitive alerts based on hydration trajectories, not solely on instantaneous states. This includes pre-emptive notifications (FIG. 89) when hydration status is forecast to deteriorate. Alerts (FIG. 89) are modulated according to contextual parameters such as time of day, user activity, and recent intake actions, ensuring clinical relevance while minimizing alert fatigue.

Hemodilution, characterized by a reduction in red blood cell concentration due to increased plasma volume, may reduce the effectiveness of fluid infusion in enhancing oxygen transport, potentially impairing oxygenation. This study aims to evaluate the relationship between RCM and PD changes during a mini Volume Loading Test (mVLT) in perioperative patients. Using retrospective data from RCTs in total knee and hip arthroplasty patients, the study explores the clinical feasibility of the Homeostatic Blood States (HBS) theory and the transcapillary reflux model for non-invasive monitoring of fluid accumulation and hydration status.

We analyzed 1,651 arterial plasma dilution (aPD), 1,645 capillary plasma dilution (cPD), and 236 equilibrated haematocrit (EQ_Hct) estimates from 236 mVLT sessions in previous randomized controlled trials (RCTs).

Three mVLT fluid protocols were applied: (a) a total of 36 total knee arthroplasty (TKA) patients received three boluses of 0.5 ml/kg, (b) 48 TKA patients received six boluses of 0.25 ml/kg, (c) 34 total hip arthroplasty (THA) patients received 0.25 ml/kg boluses, with the number determined by an automated decision support system. Boluses were administered before the induction of regional anesthesia and again postoperatively-on the next morning for TKA patients and in the evening of surgery for THA patients.

The primary endpoint was the relationship between RCM and PD changes during the mVLT. This test involved stepwise crystalloid infusion followed by a 20-minute equilibration period without fluids. The EQ_Hct measured after this period was assumed as optimized or homeostatic target plasma dilution (tPD), with variations in EQ_Hct reflecting differences in RCM across mVLT sessions.

The secondary endpoint was fluid extravasation during the equilibration period, inferred from the difference in PD before and after this phase. Arterial plasma dilution (aPD) and EQ_Hct were estimated invasively using arterial hemoglobin concentration (aHb), while capillary plasma dilution and EQ_Hct were estimated noninvasively using total hemoglobin (SpHb; Radical 7, Masimo Corp., CA).

The primary hypothesis—that aPD decreases as EQ_Hct decreases when EQ_Hct<0.4 (40%)—was confirmed. A very weak but statistically significant positive correlation was found between EQ_Hct and absolute aPD (Spearman's correlation coefficient: 0.1025, p<0.001).

The secondary hypotheses were also confirmed: (a) different numbers of boluses with equal net crystalloid volumes resulted in similar fluid extravasation during the equilibration period. There was no statistically significant difference between the positive median aPD values of the 36 and 48 TKA patients (Welch's t-statistic: −1.1081, p=0.2721), (b) the automated decision support system, which guided the number of boluses, led to less fluid extravasation than a fixed number of fluid challenges. The mean amplitude of positive aPD values in the 34 THA patients (0.0427) was significantly lower than in the pooled group of 36 and 48 TKA patients (0.0752) (Mann-Whitney U test: 5327.5, p<0.001). When non-invasive data sets were used, all hypotheses were partially confirmed.

This study provides preliminary evidence for the feasibility of using the HBS theory and the transcapillary reflux model for noninvasive, continuous monitoring of plasma hydration and intravascular fluid accumulation in perioperative patients. Our results support the hypothesis that PD fluctuations are linked to RCM and that safe limits of PD depend on EQ_Hct values. In addition, we found that varying bolus numbers in fluid loading protocols did not significantly affect fluid extravasation provided that net infused volume is the same, and that controlled infusion can minimize extravasation and reduce the risk of excessive fluid accumulation. The findings emphasize the dermis's role in managing fluid overload and highlight the potential of MW PPG technology for improving fluid management in clinical settings In embodiments, a method for determining extravascular water volume (eH2O) in a subject, which is an indication of hydration status of a subject, and its trend which indicates changes in total body water TBW, includes a processing step configured to perform continuously or intermittently (occlusion method) obtaining MW PPG information from light that has passed through a tissue of the subject; continuously or intermittently (occlusion method) processing the obtained MW PPG information to derive a parameter of eH2O of the subject and its changes (trend) based on the MW PPG information, thereby determining the hydration status of the subject, and changes in TBW based on one or more of the derived parameters.

In embodiments, a method for determining the iH2O, which is an indication of plasma dilution status of a subject, and its trend which indicates changes in PD and total body blood volume TBV, includes a processing step configured to perform continuously or intermittently (occlusion method) obtaining MW PPG information from light that has passed through a tissue of the subject and continuously or intermittently (occlusion method) processing the obtained MW PPG information to derive a parameter of iH2O, and changes in PD and TBV based on the MW PPG information.

In embodiments, a method for determining changes in the transcapillary FAR of a subject which is an indication of changes in transcapillary fluid equilibration, fluid accumulation in tissues, and the present or imminent edema or dehydration, including continuously or intermittently (occlusion method) obtaining MW PPG information from light that has passed through a tissue of the subject; continuously or intermittently (occlusion method) processing the obtained MW PPG information to derive a parameter of transcapillary filtration absorption ratio (iH2O) based on assessing the difference between the changes (trends) of iH2O and extravascular water volume eH2O based on the MW PPG information.

In embodiments, a method for determining the total hemoglobin volume tHb of a subject which is the sum of pulsatile aHb, nHb, cHb, vHb, and tHb trend which indicates changes in large vessel hemoglobin concentration lvHb, PD, TBV, perfusion of tissues (microcirculation), and changes in the wbHb, which is an indication of reduction in red cell volume (e.g. hemorrhage) or increase in red cell volume (e.g. transfusion), including continuously or intermittently (occlusion method) obtaining MW PPG information from light that has passed through a tissue of the subject; continuously or intermittently (occlusion method) processing the obtained MW PPG information to derive a parameter of tHb of the subject which is the sum of pulsatile aHb, non-pulsatile arterial nHb, cHb, vHb, and tHb trend which indicates changes in in lvHb, PD, perfusion of tissues (microcirculation), and changes in the wbHb based on the MW PPG information, thereby determining the hydration status of the subject based on one or more of the derived parameters.

In embodiments, the light includes (i) low wavelength light (LWL), preferably 400 nm to 600 nm light; and (ii) high wavelength light (HWL), preferably 850 nm to 1100 nm light, preferably wherein there is an inverse relationship between light absorption by hemoglobin and water at LWL and HWL; preferably wherein this is applied for calibration, more specifically light absorption by hemoglobin at LWL is adjusted by ratio light absorption by water to hemoglobin at HWL (this minimizes the impact of light absorption by water in hemoglobin measurements, and vice versa when water is being measured).

In embodiments, the light includes (i) low wavelength light (LWL), preferably 400 nm to 600 nm light; and (ii) high wavelength light (HWL), preferably 850 nm to 1100 nm light.

In embodiments, the MW PPG information includes at least one pulsatile (AC) component and at least one non-pulsatile (DC) component.

In embodiments, a net high wavelength (HWL) DC component value (a whole DC (wDC) component value) is a net light absorption by total non-pulsatile water value calculated during step (ii) by adding an intravascular (sH2O) light absorption value, an extravascular (eH2O) light absorption value, and a non-expandable water compartment (nDC) light absorption value.

In embodiments, a net high wavelength (HWL) DC component value—the total non-pulsatile intravascular water (sH2O)—is a net absorption by non-pulsatile water value calculated during step (ii) by adding an arterial (nH2O) light absorption value, a venous (vH2O) light absorption value, and a capillary (cH2O) light absorption value; wherein each of these values include light absorption by water in plasma (PV, plasma volume) and water inside red blood cells (RCV, red cell volume).

In embodiments, a high wavelength (HWL) AC component value includes a pulsatile arterial water (aH2O) light absorption value, and optionally comprising other light absorption values of other constituents with lower absorption coefficients such as hemoglobin, melanin, and myoglobin (other high-wavelength AC components (oHAC)), and is calculated during step (ii).

In embodiments, a non-pulsatile low wavelength (LWL) DC component value includes a non-pulsatile hemoglobin (sHb) light absorption value, optionally and light absorption values of other constituents such as melanin and myoglobin (other DC components (oDC)), and is calculated during step (ii).

In embodiments, the sHb value a is net LWL light absorption DC component value by hemoglobin includes a non-pulsatile arterial (nHb) light absorption value, a capillary (cHb) light absorption value, and a venous (vHb) light absorption value, and is calculated during step (ii).

In embodiments, a LWL AC component value includes a pulsatile arterial hemoglobin (aHb) light absorption value, optionally comprising and light absorption values of other constituents with much lower absorption coefficients including w ater (other low-wavelength AC components (oLAC)), and is calculated during step (ii).

In embodiments, a total hemoglobin (tHb) value is the sum of aHb, sHb, oDC, and oLAC and is calculated during step (ii).

In embodiments, a lwDC value is measured when compression of the tissue and its blood vessels is applied, wherein the lwDC value is a HWL DC component value and is the net light absorption value calculated during step (ii) by adding a extravascular water (eH2O) light absorption value and a non-expandable water compartment (nDC) light absorption value.

In embodiments, a pre-occlusion non-pulsatile water net baseline light absorption value (bwDC) is calculated during step (ii) as:

$$bw\mathrm{DC} = s\mathrm{H2O} + e\mathrm{H2O} + n\mathrm{DC} = n\mathrm{H2O} + v\mathrm{H2O} + c\mathrm{H2O} + e\mathrm{H2O} + n\mathrm{DC} \quad [29]$$

where sH2O is all non-pulsatile intravascular water, eH2O is extravascular water in expandable tissues, nDC is water in non-expandable tissues, nH2O is non-pulsatile arterial water, vH2O is venous, and cH2O is capillary.

In embodiments, an occlusion phase HWL DC component light absorption by water value (lwDC) is calculated during step (ii) as:

$$lw\mathrm{DC} = e\mathrm{H2O} + n\mathrm{DC} \quad [30]$$

where lwDC is net HWL DC light absorption by water, eH2O is all non-pulsatile water which is net extravascular water in expandable fluid compartments (interstitial and intracellular), and nDC is water in non-expandable tissues.

In embodiments, HWL DC component light absorption by water value nDC is constant in short term and does not affect evaluation of changes in eH2O based on changes in lwDC in consecutive occlusion sessions such that:

$$\Delta lwDC = \Delta eH2O; \text{ and} \quad [31]$$

$$QlwDC = QeH2O \quad [32]$$

In embodiments, a pre-occlusion (baseline) LWL DC component light absorption by hemoglobin value wDC net light absorption value (bsHb, baseline sHb) is calculated during step (ii) as $$bsHb = sHb + \text{melanin} + \text{myoglobin} = sHb + oDC \quad [33]$$

where bsHb is baseline static hemoglobin, sHb is static (non-pulsatile) hemoglobin and oDC is myoglobin and/or melanin.

In embodiments, a true baseline LWL DC component light absorption by hemoglobin value sHb value (tbsHb) is calculated during step (ii) as $$tbsHb = bsHb - oDC = bsHb - lsHb \quad [34]$$

wherein tbsHb is true baseline static hemoglobin, bsHb is baseline static hemoglobin, lsHb is a LWL DC signal which indicates net absorption by non-hemoglobin constituents.

In embodiments, wherein light absorption LWL DC component light absorption by other constituents, preferably melanin and/or myoglobin, are ignored in extrapolating/estimating changes in sHb such that $$\Delta sHb = \Delta(nHb + cHb + vHb) \quad [35]$$

$$QsHb = Q(nHb + cHb + vHb) \quad [36]$$

where sHb is absorption by static hemoglobin, nHb is non-pulsatile arterial hemoglobin, cHb is capillary and vHb is venous hemoglobin.

In embodiments, a pre-occlusion/baseline HWL AC component light absorption by pulsatile arterial water aH2O net light absorption value (baH2O) is calculated during step (ii) as:

$$baH2O = aH2O + oHAC \quad [37]$$

wherein aH2O is pulsatile arterial water and oHAC is other pulsatile HWL light absorbing constituents with a lower absorption coefficient preferably hemoglobin, melanin, and/or myoglobin.

In embodiments, an adjusted true pre-occlusion/baseline HWL AC component light absorption by pulsatile arterial water bH2O value (tbaH2O) is calculated during step (ii) as:

$$tbaH2O = baH2O - oHAC = baH2O - laH2O \quad [38]$$

wherein baH2O is baseline pulsatile arterial water, oHAC is other pulsatile HWL light absorbing constituents, laH2O is lowest aH2O value in an occlusion phase measurements In embodiments, a pre-occlusion baseline LWL AC component light absorption Hb (baHb) is calculated during step (ii) as:

$$baHb = aHb + oLAC \quad [39]$$

wherein aHb is pulsatile arterial hemoglobin and oLAC is other low-wavelength light absorbing constituents with a lower absorption coefficient.

In embodiments, an adjusted or true pre-occlusion/baseline HWL AC component light absorption by pulsatile arterial hemoglobin (tbaHb) is calculated during step (ii) as:

$$tbaHb = baHb - oLAC = baHb - laHb \quad [40]$$

wherein baHb is pre-occlusion/baseline pulsatile arterial hemoglobin, oLAC is other LWL light absorbing constituents with a lower absorption coefficient, laHb is an occlusion phase measurement of the lowest aHb value.

In embodiments, a non-pulsatile intravascular water value (sH2O) is calculated during step (ii) as:

$$sH2O = nH2O + vH2O + cH2O = bwDC - lwDC \quad [41]$$

where nH2O is non-pulsatile arterial water, vH2O is non-pulsatile venous, cH2O is non-pulsatile capillary, bwDC is pre-occlusion/baseline HWL DC component, and lwDC is lowest HWL DC component during occlusion phase.

In embodiments, a net intravascular water value (iH2O) is the sum of non-pulsatile (sH2O) and pulsatile (aH2O) intravascular water and is calculated during step (ii) as:

$$iH2O = sH2O + aH2O = bwDC - lwDC + aH2O \quad [42]$$

where bwDC is pre-occlusion/baseline HWL DC value, lwDC is the lowest HWL DC component value during the inflation phase.

In embodiments, a total hemoglobin value (itHb) indicates the sum of true non-pulsatile and pulsatile hemoglobins and is calculated during step (ii) as:

$$tHb = tbsHb + tbaHb \quad [43]$$

where tsHb is the sum of non-pulsatile arterial, capillary and venous hemoglobins (nHb+cHb+vHb).

In embodiments, a Total Blood Volume value (TBV) is the sum of AC and DC components of LWL light absorption by hemoglobin and HWL absorption by water and is calculated during step (ii) as:

$$TBV = tHb + iH2O = tHb + bwDC - lwDC \quad [44]$$

where tHb is total hemoglobin (preferably calculated by equation 15), iH2O is total intravascular water which is the sum of plasma volume (PV) and intracellular water (RCV, red cell volume), bwDC is baseline non-pulsatile water (preferably calculated in equation 1) and lwDC is non-pulsatile water in occlusion phase (preferably calculated in equation 2) and it is the lowest HWL DC component value during the inflation phase.

In embodiments, a non-pulsatile Tissue Perfusion Index (nTPI) value indicates a non-pulsatile tissue perfusion reserve which is (i) a difference (A) between maximized value of light absorption by non-pulsatile hemoglobin (msHb) in hyperemia phase and its baseline (bsHb), (ii) a reserve of net tissue perfusion by net non-pulsatile flow in all types of micro-vessels, arterioles, metarterioles, true capillaries, and venules, and (iii) is calculated during step (ii) as:

$$nTPI = msHb - bsHb. \quad [45]$$

preferably wherein equation is used and absorption by non-hemoglobin constituents is ignored; more preferably wherein pulsatile hemglobin is ignored.

In embodiments, a total Tissue Perfusion Index (tTPI) value indicates net or total tissue perfusion reserve which is a difference (Δ) between the maximized TBV (mTBV) in hyperemia phase and baseline TBV (bTBV), wherein tTPI is a reserve of net tissue perfusion by net pulsatile and non-pulsatile hemoglobin and water in arterioles, metarterioles, true capillaries and venules; preferably wherein tTPI is more specific to change in perfusion compared to nTPI; and is calculated during step (ii) as:

$$tTPI = mTBV - bTBV \quad [46]$$

preferably wherein equation is used and the light absorption by non-hemoglobin constituents (optionally oLAC and/or oHAC) and water in non-expandable water compartments (nDC) are ignored.

In embodiments, a total Tissue Perfusion Index (tTPI) value indicates net or total tissue perfusion reserve which is a difference (A) between the maximized TBV (mTBV) in hyperemia phase and baseline TBV (bTBV), wherein tTPI is a reserve of net tissue perfusion by net pulsatile and non-pulsatile hemoglobin and water in arterioles, metarterioles, true capillaries and venules; preferably wherein tTPI is more specific to change in perfusion compared to nTPI; and is calculated during step (ii) as:

$$tTPI = mTBV - bTBV \quad [47]$$

preferably wherein equation is used and the light absorption by non-hemoglobin constituents (optionally oLAC and/or oHAC) and water in non-expandable water compartments (nDC) are ignored.

In embodiments, a difference between light absorption by non-pulsatile water at baseline in two occlusion sessions n and n+1 (ΔbwDCn+1) is calculated during step (ii), such that if:

$$\Delta bwDCn+1 = bwDCn+1 - \Delta bwDCn \quad [48]$$

$$\Delta bwDCn+1 = (-2);$$

-continued $$\Delta eH2On+1 = \Delta lwDCn+1 = lwDCn+1 - lwDCn \quad [49]$$

$$\Delta lwDCn+1 = (-3);$$

$$\Delta sH2On+1 = \Delta bwDCn+1 \quad [50]$$

$$\Delta sH2On+1 == (-2) - (-3) = (+1);$$

and wherein a transcapillary fluid shift that occurs due to net fluid Filtration Absorption Ratio (FAR) in a period between two sessions is approximated as follows:

$$FAR = \Delta eH2On+1 - \Delta sH2On+1 = lwDCn+1 - lwDCn - bwDCn+1 + bwDCn$$

and/or using net intravascular water estimate (iH2O) rather than net non-pulsatile:

$$FAR = \Delta eH2On+1 - \Delta iH2On+1. \quad [51]$$

In embodiments, a change in extravascular water between occlusion session n and n+1 (ΔeH2O) is calculated during step (ii), such that:

$$\Delta eH2On+1 = eH2On+1 - eH2On = \Delta lwDCn+1 = lwDCn+1 - lwDCn \quad [52]$$

preferably wherein equations [2,3] are used and light absorption by water in non-expandable water compartments (nDC) is ignored.

In embodiments, a difference between non-pulsatile Tissue Perfusion Index in session n and n+1 (ΔnTPI) indicates changes in non-pulsatile tissue perfusion reserve and is calculated during step (ii) as:

$$\Delta nTPIn+1 = nTPIn+1 - nTPIn \quad [53]$$

preferably using equation [17].

In embodiments a difference between total Tissue Perfusion Index in session n and n+1 (ΔtTPI) indicates changes in total tissue perfusion reserve and is calculated during step (ii) as:

$$\Delta tTPIn+1 = tTPIn+1 - tTPIn \quad [54]$$

preferably using equation [18].

In embodiments, an intra-session Q fractional change of light absorption value of the same MW PPG characteristics in different phases of occlusion, preferably lowest, maximal, or residual, in respect to pre-inflation baseline, optionally Q lwDC in session number n, is calculated during step (ii) as:

$$Q\, lwDCn = (lwDCn - bwDCn)/bwDCn \quad [55]$$

preferably using equations and [30].

In embodiments, a difference between fractional changes of signals with different MW PPG characteristics in a same session is used for extrapolation of variables A of the Q values of maximized non-pulsatile hemoglobin (QmsHb), and maximized pulsatile hemoglobin (QmaHb) in reactive hyperemia phase indicates a true capillary perfusion state, labeled as Capillary Perfusion Index (CPI) which is defined as reserve of perfusion in true capillaries, or the only capillary type where transcapillary fluid shifts take place, and is calculated during step (ii) as:

$$CPI = Q\,msHb - Q\,maHb \quad [56]$$

preferably using equations [33], [34], [39], and/or [40].

In embodiments Inter-session Q refers to fractional change of light absorption value of the same MW PPG characteristics at the same phase of two occlusion sessions, preferably values either at baseline, or lowest, or maximal, or residual phase, so that only corresponding values, preferably baseline values or lowest values, are used in a single equation, optionally wherein Q maHbn+1 refers to fractional change of maHbn+1 in respect to maHbn, wherein maHbn is a baseline for calculating during step (ii) Q maHbn+1 as:

$$Q\,maHbn+1 = (maHbn+1 - maHbn)/maHbn \quad [57]$$

where n is the number of a preceding session to session number n+1.

In embodiments, extrapolation calculation of fractional change of maximized light absorption by TBV (QmTBV) in reactive hyperemia phase indicates change in Total Perfusion Index (TPI) and is calculated during step (ii) as:

$$Q\,tTPIn+1 = (tPIn+1 - tPIn)/tPIn \quad [58]$$

preferably using equation [46].

In embodiments, an extrapolation calculation of Q TBV value, which is a fractional change of TBV where baseline TBV value, is calculated during step (ii) as either (1) a first occlusion session (n), optionally wherein:

$$QTBVn+3 = (QTBVn+3 - QTBVn)/QTBVn, \quad [59]$$

or (2) a preceding session:

$$QTBVn+3 = (QTBVn+3 - QTBVn+2)/QTBVn+2 \quad [60]$$

where TBV is net AC and DC components (TBV, preferably calculated from equation 44) of LWL light absorption by hemoglobin within a PPG scan area (tHb, preferably calculated from equation 15) and HWL absorption by intravascular water (iH2O, preferably calculated from equation 14); wherein n, n+1 and so on are numbers of occlusion sessions.

In embodiments extrapolation calculation of Q iH2O, which is a fractional change of iH2O, wherein its baseline value is calculated during step (ii) as either a first occlusion session (n), optionally wherein:

$$Q\,iH2On+3 = (Q\,iH2On+3 - Q\,iH2On)/Q\,iH2On, \quad [61]$$

or (2) the preceding session:

$$Q\,iH2On+3 = (Q\,iH2On+3 - Q\,iH2On+2)/Q\,iH2On+2 \quad [62]$$

where iH2O is net AC and DC components of HWL absorption by total intravascular water (iH2O, equation 14); n, n+1 and so on are numbers of occlusion sessions.

The method of any one of the above, wherein extrapolation of Q tHb, which is a fractional change of tHb, where its baseline value is calculated during step (ii) as either very first occlusion session (n), optionally wherein:

(1)

$$Q\,tHbn+3 = (Q\,tHbn+3 - Q\,tHbn)/Q\,tHbn, \quad [63]$$

or (2) the preceding session, optionally wherein:

$$Q\,tHbn+3 = (Q\,tHbn+3 - Q\,tHbn+2)/Q\,tHbn+2 \quad [64]$$

where tHb is net AC and DC components of LWL absorption by total hemoglobin (tHb, preferably calculated equation 15); wherein n and n+1 are numbers of sessions.

In embodiments, Inter-session changes in plasma dilution (APD) are calculated during step (ii), optionally wherein:

$$\Delta PDn+3 = Q\,iH2On+3 - Q\,tHbn \quad [65]$$

where Q iH2On+3 is preferably calculated by equation or [62], and Q tHbn is preferably calculated by equations or [64].

In embodiments, an Inter-session change in predicted perfusion index (pPI) is calculated during step (ii) as:

$$\Delta PPI = \Delta\,QtHbn+1 - (\Delta\,QTBVn+1 - \Delta\,QiH2On+1) \quad [66]$$

In embodiments a negative arterio-venous plasma dilution difference (a-vPDD) value is calculated during step (ii) as: a negative difference between changes in pulsatile arterial water (aH2O) and non-pulsatile intravascular water (sH2O) in consecutive occlusion sessions:

$$0 < \Delta\,a - vPDDn+1 = \Delta\,baH2On+1 - \Delta\,bsH2On+1; \quad [67]$$

a negative difference between fractional changes of non-pulsatile intravascular water (QiH2O) and pulsatile arterial water (QaH2O):

$$\Delta Qa - vPDDn + 1 = QbsH2On + 1 - QbaH2On + 1 \quad [68]$$

$$QbaH2On + 1 = (baH2On + 1 - baH2On)/baH2On \quad [69]$$

$$QbsH2On + 1 = (bsH2On + 1 - bsH2On)/bsH2On \quad [70]$$

$$bsH2On + 1 = (bwDCn + 1 - lwDCn + 1), \text{ where} \quad [71]$$

$$bwDCn + 1 = bwDCn + 1 - bwDCn \quad [72]$$

$$lwDCn + 1 = lwDCn + 1 - lwDCn \quad [73]$$

In embodiments, a Homeostatic Blood States (HBS) method is used to determine the hydration status of the subject in step (b) (iii).

In embodiments, the method includes calculating an extrapolated predicted large vessel haematocrit (plvHct) vale, wherein (a) the large vessel hemoglobin concentration (lvHb) to hematocrit (lvHct) ratio provides an MCHC value as follows:

$$MCHC = lvHb \cdot lvHct - 1 \quad [74]$$

wherein the normal MCHC intervals are 310-360 (g/L), preferably wherein the mean normal MCHC value (mMCHC)=330 (g/L); and (b) a capillary haematocrit (cHct) approximation is calculated as:

$$cHct = cHb/mMCHC, \quad [75]$$

$$\text{where } cHb = 1000(aHb \cdot aH2O - 1) = 1000(sHb \cdot sH2O - 1); \quad [76]$$

and (c) these values are applied and the arbitrary f-ratio (f-cell ratio) of 0.3 in the following equation for plvHct:

$$plvHct = cHct/f\text{-ratio} = 1000\ aHb \cdot (330 \cdot aH2O) - 1 \quad [77]$$

wherein the plvHct is compared to the HBS nomogram table shown in FIG. 39 and limits of homeostatic Hct shifts or related changes in body hydration status are determined; and corresponding limits of cHct are determined by reverse calculation and applied to determine the hydration status of the subject.

In embodiments, the capillary plasma dilution efficacy difference is the difference between metarteriolar and true capillary plasma dilution efficacies of the same 5-minute averaging period and is calculated during step (ii) as:

$$mtcPEDi = mPDEi - tcPDEi \quad [78]$$

where mtcPEDi is the metarteriolar-true capillary plasmadilution efficacy difference at time-point i, mPDEi is the metarteriolar plasma dilution efficacy at time-point i, and tcPDEi is the true capillary plasma dilution efficacy at time-point i.

In embodiments, an Overlapping Light Absorption (OLA) math model is employed to derive a parameter in step (ii).

In embodiments, in step (ii), a derived parameter is selected from any one of cHb-hemoglobin in capillaries;

eH2O-extravascular water (water in extravascular cells and extracellular tissue);

iH2O-intravascular water is the sum of light absorption by water in the pulsatile and non-pulsatile blood flows;

nHb-static (non-pulsatile) hemoglobin in the non-pulsatile part of blood flow of in arteries;

oH2O-water within compartments other than blood and soft tissues;

sH2O-intravascular water in the non-pulsatile blood flow;

tH2O-total water of intravascular (pulsatile and non-pulsatile) and extravascular water (tDC); and/or vHb—hemoglobin in veins.

In embodiments, the method includes a trend in hemoglobin volume, fluid volume in circulation (plasma volume plus intracellular water in red blood cells), fluid volume in tissues (interstitial fluid), and/or perfusion status (microcirculation) of the subject, preferably by determining a Fluid Accumulation Trend (FAT), and/or any one of:

an Intravascular Fluid Accumulation Trend (IFAT);

an Extravascular Fluid Accumulation Trend (EFAT);

a Microcirculation & Perfusion Trend (MPT); and/or a Total Hemoglobin Trend (THT);

based on the parameters derived in ((ii).

In embodiments, the method further determines if fluid intake, fluid restriction, fluid removal, co-administration of cardiovascular medication, and/or red cell transfusion would improve the intravascular fluid volume, extravascular fluid volume, and/or hydration status of the subject.

In embodiments, determining the hydration status of the subject includes determining intravascular fluid volume, extravascular fluid volume, and/or hemoglobin level of the subject.

In embodiments, the method includes determining the subject is experiencing occult bleeding based on the derived parameters, and/or where the method further determines the plasma dilution, blood volume, microcirculation and/or whole body hemoglobin status of the subject based on the derived parameters.

In embodiments, the method extrapolates/estimates the hydration, plasma dilution, blood volume, microcirculation and/or whole body hemoglobin status of the subject.

In embodiments the method includes treating the subject, preferably by subjecting them to fluid intake, fluid restriction, fluid removal, and/or administration of a drug.

In embodiments, the method includes treating the subject for suspected edema, dehydration, or blood loss.

In embodiments, the treating is determined based on treatment option guidance provided by the an artificial intelligence algorithm.

A device for determining a hydration status of a subject in accordance with an embodiment, of the present disclosure includes: a multi-wavelength (MW) plethysmography (PPG) Swapping-Layer Sensor System (SLSS), wherein the SLSS includes at least two light emitting diodes (LEDs) including at least one low wavelength light (LWL)-emitting diode, which preferably emits about 400 nm to 600 nm light; and at least one high wavelength light (HWL)-emitting diode, which preferably emits about 850 nm to 1100 nm light; and at least one photodiode detector positioned to detect light emitted from the at least one LWL-emitting diode and/or light emitted from the at least one HWL-emitting diode that has passed through a tissue of the subject; and processing means configured to obtain MW PPG information from the at least one photodiode detector;

derive a parameter of hemoglobin, plasma volume, interstitial fluid volume, blood volume, and/or microcirculation of the subject based on the MW PPG information; and determine the hydration status of the subject based on the derived parameters.

In embodiments, the at least one photodiode detector is separated by a distance of 2.5 cm or less from the at least one LWL-emitting diode and/or the at least one HWL-emitting diode for a Low Width Scan (LWS) mode.

In embodiments, the at least one photodiode detector is separated by a distance of greater than 2.5 cm, preferably 2.5 cm to 20 cm, from the at least one LWL-emitting diode and/or the at least one HWL-emitting diode for a Wide Width Scan (WWS) mode.

In embodiments, the device includes a LWL-emitting diode in LWS mode ("ShallowNarrowScan" type sensor system); a LWL-emitting diode in WWS mode ("ShallowWideScan" type sensor system); a HWL-emitting diode in LWS mode ("DeepNarrowScan" type sensor system); and/or a HWL-emitting diode in WWS mode ("DeepWideScan" type sensor system).

In embodiments, the at least one photodiode detector is positioned on the same side of the tissue as the at least one LWL-emitting diode and/or the at least one HWL-emitting diode (reflectance mode setup); or on opposite sides of the tissue relative to the at least one LWL-emitting diode and/or the at least one HWL-emitting diode (transmission mode setup).

In embodiments, the SLSS is placed on the finger, fingertip, earlobe, wrist, forehead, or torso of the subject, and/or the tissue is a finger, fingertip, earlobe, wrist, forehead, torso, or a portion thereof, of the subject.

In embodiments the SLSS includes a Swapping Signal Processing (SSP) component and one or more Triplet Sensor Array (TSA) systems.

In embodiments, the one or more TSA systems are connected to the SSP module via different links, preferably wherein the different links are wired and/or wireless modalities or connections.

In embodiments, the TSA system includes three independently driven LEDs and a single photodiode detector dedicated to the three independently driven LEDs.

In embodiments, the TSA system includes two HWL-emitting diodes and one LWL-emitting di ode.

In embodiments, all three independently driven LEDs are located at the same distance from the photodiode detector.

In embodiments, the LWL-emitting diode and a first HWL-emitting diode are positioned at the same distance from each other, preferably alongside each other, preferably wherein the LWL-emitting diode and a first HWL-emitting diode are both less than or equal to 2.5 cm from the photodiode detector, and a second HWL-emitting diode is positioned at a longer distance from the dedicated detector compared to the other two LEDs, preferably more than 2.5 cm from the photodiode detector.

In embodiments, the LWL-emitting diode is used for the "ShallowNarrowScan" function (LWL-LWS technique) in the measurement of light absorption by hemoglobin in the subject.

In embodiments, the first HWL-emitting diode is used for the "DeepNarrowScan" function (HWL-LWS technique) in the measurement of light absorption by water in the subject.

In embodiments, the second HWL-emitting diode is used for the "Deep WideScan" function (HWL-WWS technique) in the measurement of light absorption by water in the subject:

In embodiments, the SLSS is mounted on a surface base and is situated as a Flat Surface Array of Sensor (FSAS), a Multi-Directional Sensor System (MDSS) on a ring shape base, or a Target-Layer Sensor System (TLSS).

In embodiments, the SLSS is mounted on a surface base and is situated as a Flat Surface Array of Sensor (FSAS), and the surface base is a solid flat base, preferably a wearable used for skin of a relatively flat anatomic surface, a watch, or a patch; or the surface base is a flexible flat base, preferably a wearable used for skin of a relatively curved anatomic surface, a watch band, a bracelet, a cuff, an inflatable cuff, a patch, or an attachable, preferably a sticky and/or single-use, surface.

In embodiments, the SLSS is mounted on a surface base and is situated as a Multi-Directional Sensor Systems (MDSS) on a ring shape base in an ACDC-2-RING format; or an ACDC-5-RING format.

In embodiments, the ring shape base is a closed ring frame, preferably a bracelet, a finger ring, preferably a soft, size-adjustable, cuffed, and/or inflatable ring, a solid frame, a solid ring, or a ring in a fixed size.

In embodiments, obtaining the MW PPG information in (b) (i) includes calculating quantity, fractional change, and/or acceleration (rate of change of speed) of LED-emitted light absorption.

In embodiments, a net high wavelength (HWL) DC component value (a whole DC (wDC) component value) is a net light absorption by total non-pulsatile water value calculated by the processing means by adding an intravascular (sH2O) light absorption value, an extravascular (eH2O) light absorption value, and a non-expandable water compartment (nDC) light absorption value.

In embodiments, sH2O is a net absorption by non-pulsatile water value calculated by the processing means by adding an arterial (nH2O) light absorption value, a venous (vH2O) light absorption value, and a capillary (cH2O) light absorption value; wherein each of these values include light absorption by water in plasma (PV) and water inside red blood cells (RCV).

In embodiments, a high wavelength (HWL) AC component value comprises a pulsatile arterial water (aH2O) light absorption value, and optionally includes other light absorption values of other constituents with lower absorption coefficients such as hemoglobin, melanin, and myoglobin (other high-wavelength AC components (oHAC)), and is calculated by the processing means.

In embodiments, a non-pulsatile LWL DC component value includes a non-pulsatile hemoglobin (sHb) light absorption value, optionally including light absorption values of other constituents such as melanin and myoglobin (other DC components (oDC)), and is calculated by the processing means.

In embodiments, the sHb value a is net LWL light absorption value by hemoglobin comprising a non-pulsatile arterial (nHb) light absorption value, a capillary (cHb) light absorption value, and a venous (vHb) light absorption value, and is calculated by the processing means.

In embodiments, a LWL AC component value comprises a pulsatile arterial hemoglobin (aHb) light absorption value, optionally comprising light absorption values of other constituents with much lower absorption coefficients including water (other low-wavelength AC components (oLAC)), and is calculated by the processing means.

In embodiments, a total hemoglobin (tHb) value is the sum of aHb, sHb, oDC, and oLAC and is calculated by the processing means.

In embodiments, a lwDC value is measured when compression of the tissue and its blood vessels is applied, wherein the lwDC value is a HWL DC component value and is the net light absorption value calculated by the processing means by adding an extravascular water (eH2O) light absorption value and a non-expandable water compartment (nDC) light absorption value.

In embodiments, a pre-occlusion non-pulsatile water net baseline light absorption value (bwDC) is calculated by the processing means as:

$$bw\mathrm{DC} = s\mathrm{H2O} + e\mathrm{H2O} + n\mathrm{DC} = n\mathrm{H2O} + v\mathrm{H2O} + c\mathrm{H2O} + e\mathrm{H2O} + n\mathrm{DC} \quad [79]$$

where sH2O is all non-pulsatile intravascular water, eH2O is extravascular water in expandable tissues, nDC is water in non-expandable tissues, nH2O is non-pulsatile arterial water, vH2O is venous, and cH2O is capillary.

In embodiments, an occlusion phase HWL DC component light absorption value (lwDC) is calculated by the processing means as:

$$lw\mathrm{DC} = e\mathrm{H2O} + n\mathrm{DC} \quad [80]$$

where eH2O is all non-pulsatile water which is net extravascular water in expandable fluid compartments (interstitial and intracellular), and nDC is water in non-expandable tissues.

In embodiments, nDC is constant in short term and does not affect evaluation of changes in eH2O based on changes in lwDC in consecutive occlusion sessions such that:

$$\Delta lw\mathrm{DC} = \Delta e\mathrm{H2O}; \quad [81]$$

and $$Qlw\mathrm{DC} = Qe\mathrm{H2O}. \quad [82]$$

In embodiments, a pre-occlusion wDC net light absorption value (bsHb) is calculated by the processing means as:

$$bsHb = sHb + \mathrm{melanin} + \mathrm{myoglobin} = sHb + o\mathrm{DC} \quad [83]$$

where sHb is static (non-pulsatile) hemoglobin and oDC is myoglobin and/or melanin.

In embodiments, a true baseline sHb value (tbsHb) is calculated by the processing means as $$tbsHb = bsHb - o\mathrm{DC} = bsHb - lsHb \quad [84]$$

wherein lsHb is a LWL DC signal which indicates net absorption by non-hemoglobin constituents.

In embodiments, light absorption by other constituents, preferably melanin and/or myoglobin, are ignored in extrapolating changes in sHb such that $$\Delta sHb = \Delta(nHb + cHb + vHb) \quad [85]$$

$$QsHb = Q(nHb + cHb + vHb) \quad [86]$$

where nHb is non-pulsatile arterial hemoglobin, cHb is capillary and vHb is venous hemoglobin.

In embodiments, a pre-occlusion baseline aH2O net light absorption value (baH2O) is calculated by the processing means as:

$$ba\mathrm{H2O} = a\mathrm{H2O} + oHAC \quad [87]$$

wherein aH2O is pulsatile arterial water and oHAC is other HWL light absorbing constituents, preferably hemoglobin, melanin, and/or myoglobin.

In embodiments, an adjusted true bH2O value (tbaH2O) is calculated by the processing means as:

$$tba\mathrm{H2O} = ba\mathrm{H2O} - oHAC = ba\mathrm{H2O} - la\mathrm{H2O} \quad [88]$$

wherein laH2O is an occlusion phase measurement of the lowest aH2O value.

In embodiments, a pre-occlusion baseline aHb net light absorption value (baHb) is calculated by the processing means as:

$$baHb = aHb + oLAC \quad [89]$$

wherein aHb is pulsatile arterial hemoglobin and oLAC is other low-wavelength constituents with a lower absorption coefficient.

In embodiments an adjusted true bHb value (tbaHb) is calculated by the processing means as:

$$tbaHB = baHb - oLAC = baHb - laHb \quad [90]$$

wherein laHb is an occlusion phase measurement of the lowest aHb value.

In embodiments, a non-pulsatile intravascular water value (sH2O) is calculated by the processing means as:

$$s\mathrm{H2O} = n\mathrm{H2O} + v\mathrm{H2O} + c\mathrm{H2O} = bw\mathrm{DC} - lw\mathrm{DC} \quad [91]$$

where bwDC is baseline HWL DC component, and lwDC is lowest HWL DC component.

In embodiments, a net intravascular water value (iH2O) is the sum of non-pulsatile (sH2O) and pulsatile (aH2O) intravascular water and is calculated by the processing means as:

$$i\mathrm{H2O} = s\mathrm{H2O} + a\mathrm{H2O} = bw\mathrm{DC} - lw\mathrm{DC} + a\mathrm{H2O} \quad [92]$$

where bwDC is baseline HWL DC value, lwDC is the lowest value in the inflation phase.

In embodiments, a total hemoglobin value (iHb) indicates the sum of true non-pulsatile and pulsatile hemoglobins and is calculated by the processing means as:

$$tHb = tbsHb + tbaHb \qquad [93]$$

where tsHb is the sum of non-pulsatile arterial, capillary and venous hemoglobins (nHb+cHb+vHb).

In embodiments, a Total Blood Volume value (TBV) is the sum of AC and DC components of LWL light absorption by hemoglobin and HWL absorption by water and is calculated by the processing means as:

$$TBV = tHb + i\mathrm{H2O} = tHb + bw\mathrm{DC} - lw\mathrm{DC} \qquad [94]$$

where tHb is total hemoglobin (preferably calculated by equation 15), iH2O is total intravascular water which is the sum of plasma volume (PV) and intracellular water (red cell volume), bwDC is baseline non-pulsatile water (preferably calculated in equation 1) and lwDC is non-pulsatile water in occlusion phase (preferably calculated in equation 2).

In embodiments, a non-pulsatile Tissue Perfusion Index (nTPI) value indicates a non-pulsatile tissue perfusion reserve which is (i) a difference (Δ) between maximized value of light absorption by non-pulsatile hemoglobin (msHb) in hyperemia phase and its baseline (bsHb), (ii) a reserve of net tissue perfusion by net non-pulsatile flow in all types of micro-vessels, arterioles, metarterioles, true capillaries, and venules, and (iii) is calculated by the processing means as:

$$nTPI = msHb - bsHb. \qquad [95]$$

preferably wherein equation [5] is used and absorption by non-hemoglobin constituents is ignored; more preferably wherein pulsatile hemoglobin is ignored.

In embodiments, a total Tissue Perfusion Index (tTPI) value indicates net or total tissue perfusion reserve which is a difference (A) between the maximized TBV (mTBV) in hyperemia phase and baseline TBV (bTBV), wherein tTPI is a reserve of net tissue perfusion by net pulsatile and non-pulsatile hemoglobin and water in arterioles, metarterioles, true capillaries and venules; preferably wherein tTPI is more specific to change in perfusion compared to nTPI; and is calculated by the processing means as:

$$tTPI = mTBV - bTBV \qquad [96]$$

preferably wherein equation is used and the light absorption by non-hemoglobin constituents (optionally oLAC and/or oHAC) and water in non-expandable water compartments (nDC) are ignored.

In embodiments, a difference between light absorption by non-pulsatile water at baseline in two occlusion sessions n and n+1 (ΔbwDCn+1) is calculated by the processing means, such that if:

$$\Delta bw\mathrm{DC}n+1 = bw\mathrm{DC}n+1 - \Delta bw\mathrm{DC}n \qquad [96]$$

$$\Delta bw\mathrm{DC}n+1 = (-2);$$

$$\Delta e\mathrm{H2O}n+1 = \Delta lw\mathrm{DC}n+1 = lw\mathrm{DC}n+1 - lw\mathrm{DC}n \qquad [97]$$

$$\Delta lw\mathrm{DC}n+1 = (-3);$$

$$\Delta s\mathrm{H2O}n+1 = \Delta bw\mathrm{DC}n+1 \qquad [98]$$

$$\Delta s\mathrm{H2O}n+1 = = (-2) - (-3) = (+1);$$

and wherein a transcapillary fluid shift that occurs due to net fluid Filtration Absorption Ratio (FAR) in a period between two sessions is approximated as follows:

$$FAR = \Delta e\mathrm{H2O}n+1 - \Delta s\mathrm{H2O}n+1 = lw\mathrm{DC}n+1 - lw\mathrm{DC}n - bw\mathrm{DC}n+1 + bw\mathrm{DC}n$$

and/or using net intravascular water estimate (iH2O) rather than net non-pulsatile:

$$FAR = \Delta e\mathrm{H2O}n+1 - \Delta i\mathrm{H2O}n+1. \qquad [99]$$

In embodiments, a change in extravascular water between occlusion session n and n+1 (ΔeH2O) is calculated by the processing means, such that:

$$\Delta e\mathrm{H2O}n+1 = e\mathrm{H2O}n+1 - e\mathrm{H2O}n = \Delta lw\mathrm{DC}n+1 = lw\mathrm{DC}n+1 - lw\mathrm{DC}n \qquad [100]$$

preferably wherein equations [2,3] are used and light absorption by water in non-expandable water compartments (nDC) is ignored.

In embodiments, a difference between non-pulsatile Tissue Perfusion Index in session n and n+1 (ΔnTPI) indicates changes in non-pulsatile tissue perfusion reserve and is calculated by the processing means as:

$$\Delta nTPIn+1 = nTPIn+1 - nTPIn \qquad [101]$$

preferably using equation [94].

The device of any of the embodiments of the present disclosure, wherein a difference between total Tissue Perfusion Index in session n and n+1 (ΔtTPI) indicates changes in total tissue perfusion reserve and is calculated by the processing means as:

$$\Delta tTPIn+1 = tTPIn+1 - tTPIn \qquad [102]$$

preferably using equation [95].

In embodiments, an intra-session Q fractional change of light absorption value of the same MW PPG characteristics in different phases of occlusion, preferably lowest, maximal, or residual, in respect to pre-inflation baseline, optionally Q lwDC in session number n, is calculated by the processing means as:

$$QlwDCn = (lwDCn - bwDCn)/bwDCn \quad [103]$$

preferably using equations and [99].

In embodiments, a difference between fractional changes of signals with different MW PPG characteristics in a same session is used for extrapolation of variables A of the Q values of maximized non-pulsatile hemoglobin (QmsHb), and maximized pulsatile hemoglobin (QmaHb) in reactive hyperemia phase indicates a true capillary perfusion state, labeled as Capillary Perfusion Index (CPI) which is defined as reserve of perfusion in true capillaries, or the only capillary type where transcapillary fluid shifts take place, and is calculated by the processing means as:

$$CPI = QmsHb - QmaHb \quad [104]$$

preferably using equations [82], [83], [88], and/or [89].

In embodiments, Inter-session Q refers to fractional change of light absorption value of the same MW PPG characteristics at the same phase of two occlusion sessions, preferably values either at baseline, or lowest, or maximal, or residual phase, so that only corresponding values, preferably baseline values or lowest values, are used in a single equation, optionally wherein Q maHbn+1 refers to fractional change of maHbn+1 in respect to maHbn, wherein maHbn is a baseline for calculating by the processing means Q maHbn+1 as:

$$QmaHbn + 1 = (maHbn + 1 - maHBn)/maHbn \quad [105]$$

where n is the number of a preceding session to session number n+1.

In embodiments, extrapolation of fractional change of maximized light absorption by TBV (QmTBV) in reactive hyperemia phase indicates change in Total Perfusion Index (TPI) and is calculated by the processing means as:

$$QtTPIn + 1 = (tPIn + 1 - tPIn)/tPIn \quad [106]$$

preferably using equation [95].

In embodiments, The device of any embodiments of the present disclosure, wherein an extrapolation of Q TBV value, which is a fractional change of TBV where baseline TBV value, is calculated by the processing means as either (1) a first occlusion session (n), optionally wherein:

$$QTBVn + 3 = (TBVn + 3 - TBVn)/TBVn, \quad [107]$$

or (2) a preceding session:

$$QTBVn + 3 = (TBVn + 3 - TBVn + 2) \quad [108]$$

In embodiments, Plasma dilution (PD) is the fractional change of haemoglobin in respect to baseline, namely the time-point zero or 1st Hb measurement at the start of continuous observation, and Metarteriolar and true capillary plasma dilution (mPD and tcPD, respectively) is calculated during step (ii) as a fractional change of mHb and tcHb at proper time-point in respect to the baseline values of mHb and tcHb, respectively:

$$xPDi = (xHb0 \cdot xHbi - 1 - 1) \cdot (1 - xHct0) - 1 \quad [109]$$

where xPDi is the plasma dilution at the time-point i; xHb0 is baseline value (mHb0 or tcHb0) which is $1^{st}$ average Hb value of the first 1-min. averaging period; xHbi is the value at the time-point i (mHbi or tcHbi); and xHct0 is the xHb0 divided by 330 which is the mean cell haemoglobin concentration (MCHC) value in the middle of the normal range; and x is the haemoglobin measuring site ("m" for metarteriolar, and "tc" for true capillary).

A system for medical trend analysis and prediction includes a machine learning and AI algorithms configured to analyze current trends in patient data, a notification module that indicates a match with predefined patterns on a main screen, a trends window that opens upon activation of the notification, allowing a medical professional to assess a patient's condition, and a prediction module that predicts standardized trends for short-term (1 hour), average-term (3 hours), and long-term (6 hours) periods In embodiments, the prediction module displays predictions on traffic light indicators for each time frame.

In embodiments, the system includes a Clinical Decision Support System (CDSS) that provides recommendations and support based on predefined decision rules, with interaction modes including normal mode, predicted mode, and copilot mode.

In embodiments, in copilot mode, the AI agents automatically display the application screen and information most relevant for decision support, considering the context of the current health status, and recommend actions based on classical CDSS system decision rules.

In embodiments, the system includes a continuous learning module that constantly learns and improves decision paths based on collected data, including patient measures, medical expert actions, and patient health outcomes.

A method for hosting AI agent core application and components on a cloud platform includes In embodiments, providing scalable computing resources to handle varying workloads, ensuring continuous access to AI services, facilitating secure data transfer and storage.

A system for clinical decision support accessible online via the cloud platform in accordance with an embodiment of the present disclosure includes an AI agent providing advanced decision support and predictive analytics, and enhancing clinical decision-making processes through real-time data analysis.

A dual storage system for measuring data in accordance with an embodiment of the present disclosure includes temporary local measurements data storage for real-time tracking and immediate access, and cloud measurements data storage for periodic transfer and ensuring data consistency and availability for analysis and reporting.

An online service for providing AI-driven predictions and recommendations in accordance with an embodiment of the present disclosure includes real-time insights and guidance based on collected data, and multiple interaction modes including traditional on-screen displays, voice communication, and free-form text chat.

An embedded clinical decision support system operating locally within a monitoring application in accordance with an embodiment of the present disclosure includes decision support based on real-time measurements and predefined rules, and periodic updates from the cloud platform to enhance functionality.

A Clinical Decision Support System (CDSS) in accordance with an embodiment of the present disclosure includes an AI agent configured to predict hemorrhage and hydration statuses for short-term (1 hour), average-term (3 hours), and long-term (6 hours) intervals, displayed using a traffic light indicator system.

In embodiments, the CDSS includes recommendations and support actions for medical personnel, including suggestions on parameters or screens to evaluate patient status and hints based on CDSS decision rules.

In embodiments, the CDSS includes three operational modes: Normal mode (no AI suggestions), Predicted mode (AI provides future health status predictions), and Copilot mode (AI recommends actions and displays relevant information).

In embodiments, the AI agent continuously learns and improves its decision paths based on collected data, including patient measures, medical expert actions, and patient health outcomes.

In embodiments, the CDSS includes multiple interaction modes, including traditional on-screen, voice communication, and free-form dialog text chat, with the AI agent providing predictions, recommendations, and guidance in each mode.

In embodiments, a software application may be adapted for use on various devices, including medical monitoring devices to ensure compatibility with medical monitoring equipment for real-time patient data tracking, mobile app devices, allowing healthcare professionals to access patient data on the go, and PC or tablet computer screens to be fully functional on personal or tablet computers, providing a comprehensive view of patient data and trends.

A method of monitoring extravascular water volume of a subject in accordance with an embodiment of the present disclosure includes: obtaining multi-wavelength photoplethysmography information associated light that has passed through tissues of the subject; processing the multi-wavelength photoplethysmography information to derive a parameter associated with extravascular water volume (eH2O) in tissues through which the light passed associated with the subject; storing the multi-wavelength photoplethysmography information, and the parameter associated with extravascular water volume; repeating these for a period of time; determining, based on the stored multi-wavelength photoplethysmography information, parameter associated with extravascular water volume, a trend associated with extravascular water volume; providing hydration status information associated with the subject based on the multi-wavelength photoplethysmography information, and the parameter associated with extravascular water volume and the trend.

In embodiments, the light that has passed through tissue of the subject includes a low wavelength of spectrum and a high wavelength spectrum.

In embodiments, a low wavelength spectrum is 400 nm to 600 nm light and the high wavelength spectrum is 850 nm to 1100 nm light.

In embodiments, the multi-wavelength photoplethysmography information includes a pulsatile PPG component (AC) and a non-pulsatile (DC) component.

In embodiments, the low wavelength spectrum is emitted before the high wavelength component of the light.

In embodiments, a net high wavelength (HWL) DC component value corresponds to net light absorption by non-pulsatile water and is calculated during step (iii) by adding an intravascular (sH2O) light absorption value, the extravascular (eH2O) light absorption value, and a non-expandable water compartment (nDC) light absorption value.

In embodiments, a non-pulsatile LWL DC component value is based on a non-pulsatile hemoglobin (sHb) light absorption value and is calculated during step (iii).

In embodiments, the non-pulsatile hemoglobin (sHb) value is a net LWL light absorption value by hemoglobin comprising a non-pulsatile arterial (nHb) light absorption value, a capillary (cHb) light absorption value, and a venous (vHb) light absorption value, and is calculated during step (iii).

In embodiments, the providing step vi) comprises providing the multi-wavelength photoplethysmography information, parameter associated with extravascular water volume as inputs to a machine learning algorithm, that is trained by a training set including prior wavelength photoplethysmography information, prior parameters associated with extravascular water volume and provides, as an output, trend information associated with the trend associated with extravascular water volume.

In embodiments, the providing step vi) uses the multi-wavelength photoplethysmography information, perfusion information and parameter associated with extravascular water volume to generate trend information associated with the trend associated with extravascular water volume.

In embodiment, the method includes generating one or more alerts based at least on the trend, the one or more alerts associated with hydration of the subject.

In embodiments, the one or more alerts include one or more recommendations associated with avoiding one of dehydration and over-hydration.

In embodiments, the one or more alerts include recommendations related to one of increasing or decreasing fluid intake.

A system for monitoring extravascular water volume of a subject in accordance with an embodiment of the present disclosure includes: a multi-wavelength photoplethysmography sensor adopted to provide multi-wavelength photoplethysmography sensor information associated light that has passed through tissue of the subject; a decision support system including a processor and memory operably connected thereto, wherein the memory incudes processor executable code, that, when executed by the processor, performs steps of: receiving the multi-wavelength photoplethysmography information; deriving a parameter associated with extravascular water volume associated with the subject based at least on the multi-wavelength photoplethysmography information; storing the multi-wavelength photoplethysmography information and the parameter in the memory; repeating these for a period of time; determining, based on the stored multi-wavelength photoplethysmography information, parameter a trend associated with extravascular water volume; providing hydration status information associated with the subject based on the multi-wavelength photoplethysmography information, the parameter associated with extravascular water volume and the trend; displaying the multi-wavelength photoplethysmography information parameter and the trend.

In embodiments, the multi-wavelength photoplethysmography sensor comprises a low wavelength light source, a high wavelength light source and a light detector configured to detect light of the low wavelength and the high wavelength.

In embodiments, the system includes a control unit operably connected to the low wavelength light source, a high wavelength light source and a light detector and configured to control at least emission of light.

In embodiments, the low wavelength light source, high wavelength light source, light detector and the control unit are mounted on a wearable accessory configured to be worn by the subject.

In embodiments, the multi-wavelength photoplethysmography sensor includes a plurality of a low wavelength light sources, a plurality of high wavelength light sources and at least one light detector configured to detect light of the low wavelength and the high wavelength.

In embodiments, further comprising a control unit operably connected to the plurality of low wavelength light sources, plurality of high wavelength light sources and at least one light detector and configured to control at least emission of light.

In embodiments, the multi-wavelength photoplethysmography sensor includes a plurality of the multi-wavelength photoplethysmography sensors, each multi-wavelength photoplethysmography sensor including a low wavelength light source, a high wavelength light source and one light detector and configured to detect light of the low wavelength and the high wavelength.

In embodiments, the system includes a control unit operably connected to the plurality of the multi-wavelength photoplethysmography sensors and configured to control at least emission of light.

In embodiments, the light that has passed through tissue of the subject includes a low wavelength spectrum and a high wavelength spectrum.

In embodiments, the low wavelength spectrum is 400 nm to 600 nm light and the high wavelength spectrum is 850 nm to 1100 nm light.

In embodiments, the multi-wavelength photoplethysmography information includes a pulsatile component and a non-pulsatile component.

In embodiments, a net high wavelength (HWL) DC component value corresponds to net light absorption by non-pulsatile water and is calculated during step (iii) by adding an intravascular (sH2O) light absorption value, the extravascular (eH2O) light absorption value, and a non-expandable tissue compartment (nDC) light absorption value.

In embodiments, a non-pulsatile LWL DC component value comprises a non-pulsatile hemoglobin (sHb) light absorption value and is calculated during step (iii).

In embodiments, the non-pulsatile hemoglobin (sHb) value is a net LWL light absorption value by hemoglobin comprising a non-pulsatile arterial (nHb) light absorption value, a capillary (cHb) light absorption value, and a venous (vHb) light absorption value, and is calculated during step (iii).

In embodiments, the decision support system includes an artificial intelligence module, the artificial intelligence module configured to receive the multi-wavelength photoplethysmography information, parameter as inputs to a machine learning algorithm, that is trained by a training set including prior wavelength photoplethysmography information, and a prior parameter and to provide, as an output, trend information associated with the trend associated with extravascular water volume.

In embodiments, the decision support system provides one or more alerts based at least on the first trend information and the second trend information, the one or more alerts associated with hydration of the subject.

In embodiments, the one or more alerts include one or more recommendations associated with avoiding one of dehydration and over hydration.

In embodiments, the system includes a main display operable to display the one or more alerts.

A method for monitoring tissue perfusion of a subject in accordance with am embodiment of the present disclosure includes: obtaining multi-wavelength photoplethysmography information associated with light that has passed through tissue of the subject; obtaining multi-wavelength photoplethysmography information associated tissue perfusion information which is a total blood volume in microcirculation of tissues through which the light passed; obtaining multi-wavelength photoplethysmography information associated tissue perfusion reserve information which is an indication of an ability of microcirculation in tissues through which the light passed to accommodate additional total blood volume; deriving from the multi-wavelength photoplethysmography information a parameter associated tissue perfusion and perfusion reserve in tissue through which the light; storing the multi-wavelength photoplethysmography information, and the parameter associated with tissue perfusion and perfusion reserve; repeating these for a period of time; determining, based on the stored multi-wavelength photoplethysmography information, parameter associated with tissue perfusion and perfusion reserve, a trend associated with tissue perfusion and perfusion reserve; providing tissue perfusion status and perfusion reserve information associated with the subject based on the multi-wavelength photoplethysmography information and the parameter associated with tissue perfusion and perfusion reserve and the trend.

A method for monitoring hemoglobin mass of a subject in accordance with an embodiment of the present disclosure includes: obtaining multi-wavelength photoplethysmography information associated light that has passed through tissues of the subject; processing the multi-wavelength photoplethysmography information to derive a parameter associated with hemoglobin mass (Hb) in tissues through which the light passed associated with the subject; storing the multi-wavelength photoplethysmography information, and the parameter associated with hemoglobin mass; repeating these steps for a period of time; determining, based on the stored multi-wavelength photoplethysmography information, parameter associated with hemoglobin mass, a trend associated with hemoglobin mass; and providing hydration status information associated with the subject based on the multi-wavelength photoplethysmography information, the parameter associated with hemoglobin mass and the trend.

In embodiments, the light that has passed through tissue of the subject includes a low wavelength spectrum and a high wavelength spectrum.

In embodiments, a low wavelength spectrum is 400 nm to 600 nm light and the high wavelength spectrum is 850 nm to 1100 nm light.

In embodiments, the multi-wavelength photoplethysmography information includes a pulsatile PPG component (AC) and a non-pulsatile (DC) component.

In embodiments, the high wavelength spectrum is emitted before the low wavelength spectrum of the light.

In embodiments, a net low wavelength (LWL) DC component value corresponds to net light absorption by hemoglobin and is calculated during step (iii) by adding pulsatile arterial hemoglobin volume (aHb), non-pulsatile arterial hemoglobin (nHb), a capillary hemoglobin (cHb), a venous hemoglobin (vHb).

In embodiments, the providing step vi) comprises providing the multi-wavelength photoplethysmography information, parameter associated with hemoglobin mass as inputs to a machine learning algorithm, that is trained by a training set including prior wavelength photoplethysmography information, prior parameters associated with extravascular water volume and provides, as an output, trend information associated with the trend associated with extravascular water volume.

In embodiments, the providing step vi) uses the multi-wavelength photoplethysmography information, perfusion information and parameter associated with hemoglobin mass to generate trend information associated with the trend associated with hemoglobin mass.

In embodiments, the method includes generating one or more alerts based at least on the trend, the one or more alerts associated with hydration of the subject.

In embodiments, the one or more alerts include one or more recommendations associated with avoiding one of dehydration and over-hydration.

In embodiments, the one or more alerts include recommendations related to one of increasing or decreasing fluid intake.

A system for monitoring hemoglobin mass of a subject in accordance with an embodiment of the present disclosure includes: a multi-wavelength photoplethysmography sensor adopted to provide multi-wavelength photoplethysmography sensor information associated light that has passed through tissue of the subject; a decision support system including a processor and memory operably connected thereto, wherein the memory incudes processor executable code, that, when executed by the processor, performs steps of: receiving the multi-wavelength photoplethysmography information; deriving a parameter associated with hemoglobin mass associated with the subject based at least on the multi-wavelength photoplethysmography information; storing the multi-wavelength photoplethysmography information and the parameter in the memory; repeating these steps for a period of time; determining, based on the stored multi-wavelength photoplethysmography information and parameter a trend associated with extravascular water volume; providing hydration status information associated with the subject based on the multi-wavelength photoplethysmography information, the parameter associated with hemoglobin mass and the trend; displaying the multi-wavelength photoplethysmography information parameter and the trend.

In embodiments, the multi-wavelength photoplethysmography sensor comprises a low wavelength light source, a high wavelength light source and a light detector configured to detect light of the low wavelength and the high wavelength.

In embodiments, a control unit operably connected to the low wavelength light source, a high wavelength light source and a light detector and configured to control at least emission of light.

In embodiments, the low wavelength light source, high wavelength light source, light detector and the control unit are mounted on a wearable accessory configured to be worn by the subject.

In embodiments, the multi-wavelength photoplethysmography sensor includes a plurality of a low wavelength light sources, a plurality of high wavelength light sources and at least one light detector configured to detect light of the low wavelength and the high wavelength.

In embodiments, the system includes a control unit operably connected to the plurality of low wavelength light sources, plurality of high wavelength light sources and at least one light detector and configured to control at least emission of light.

In embodiments, the multi-wavelength photoplethysmography sensor includes a plurality of the multi-wavelength photoplethysmography sensors, each multi-wavelength photoplethysmography sensor including a low wavelength light source, a high wavelength light source and one light detector and configured to detect light of the low wavelength and the high wavelength.

In embodiments, the system includes a control unit operably connected to the plurality of the multi-wavelength photoplethysmography sensors and configured to control at least emission of light.

In embodiments, the light that has passed through tissue of the subject includes a low wavelength spectrum and a high wavelength spectrum.

In embodiments, the low wavelength spectrum is 400 nm to 600 nm light and the high wavelength spectrum is 850 nm to 1100 nm light.

In embodiments, the multi-wavelength photoplethysmography information includes a pulsatile component and a non-pulsatile component.

In embodiments, a non-pulsatile LWL DC component value comprises a non-pulsatile hemoglobin (sHb) light absorption value and is calculated during step (iii).

In embodiments, the non-pulsatile hemoglobin (sHb) value is a net LWL light absorption value by hemoglobin comprising a non-pulsatile arterial (nHb) light absorption value, a capillary (cHb) light absorption value, and a venous (vHb) light absorption value, and is calculated during step (iii).

In embodiments, the decision support system includes an artificial intelligence module, the artificial intelligence module configured to receive the multi-wavelength photoplethysmography information, parameter as inputs to a machine learning algorithm, that is trained by a training set including prior wavelength photoplethysmography information, and a prior parameters and to provide, as an output, trend information associated with the trend associated with extravascular water volume.

In embodiments, the decision support system provides one or more alerts based at least on the trend information and the one or more alerts are associated with hydration of the subject.

In embodiments, the one or more alerts include one or more recommendations associated with avoiding one of dehydration and over hydration.

In embodiments, the system includes a main display operable to display the one or more alerts.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

ABBREVIATIONS

MW—multi-wavelength
PPG—photoplethysmography wbHb—whole body hemoglobin mass
wbi$H_2O$—whole body intravascular water
wbBV-whole body blood volume
wbe$H_2O$—whole body extravascular water
tHb—total hemoglobin mass in microcirculation
tiw$H_2O$-$_1$ntravascular water in microcirculation
tBV—total blood volume in microcirculation (an indication of tissue perfusion) which is a sum of tiw$H_2O$ and tHb
eH2O—extravascular water
thA—light attenuation by total hemoglobin mass
tiwA—light attenuation by intravascular water
cbvA—light attenuation by capillary blood volume (an indication of tissue perfusion) which is a sum of thA and tiwA, light attenuation by extravascular water (ewA)
PD—plasma dilution
PV—plasma volume
BV—blood volume
FAR—transcapillary fluid filtration absorption ratio
$H_2O$—water
Hα-hemoglobin mass
LED-light emitting diode
PI—perfusion index
WL—wavelength
LWL—Low Wave-Length spectrum
HWL—High Wave-Length spectrum
Low Width Scan (LWS) mode, the distance between LEDs and the detector is approximately 2.5 cm or less and is used for measuring the AC and DC components of PPG.
TSA—triplet sensor array
non-pulsatile intravascular water (s$H_2O$) which includes: non-pulsatile water in veins (v$H_2O$) and capillaries (cH2O)
n$H_2O$—non-pulsatile component of arterial flow
aHb—arterial hemoglobin
a$H_2O$—pulsatile (arterial) water
wDc—light absorption by non-pulsatile water
TTCS—Titrated Tissue Compression Spectroscopy module
MDSS—Multi—Directional Sensor Systems
revHBS—revised Homeostatic Blood States method
HBS—Homeostatic Blood States method
VLT—Volume Loading Test
Hct—blood hematocrit
$Hct_{min}$—minimal physiologically acceptable hematocrit (13.3%),
$Hct_{max}$—maximal acceptable hematocrit (60%).
IBV—deal (normal) blood volume
IPV—ideal (normal) plasma volume
$Hct_{PM}$—hematocrit of Perfect Match (40%),
optimized values of RCM, BV, PV and PD: oHct, oBV, oPV and oPD
wbPD or lvPD—whole body plasma dilution (or large vessel PD)
wbPV or lvPV—whole body plasma volume (or large vessel PV)
oHct—optimised hematocrit
oPD—optimised plasma dilution
oPV—optimised plasma volume
oBV—optimised blood volume
oEFV—optimised extravascular fluid volume
dHct—dehydrated hematocrit
dPD—dehydrated plasma dilution
dPV—dehydrated plasma volume
dBV—dehydrated blood volume
dEFV—dehydrated extravascular fluid volume
eHct—excess-hydrated blood hematocrit
ePD—excess-hydrated plasma dilution
ePV—excess-hydrated plasma volume
eBV—excess-hydrated blood volume
eEFV—excess-hydrated extravascular fluid volume
EQ_Hct—equilibrated hematocrit is Het after equilibration which implies net effect of fluid distribution and elimination on PD
EQ_PD—equilibrated plasma dilution is wbPD after equilibration
Quantity of water is referred to as water amount (p.d.u.), and quantity of hemoglobin is referred to as hemoglobin mass (p.d.u.). These terms refer to the quantity of media which is saturated with photons from the passing light rather than quantity of media. Changes in light attenuation are used as approximation of changes in saturated quantity of media, which is context sensitive. The terms "water" and "hemoglobin" are used accordingly.
DOS—Depth of Scan is a function of an attenuation coefficient which is a measure of the light loss from the combined effects of scattering and absorption over a unit length of travel in light attenuating medium on the path from LED to sensor.
SSP—Spectrophotometric Signal Processing (math) model
V—amount of media
A—light attenuation (reflects the net effect of light absorption and scattering which is estimated as a difference between the energy of LED-emitted light (EL) and energy sensed by the light detector; A is a sum of AC and DC components in PPG measurements with specific wavelength)
QhA and QwA—fractional changes of attenuation by hemoglobin (QhA) and water (QwA) are used for comparison of changes in their amount over time or due to changes in WL, the site of measurement, the DOS, etc.,
BOL model—Beam of Light model is theoretical background for estimating changes in Hb and i$H_2O$ and e$H_2O$ in a living tissue based on WL-specific fractional changes in light attenuation over time,
LAE—light absorption efficacy
Hbc—hemoglobin concentration
lvHbc—large vessel hemoglobin concentration
cHbc—capillary hemoglobin concentration
nhA—light attenuation by non-pulsatile hemoglobin
RBC—red blood cells
RCM—red cell mass
lvPD—large vessel plasma dilution
RL—Radiating Lines; the SoA HBS Nomogram includes radiating lines (RL) which indicate mean cell hemoglobin concentration (MCHC); hemoglobin concentration (Hb) is in axis X, and Hct in axis Y
cPD—capillary plasma dilution
EFV—extravascular fluid volume
e$H_2O$—extravascular (interstitial) water
RRT—renal replacement therapy
MAD—is RCM and oHct specific maximal acceptable plasma hydration origin deviation in plasma volume (ΔPV)
thA—light attenuation (p.d.u.) by total hemoglobin (mass) as indication of net capillary hemoglobin mass (measurable by invented technique)

tiwA—light attenuation (p.d.u.) by net intravascular water as indication of the amount of capillary water (cH2O) (measurable by invented technique)

ewA—light attenuation (p.d.u.) by extravascular water as indication of the amount of extravascular water (eH2O) (measurable by invented technique)

cHb—capillary hemoglobin concentration (p.d.u.) (estimated by invented technique)

cHct—capillary hematocrit (%) (estimated by invented technique)

plvHct—predicted large vessel hematocrit (%) (estimated by invented technique)

plvHb—predicted (estimated) large vessel hemoglobin concentration (g/L)

oPVD—oPV deviation from IPV oBVD—oBV deviation from IBV dPVD—dPV deviation from IPV dBVD dBV deviation from IBV ePVD—ePV deviation from IPV eBVD—eBV deviation from IBV CDSS—Clinical Decision Support System

What is claimed is:

1. A method for monitoring hydration status and detection of changes in whole body hemoglobin mass of a subject comprising:

i) obtaining multi-wavelength photoplethysmography information associated with light that has passed through the derma of the subject;

ii) setting a minimum hemocrit (Hct) value and a maximum Hct value defining lateral boundaries;

iii) setting dehydrated plasma dilution (dPD) value as a lower boundary;

iv) setting an optimal plasma dilution (oPD) as an upper boundary;

v) processing the multi-wavelength photoplethysmography information to derive:

(1) a first parameter associated with plasma dilution (PD); and (2) a second parameter associated with Hct, vi) generating a nomogram including a rhombus shape defined by the minimum Hct, maximum Hct, dehydrated plasma dilution and optimal plasma dilution, and vii) fitting the first parameter and the second parameter on the nomogram, wherein normal hydration is indicated where the first parameter and second parameter fit inside the rhombus shape, wherein a reduction in whole body hemoglobin mass is indicated where the first parameter and second parameter fit outside the rhombus shape above the optimal plasma dilution (oPD) as the upper boundary, and/or wherein an increase in the whole body hemoglobin mass is indicated where the first parameter and second parameter fit outside the rhombus shape below the dehydrated plasma dilution (dPD) value as the lower boundary.

2. The method of claim 1, wherein the nomogram is displayed on a display to a user such that the rhombus shape is visible.

3. The method of claim 2, wherein the nomogram includes a zoom feature to allow a user a more detailed view of the parameters represented on the nomogram.

4. The method of claim 1, wherein the nomogram includes indicia indicating warning areas on the nomogram associated with hydration or circulation risks, or body dehydration, overhydration, a change the in whole body hemoglobin mass, bleeding, red cell transfusion.

5. The method of claim 1, wherein the nomogram includes patient identification information identifying the subject.

6. The method of claim 1, further comprising, prior to the step of obtaining multi-wavelength photoplethysmography information, a step of calibrating a plurality of multi-wavelength photoplethysmography sensor devices arranged in parallel in a system for monitoring changes in a quantity of hemoglobin and water in derma of the subject, wherein the step of calibrating comprises:

I) activating a first light source emitting light of a first wavelength toward tissue of the subject;

II) activating a second light source emitting light of a second wavelength toward tissue of the subject;

wherein the first light source is positioned parallel to the second light source;

III) receiving, by a first light detector first wavelength spectra associated with the first wavelength and by a second light detector second wavelength spectra associated with the second wavelength;

IV) generating multi-wavelength photoplethysmography information based on receipt of the first spectra and the second spectra;

V) analyzing the multi-wavelength photoplethysmography (PPG) information to select a first desired wavelength specifically for measuring light attenuation by hemoglobin based on signal quality, patterns and features, where the first desired wavelength is referred to as individual low wavelength (ILWL);

VI) analyzing the multi-wavelength photoplethysmography information to select a second desired wavelength specifically for measuring light attenuation by water based signal quality, patterns and features, the second desired wavelength is referred to as individual high wavelength (IHWL);

VII) indicating the individual low wavelength (ILWL) and the individual high wavelength (IHWL) which are associated with the best suitable features, where ILWL is used for the multi-wavelength PPG measurements that estimate changes in hemoglobin and IHWL is used for the multi-wavelength PPG measurements that estimate changes in water, wherein the individual low wavelength (ILWL) and the individual high wavelength (IHWL) are used by the plurality of multi-wavelength photoplethysmography sensor devices to provide the multi-wavelength photoplethysmography information obtained in the step of obtaining multi-wavelength photoplethysmography information.

7. The method of claim 6, wherein there is an inverse relationship between light absorption by the hemoglobin and water at ILWL and IHWL.

8. The method of claim 6, further comprising, after the step of obtaining multi-wavelength photoplethysmography information, a step of monitoring measurable changes in quantities of hemoglobin, intravascular water and extravascular water in derma of the subject comprising:

A) processing the multi-wavelength photoplethysmography information to derive:

(1) a first parameter associated with a quantity of non-pulsatile hemoglobin (sHb) as indicated by a PPG DC component associated with ILWL light attenuation (nhA) in tissues through which the light passed in the subject, (2) a second parameter associated with net non-pulsatile water volume (wDC) as indicated by the PPG DC component that associated with IHWL light attenuation by non-pulsatile water (nwA) in tissues through which the light passed in the subject, (3) a third parameter associated with a quantity of pulsatile hemoglobin (aHb) as indicated by a PPG AC component associated with ILWL light attenuation (phA) in tissues through which the light passed in the subject, (4) a fourth parameter associated with net pulsatile water volume (wDC) as indicated by the PPG AC component associated with THWL light attenuation (pwA) in tissues through which the light passed in the subject, B) storing the multi-wavelength photoplethysmography information, and the first, second, third and fourth parameters associated with the changes in quantity of hemoglobin, intravascular water and extravascular water in derma of the subject over time;

C) repeating steps A) through B) for a period of time;

D) determining, based on the stored multi-wavelength photoplethysmography information and the stored first, second, third and fourth parameters associated with the changes in quantity of hemoglobin, intravascular water and extravascular water in derma of the subject, trends associated with the changes in quantity of hemoglobin, intravascular water and extravascular water in derma of the subject; and E) providing hydration status information associated with the subject based on the multi-wavelength photoplethysmography information, the parameters associated with hemoglobin, intravascular water and extravascular water in derma of the subject and the trends, wherein the hydration status information is used in the step of fitting the first parameter and the second parameter on the nomogram.

9. The method of claim 8, wherein a IHWL DC component value corresponds to net light attenuation by non-pulsatile water (niwA) in the subject and is obtained during step B) by adding an intravascular water (sH2O) quantity-related light attenuation value, extravascular water (eH2O) quantity-related light attenuation value, and a non-expandable water containing media (nDC) quantity-related light attenuation value (nHDC), where light attenuation by nDC has no impact on changes in niwA because the quantity of nDC is not changing in short term.

10. The method of claim 8, wherein a IHWL AC component value corresponds to net light attenuation by pulsatile water (pwA) in the subject and is obtained during step B) by adding a non-expandable water containing media (oLAC) quantity-related light attenuation value (pHAC) where light attenuation by nDC has no impact on changes in niwA because the quantity of nDC is not changing in short term.

11. The method of claim 8, wherein a ILWL DC component value corresponds to net light attenuation by non-pulsatile hemoglobin (nhA) in the subject and is obtained during step B) by adding attenuation by non-expandable media (oDC) quantity-related light attenuation value (iLDC) where light attenuation by oDC has no impact on changes in nhA because the quantity of oDC is not changing in short term.

12. The method of claim 8, wherein a ILWL AC component value corresponds to net light attenuation by pulsatile hemoglobin (phA) in the subject and is obtained during step B) by adding a attenuation by non-expandable media (oLAC) quantity-related light attenuation value (pLAC); light attenuation by oLAC has no impact on changes in phA because the quantity of oLAC is not changing in short term.

13. The method of claim 8, wherein the providing step E) comprises providing the stored multi-wavelength photoplethysmography information and stored first, second, third and fourth parameters to a machine learning algorithm, that is trained by a training set including prior wavelength photoplethysmography information, prior parameters associated with extravascular water volume and provides, as an output, trend information associated with the trend associated with extravascular water volume.

14. The method of claim 8, wherein the light comprises (i) individual i low wavelength (ILWL) light in a wavelength spectrum most sensitive to absorption by hemoglobin, and (ii) individual high wavelength (IHWL) light in a wavelength spectrum most sensitive to absorption by water.

15. The method of claim 14, wherein there is an inverse relationship between light absorption by the hemoglobin and water at ILWL and IHWL.

16. The method of claim 8, wherein the individual low wavelength (ILWL) light and individual high wavelength (IHWL) light are determined in the calibrating step and the light absorption by hemoglobin at ILWL is adjusted by a ratio of the light absorption by water of hemoglobin at IHWL to minimize impact of light absorption by water in hemoglobin measurements, and impact of light absorption by hemoglobin in water measurements.

17. The method of claim 8, wherein the ILWL is determined as a wavelength at which light attenuation prior to induced obstruction of circulation is lower than at any other wavelength and at which reduction of light attenuation is greater than reduction of light attenuation at any other wavelength during an induced obstruction of circulation under a photoplethysmography sensor, and/or wherein the IHWL is determined as a wavelength at which light attenuation prior to induced obstruction of circulation is higher than at any other wavelength and at which reduction of light attenuation is less than reduction of light attenuation at any other wavelength during an induced obstruction of circulation under the photoplethysmography sensor.

18. The method of claim 8, wherein the determining step includes providing the stored multi-wavelength photoplethysmography information and the stored first, second, third and fourth parameters associated with the changes in quantity of hemoglobin, intravascular water and extravascular water in derma of the subject as inputs to a machine learning algorithm trained using prior multi-wavelength photoplethysmography information and parameters and providing, as an output, trend information associated with the trends.

19. The method of claim 8, further comprising, after the step of providing hydration status information, a step of monitoring changes in a non-measurable quantity of extravascular (tissue) water of the subject and its changes comprising:

a) obtaining IHWL photoplethysmography information associated with light that has passed through tissue of the subject;

b) obtaining the multi-wavelength photoplethysmography information associated with the net pulsatile water volume (wDC), non-pulsatile water volume (WDC), pulsatile hemoglobin (aHb) and non-pulsatile hemoglobin (sHb), as indicated by the pwA, nwA, phA and nhA, and c) deriving from the above information an estimated quantity of non-pulsatile intravascular water (sH2O) as indicated by a net DC component either during an induced obstruction of circulation under a photoplethysmography sensor providing the photoplethysmography information, or d) without compression by deriving an estimated quantity of non-pulsatile intravascular water (sH2O) by applying an arterial hemodilution value, which is a ratio of measurable phA to pwA, to a ratio of measurable nhA to non-measurable niwA, with niwA estimated as a result;

e) storing the multi-wavelength photoplethysmography information and the estimated quantities;

f) repeating steps a) through e) for a period of time;

g) determining, based on the stored multi-wavelength photoplethysmography information and the stored estimated quantities associated with extravascular water amount and accumulation a trend; and h) providing changes in tissue hydration information associated with the subject based on the multi-wavelength photoplethysmography information and the trend, wherein the changes in tissue hydration information is used in the step of fitting the first parameter and the second parameter on the nomogram.

20. The method of claim 19, wherein the determining step g) comprises providing the multi-wavelength photoplethysmography information and the stored estimated quantities associated with extravascular water amount and accumulation as inputs to a machine learning algorithm trained by a training set including multi-wavelength photoplethysmography information and the stored estimated quantities and providing as an output trend information associated with the trend.

* * * * *